US012478635B2

(12) United States Patent
Machielse et al.

(10) Patent No.: US 12,478,635 B2
(45) **Date of Patent: *Nov. 25, 2025**

(54) HYDROXYPROPYL BETA-CYCLODEXTRIN COMPOSITIONS AND METHODS

(71) Applicant: Mandos LLC, West Hollywood, CA (US)

(72) Inventors: Bernardus Nicolaas Machielse, North Potomac, MD (US); Allan Darling, North Potomac, MD (US)

(73) Assignee: MANDOS LLC, Thousand Oaks, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/219,596

(22) Filed: May 27, 2025

(65) Prior Publication Data

US 2025/0281522 A1 Sep. 11, 2025

Related U.S. Application Data

(63) Continuation of application No. 19/028,631, filed on Jan. 17, 2025, which is a continuation of application No. 18/533,373, filed on Dec. 8, 2023, which is a continuation of application No. 17/970,080, filed on Oct. 20, 2022, now Pat. No. 11,938,144, which is a continuation of application No. 17/745,464, filed on May 16, 2022, now Pat. No. 11,590,159, which is a continuation of application No. 17/036,148, filed on Sep. 29, 2020, now Pat. No. 11,406,657, which is a continuation of application No. 16/430,664, filed on Jun. 4, 2019, now Pat. No. 10,933,083, which is a continuation of application No. 16/372,899, filed on Apr. 2, 2019, now Pat. No. 10,709,730, which is a continuation of application No. 16/134,028, filed on Sep. 18, 2018, now Pat. No. 10,300,086, which is a continuation of application No. 15/499,831, filed on Apr. 27, 2017, now Pat. No. 10,258,641, which is a continuation of application No. 15/288,876, filed on Oct. 7, 2016, now Pat. No. 9,675,634, which is a continuation of application No. 15/178,153, filed on Jun. 9, 2016, now abandoned.

(60) Provisional application No. 62/345,721, filed on Jun. 3, 2016, provisional application No. 62/331,385, filed on May 3, 2016, provisional application No. 62/314,765, filed on Mar. 29, 2016, provisional application No. 62/308,736, filed on Mar. 15, 2016, provisional application No. 62/276,728, filed on Jan. 8, 2016, provisional application No. 62/263,599, filed on Dec. 4, 2015, provisional application No. 62/249,876, filed on Nov. 2, 2015, provisional application No. 62/245,974, filed on Oct. 23, 2015, provisional application No. 62/189,114, filed on Jul. 6, 2015, provisional application No. 62/175,075, filed on Jun. 12, 2015, provisional application No. 62/173,889, filed on Jun. 10, 2015.

(51) Int. Cl.

| | |
|---|---|
| *A61K 31/724* | (2006.01) |
| *A61K 9/00* | (2006.01) |
| *A61K 9/08* | (2006.01) |

(52) U.S. Cl.
CPC .......... *A61K 31/724* (2013.01); *A61K 9/0019* (2013.01); *A61K 9/0085* (2013.01); *A61K 9/08* (2013.01)

(58) Field of Classification Search
CPC .................................................... A61K 31/724
See application file for complete search history.

(56) References Cited

U.S. PATENT DOCUMENTS

| | | | |
|---|---|---|---|
| 4,727,064 | A | 2/1988 | Pitha |
| 4,877,778 | A | 10/1989 | Carpenter et al. |
| 5,262,404 | A | 11/1993 | Weisz et al. |
| 5,376,645 | A | 12/1994 | Stella et al. |
| 5,624,914 | A | 4/1997 | Patel et al. |
| 6,407,079 | B1 | 6/2002 | Müller et al. |
| 6,528,642 | B1 | 3/2003 | Duval et al. |
| 6,878,695 | B2 | 4/2005 | Woo et al. |
| 9,044,451 | B2 | 6/2015 | Zheng et al. |
| 9,675,634 | B2 | 6/2017 | Machielse et al. |

(Continued)

FOREIGN PATENT DOCUMENTS

| | | | |
|---|---|---|---|
| CN | 1073359 | A | 6/1993 |
| CN | 102040675 | A | 5/2011 |

(Continued)

OTHER PUBLICATIONS

Abi-Mosleh L., et al., "Cyclodextrin Overcomes Deficient Lysosome-To-Endoplasmic Reticulum Transport of Cholesterol in Niemann-Pick Type C Cells," Proceedings of the National Academy of Sciences, Nov. 17, 2009, vol. 106, No. 46, pp. 19316-19321.

(Continued)

*Primary Examiner* — Layla D Berry
(74) *Attorney, Agent, or Firm* — POLSINELLI PC

(57) ABSTRACT

This disclosure provides mixtures of beta-cyclodextrin molecules substituted at one or more hydroxyl positions by hydroxypropyl groups, the mixture optionally including unsubstituted beta-cyclodextrin molecules, for use as a pharmaceutically active ingredient; methods of making such mixtures; methods of qualifying such mixtures for use in a pharmaceutical composition suitable for intrathecal or intracerebroventricular administration; pharmaceutical compositions suitable for intrathecal or intracerebroventricular administration comprising such mixtures; and methods of using the pharmaceutical compositions for treatment of Niemann-Pick disease Type C.

30 Claims, 58 Drawing Sheets

(56) References Cited

U.S. PATENT DOCUMENTS

| | | | |
|---|---|---|---|
| 11,633,423 B2 | 4/2023 | Machielse et al. |
| 11,744,848 B2 | 9/2023 | Machielse et al. |
| 11,958,917 B2 | 4/2024 | Pfeiffer et al. |
| 2001/0056080 A1 | 12/2001 | Woo et al. |
| 2004/0076591 A1 | 4/2004 | Anthony Nelson et al. |
| 2006/0025380 A1 | 2/2006 | Thorsteinsson et al. |
| 2011/0028432 A1 | 2/2011 | Cataldo et al. |
| 2015/0065457 A1 | 3/2015 | Fornoni et al. |
| 2015/0216895 A1 | 8/2015 | McKew et al. |

FOREIGN PATENT DOCUMENTS

| | | | |
|---|---|---|---|
| CN | 109675054 | A | 4/2019 |
| EP | 1747785 | A1 | 1/2007 |
| JP | 2007504166 | A | 3/2007 |
| TW | 491715 | B | 6/2002 |
| WO | 2007013123 | A1 | 2/2007 |
| WO | 2010138802 | A2 | 12/2010 |
| WO | 2012012473 | A1 | 1/2012 |
| WO | 2013155485 | A2 | 10/2013 |
| WO | 2014022841 | A1 | 2/2014 |
| WO | 2015087016 | A1 | 6/2015 |
| WO | 2016201137 | A1 | 12/2016 |
| WO | 2021050890 | A1 | 3/2021 |
| WO | 2022047241 | A1 | 3/2022 |

OTHER PUBLICATIONS

Acucena R.W., "Defining a strategy for the Validation and Qualification of Sterile Filtration Processes of Investigational Medicinal Compounds," PDA Metro Chapter Dinner, Mar. 4, 2014, 45 pages.

Alvarez A.R., et al., "Imatinib Therapy Blocks Cerebellar Apoptosis and Improves Neurological Symptoms in A Mouse Model of Niemann-Pick Type C Disease," The FASEB Journal, Oct. 2008, vol. 22, pp. 3617-3627.

Aqul A., et al., "Unesterified Cholesterol Accumulation in Late Endosomes/Lysosomes Causes Neurodegeneration and Is Prevented by Driving Cholesterol Export from This Compartment," The Journal of Neuroscience, Jun. 22, 2011, vol. 31, No. 25, pp. 9404-9413.

Beers M.H., et al., "Hydroxypropyl Beta-Cyclodextrin Compositions and Methods," The Merck Manual of Diagnosis and Therapy, 1992, pp. 1049-1051.

Bhandari T., "Protein Linked to Alzheimer's, Strokes Cleared from Brain Blood Vessels," Washington University School of Medicine, Feb. 17, 2021,6 pages, Retrieved from the Internet: URL: https://medicine.wustl.edu/news/protein-linked-to-alzheimers-strokes-cleared-from-brain-blood-vessels/.

Boldrini R., et al., "Wolman Disease and Cholesteryl Ester Storage Disease Diagnosed by Histological and Ultrastructural Examination of Intestinal and Liver Biopsy," Pathology—Research and Practice, 2004, vol. 200, pp. 231-240.

Brewster M. E., et al., "An Intravenous Toxicity Study of 2-Hydroxypropyl-Cyclodextrin, a Useful Drug Solubilizer, in Rats and Monkeys," International Journal of Pharmaceutics, 1990, vol. 59, pp. 231-243.

Byun K., et al., "Alteration of the Glutamate and GABA Transporters in the Hippocampus of the Niemann-Pick Disease, Type C Mouse Using Proteomic Analysis," Proteomics, 2006, vol. 6, pp. 1230-1236.

Camargo F., et al., "Cyclodextrins in the Treatment of a Mouse Model of Niemann-Pick C Disease," Life Sciences, 2001, vol. 70, No. 2, pp. 131-142.

Cantz M., et al., Disorders of Glycoprotein Degradation, Journal of Inherited Metabolic Disease, 1990, vol. 13 pp. 523-537.

Carstea E.D., et al., "Niemann-Pick C1 Disease Gene: Homology to Mediators of Cholesterol Homeostasis," Science, Jul. 11, 1997, vol. 277, pp. 228-231.

Chen F.W., et al., "Cyclodextrin Induces Calcium-Dependent Lysosomal Exocytosis," PLOS One, Nov. 2010, vol. 5, No. 11, 7 Pages.

Chien Y.H., et al., "Long-Term Efficacy of Miglustat in Paediatric Patients with Niemann-Pick Disease Type C," Journal of Inherited Metabolic Disease, 2013, vol. 36, pp. 129-137.

Choi H.Y., et al., "Impaired ABCA1-Dependent Lipid Efflux and Hypoalphalipoproteinemia in Human Niemann-Pick Type C Disease," Journal of Biological Chemistry, Aug. 29, 2003, vol. 278, No. 35, pp. 32569-32577.

Cluzeau C.V.M., et al., "Microarray Expression Analysis and Identification of Serum Biomarkers for Niemann-Pick Disease, Type C1," Human Molecular Genetics, 2012, vol. 21, No. 16, pp. 3632-3646.

Coisne C., et al., "Cyclodextrins as Emerging Therapeutic Tools in the Treatment of Cholesterol-Associated Vascular and Neurodegenerative Diseases," Molecules, Dec. 20, 2016, vol. 21, No. 12, pp. 1-22, XP055548026, DOI: 10.3390/molecules21121748.

Cologna S.M., et al., "Quantitative Proteomic Analysis of Niemann-Pick Disease, Type C1 Cerebellum Identifies Protein Biomarkers and Provides Pathological Insight," PLoS One, Oct. 2012, vol. 7, No. 10, 13 pages.

Crumling M.A., et al., "Hearing Loss and Hair Cell Death in Mice Given the Cholesterol-Chelating Agent Hydroxypropyl-Cyclodextrin," PLoS One, Dec. 2012, vol. 7, No. 12, 8 pages.

Cruz-Pardos S., et al., "Treatment with Cyclodextrin for Niemann Pick's Disease," Farm Hospital, 2013, vol. 37, No. 3, pp. 263-272.

CTD, Inc., "Cyclo Powder, Product Brochure," Retrieved from the Internet on Nov. 21, 2023, 3 pages.

Davidson, C. D., et al., "Efficacy of Different Cyclodextrins in the Treatment of Niemann-Pick type C Disease," Jun. 2012, Abstract, Retrieved from the Internet: URL: http://niemannpick.nd.edu/assets/69394/abstracts_in_speaking_order.pdf, on Jul. 20, 2016.

Davidson C., et al., "Chronic Cyclodextrin Administration Ameliorates Clinical Symptoms and Storage Accumulation in Niemann-Pick Type C1 Mice," Lysosomal Disease Network Annual Meeting, Feb. 18-20, 2009, 1 page.

Davidson C., et al., "Different Cyclodextrins for the Treatment of Niemann-Pick Disease Type C," Molecular Genetics and Metabolism, 2016, vol. 117, 1 page.

Davidson C., et al., "Poster: Combinatorial Therapy for Niemann-Pick Type C Disease: Treatment of an NPC1 Murine Model with 2-Hydroxypropyl-Beta-Cyclodextrin and Miglustat," World Symposium, 2015.

Davidson C.D., et al., "Chronic Cyclodextrin Treatment of Murine Niemann-Pick C Disease Ameliorates Neuronal Cholesterol and Glycosphingolipid Storage and Disease Progression," PLoS One, Sep. 2009, vol. 4, No. 9, 15 Pages.

Davidson C.D., et al., "Efficacy and Ototoxicity of Different Cyclodextrins in Niemann-Pick C Disease," Annals of Clinical and Translational Neurology, 2016, vol. 3, No. 5, pp. 366-380.

De Windt A., et al., "Gene Set Enrichment Analyses Revealed Several Affected Pathways in Niemann-Pick Disease Type C Fibroblasts," DNA and Cell Biology, 2007, vol. 26, No. 9, pp. 665-671.

Decroocq C., et al., "Cyclodextrin-Based Iminosugar Click Clusters: The First Examples of Multivalent Pharmacological Chaperones for the Treatment of Lysosomal Storage Disorders," ChemBioChem, 2012, vol. 13, No. 5, pp. 661-664.

Dekaban A.S., et al., "Changes in Brain Weights during the Span of Human Life: Relation of Brain Weights to Body Heights and Body Weights," Annals of Neurology, 1978, vol. 4, pp. 345-356.

Elrick M.J., et al., "Autophagic Dysfunction in a Lysosomal Storage Disorder Due To Impaired Proteolysis," Autophagy, Feb. 2013, vol. 9, No. 2, 2 pages.

European Medicines Agency, "Background Review for Cyclodextrins Used as Excipients," Committee for Human Medicinal Products (CHMP), Nov. 20, 2014, 17 pages, Retrieved from the Internet: URL: http://www.ema.europa.eu/docs/en_GB/document_library/Report/2014/12/WC500177936. pdf.

European Medicines Agency, "Background Review for the Excipient Propylene Glycol," Committee for Human Medicinal Products (CHMP), Nov. 20, 2014, 96 pages.

Favier M.L., et al., "Effect of Cyclodextrin on Plasma Lipids and Cholesterol Metabolism in the Rat," Metabolism, Feb. 1995, vol. 44, No. 02, pp. 200-206.

(56) References Cited

OTHER PUBLICATIONS

Fenyvesi F., et al., "Fluorescently Labeled Methyl-Beta-Cyclodextrin Enters Intestinal Epithelial Caco-2 Cells By Fluid-Phase Endocytosis," PLoS One, Jan. 2014, vol. 9, No. 1,11 pages.
First Examination Report for Australian Application No. 2013296170, mailed on May 5, 2017, 4 pages.
Fromming K.H., et al., "Pharmacokinetics and Toxicology of Cyclodextrins," Cyclodextrins in Pharmacy, Chapter 3, 1994, pp. 33-44.
Garcia-Robels A.A., et al., "Use of 2 Hydroxypropyl-Beta-Cyclodextrin Therapy in Two Adult Niemann Pick Type C Patients," Journal of the Neurological Sciences, 2016, vol. 366, pp. 65-67.
Gelsthorpe M.E., et al., "Niemann-Pick Type C1 11061T Mutant Encodes A Functional Protein That Is Selected For Endoplasmic Reticulum-Associated Degradation Due To Protein Misfolding," The Journal of Biological Chemistry, Mar. 28, 2008, vol. 283, No. 13, pp. 8229-8236.
Ginocchio V.M., et al., "Efficacy of Miglustat in NiemannPick C Disease: A Single Centre Experience," Molecular Genetics and Metabolism, 2013, vol. 110, No. 3, pp. 329-335.
Gould S., et al., "2-Hydroxypropyl-Cyclodextrin (HP-CD): A Toxicology Review," Food and Chemical Toxicology, 2005, vol. 43, pp. 1451-1459.
Grebe A., "Targeting Cholesterol Crystals in Atherosclerosis with Cholesterol Solubilizing 2-Hydroxypropyl—Cyclodextrin," Dissertation, Mar. 2016, 157 pages.
Hastings C. A., et al., "Clinical Experience with Intravenous and Intrathecal Infusions of Hydroxy-Propyl-Beta-Cyclodextrin in Identical Twin Patients with Niemann-Pick Type C Disease," Jun. 2011, Abstract, Retrieved from the Internet: URL: http://niemannpick.nd.edu/assets/52702/all_abstracts.pdf, on Jul. 20, 2016.
Hempel C., "Dear British Media—Feel Free to Call or Email!," Mar. 26, 2009, 2 pages, Retrieved from the Internet: URL http://addiandcassi.com/dear-british-media/.
Hempel C., "Dr. Caroline Hastings Submission Letter to FDA: Investigational New Drug Application," May 2009, 23 pages, Retrieved from the Internet: URL: http://addiandcassi.com/wordpress/wp-content/uploads/2009/09/FDA-Caroline-Hastings-Submission-Letter-May 2009.pdf, on Sep. 16, 2016.
Hempel C., "FDA Filing Requesting to put Cyclodextrin into the Brains of the Addi and Cassi," Aug. 2010, 239 pages, Retrieved from the Internet: URL: http://addiandcassi.com/wordpress/wp-content/uploads/Hempel-Cyclodextrin-Intrathecal-FDA-Filing-2010-Aug.pdf, on Sep. 16, 2016.
Hempel C., "FDA Investigational New Drug Application Documents for Cyclodextrin Treatment for Niemann Pick Type C Disease," Addi Cassi Fund [Online], Sep. 13, 2009, pp. 1-5, Retrieved from the Internet: URL: https://addiandcassi.com/fda-investigational-new-drug-application-documents-for-cyclodextrin-treatment-for-niemann-pick-type-c-disease/.
Heron B., et al., "Miglustat Therapy in the French Cohort of Paediatric Patients with Niemann-Pick Disease Type C," Orphanet Journal of Rare Diseases, 2012, vol. 7, No. 36, 14 Pages.
Herrmann H.C., et al., "Inhibition of Smooth Muscle Cell Proliferation and Experimental Angioplasty Restenosis by Beta-Cyclodextrin Tetradecasulfate," Arteriosclerosis and Thrombosis, Jun. 1993, vol. 13, No. 6, pp. 924-931.
Hospira, "0.9% Sodium Chloride Injection," USP, May 2014, 13 pages.
Walenbergh S.M.A, et al., "Weekly Treatment of 2-Hydroxypropyl-cyclodextrin Improves Intracellular Cholesterol Levels in LDL Receptor Knockout Mice," International Journal of Molecular Sciences, 2015, vol. 16, No. 9, pp. 21056-21069.
Walkley S., et al., "141. Cyclodextrin Treatment Not Only Delays but also Reduces Established Intraneuronal Storage in Niemann-Pick Type C Disease," Molecular Genetics and Metabolism, 2010, vol. 99, No. 2, 1 page.
Walkley S.U., "Cellular Pathology of Lysosomal Storage Disorders," Brain Pathology, 1998, vol. 8, pp. 175-193.
Walkley S.U., et al., "Consequences of NPC1 and NPC2 Loss of Function in Mammalian Neurons," Biochimica et Biophysica Acta (BBA)—Molecular and Cell Biology of Lipids, 2004, vol. 1685, No. 1-3, pp. 48-62.
Walkley S.U., et al., "Gangliosides as Modulators of Dendritogenesis in Normal and Storage Disease-affected Pyramidal Neurons," Cerebral Cortex, Oct. 2000, vol. 10, No. 10, pp. 1028-1037.
Walkley S.U., et al., "Lysosomal Compromise and Brain Dysfunction: Examining the Role of Neuroaxonal Dystrophy," Biochemical Society Transactions, Dec. 2010, vol. 38, No. 6, 13 pages.
Walpole S.C., et al., "The Weight of Nations: An Estimation of Adult Human Biomass," BMC Public Health, 2012, vol. 12, No. 439, 6 pages.
Wang M.L., et al., "Identification of Surface Residues on Niemann-Pick C2 Essential for Hydrophobic Handoff of Cholesterol to NPC1 in Lysosomes," Cell Metabolism, Aug. 4, 2010, vol. 12, No. 2, pp. 166-173.
Ward S., et al., "2-hydroxypropyl-beta-Cyclodextrin Raises Hearing Threshold in Normal Cats and in Cats with Niemann-pick Type C Disease," Pediatric Research, 2010, vol. 68, No. 1, pp. 52-56.
Wehrmann Z.T., et al., "Quantitative Comparison of the Efficacy of Various Compounds in Lowering Intracellular Cholesterol Levels in Niemann-Pick Type C Fibroblasts," PLoS One, Oct. 2012, vol. 7, No. 10, 9 pages.
Wistrand L.G., et al., "A Method for Removal of Endotoxin from Pharmaceutical Formulation," BioPharm Interntional, Nov. 1, 2012, vol. 25, No. 9, 26 pages.
Wraith J.E., et al., "Miglustat in Adult and Juvenile Patients with NiemannPick Disease Type C: Long-term Data from a Clinical Trial," Molecular Genetics and Metabolism, 2009, 7 pages.
Xu M., et al., "A Phenotypic Compound Screening Assay for Lysosomal Storage Diseases," Journal of Biomolecular Screening, 2014, vol. 19, No. 1, pp. 168-175.
Xu M., et al., "-Tocopherol Reduces Lipid Accumulation in Niemann-Pick Type C1 and Wolman Cholesterol Storage Disorders," The Journal of Biological Chemistry, Nov. 16, 2012, vol. 287, No. 47, pp. 39349-39360.
Yanjanin N.M., et al., "Linear Clinical Progression, Independent of Age of Onset, in NiemannPick Disease, Type C," American Journal of Medical Genetics Part B: Neuropsychiatric Genetics, Jan. 5, 2010, vol. 153B, No. 1, 17 pages.
Yergey A.L., et al., "Characterization of Hydroxypropyl-Beta-Cyclodextrins by ESI lon Mobility Mass Spectrometry," Michael, Marcia, and Christa Parseghian Scientific Conference for Niemann-Pick Type C Research, 2016,1 page.
Yergey A.L., et al., "Characterization of Hydroxypropyl-Beta-Cyclodextrins Used in the Treatment of Niemann-Pick Disease Type C1," PLOS One, Apr. 17, 2017, vol. 12, No. 4, pp. 1-13.
Yu D., et al., "NiemannPick Disease Type C: Induced Pluripotent Stem CellDerived Neuronal Cells for Modeling Neural Disease and Evaluating Drug Efficacy," Journal of Biomolecular Screening, 2014, vol. 19, No. 8, pp. 1164-1173.
Yuan C., et al., "Characterization of Hydroxypropyl-Cyclodextrins with Different Substitution Patterns via FTIR, GCMS, andTGDTA," Carbohydrate Polymers, 2015, vol. 118, pp. 36-40.
Zervas M., et al., "Critical Role for Glycosphingolipids in Niemann-Pick Disease Type C," Current Biology, 2001, vol. 11, No. 16, pp. 1283-1287.
Zimmer S., et al., "Cyclodextrin Promotes Atherosclerosis Regression via Macrophage Reprogramming," Science Translational Medicine, Apr. 6, 2016, vol. 8, No. 333, 12 pages.
Zimmer S., et al., "Cyclodextrin Promotes Atherosclerosis Regression via Macrophage Reprogramming," Science Translational Medicine, 2016, vol. 8, No. 333, pp. 1-31.
"Hydroxypropyl Beta Cyclodextrin for Niemann-Pick Type C1 Disease," Dec. 10, 2012, retrieved from the Internet: URL: http://clinicaltrials.gov/archive/NCTO1747135/2012_12_10, 6 pages.
"Hydroxypropyl Betadex"., Official Monographs, The United States Pharmacopeial Convention, May 1, 2012, pp. 1819-1821.
Innovation Hub., "KLEPTOSE HPB parenteral Grade Hydroxypropyl Beta-Cyclodextrin—Pyrogen-Free-Low Molar Substitution," Pharma Virtual lab by Roquette, retrieved on Mar. 13, 2025, 5 pages,

(56) References Cited

OTHER PUBLICATIONS

Retrieved from Internet URL: https://www.roquette.com/innovation-hub/pharma/product-profile-pages/kleptose-hpb-parenteral-grade.
International Preliminary Report on Patentability for Application No. PCT/IB2023/051462, mailed on Aug. 29, 2024, 5 pages.
International Preliminary Report on Patentability for Application No. PCT/US2013/053527, mailed on Feb. 3, 2015, 10 Pages.
International Preliminary Report on Patentability for International Application No. PCT/US2016/036753, mailed Dec. 21, 2017, 09 Pages.
International Search Report and Written Opinion for Application No. PCT/US2013/053527, mailed on Oct. 16, 2013, 14 Pages.
International Search Report and Written Opinion for International Application No. PCT/US2016/036753, mailed Aug. 30, 2016, 11 Pages.
Irie T., et al., "Hydroxypropylcyclodextrins in Parenteral Use. II: Effects on Transport and Disposition of Lipids in Rabbit and Humans," Journal of Pharmaceutical Sciences, Jun. 1992, vol. 81, No. 6, pp. 524-528.
Irie T., et al., "Pharmaceutical Applications of Cyclodextrins. III. Toxicological Issues and Safety Evaluation," Journal of Pharmaceutical Sciences, Feb. 1997, vol. 86, No. 2, pp. 147-162.
Jiang H., et al., "Development and Validation of Sensitive LC-MS/MS Assays for Quantification of HP-CD in Human Plasma and CSF," Journal of Lipid Research, 2014, vol. 55, No. 7, pp. 1537-1548.
Jiang X., et al., "Development of a Bile Acid-Based Newborn Screen for Niemann-Pick C Disease," Science Translational Medicine, May 4, 2016, vol. 8, No. 337, 26 Pages.
Kali G., et al., "Cyclodextrins and Derivatives in Drug Delivery: New Developments, Relevant Clinical Trials, and Advanced Products," Carbohydrate Polymers, 2024, vol. 324, pp. 1-23.
King K., et al., "Auditory Phenotype of Niemann-Pick Disease, Type C1," Ear and Hearing, 2014, vol. 35, No. 1, 17 pages.
Ko D.C., et al., "Cell-Autonomous Death of Cerebellar Purkinje Neurons with Autophagy in Niemann-Pick Type C Disease," PLoS Genetics, Jul. 2005, vol. 1, No. 1, pp. 81-95.
Kondo Y., et al., "In Vitro Evaluation of 2-Hydroxyalkylated -Cyclodextrins as Potential Therapeutic Agents for Niemann-Pick Type C Disease," Molecular Genetics and Metabolism, 2016, vol. 118, pp. 214-219.
Lachmann R.H., et al., "Treatment with Miglustat Reverses the Lipid-Trafficking Defect in NiemannPick Disease Type C," Neurobiology of Disease, 2004, vol. 16, No. 3, pp. 654-658.
Leigh-Paffenroth E., et al., "Objective Measures of Ototoxicity," Hearing and Hearing Disorders: Research and Diagnostics, Sep. 2005, vol. 9, No. 1,7 pages.
Liao G., et al., "Allopregnanolone Treatment Delays Cholesterol Accumulation and Reduces Autophagic/Lysosomal Dysfunction and Inflammation in Npc1−/− Mouse Brain," Brain Research, May 13, 2009, vol. 1270, 20 pages.
Lieberman A.P., et al., "Autophagy in Lysosomal Storage Disorders," Autophagy, 2012, vol. 8, No. 5, pp. 719-730.
Liu B., et al., "Cyclodextrin Overcomes the Transport Defect in Nearly Every Organ of NPC1 Mice Leading to Excretion of Sequestered Cholesterol as Bile Acid," Journal of Lipid Research, 2010, vol. 51, pp. 933-944.
Liu B., et al., "Genetic Variations and Treatments that Affect the Lifespan of the NPC1 Mouse," Journal of Lipid Research, 2008, vol. 49, pp. 663-669.
Liu B., et al., "Reversal of Defective Lysosomal Transport in NPC Disease Ameliorates Liver Dysfunction and Neurodegeneration in the npc1−/− Mouse," Proceedings of the National Academy of Sciences (PNAS), Feb. 17, 2009, vol. 106, No. 7, pp. 2377-2382.
Loftsson T., et al., "Pharmaceutical Applications of Cyclodextrins: Basic Science and Product Development" Journal of Pharmacy and Pharmacology, 2010, vol. 62, pp. 1607-1621.
Lopez A. M., et al., "Systemic Administration of 2-Hydroxypropyl-Beta-Cyclodextrin to Symptomatic Npc1-Deficient Mice Slows Cholesterol Sequestration in the Major Organs and Improves Liver Function," Clinical and Experimental Pharmacology and Physiology, 2014, vol. 41, pp. 780-787.
Maarup T.J., et al., "Intrathecal 2-Hydroxypropyl-Beta-Cyclodextrin in a Single Patient with Niemann-Pick C1," Molecular Genetics Metabolism, 2015, vol. 116, 13 pages.
Machine Translation for CN102040675A, 2011, 12 pages.
Maetzel D., et al., "Genetic and Chemical Correction of Cholesterol Accumulation and Impaired Autophagy in Hepatic and Neural Cells Derived From Niemann-Pick Type C Patient-Specific iPS Cells," Stem Cell Reports, Jun. 3, 2014, vol. 2, pp. 866-880.
Malanga M., et al., ""Back to the Future": A New Look at Hydroxypropyl Beta-Cyclodextrins," Journal of Pharmaceutical Sciences, 2016, vol. 105, No. 9, pp. 2921-2931.
Marcus A.D., "A Mom Brokers Treatment for Her Twins' Fatal Illness," The Wall Street Journal, Apr. 3, 2009, 4 pages, Retrieved from the Internet: URL: https://www.wsj.com/articles/SB123871183055784317.
Marcus A.D., "Small Biotech Gets Rights to Rare Disease Drug," Press Release, Jan. 7, 2015, 3 pages, Retrieved from the Internet: URL: http://www.wsj.com/articles/small-biotech-vtesse-gets-rights-to-rare-disease-drug-1420606861.
Matsuo M., et al., "Effects of Cyclodextrin in Two Patients with Niemann-Pick Type C Disease," Molecular Genetics and Metabolism, 2013, vol. 108, pp. 76-81.
Matsuo M., et al., "Effects of Intracerebroventricular Administration of 2-Hydroxypropyl-B-Cyclodextrin in a Patient with Niemann-Pick Type C Disease," Molecular Genetics and Metabolism Reports, 2014, vol. 1, pp. 391-400.
Maue R.A., et al., "A Novel Mouse Model of Niemann-Pick Type C Disease Carrying a D1005G-Npc1 Mutation Comparable to Commonly Observed Human Mutations," Human Molecular Genetics, 2012, vol. 21, No. 4, pp. 730-750.
McCook A., "Twin Disorders," The Scientist, Nov. 1, 2008, 7 pages.
Mendelsohn A.R., et al., "Preclinical Reversal of Atherosclerosis by FDA-Approved Compound that Transforms Cholesterol into an Anti-Inflammatory "Prodrug"," Rejuvenation Research, Jun. 20, 2016 [Published Online], vol. 19, No. 3, pp. 1-9.
Mengel E., et al., "Niemann-Pick Disease Type C Symptomatology: An Expert-Based Clinical Description," Orphanet Journal of Rare Diseases, 2013, vol. 8, No. 166,11 Pages.
Meske V., et al., "How To Reduce The Accumulation of Autophagic Vacuoles In NPC1-Deficient Neurons: A Comparison of Two Pharmacological Strategies," Neuropharmacology, 2015, vol. 89, pp. 282-289.
Meske V., et al., "The Autophagic Defect in Niemann-Pick Disease Type C Neurons Differs from Somatic Cells and Reduces Neuronal Viability," Neurobiology of Disease, 2014, vol. 64, pp. 88-97.
Millat G., et al., "Niemann-Pick C1 Disease: The I1061T Substitution is a Frequent Mutant Allele in Patients of Western European Descent and Correlates with a Classic Juvenile Phenotype," American Journal of Human Genetics, 1999, vol. 65, pp. 1321-1329.
Mller B.W., et al., "Solubilization of Drugs by Modified -Cyclodextrins," International Journal of Pharmaceutics, 1985, vol. 26, pp. 77-88.
Montecucco F., et al. "Treatment with KLEPTOSE CRYSMEB Reduces Mouse Atherogenesis by Impacting on Lipid Profile and Th1 Lymphocyte Response," Vascular Pharmacology, 2015, vol. 72, pp. 197-208.
Munkacsi A.B., et al., "An "Exacerbate-Reverse" Strategy in Yeast Identifies Histone Deacetylase Inhibition as a Correction for Cholesterol and Sphingolipid Transport Defects in Human Niemann-Pick Type C Disease," The Journal of Biological Chemistry, Jul. 8, 2011, vol. 286, No. 27, pp. 23842-23851.
Nah J., et al., "Autophagy in Neurodegenerative Diseases: From Mechanism to Therapeutic Approach," Molecules and Cells, 2015, vol. 38, No. 5, pp. 381-389.
NanoSonic Products, Inc. and CTD, Inc., "Certificate of Analysis, Trappsol THPB-EC," dated Apr. 22, 2015.
Non Final Office action for U.S. Appl. No. 18/141,832, mailed on Sep. 14, 2023, 12 pages.
Non Final Office action for U.S. Appl. No. 19/028,631, mailed on Mar. 19, 2025, 30 pages.

(56) References Cited

OTHER PUBLICATIONS

Non-Final Office Action for U.S. Appl. No. 18/633,063, mailed on Jun. 28, 2024, 21 Pages.
Notice of Allowance for U.S. Appl. No. 17/745,487, mailed on Sep. 8, 2022, 8 pages.
Notice of Allowance for U.S. Appl. No. 17/970,080, mailed on Dec. 7, 2023, 10 pages.
Rauniyar N., et al., "Quantitative Proteomics of Human Fibroblasts with I1061T Mutation in NiemannPick C1 (NPC1) Protein Provides Insights into the Disease Pathogenesis," Molecular Cellular Proteomics, 2015, vol. 14, No. 7, pp. 1734-1749.
Reagan J.W., et al., "Posttranslational Regulation of Acid Sphingomyelinase in Niemann-Pick Type C1 Fibroblasts and Free Cholesterol-enriched Chinese Hamster Ovary Cells," The Journal of Biological Chemistry, Dec. 1, 2000, vol. 275, No. 48, pp. 38104-38110.
Reddy J.V., et al., "Clues to Neuro-Degeneration in Niemann-Pick Type C Disease from Global Gene Expression Profiling," PLoS One, Dec. 2006, vol. 1, No. 1, 7 pages.
Rodal S.K., et al., "Extraction of Cholesterol with Methyl—Cyclodextrin Perturbs Formation of Clathrin-Coated Endocytic Vesicles," Molecular Biology of the Cell, Apr. 1999, vol. 10, pp. 961-974.
Roquette, Brochure: "Kleptose HP / Kleptose HPB, multifunctional excipients for molecular encapsulation," 2005, retrieved from the Internet: URL: http://www.roquette-pharma.com/brochures/23/visio.html, on Sep. 16, 2016.
Roquette, "Kleptose HPB Parenteral Grade product specification sheet," dated Jul. 28, 2014.
Roquette, "Kleptose HPB Parenteral Grade product specification sheet," dated Mar. 2, 2015, 2 pages.
Rosenbaum A.I., et al., "Endocytosis of Beta-Cyclodextrins is Responsible for Cholesterol Reduction in Niemann-Pick Type C Mutant Cells," Proceedings of the National Academy of Sciences, Mar. 23, 2010, vol. 107, No. 12, pp. 5477-5482.
Rosenbaum A.I., et al., "Niemann-Pick Type C Disease: Molecular Mechanisms and Potential Therapeutic Approaches," Journal of Neurochemistry, 2011, vol. 116, No. 5, pp. 789-795.
Rosseels M.L.A., et al., "Hydroxypropyl-Cyclodextrin Impacts Renal and Systemic Hemodynamics in the Anesthetized Dog," Regulatory Toxicology and Pharmacology, 2013, vol. 67, No. 3, pp. 1-9.
Sakiyama Y., et al., "Intrathecal 2-Hydroxypropyl-Beta-Cyclodextrin (HPBCD) Therapy in Adult-Onset Niemann-Pick Disease Type C (NPC)," Journal of the Neurological Sciences, 2015, vol. 357, pp. e193-e214.
Sarkar S., et al., "Impaired Autophagy in the Lipid-Storage Disorder Niemann-Pick Type C1 Disease," Cell Reports, Dec. 12, 2013, vol. 5, pp. 1302-1315.
Sarkar S., et al., "Restarting Stalled Autophagy a Potential Therapeutic Approach for the Lipid Storage Disorder, Niemann-Pick Type C1 Disease," Autophagy, Jun. 2014, vol. 10, No. 6, pp. 1137-1140.
Schonbeck C., et al., "Hydroxypropyl-Substituted Beta-Cydodextrins: Influence Of Degree of Substitution on the Thermodynamics of Complexation with Tauroconjugated and Glycoconjugated Bile Salts," Langmuir, 2010, vol. 26, No. 23, pp. 17949-17957.
Schultz M.L., et al., "Clarifying Lysosomal Storage Diseases," Trends in Neurosciences, Aug. 2011, vol. 34, No. 8, 20 pages.
Soga M., et al., HPGCD Outperforms HPBCD as a Potential Treatment for Niemann-Pick Disease Type C During Disease Modeling with iPS Cells, Stem Cells, 2015, vol. 33, pp. 1075-1088.
Song W., et al., "2-Hydroxypropyl-Cyclodextrin Promotes Transcription Factor EB-Mediated Activation of Autophagy," The Journal of Biological Chemistry, Apr. 4, 2014, vol. 289, No. 14, pp. 10211-10222.
Stella V., et al., "Cyclodextrins," Toxicologic Pathology, 2008, vol. 36, pp. 30-42.
Study NCT01747135, Clinical Trials, Comparison of Dec. 8, 2012 version and Apr. 2, 2014 version, retrieved from the internet: URL: https://clinicaltrials.gov/ct2/history/NCT01747135?A=1&B=19&C-Side-by-Side, 18 pages.
Sun D., et al., "Effect of the Platelet-Activating Factor Antagonist BN 50739 and Its Diluents on Mitochondrial Respiration and Membrane Lipids During and Following Cerebral Ischemia," Journal of Neurochemistry, 1994, vol. 62, No. 5, pp. 1929-1938.
Swaroop M., et al., "Evaluation of Cholesterol Reduction Activity of Methyl-cyclodextrin Using Differentiated Human Neurons and Astrocytes," Journal of Biomolecular Screening, 2012, vol. 17, No. 9, pp. 1243-1251.
Szejtli J_, "Medicinal Applications of Cyclodextrins," Medicinal Research Reviews, 1994, vol. 14, No. 3, pp. 353-386.
Tamura A., et al., "-Cyclodextrin-Threaded Biocleavable Polyrotaxanes Ameliorate Impaired Autophagic Flux in Niemann-Pick Type C Disease," The Journal of Biological Chemistry, Apr. 10, 2015, vol. 290, No. 15, pp. 9442-9454.
Tanaka Y., et al., "Efficacy of 2-Hydroxypropyl-p-cyclodextrin in Niemann-Pick Disease Type C Model Mice and Its Pharmacokinetic Analysis in a Patient with the Disease," Biological and Pharmaceutical Bulletin, 2015, vol. 38, No. 6, pp. 844-851.
Thackaberry E.A., et al., "Comprehensive Investigation of Hydroxypropyl Methylcellulose, Propylene Glycol, Polysorbate 80, and Hydroxypropyl-Beta-Cyclodextrin for use in General Toxicology Studies," Toxicological Sciences, 2010, vol. 117, No. 2, pp. 485-492.
Thein P., et al., "In Vitro Assessment of Antiretroviral Drugs Demonstrates Potential for Ototoxicity," Hearing Research, Apr. 2014, vol. 310, 19 pages.
Tortelli B., et al., "Cholesterol Homeostatic Responses Provide Biomarkers for Monitoring Treatment for the Neurodegenerative Disease NiemannPick C1 (NPC1)," Human Molecular Genetics, 2014, vol. 23, No. 22, pp. 6022-6033.
United States Pharmacopeia Convention, "Hydroxypropyl Betadex," NF Monographs, 2023, 1 page.
Vance J.E., et al., "Function of the NiemannPick type C proteins and their bypass by cyclodextrin," Current Opinion in Lipidology, 2011, vol. 22, pp. 204-209.
Vance J.E., et al., "Niemann-Pick C Disease and Mobilization of Lysosomal Cholesterol by Cyclodextrin," Journal of Lipid Research, 2014, vol. 55, pp. 1609-1621.
Vanier M.T., et al., "NiemannPick disease type C," Clinical Genetics, 2003, vol. 64, pp. 269-281.
Vanier M.T., "Niemann-Pick Disease Type C," Orphanet Journal of Rare Diseases, 2010, vol. 5, No. 16, 18 pages.
Vazquez M.C., et al., "Alteration of Gene Expression Profile in Niemann-Pick Type C Mice Correlates with Tissue Damage and Oxidative Stress," PLoS One, Dec. 2011, vol. 6, No. 12, 9 pages.
Vieira C., "APMRF 2011 Meeting Summary for Npc Families and the NPC Community," Jun. 2011, retrieved from the Internet: URL: http://niemannpick.nd.edu/assets/52704/apmrf_2011_summary_for_npc_families_and_the_npc_community.pdf, on Jul. 20, 2016.
Vieira C., et al., "Use of Cyclodextrin in Two Brazilian Girls With Niemann-Pick Type C-Intrathecal Report," Jun. 2012, retrieved from the Internet URL: http://niemannpick.nd.edu/assets/69394/abstracts_in_speaking_order.pdf, on Jul. 20, 2016.
Vieira C., "The Use of Cyclodextrin in Niemann-pick Type C Disease in Two Girls-Report After One Year of Treatment," Jun. 2011, Abstract, retrieved on Jul. 20, 2016] Retrieved from the Internet URL: http://niemannpick.nd.edu/assets/52702/all_abstracts.pdf.
Vite C.H., et al., "Clinical, Electrophysiological, and Serum Biochemical Measures of Progressive Neurological and Hepatic Dysfunction in Feline Niemann-Pick Type C Disease," Pediatric Research, 2008, vol. 64, No. 5, pp. 544-549.
Vite C.H., et al., "Intracisternal Cyclodextrin Prevents Cerebellar Dysfunction and Purkinje Cell Death in Feline Niemann-Pick Type C1 Disease," Science Translational Medicine, Feb. 25, 2015, vol. 7, No. 276, 35 pages.
Vite C.H., et al., "Intrathecal Cyclodextrin Therapy of Feline Niemann-pick Type C Disease," Molecular Genetics and Metabolism, 2011, vol. 102, 4 pages.
Vtesse Inc., "Leading Life Science Syndicate Commits $25 Million to Series A Funding to Launch Vtesse, Inc., the First Rare Disease Company Spun Out of Cydan Development, Inc.," Press Release, Jan. 7, 2015, 5 pages.

(56) References Cited

OTHER PUBLICATIONS

Vtesse Inc., "NIH Teams with Industry to Develop Treatments for Niemann-pick Type C Disease.," Press Release, Jan. 7, 2015, 4 pages, Retrieved from the Internet: URL: https://www.nih.gov/news-events/news-releases/nih-teams-industry-develop-treatments-niemann-pick-type-c-disease.
Vtesse Inc., "Vtesse Advances Phase 2b/3 Clinical Trial of VTS-270 in Niemann-Pick Type C1 Disease with Dose Selection for Evaluation in Second and Final Portion of Trial and Expansion into Europe," Press Release, May 23, 2016, 3 pages.
Vtesse Inc., "Vtesse, Inc. Announces FDA's Granting of Breakthrough Therapy Designation for VTS-270 in Niemann-Pick Type C1 Disease," Press Release, Jan. 6, 2016, 4 pages.
Vtesse Inc., "Vtesse, Inc. Announces Phase 1/2 Clinical Data Showing Slowing of Disease Progression from VTS-270 Treatment for Niemann-Pick Type C1 Disease," Press Release, Mar. 4, 2016, 3 pages.
Vtesse Inc., "Vtesse, Inc. Announces Preliminary Data from Ongoing Phase 1 Study of VTS-270 for Treatment of Niemann-Pick Disease Type C," Press Release, Aug. 6, 2015, 4 pages.
Vtesse Inc., "Vtesse, Inc. Expands Scientific Advisory Board and Appoints New VP of Clinical Operations to Support Late-Stage Clinical Study of Lead Drug Candidate VTS-270," Press Release, Oct. 22, 2015, 4 pages.
Vtesse Inc., "Vtesse, Inc. Expands Scientific Advisory Board, Fills Key Patient Advocacy Position to Prepare for Further Clinical Development of VTS-270 in Niemann-Pick Disease Type C (NPC)," Press Release, Jun. 15, 2015, 4 pages.
Vtesse Inc., "Vtesse, Inc. Forms Scientific Advisory Board," Press Release, Mar. 25, 2015, 3 pages.
Vtesse Inc., "Vtesse, Inc. Initiates Phase 2b/3 Clinical Trial of VTS-270 for Treatment of Niemann-Pick Type C1 (NPC) Disease," Press Release, Sep. 28, 2015, 4 pages.
Vtesse Inc., "Vtesse Secures Additional $17 Million in Series A Extension to Support Further Product Development and Expand the Ongoing Clinical Trial of VTS-270 for the Treatment of Niemann-Pick Type C1 Disease," Press Release, Jul. 25, 2016, 4 pages.
Notice of Allowance for U.S. Appl. No. 18/072,260, mailed on Jun. 30, 2023, 22 pages.
Notice of Allowance for U.S. Appl. No. 18/115,897, mailed on May 5, 2023, 10 pages.
Notice of Allowance for U.S. Appl. No. 18/115,898, mailed on Jun. 7, 2023, 49 pages.
Notice of Allowance for U.S. Appl. No. 18/115,901, mailed on Jun. 29, 2023, 55 pages.
Notice of Allowance for U.S. Appl. No. 18/130,132, mailed on Jul. 11, 2023, 09 pages.
Notice of Allowance for U.S. Appl. No. 18/141,832, mailed on Oct. 25, 2023, 13 pages.
Notice of Allowance for U.S. Appl. No. 19/028,631, dated May 27, 2025, 7 pages.
Notice of Allowance for U.S. Appl. No. 19/061,509, dated May 7, 2025, 8 pages.
Notice of Allowance for U.S. Appl. No. 19/061,577, dated May 19, 2025, 9 pages.
Nunes M.J., et al., "Histone Deacetylase Inhibition Decreases Cholesterol Levels in Neuronal Cells by Modulating Key Genes in Cholesterol Synthesis, Uptake And Efflux," PLOS One, Jan. 2013, vol. 8, No. 1,10 pages.
Office Action for Chinese Application No. 201380052023.0, mailed on Jul. 28, 2016, 14 Pages.
Office action for Chinese Application No. 201680041193.2, mailed on Jul. 11, 2019, 12 pages.
Office action for Eurasian Application No. 201792487/28, mailed on Nov. 29, 2018, 2 pages.
Office action for European Application No. 16808313.7, mailed on Feb. 8, 2019, 4 pages.
Office action for European Application No. 16808313.7, mailed on May 29, 2018, 10 pages.
Office action for Israell Application No. 255991, mailed on Jun. 3, 2019, 6 pages.
Office action for Singapore Application No. 11201710032U, mailed on Dec. 13, 2018, 10 pages.
Office Action for U.S. Appl. No. 14/419,471, mailed on Apr. 19, 2016, 18 Pages.
Office Action for U.S. Appl. No. 14/419,471, mailed on Dec. 12, 2016, 16 Pages.
Office action for U.S. Appl. No. 16/134,028, mailed on Nov. 16, 2018, 10 pages.
Office action for U.S. Appl. No. 16/372,899, mailed on Nov. 21, 2019, 6 pages.
Office action for U.S. Appl. No. 16/430,664, mailed on Feb. 18, 2020, 9 pages.
Office Action for U.S. Appl. No. 17/985,762, mailed on Mar. 13, 2023, 14 pages.
Office Action for U.S. Appl. No. 18/072,260, mailed on Apr. 18, 2023, 26 pages.
Office Action for Venezuela Application No. 2016000260, mailed on Dec. 1, 2022, 4 pages.
Ordonez M.P., et al., "Disruption and Therapeutic Rescue of Autophagy in a Human Neuronal Model of Niemann PickType C1," Human Molecular Genetics, 2012, vol. 21, No. 12, pp. 2651-2662.
Ottinger E.A., et al., "Collaborative Development of 2-Hydroxypropyl-Cyclodextrin for the Treatment of Niemann-Pick Type C1 Disease," Current Topics in Medicinal Chemistry, 2014, vol. 14, No. 3, 20 pages.
Ozkok A., "Cholesterol-Embolization Syndrome: Current Perspectives," Vascular Health and Risk Management [Online], Jul. 2019, vol. 15, pp. 209-220, XP093169720, DOI: 10.2147/VHRM.S175150, Retrieved from the Internet: URL: https://www.dovepress.com/getfile.phpfileID=51025.
Pacheco C.D., et al., "Autophagy in NiemannPick C Disease is Dependent Upon Beclin-1 and Responsive to Lipid Trafficking Defects," Human Molecular Genetics, 2007, vol. 16, No. 12, pp. 1495-1503.
Papandreou A., et al., "Diagnostic Workup and Management of C Patients with Suspected Niemann-Pick Type C Disease," Therapeutic Advances in Neurological Disorders, 2016, vol. 9, No. 3, pp. 216-229.
Patterson M., "Niemann-Pick Disease Type C," GeneReviews [Online], 2000, 24 pages, Retrieved from the Internet: URL: https://www.ncbi.nlm.nih.gov/books/NBK1296/.
Patterson M.C., et al., "Long-Term Miglustat Therapy in Children With Niemann-Pick Disease Type C," Journal of Child Neurology, Mar. 2010, vol. 25, No. 3, pp. 300-305.
Patterson M.C., et al., "Recommendations for the Diagnosis and Management of Niemann-Pick Disease Type C: An Update," Molecular Genetics and Metabolism, 2012, vol. 106, No. 3, 15 pages.
Patterson M.C., "Miglustat for Treatment of Niemann-Pick C Disease: A Randomised Controlled Study," The Lancet Neurology, 2007, vol. 6, 8 pages.
Peake K.B., et al., "Normalization of Cholesterol Homeostasis by 2-Hydroxypropyl-cyclodextrin in Neurons and Glia from Niemann-Pick C1 (NPC1)-deficient Mice," The Journal of Biological Chemistry, Mar. 16, 2012, vol. 287, No. 12, pp. 9290-9298.
Pharmacopeia Online, "Hydroxypropyl Betadex," USP32-NF27 p. 1250, Pharmacopeial Forum: retrieved on Oct. 19, 2023, vol. 32, No. 5, 4 pages, Retrieved from the Internet URL: http://www.uspbpep.com/usp32/pub/data/v32270/usp32nf27s0_m39130.html.
Pillai B.K., et al., "Fast Diffusion of Very Long Chain Saturated Fatty Acids across a Bilayer Membrane and Their Rapid Extraction by Cyclodextrins: Implications for Adrenoleukodystrophy," The Journal of Biological Chemistry, Nov. 27, 2009, vol. 284, No. 48, pp. 33296-33304.
Pipalia N.H., et al., "Histone Deacetylase Inhibitor Treatment Dramatically Reduces Cholesterol Accumulation in Niemann-Pick Type C1 Mutant Human Fibroblasts," Proceedings of the National Academy of Sciences (PNAS), Apr. 5, 2011, vol. 108, No. 14, pp. 5620-5625.
Pitha J., et al., "Distribution of Substituents in Hydroxypropyl Ethers of Cyclomaltoheptaose," Carbohydrate Research, 1990, vol. 200, pp. 429-435.

(56) References Cited

OTHER PUBLICATIONS

Pitha J., et al., "Drug Solubilizers to Aid Pharmacologists: Amorphous Cylodextrin Derivatives," Life Sciences, 1988, vol. 43, No. 6, pp. 493-502.
Pitha J., et al., "Hydroxypropyl-Cyclodextrin: Preparation and Characterization; Effects on Solubility of Drugs," International Journal of Pharmaceutics, 1986, vol. 29, No. 1, pp. 73-82.
Pontikis C.C., et al., "Cyclodextrin Alleviates Neuronal Storage of Cholesterol in Niemann-Pick C Disease Without Evidence of Detectable Blood-Brain Barrier Permeability," Journal of Inherited Metabolic Disease, May 2013, vol. 36, No. 3, 14 pages.
Porter F.D., et al., "Phase 1/2 Evaluation of Intrathecal 2-Hydroxypropyl-Cyclodextrin for the Treatment of Niemann-Pick Disease Type C1," Molecular Genetics and Metabolism, 2016, vol. 117, 1 page.
Puskas I., et al., "Aggregation Behavior of Cyclodextrin and Cholesterol in Simulated Human Cerebrospinal Fluid," Bioactive Carbohydrates and Dietary Fibre, 2013, vol. 2, No. 2, pp. 157-163.
Raal F.J., et al., "Familial Hypercholesterolemia Treatments: Guidelines and New Therapies," Atherosclerosis, Oct. 2018, vol. 277, pp. 483-492.
Ramirez C.M., et al., "Quantitative Role of LAL, NPC2, and NPC1 in Lysosomal Cholesterol Processing Defined by Genetic and Pharmacological Manipulations," Journal of Lipid Research, 2011, vol. 52, No. 4, pp. 688-698.
Ramirez C.M., et al., "Weekly Cyclodextrin Administration Normalizes Cholesterol Metabolism in Nearly Every Organ of the Niemann-Pick Type C1 Mouse and Markedly Prolongs Life," Pediatric Research, 2010, vol. 68, No. 4, pp. 309-315.
Rao C.T., et al., "Distribution of Substituents in O-(2-hydroxypropyl) Derivatives of Cyclomalto-oligosaccharides Cyclodextrins): Influence of Increasing Substitution, of the Base Used in the Preparation, and of Macrocyclic Size," Carbohydrate Research, 1992, vol. 223, pp. 99-107.
Rao C.T., et al., "Substitution in Beta-Cyclodextrin Directed by Basicity: Preparation of 2-O-and 6-O-[(R)-and (S)-2-hydroxypropyl] Derivatives," The Journal of Organic Chemistry, 1991, vol. 56, No. 1, pp. 1327-1329.
Rao T.C., et al., "Pharmaceutical Usefulness of Hydroxypropylcyclodextrins: "E Pluribus Unum" Is an Essential Feature," Pharmaceutical Research, 1990, vol. 7, No. 6, 4 pages.
Notice of Allowance for U.S. Appl. No. 19/175,757, dated Jul. 1, 2025, 8 pages.

Yanjanin *et al.*, "Linear Clinical Progression, Independent of Age of Onset, in Niemann-Pick Disease, Type C," *Am. J. Med. Genet. Part B* 153B:132-140 (2010).

| NPC score | VTS-270 | Natural History | p-value for difference in slopes |
|---|---|---|---|
| | Avg change over one year (std. error) | | |
| Total | 0.74 (0.67) | 2.53 (0.27) | 0.02 |
| Total with hearing/ ABR removed | -0.02 (0.69) | 2.23 (0.28) | 0.004 |
| | | | |
| Ambulation | 0.001 (0.18) | 0.27 (0.07) | **0.18** |
| Fine Motor | 0.03 (0.10) | 0.11 (0.04) | 0.34 |
| Cognition | -0.04 (0.16) | 0.31 (0.06) | **0.04** |
| Swallowing | -0.11 (0.23) | 0.20 (0.09) | 0.22 |
| Speech | -0.16 (0.13) | 0.09 (0.05) | 0.09 |
| Eye Movement | 0.22 (0.16) | 0.08 (0.06) | 0.42 |
| Hearing | 0.44 (0.16) | 0.17 (0.06) | 0.13 |
| Memory | -0.04 (0.12) | 0.18 (0.05) | 0.10 |
| Seizures | NA | NA | NA |

FIG. 2

◦ *12 patients on monthly dosing and 3 patients on biweekly dosing*
◦ *Analysis includes doses up to 900 mg*

*NPC07, NPC18, NPC24, NPC44, NPC56 and CDA105 are not on Miglustat*

*NPC07, NPC18, NPC24, NPC44, NPC56 and CDA105 are not on Miglustat*

New "NPC Composite" Endpoint

- Composite score with
  - Ambulation
  - Fine Motor
  - Cognition
  - Swallowing

FIG. 7

Mass Spectrum (38.72-51.30 ms)(1.557 min) - 2OH-Pr-bCD_Kleptose_Single frame_POS_001_condensed[1].d Mass Spectrum (39.21-50.97 ms)(1.557 min) - 2OH-Pr-bCD_Trappsol_Single frame_POS_001_condensed[1].d Numbers denote presence of hydroxypropyl moieties

| Kleptose® HPB 1.0mM | Batch CYL-4063 1.0mM |
|---|---|
| Top Biological Pathways | Top Biological Pathways |
| ErbB signaling pathway | MAPK signaling pathway |
| MAPK signaling pathway | Steroid biosynthesis |
| GnRH signaling pathway | GnRH signaling pathway |
| Estrogen signaling pathway | ErbB signaling pathway |
| Non-alcoholic fatty liver disease (NAFLD) | Metabolic pathways |
| Steroid biosynthesis | ABC transporters |
| Epithelial cell signaling in Helicobacter pyl... | PPAR signaling pathway |
| Alcoholism | T cell receptor signaling pathway |
| Protein processing in endoplasmic reticulum | B cell receptor signaling pathway |
| Melanoma | Herpes simplex infection |

FIG. 39

Parent Lot

Low DS ("L") Pooled Fraction

Medium DS ("M") Pooled Fraction

High DS ("H") Pooled Fraction

| "L" 1.0mM | "M" 1.0mM | "H" 1.0mM |
|---|---|---|
| Top Biological Pathways | Top Biological Pathways | Top Biological Pathways |
| Epithelial cell signaling in Helicobacter pyl... | Steroid biosynthesis | Estrogen signaling pathway |
| Estrogen signaling pathway | Estrogen signaling pathway | Steroid biosynthesis |
| ErbB signaling pathway | Epithelial cell signaling in Helicobacter pyl... | Epithelial cell signaling in He... |
| MAPK signaling pathway | ErbB signaling pathway | p53 signaling pathway |
| GnRH signaling pathway | GnRH signaling pathway | Apoptosis |
| Transcriptional misregulation in cancer | Apoptosis | GnRH signaling pathway |
| MicroRNAs in cancer | MAPK signaling pathway | MAPK signaling pathway |
| NF-kappa B signaling pathway | Transcriptional misregulation in cancer | HTLV-I infection |
| TNF signaling pathway | MicroRNAs in cancer | Amphetamine addiction |
| Cytokine-cytokine receptor interaction | HTLV-I infection | Cocaine addiction |

FIG. 42

Impact on Hearing
*Conclusions To Date*

- No quality of living impact to date
- Variable sensitivity
  - Acute effect, with partial or complete recovery
- Symptoms are correctable with hearing aids
  - Majority were candidates for hearing aids prior to exposure
  - All are candidates now
- Etiology and impact
  - Impact on high frequency hearing is due to the impairment of outer hair cell function
  - Impact on hearing is not correlated to dose of VTS-270; seems to accelerate the impact on hearing caused by the disease

FIG. 50

KLEPTOSE® HPB PARENTAL GRADE (EXEMPLARY BATCH 1) PAGE 1/4

DEFINITION:

HYDROXYPROPYLBETADEX is a partially substituted Poly (hydroxypropyl) ether of betadex.
CAS n°: 128446-35-5
EINECS: 420-920-1
INCI: HYDROXYPROPYL CYCLODEXTRIN

SPECIFICATIONS:

A) CHARACTERS

| | |
|---|---|
| APPEARANCE | White or almost white, amorphous or crystalline powder. |
| SOLUBILITY | Freely soluble in water and in propylene glycol. |

B) IDENTIFICATION

| | | |
|---|---|---|
| IDENTIFICATION-TEST A | EP-USP/NF | See test |
| IDENTIFICATION-TEST B | EP-USP/NF | See test |

C) TESTS

| | | | |
|---|---|---|---|
| INFRA-RED | EP-USP/NF | Conforms | |
| APPEARANCE IN SOLUTION | EP-USP/NF | Clear, colourless | |
| CONDUCTIVITY | EP-USP/NF | 200 µS/cm max. | |
| RELATED SUBSTANCES | | | |
| -IMPURITY A: BETA CYCLODEXTRIN | EP | 1.5 | % max. |
| -IMPURITY A: BETA CYCLODEXTRIN | USP/NF | 1.5 | % max. |
| -IMPURITY B: PROPANE 1, 2 DIOL | EP | 2.5 | % max. |
| -IMPURITY B: PROPANE 1, 2 DIOL | USP/NF | 2.5 | % max. |

FIG. 51A

KLEPTOSE® HPB PARENTAL GRADE (EXEMPLARY BATCH 1) Page 2/4

| | | |
|---|---|---|
| -SUM OF IMPURITIES OTHER THAN A | EP | 1.0 % max. |
| -ANY OTHER IMPURITY | USP/NF | 0.25 % max. |
| -TOTAL OF OTHER IMPURITIES | USP/NF | 1 % max. |
| HEAVY METALS | EP-USP/NF | 20 ppm max. |
| LOSS ON DRYING | EP-USP/NF | 10.0 % max. |
| MOLAR SUBSTITUTION | EP-USP/NF | 0.40 - 1.50 |
| PROPYLENE OXIDE (**) | USP/NF | 0.0001 % |
| | | |
| MICROBIAL CONTAMINATION: | | |
| -TOTAL AEROBIC MICROBIAL COUNT | EP-USP/NF | 100 CPU/g max. |
| -TOTAL YEASTS AND MOULD COUNT | EP-USP/NF | 100 CPU/g max. |

* Compliance data - Tests not performed

** Monitoring plan

FIG. 51B

| | | |
|---|---|---|
| -ESCHERICHIA | EP-USP/NF | Absence in 10 g. |
| -SALMONELLA | EP-USP/NF | Absence in 10 g. |
| BACTERIAL ENDOTOXINS | EP-USP/NF | 10 IU/g max |

TYPICAL VALUES:

| | |
|---|---|
| MOLAR SUBSTITUTION NOMINAL VALUE | 0.62 |
| MOLAR SUBSTITUTION (MS) | 0.58 – 0.68 |

| | | |
|---|---|---|
| INTERNAL REQUIREMENTS ON RELATED SUBSTANCES: | | |
| -IMPURITY A: BETA CYCLODEXTRIN | Internal method (/com) | 1.0 % max |
| -IMPURITY B: PROPANE 1.2 DIOL | Internal method (/com) | 0.5 % max |
| -ANY OTHER INPURITY | Internal method (/com) | 0.1 % max |
| PARTICLE SIZE: | Sieve | |
| - RESIDUE ON 315 mic. | | 20 % max |
| - RESIDUE ON 100 mic. | | 50 % max |

COMMENTS:

Methods used by Roquette may be EP or USP or internal validated methods which have been compared to the pharmacopeia monograph.

This substance is suitable for use in the manufacture of parenteral preparations.

CONFORMITY:

Current pharmacopeia: E.P. (1804) and U.S.P / N.F.

FIG. 51C

STORAGE:

STORAGE:

- Preserve in well-closed containers.
- Hygroscopic product: handle under controlled room conditions.

RETEST DATE:

- 3 years in its original packaging.

* Compliance data – Tests not performed

** Monitoring plan

FIG. 51D

KLEPTOSE® HPB PARENTAL GRADE (Exemplary batch 2) Page 1/4

DEFINITION:

HYDROXYPROPYLBETADEX is a partially substituted Poly (hydroxypropyl) ether of betadex.

CAS n°: 128446-35-5

EINECS: 420-920-1

INCI: HYDROXYPROPYL CYCLODEXTRIN

SPECIFICATIONS:

A) CHARACTERS

| | |
|---|---|
| APPEARANCE | White or almost white, amorphous or crystalline powder. |
| SOLUBILITY | Freely soluble in water and in propylene glycol. |

B) IDENTIFICATION

| | | |
|---|---|---|
| IDENTIFICATION-TEST A | EP-USP/NF | See test |
| IDENTIFICATION-TEST B | EP-USP/NF | See test |

C) TESTS

| | | |
|---|---|---|
| | EP-USP/NF | Conforms |
| INFRA-RED | | |
| APPEARANCE IN SOLUTION | EP-USP/NF | Clear, colourless |
| CONDUCTIVITY | EP-USP/NF | 200 µS/cm max. |
| | | |
| RELATED SUBSTANCES | | |
| IMPURITY A: BETA CYCLODEXTRIN | EP-USP/NF | 1.0 % max. |
| IMPURITY B: PROPANE 1, 2 DIOL | EP-USP/NF | 0.50 % max. |
| ANY OTHER IMPURITY | EP-USP/NF | 0.1 % max. |
| TOTAL OF OTHER IMPURITIES | EP-USP/NF | 1.0 % max. |
| HEAVY METALS | EP-USP/NF | 20 ppm max. |
| LOSS ON DRYING | EP-USP/NF | 10.0 % max. |

FIG. 51E

KLEPTOSE® HPB PARENTAL GRADE (Exemplary batch 2) Page 2/4

| | | |
|---|---|---|
| MOLAR SUBSTITUTION | EP-USP/NF | 0.40 - 1.50 |
| PROPYLENE OXIDE (**) | EP-USP/NF | 1 ppm max. |

* Compliance data - Tests not performed

** Monitoring plan

FIG. 51F

KLEPTOSE® HPB PARENTAL GRADE (Exemplary batch 2) Page 3/4

| | | |
|---|---|---|
| -MICROBIAL CONTAMINATION: | | |
| TOTAL AEROBIC MICROBIAL COUNT | EP-USP/NF | 100 CPU/g max. |
| TOTAL YEASTS AND MOULS COUNT | EP-USP/NF | 100 CPU/g max. |
| ESCHERICHIA | EP-USP/NF | Absence in 10g. |
| SALMONELLA | EP-USP/NF | Absence in 10g. |
| BACTERIAL ENDOTOXINS | EP-USP/NF | 10 IU/g max. |

TYPICAL VALUES:

| | | |
|---|---|---|
| MOLAR SUBSTITUTION NOMINAL VALUE | | 0.62 |
| MOLAR SUBSTITUTION (MS) | | 0.58 – 0.68 |
| PARTICLE SIZE: | Sieve | |
| - RESIDUE ON 315 mic. | | 20 % max |
| - RESIDUE ON 100 mic. | | 50 % max |

COMMENTS:

Methods used by Roquette may be EP or USP or internal validated method which have been compared to the pharmacopeia monograph.

This substance is suitable for use in the manufacture of parenteral preparations.

CONFORMITY:

Current pharmacopeia: E.P. (1804) and U.S.P / N.F.

FIG. 51G

KLEPTOSE® HPB PARENTAL GRADE (Exemplary batch 2) Page 4/4

STORAGE:

- Preserve in well-closed containers.
- Hygroscopic product: handle under controlled room conditions.

RETEST DATE:

- 3 years in its original packaging.

* Compliance data – Tests not performed

** Monitoring plan

FIG. 51H

HYDROXYPROPYL BETA-CYCLODEXTRIN COMPOSITIONS AND METHODS

1. CROSS REFERENCE TO RELATED APPLICATIONS

This application is a continuation of U.S. patent application Ser. No. 19/028,631, filed Jan. 17, 2025, which is a continuation of U.S. patent application Ser. No. 18/533,373, filed Dec. 8, 2023, which is a continuation of U.S. patent application Ser. No. 17/970,080, filed Oct. 20, 2022, now U.S. Pat. No. 11,938,144, which is a continuation of U.S. patent application Ser. No. 17/745,464, filed May 16, 2022, now U.S. Pat. No. 11,590,159, which is a continuation of U.S. patent application Ser. No. 17/036,148, filed Sep. 29, 2020, now U.S. Pat. No. 11,406,657, which is a continuation of U.S. patent application Ser. No. 16/430,664, filed Jun. 4, 2019, now U.S. Pat. No. 10,933,083, which is a continuation of U.S. patent application Ser. No. 16/372,899, filed Apr. 2, 2019, now U.S. Pat. No. 10,709,730, which is a continuation of U.S. patent application Ser. No. 16/134,028, filed Sep. 18, 2018, now U.S. Pat. No. 10,300,086, which is a continuation of U.S. patent application Ser. No. 15/499,831, filed Apr. 27, 2017, now U.S. Pat. No. 10,258,641, which is a continuation of U.S. patent application Ser. No. 15/288,876, filed Oct. 7, 2016, now U.S. Pat. No. 9,675,634, which is a continuation of U.S. patent application Ser. No. 15/178,153, filed Jun. 9, 2016, now abandoned, which claims the benefit of U.S. Provisional Application Nos. 62/345,721, filed Jun. 3, 2016; 62/331,385, filed May 3, 2016; 62/314,765, filed Mar. 29, 2016; 62/308,736, filed Mar. 15, 2016; 62/276,728, filed Jan. 8, 2016; 62/263,599, filed Dec. 4, 2015; 62/249,876, filed Nov. 2, 2015; 62/245,974, filed Oct. 23, 2015; 62/189,114, filed Jul. 6, 2015; 62/175,075, filed Jun. 12, 2015; and 62/173,889, filed Jun. 10, 2015, each of which is incorporated in its entirety by reference.

2. STATEMENT REGARDING FEDERALLY SPONSORED RESEARCH OR DEVELOPMENT

This invention was created in the performance of a Cooperative Research and Development Agreement (Agreement Ref. No. 02947) with the National Institutes of Health, an Agency of the Department of Health and Human Services. The Government of the United States has certain rights in this invention.

3. BACKGROUND

Niemann-Pick disease Type C (NPC) is a lysosomal lipid storage disorder caused by autosomal recessive mutations in either the NPC1 or NPC2 gene. Symptoms typically manifest beginning in the perinatal period and progress throughout life. The disorder often includes neurological symptoms, such as cerebellar ataxia, dysarthria, seizures, vertical gaze palsy, motor impairment, dysphagia, psychotic episodes, and progressive dementia, as well as systemic symptoms in other organs, such as the liver, spleen, or lung. NPC has been described as a cellular cholesterol transport defect, although in the brain accumulation of other lipids, such as GM2 and GM3 gangliosides, also occurs (Vanier, 2010, *Orphanet Journal of Rare Diseases*, vol. 5:16). Owing to different clinical presentations and course of disease, NPC1 disease is typically categorized as early-infantile onset (<2 yrs), late-infantile onset (2 to <6 years), juvenile onset (6 to <15 years), and adolescent/adult onset (>15 years).

Efforts to treat NPC in humans have focused on substrate reduction therapy, such as inhibiting glycosphingolipid synthesis, for example with N-butyldeoxynojirimycin (miglustat, Zavesca®), or on ameliorating overall lipid storage, particularly storage of cholesterol and glycosphingolipids, through clearance mechanisms.

2-Hydroxypropyl-beta-cyclodextrins have been shown to alleviate excess cholesterol storage in NPC cells (Abi-Mosleh, L. et al., *Proceedings of the National Academy of Sciences USA,* 2009, vol. 106 (46), pages 19316-19321), consistent with a previous report of related cyclodextrins extracting cholesterol from the plasma membrane of cells (Rodal, S. K. et al., 1999, *Molecular Biology of the Cell*, vol. 10, pages 961-974). Hydroxypropyl beta-cyclodextrins have also been observed to have beneficial effects in animal models of NPC. For example, a composition comprising 2-hydroxypropyl-beta-cyclodextrins was reported to reverse defective lysosomal transport of cholesterol in the liver and brains of Npc1 knockout mice, and led to a prolongation of life in these mutants compared with no treatment (Liu, B. et al., 2009, *Proceedings of the National Academy of Sciences USA*, vol. 106 (7), pages 2377-2382; Davidson et al., 2009, *PLoS One* 4: e6951).

Various hydroxypropyl beta-cyclodextrin compositions have been administered to human NPC patients in the United States, Brazil, and Japan under compassionate use exemptions, with anecdotal reports of some improvement in various signs and symptoms. However, blinded clinical trials of hydroxypropyl beta-cyclodextrin compositions to determine safety and efficacy have not been completed (Ottinger, E. A. et al., 2014, *Current Topics in Medicinal Chemistry*, vol. 14 (3), pages 330-339). Given likely observer bias in the anecdotal reports, there is a need for controlled clinical studies to confirm that hydroxypropyl beta-cyclodextrin provides clinical benefit.

Effective treatment of NPC will require chronic intrathecal or intracerebroventricular administration beginning in infancy, and parenteral grade compositions of hydroxypropyl beta-cyclodextrins used previously in human patients contain impurities that make them unsuitable for chronic administration directly to the cerebrospinal fluid of infants and children: propylene glycol, which is thought to be ototoxic; beta-cyclodextrin molecules having no hydroxypropyl substitutions, which are known to form precipitates and to have an acute toxicity (Muller and Brauns, 1985, *International Journal of Pharmaceutics*, vol. 26, pages 77-88); and bacterial endotoxin, which is highly inflammatory. There is, therefore, a need for pharmaceutical compositions of hydroxypropyl beta-cyclodextrins of higher purity.

In addition, all existing parenteral grade compositions of hydroxypropyl beta-cyclodextrins contain complex mixtures of hydroxypropyl beta-cyclodextrin species having different degrees of hydroxypropyl substitution. The ratios of these species within the mixture differ widely among the various suppliers, and vary even among batches from a single supplier. It is not known how these different species contribute to the pharmacological effects of the complex mixture. There is, therefore, a need for pharmaceutical compositions of hydroxypropyl beta-cyclodextrins having more precisely defined and precisely controlled mixtures, or fingerprints, of such species.

There is, finally, a need for methods of manufacturing at commercial scale under GMP conditions pharmaceutical compositions of hydroxypropyl beta-cyclodextrins suitable for chronic intrathecal or intracerebroventricular administration, having low levels of impurities, and having specific and structurally-defined composition.

4. SUMMARY

We analyzed initial data from a phase I clinical trial in which patients with NPC type 1 disease are being treated by intrathecal administration of 2-hydroxypropyl beta-cyclodextrin ("HPBCD") using an existing parenteral grade composition, Kleptose® HPB (Roquette). In this non-randomized, open-label, single-center study conducted by the NIH, Kleptose® HPB is being administered via lumbar injection to drug-naive cohorts of patients at escalating doses. In certain of our analyses, we also included data from three patients being treated with intrathecal Kleptose® HPB at another institution under individual INDs.

Our analyses confirmed that intrathecal administration of Kleptose® HPB provides therapeutic benefit in NPC type 1 disease. Using a standard aggregate outcome measure, the NPC Clinical Severity Scale, 7/15 patients were observed to have stable or improving disease, as compared to 0/13 in a cohort of patients in whom the natural history of untreated disease has been studied. Using a new composite endpoint informed by post-hoc analysis of the data, we found that 11/15 study patients showed stable or improving disease versus only 4/13 with stable disease in the Natural History cohort.

More detailed analyses, however, showed that while intrathecal administration of HPBCD improves certain signs and symptoms of NPC type 1 disease, it merely slows progression of others, and paradoxically appears to accelerate progression in other symptoms. In particular, hearing loss appears to have been accelerated in patients receiving intrathecal Kleptose® HPB. Our analysis of representative batches of Kleptose® HPB revealed that this parenteral grade product comprises a complex mixture of beta-cyclodextrin molecules having different degrees of substitution; it is not known which of these species contributes to the observed improvement, the slowing of progression, and the acceleration in progression of the various clinical domains.

To prepare for clinical trials in which HPBCD will be administered directly to the cerebrospinal fluid for longer periods of time, and with more frequent dosing, we developed methods to reduce levels of propylene glycol, which is a presumed ototoxin; beta-cyclodextrin molecules having no hydroxypropyl substitutions, which are known to form precipitates; and bacterial endotoxin, which is highly inflammatory. Although the methods were successful in reducing the specified impurities, we observed that absorption chromatography with alumina, whether used alone or in combination with solvent precipitation, also changed the compositional fingerprint, substantially reducing the amount of beta-cyclodextrin molecules having a single hydroxypropyl substitution (DS-1) and reducing the amount of beta-cyclodextrin molecules having two hydroxypropyl groups (DS-2). Reduction in the prevalence of molecules with low degrees of substitution (DS-0, as intended; and DS-1 and DS-2, unintended) increased the average degree of substitution ($DS_a$) of the mixture.

Despite the change in fingerprint from Kleptose® HPB there was, surprisingly, no change in the expression of genes known to be involved in cholesterol metabolism and transport, as assessed by in vitro gene expression profiling experiments. This discovery will allow the more highly purified and compositionally distinct HPBCD composition to be administered by intrathecal or intracerebroventricular route to the CSF of patients with NPC disease for longer periods, optionally with more frequent dosing, with therapeutic effect and improved safety.

Accordingly, in a first aspect, mixtures of beta-cyclodextrin molecules substituted at one or more hydroxyl positions by hydroxypropyl groups, the mixture optionally including unsubstituted beta-cyclodextrin molecules, are provided. The mixture comprises less than 1% unsubstituted beta-cyclodextrin ("DS-0") and beta-cyclodextrin substituted with one hydroxypropyl group ("DS-1"), collectively; at least 85% beta-cyclodextrin substituted with three hydroxypropyl groups ("DS-3"), beta-cyclodextrin substituted with four hydroxypropyl groups ("DS-4"), beta-cyclodextrin substituted with five hydroxypropyl groups ("DS-5"), and beta-cyclodextrin substituted with six hydroxypropyl groups ('DS-6"), collectively; and less than 1% beta-cyclodextrin substituted with nine hydroxypropyl groups ("DS-9") and beta-cyclodextrin substituted with ten hydroxypropyl groups ("DS-10"), collectively, each as determined by peak height of an electrospray MS spectrum.

In certain embodiments, less than 0.1% of the beta-cyclodextrin mixture is DS-0 and DS-1, collectively. In some embodiments, less than 0.01% of the beta-cyclodextrin mixture is DS-0 and DS-1, collectively. In some embodiments, at least 87% of the beta-cyclodextrin mixture is DS-3, DS-4, DS-5, and DS-6, collectively. In some embodiments, at least 90% of the beta-cyclodextrin mixture is DS-3, DS-4, DS-5, and DS-6, collectively. In some embodiments, less than 0.1% of the beta-cyclodextrin mixture is DS-9 and DS-10, collectively. In certain embodiments, less than 0.01% of the beta-cyclodextrin mixture is DS-9 and DS-10, collectively.

In another aspect, the mixture comprises less than 1% unsubstituted beta-cyclodextrin ("DS-0") and beta-cyclodextrin substituted with one hydroxypropyl group ("DS-1"), collectively, and less than 1% beta-cyclodextrin substituted with nine hydroxypropyl groups ("DS-9") and beta-cyclodextrin substituted with ten hydroxypropyl groups ("DS-10"), collectively, each as determined by peak height of an electrospray MS spectrum, and the mixture has an average molar substitution ("MS") in the range of 0.50 to 0.80.

In certain embodiments, less than 0.1% of the beta-cyclodextrin mixture is DS-0 and DS-1, collectively. In some embodiments, less than 0.01% of the beta-cyclodextrin mixture is DS-0 and DS-1, collectively. In some embodiments, less than 0.1% of the beta-cyclodextrin mixture is DS-9 and DS-10, collectively. In certain embodiments, less than 0.01% of the beta-cyclodextrin mixture is DS-9 and DS-10, collectively. In various embodiments, the MS is in the range of 0.60 to 0.70. In some of these embodiments, the MS is in the range of 0.64 to 0.68. In certain embodiments, the MS is about 0.66-0.67.

In another aspect, pharmaceutical compositions are provided, the pharmaceutical compositions comprising the beta-cyclodextrin mixture described herein and a pharmaceutically acceptable diluent.

In some embodiments, the composition comprises no more than 0.5% propylene glycol, as measured by the HPLC method set forth in the USP Hydroxypropyl Betadex monograph. In some embodiments, the composition comprises no more than 0.01% propylene glycol, as measured by the HPLC method set forth in the USP Hydroxypropyl Betadex monograph. In some embodiments, the pharmaceutical composition comprises no more than ("NMT") 5 EU of endotoxins per gram of beta-cyclodextrin mixture. In specific embodiments, the pharmaceutical composition comprises NMT 1.5 EU of endotoxins per gram of beta-cyclodextrin mixture. In some embodiments, the pharmaceutical composition comprises no more than 1 ppm propylene oxide, determined according to the USP Hydroxypropyl Betadex monograph.

In typical embodiments, the pharmaceutical composition is suitable for intrathecal or intracerebroventricular administration. In some embodiments, the pharmaceutical composition has an osmolality of about 300 to about 450 mOsm/kg. In some embodiments, the composition comprises about 10 mg/mL to about 200 mg/mL of the beta-cyclodextrin mixture.

In another aspect, the pharmaceutical composition comprises a mixture of beta-cyclodextrin molecules substituted at one or more hydroxyl positions by hydroxypropyl groups, the mixture optionally including unsubstituted beta-cyclodextrin molecules, and a diluent that is pharmaceutically acceptable for intrathecal, intracerebroventricular, or intravenous administration. The composition comprises no more than ("NMT") 5 EU of endotoxins per gram of beta-cyclodextrin mixture, no more than 0.5% propylene glycol, as measured by the HPLC method set forth in the USP Hydroxypropyl Betadex monograph, and no more than 1 ppm propylene oxide, determined according to the USP Hydroxypropyl Betadex monograph.

In some embodiments, the composition comprises NMT 1.5 EU of endotoxins per gram of beta-cyclodextrin mixture. In some embodiments, the composition comprises no more than 0.01% propylene glycol, as measured by the HPLC method set forth in the USP Hydroxypropyl Betadex monograph. In certain embodiments, the mixture comprises less than 3% unsubstituted beta-cyclodextrin ("DS-0"), beta-cyclodextrin substituted with one hydroxypropyl group ("DS-1"), and beta-cyclodextrin substituted with two hydroxypropyl groups ("DS-2"), collectively; at least 65% beta-cyclodextrin substituted with five hydroxypropyl groups ("DS-5"), beta-cyclodextrin substituted with six hydroxypropyl groups ('DS-6"), and beta-cyclodextrin substituted with seven hydroxypropyl groups ('DS-7"), collectively; and less than 3% beta-cyclodextrin substituted with nine hydroxypropyl groups ("DS-9") and beta-cyclodextrin substituted with ten hydroxypropyl groups ("DS-10"), collectively, as determined by peak heights of an electrospray MS spectrum.

In another aspect, methods of treating Niemann-Pick disease Type C are provided, the methods comprising administering to a patient in need thereof a therapeutically effective amount of the pharmaceutical composition.

In typical embodiments, the composition is administered intrathecally or by intracerebroventricular administration. In some embodiments, the method comprises administering about 300 mg to about 2000 mg of the beta-cyclodextrin mixture to the patient. In certain embodiments, the composition is administered once every week, once every two weeks, once every three weeks, once every month, once every two months, or once every three months. In certain embodiments, the method comprises administering about 900 mg to about 1800 mg of the beta-cyclodextrin mixture to the patient once every two weeks. In certain embodiments, the method comprises administering about 900 mg of the beta-cyclodextrin mixture to the patient once every two weeks.

In some embodiments, the method comprises administering an amount of the beta-cyclodextrin mixture sufficient to modulate the level in cerebrospinal fluid of one or more of: tau protein, amyloid peptide, neurofilament light protein (NFL), glial fibrillary acidic protein (GFAP), sterol, oxysterol, chitotriosidase activity, calbindin, lysosomal-associated membrane protein 1 (LAMP-1), GM2 or GM3 ganglioside, sphingosine, and sphingosine-1-phosphate (S1P).

In some embodiments, the method comprises administering an amount of the beta-cyclodextrin mixture sufficient to modulate the level in plasma of one or more of: 7-ketocholesterol, 7β-hydroxycholesterol, 24S-hydroxycholesterol, 25-hydroxycholesterol, 27-hydroxycholesterol, and cholestane-3β,5α,6β-triol.

In some embodiments, the method comprises administering an amount of the beta-cyclodextrin mixture sufficient to modulate the level in urine of one or more of 3β-sulfoxy-7β-N-acetylglucosaminyl-5-cholen-24-oic acid (SNAG-$\Delta^5$-CA), glycine-conjugated 3β-sulfoxy-7β-N-acetylglucosaminyl-5-cholen-24-oic acid (SNAG-$\Delta^5$-CG), and taurine-conjugated 3β-sulfoxy-7β-N-acetylglucosaminyl-5-cholen-24-oic acid (SNAG-$\Delta^5$-CT).

In some embodiments, the method comprises administering the beta-cyclodextrin mixture in an amount sufficient to maintain or reduce one or more domain scores of the NPC Severity Scale selected from: ambulation, fine motor skills, cognition, speech, swallowing, eye movement, memory, hearing, and seizures.

In another aspect, a process for preparing the beta-cyclodextrin mixture is presented, comprising treating Kleptose® HBP with absorption chromatography on alumina.

In some embodiments, the process comprises a combination of absorption chromatography on alumina and solvent precipitation. In some embodiments, the solvent precipitation is performed using water with acetone as precipitating agent. In other embodiments, the solvent precipitation is performed using methanol with acetone as precipitating agent.

In another aspect, mixtures of beta-cyclodextrin molecules substituted at one or more hydroxyl positions by hydroxypropyl groups, the mixture optionally including unsubstituted beta-cyclodextrin molecules, made by treating Kleptose® HBP with a combination of absorption chromatography on alumina and solvent precipitation.

In a further aspect, methods are provided for qualifying a mixture of beta-cyclodextrin molecules substituted at one or more hydroxyl positions by hydroxypropyl groups, the mixture optionally including unsubstituted beta-cyclodextrin molecules, for use in a pharmaceutical composition for intrathecal or intracerebroventricular administration. The method comprises (a) performing electrospray MS analysis of the mixture; (b) measuring peak heights; and (c) calculating the percentage of each beta-cyclodextrin species in the entire mixture based on peak heights. The mixture is qualified for use—that is, is of quality sufficient for use—if wherein the mixture comprises less than 1% DS-0 and DS-1, collectively; at least 85% DS-3, DS-4, DS-5, and DS-6, collectively; and less than 1% DS-9 and DS-10, collectively.

In another aspect, the present disclosure provides a pharmaceutical composition comprising, as a pharmaceutically active ingredient, a mixture of unsubstituted beta-cyclodextrin molecules and beta-cyclodextrin molecules substituted at one or more hydroxyl positions by hydroxypropyl groups, wherein the mixture has an average number of hydroxypropyl groups per beta-cyclodextrin ("DSa") of about 3 to about 7. In preferred embodiments, the pharmaceutical composition comprises no more than 0.5% propylene glycol, no more than ("NMT") 1.5 EU of endotoxin per gram of beta-cyclodextrin mixture, and no more than 1% of the mixture is unsubstituted with a hydroxypropyl group ("DS-0"). In various preferred embodiments, the beta-cyclodextrin mixture has an average molar substitution (MS) in the range of about 0.58—about 0.68 (DSa in the range of about 4.06-4.76). In certain of these preferred embodiments, the mixture has an MS of 0.58-0.68 (DSa of 4.06-4.76), and in some embodiment an MS of about 0.63. In various preferred embodiments, the mixture has an average molar substitution (MS) in the range of about 0.65 to about 0.68 (DSa 4.6-4.7), and in some embodiments, an average molar substitution of about 0.67.

In some embodiments, the beta-cyclodextrins in the mixture consist of glucose units of the structure:

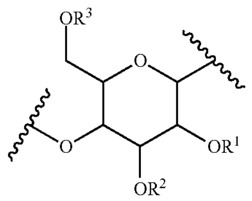

wherein $R^1$, $R^2$, and $R^3$, independently for each occurrence, are —H or —HP, wherein HP comprises one or more hydroxypropyl groups.

In some embodiments, the average number of occurrences of HP per beta-cyclodextrin is about 3 to about 7.

In some embodiments, at least 15% of total occurrences of $R^1$ and $R^2$ combined are HP. In some embodiments, at least 30% of occurrences of $R^3$ are HP.

In some embodiments, at least 70% of the beta-cyclodextrins collectively have an average number of occurrences of HP per beta-cyclodextrin of about 4 to about 6.

In some embodiments, the DSa is about 3 to about 4. In some embodiments, the DSa is 3.3±0.3. In some embodiments, the DSa is 3.7±0.3.

In some embodiments, the DSa is about 3.5 to about 4.5. In some embodiments, the DSa is 3.8±0.3. In some embodiments, the DSa is 4.2±0.3.

In some embodiments, the DSa is about 4 to about 5. In some embodiments, the DSa is 4.3±0.3. In some embodiments, the DSa is 4.7±0.3.

In some embodiments, the DSa is about 4.5 to about 5.5. In some embodiments, the DSa is 4.8±0.3. In some embodiments, the DSa is 5.2±0.3.

In some embodiments, the DSa is about 5 to about 6. In some embodiments, the DSa is 5.3±0.3. In some embodiments, the DSa is 5.7±0.3.

In some embodiments, the DSa is about 5.5 to about 6.5. In some embodiments, the DSa is 5.8±0.3. In some embodiments, the DSa is 6.2±0.3.

In some embodiments, the DSa is about 6 to about 7. In some embodiments, the DSa is 6.3±0.3. In some embodiments, the DSa is 6.7±0.3.

In some embodiments, at least 70% of the beta-cyclodextrins have a DS within DSa+1. In some embodiments, at least 90% of the beta-cyclodextrins have a DS within DSa+1.

In some embodiments, the hydroxypropyl groups are substituted at the hydroxyl positions of the beta-cyclodextrins as hydroxypropyl chains of the structure $[CH2CH(CH3)O]_nH$, wherein n≥1 and the average number of hydroxypropyl chains per beta-cyclodextrin is about 3 to about 7. In some embodiments, at least 70% of the hydroxypropyl chains have n=1. In some embodiments, less than 30% of the hydroxypropyl chains have n=2. In some embodiments, less than 10% of the hydroxypropyl chains have n>2. In some embodiments, the average number of hydroxypropyl chains per beta-cyclodextrin is about 4 to about 6. In some embodiments, at least 70% of the beta-cyclodextrins collectively have an average number of hydroxypropyl chains per beta-cyclodextrin of about 4 to about 6.

In some embodiments, the pharmaceutical composition disclosed herein contains less than about 10 International Units (IU), such as less than about 6 IU, less than about 3 IU, or less than about 1.5 IU, of endotoxins per gram of the pharmaceutically active ingredient. The level of endotoxins is determined by Limulus amoebocyte lysate test.

In some embodiments, the pharmaceutically active ingredient contains less than about 2% by weight, such as less than about 1% by weight unsubstituted beta-cyclodextrin.

In some embodiments, the pharmaceutically active ingredient contains less than about 0.5% by weight, such as less than about 0.2% by weight propylene glycol or propylene glycol oligomers.

In some embodiments, the pharmaceutically active ingredient contains less than about 1 ppm propylene oxide.

In some embodiments, the pharmaceutical composition comprises a pharmaceutically active ingredient wherein a 20% (w/v) solution of the pharmaceutically active ingredient in 1 mL of distilled water solubilizes at least 2 mg, such as at least 3 mg, at least 4 mg, or at least 5 mg, unesterified cholesterol at room temperature when measured by UV spectrometry after about 24 hours.

In some embodiments, the pharmaceutical composition exhibits a lower ototoxicity than Trappsol® Cyclo. In some embodiments, the ototoxicity is determined in vitro by toxicity in a House Ear Institute-organ of *Corti* 1 (HEI-OC1) cell. In some embodiments, ototoxicity is determined in vivo by a brainstem auditory evoked response (BAER) test in a subject, such as a mouse, a rat, a cat, a dog, or a human.

In some embodiments, the pharmaceutical composition is suitable for intrathecal or intracerebroventricular administration.

In some embodiments, the pharmaceutical composition has an osmolality of about 300 to about 450 mOsm/kg.

In some embodiments, the pharmaceutical composition comprises about 10 mg/mL to about 200 mg/mL of the pharmaceutically active ingredient.

In some embodiments, the sole pharmaceutically active ingredient of the pharmaceutical composition is obtained by purifying Kleptose® HBP, Kleptose® HP, Trappsol® Cyclo, or Cavasol® W7 HP Pharma. In certain embodiments, the sole pharmaceutically active ingredient of the pharmaceutical composition is obtained by purifying Kleptose® HBP. In certain embodiments, the sole pharmaceutically active ingredient of pharmaceutical composition is obtained by purifying Trappsol® Cyclo. In some embodiments, purifying comprises hydrophilic or hydrophobic interaction or affinity purification and can involve chromatographic methods, such as purification by HPLC or gel chromatography.

The disclosure also provides a method of treating Niemann-Pick disease Type C, comprising administering to a subject in need thereof, e.g., by intrathecal or intracerebroventricular administration, a therapeutically effective amount of a pharmaceutical composition as described herein. In some embodiments, the method comprises administering about 300 to about 3000 mg of the pharmaceutically active ingredient to the patient. In some embodiments, the administering occurs every week, every two weeks, every three weeks, every month, every two months, or every three months. For example, the method can comprise administering about 600 to about 1800 mg of the pharmaceutically active ingredient to the subject every two weeks.

In some embodiments, the method comprises administration of an amount of the pharmaceutically active ingredient sufficient to modulate the level in cerebrospinal fluid of one or more of: tau protein, amyloid peptide, neurofilament light protein (NFL), glial fibrillary acidic protein (GFAP), sterol, oxysterol, chitotriosidase activity, calbindin, lysosomal-associated membrane protein 1 (LAMP-1), GM2 or GM3 ganglioside, sphingosine, and sphingosine-1-phosphate (S1P).

In some embodiments, the method comprises administration of an amount of the pharmaceutically active ingredient sufficient to modulate the level in plasma of one or more of: 7-ketocholesterol, 7-hydroxycholesterol, 24S-hydroxycholesterol, 25-hydroxycholesterol, 27-hydroxycholesterol, and cholestane-3β,5α,6β-triol.

In some embodiments, the method comprises administration of an amount of the pharmaceutically active ingredient sufficient to modulate the level in urine of one or more of: 3-sulfoxy-7-N-acetylglucosaminyl-5-cholen-24-oic acid (SNAG-$\Delta^5$-CA), glycine-conjugated 3-sulfoxy-7-N-acetylglucosaminyl-5-cholen-24-oic acid (SNAG-$\Delta^5$-CG), and taurine-conjugated 3-sulfoxy-7-N-acetylglucosaminyl-5-cholen-24-oic acid (SNAG-$\Delta^5$-CT).

In some embodiments, the method further comprises maintaining or reducing one or more domain scores of NPC Severity Scale selected from: ambulation, fine motor skills, cognition, speech, swallowing, eye movement, memory, hearing, and seizures.

5. BRIEF DESCRIPTION OF THE FIGURES

FIG. 1 illustrates the clinical domains contributing to the standard NPC Clinical Severity Scale according to Yanjanin et al., "Linear Clinical Progression, Independent of Age of Onset, in Niemann-Pick Disease, Type C," Am. J. Med. Genet. Part B 153B: 132-140 (2010).

FIG. 2 summarizes the results from initial analyses of the Phase I clinical trial described in Example 1.

FIG. 3 summarizes further analyses of the Phase I clinical trial described in Example 1.

FIG. 4 summarizes analyses of the Phase I clinical trial data using change from baseline.

FIG. 5 summarizes early results from the Phase I clinical trial using overall NPC Scores.

FIG. 6 summarizes early results from the Phase I clinical trial with hearing impact removed.

FIG. 7 summarizes the clinical domains contributing to a novel "NPC Composite" Endpoint, or severity score;

FIG. 8 summarizes early results from the Phase I clinical trial using a novel NPC Composite Endpoint.

Figure 22:
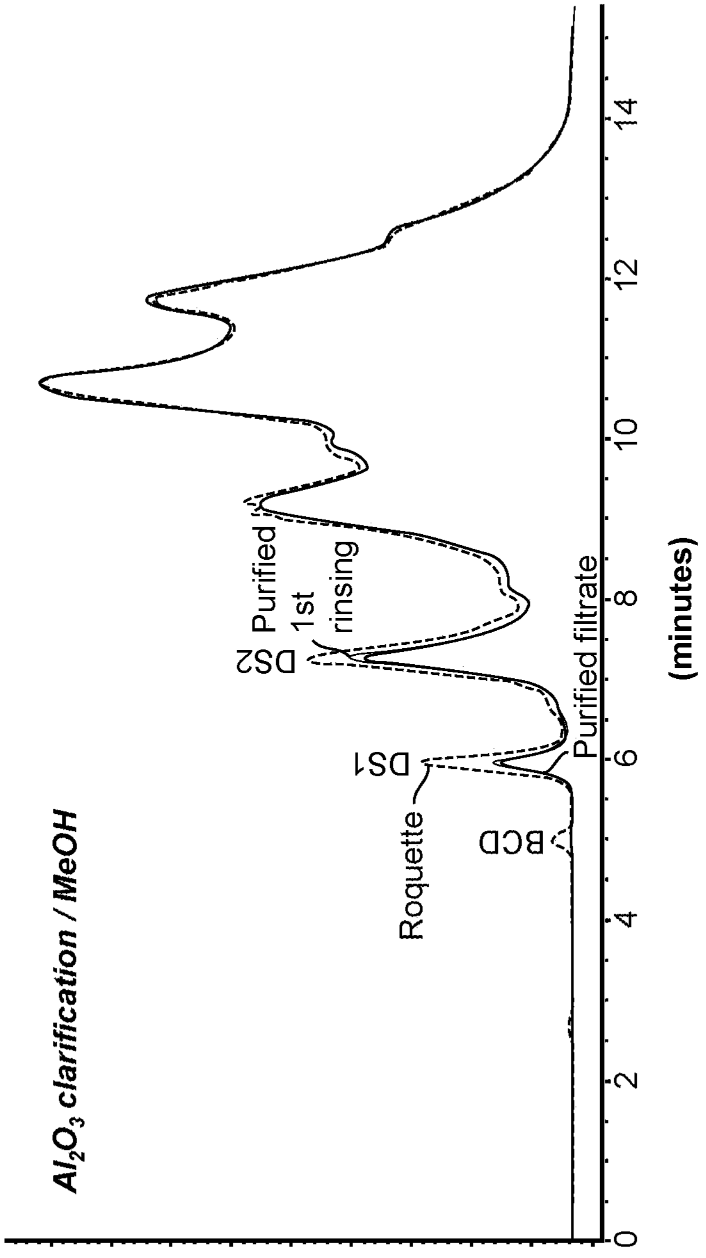

FIG. 22 shows overlay HPLC traces for the commercial Kleptose HPB® (Roquette, batch E0223) (upper trace), and after purification by alumina clarification. Lower trace shows data for the purified filtrate after alumina clarification; middle trace shows data for the purified $1^{st}$ rinsing after alumina clarification. X-axis shows retention time in minutes.

Figure 23:
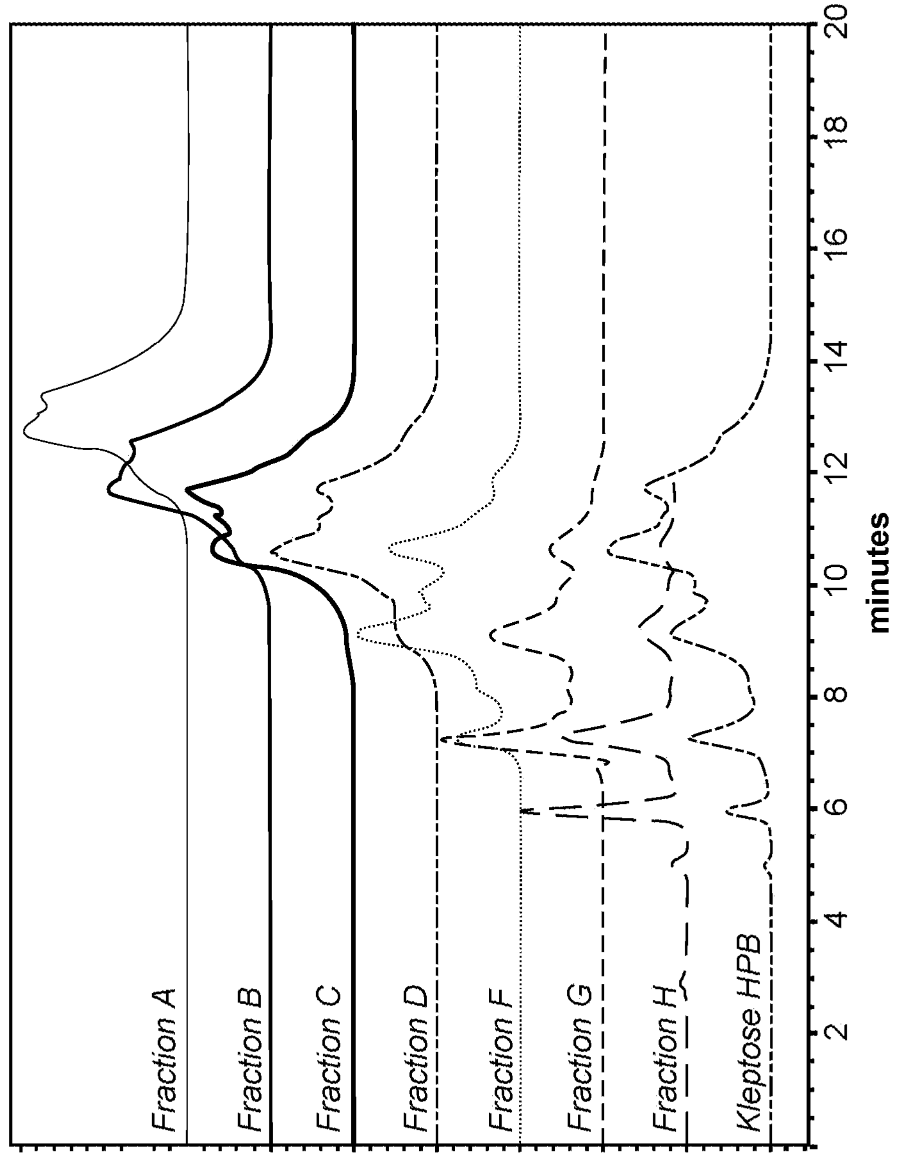

FIG. 23 shows comparative HPLC traces for each of Fractions A through H (excluding E) obtained from alumina chromatography of Kleptose® HPB. Fractions A through H correspond to Samples 5.4.3.2.2A through 5.4.3.2.2H, respectively (excluding E). X-axis shows retention time in minutes.

Figure 24:
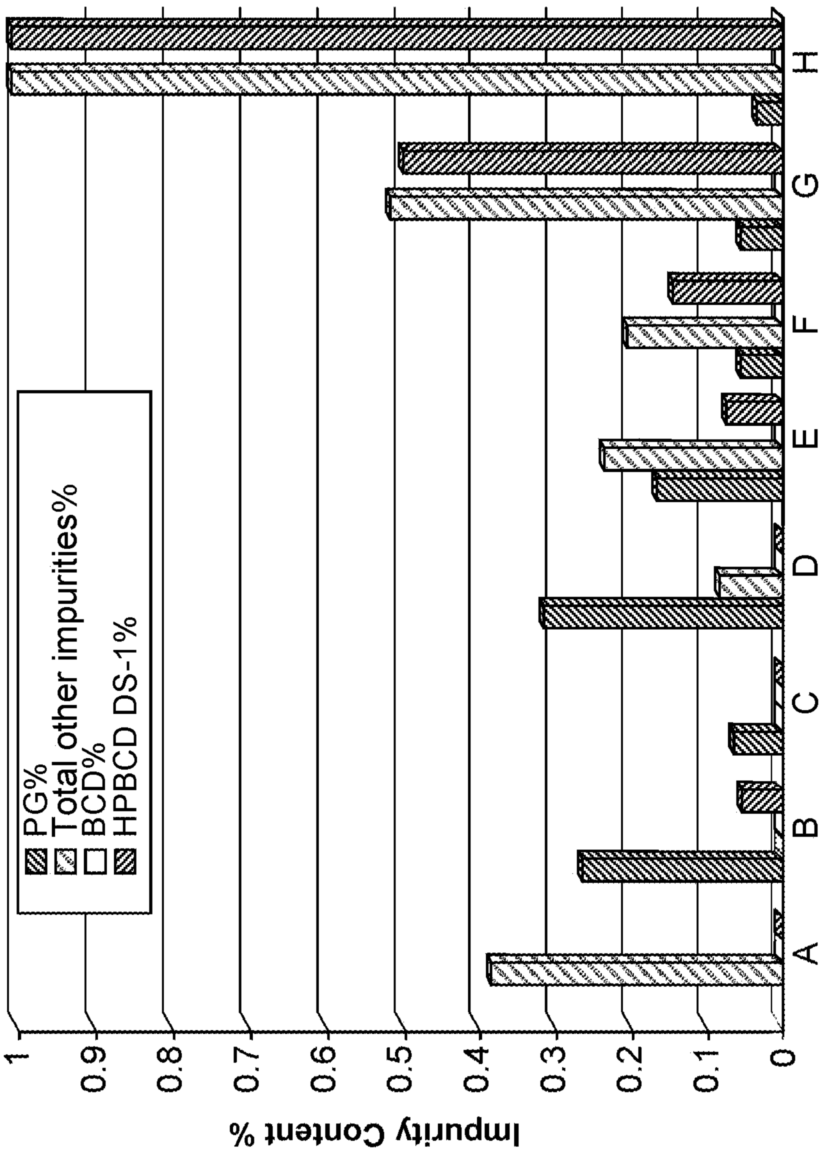

FIG. 24 shows a graph of the percentage impurity content in each of Fractions A through H collected from purification by alumina chromatography of Kleptose HPB®. A through H on the x-axis correspond to Samples 5.4.3.2.2A through 5.4.3.2.2H, respectively. Y-axis shows percent impurity content. PG %=percent propylene glycol (diagonal lined bars); total other impurities %=percent of total cyclodextrin-related impurities (black bars); BCD %=percent unsubstituted beta-cyclodextrin (hollow bars); HPBCD DS-1%=percent of monosubstituted beta-cyclodextrins (reverse diagonal lined bars).

Figure 25:
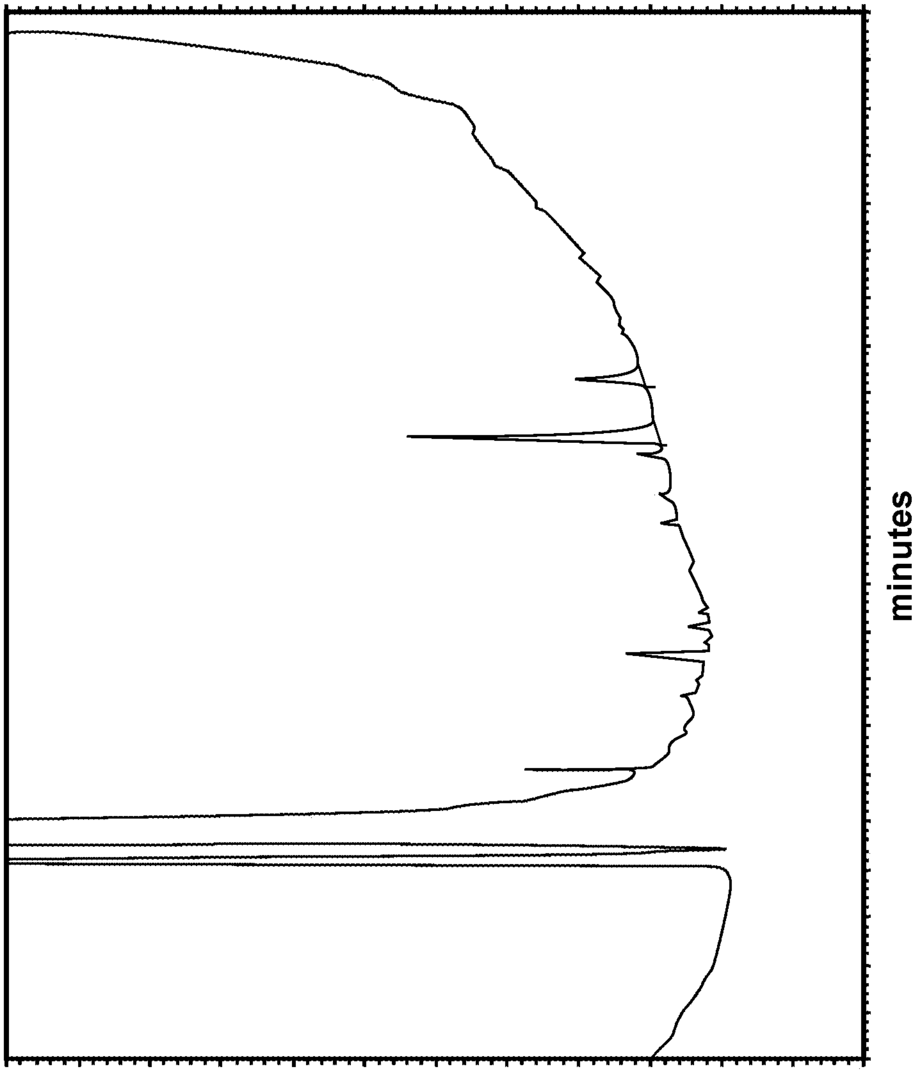

FIG. 25 depicts an exemplary gas chromatogram of Kleptose HPB® identifying propylene glycol (impurity to be measured) and ethylene glycol (internal standard). X-axis shows time in minutes; y-axis shows response.

Figure 26:
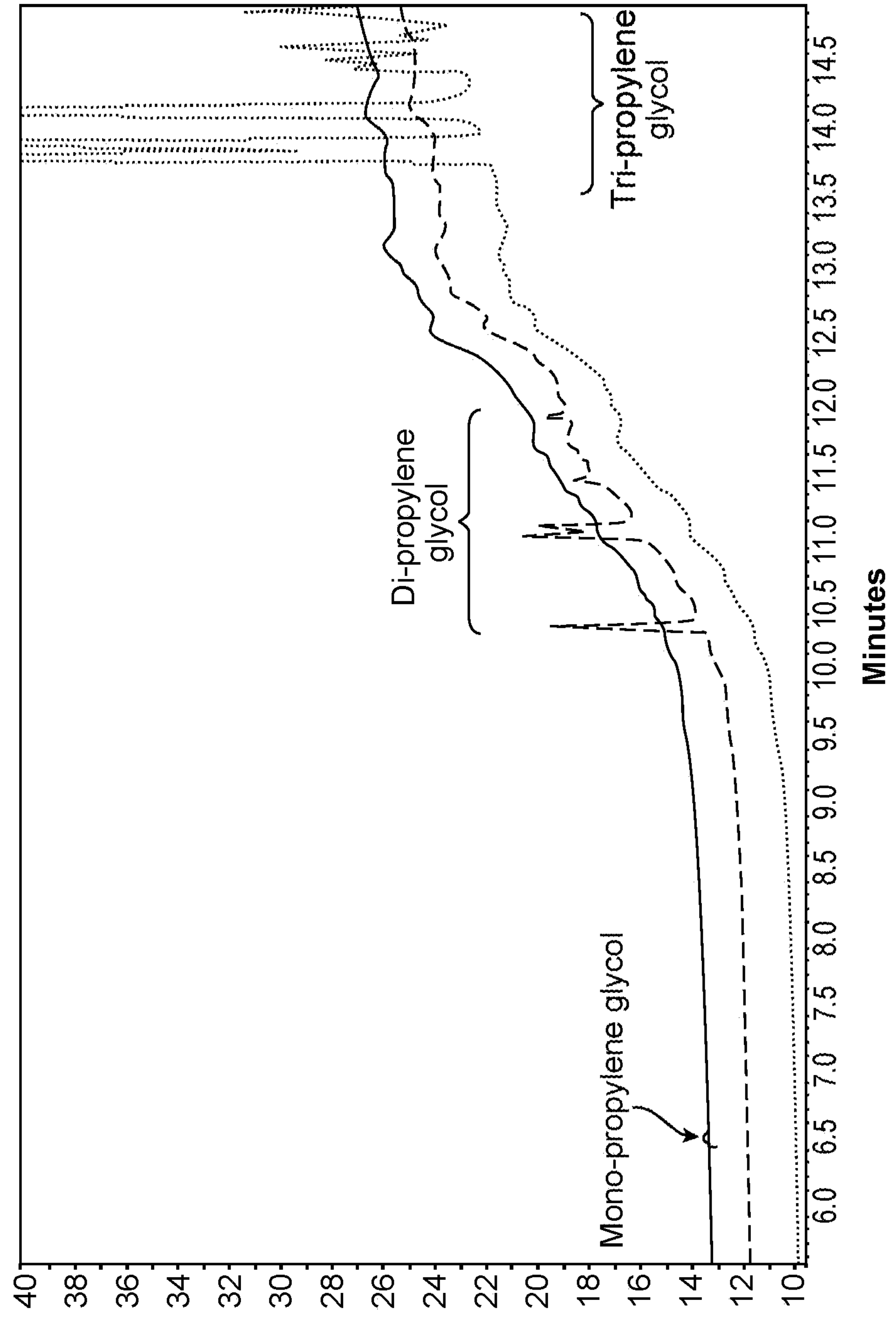

FIG. 26 depicts exemplary gas chromatograms of propylene glycol derivatives. X-axis shows time in minutes; y-axis shows response in millivolts.

Figure 27:
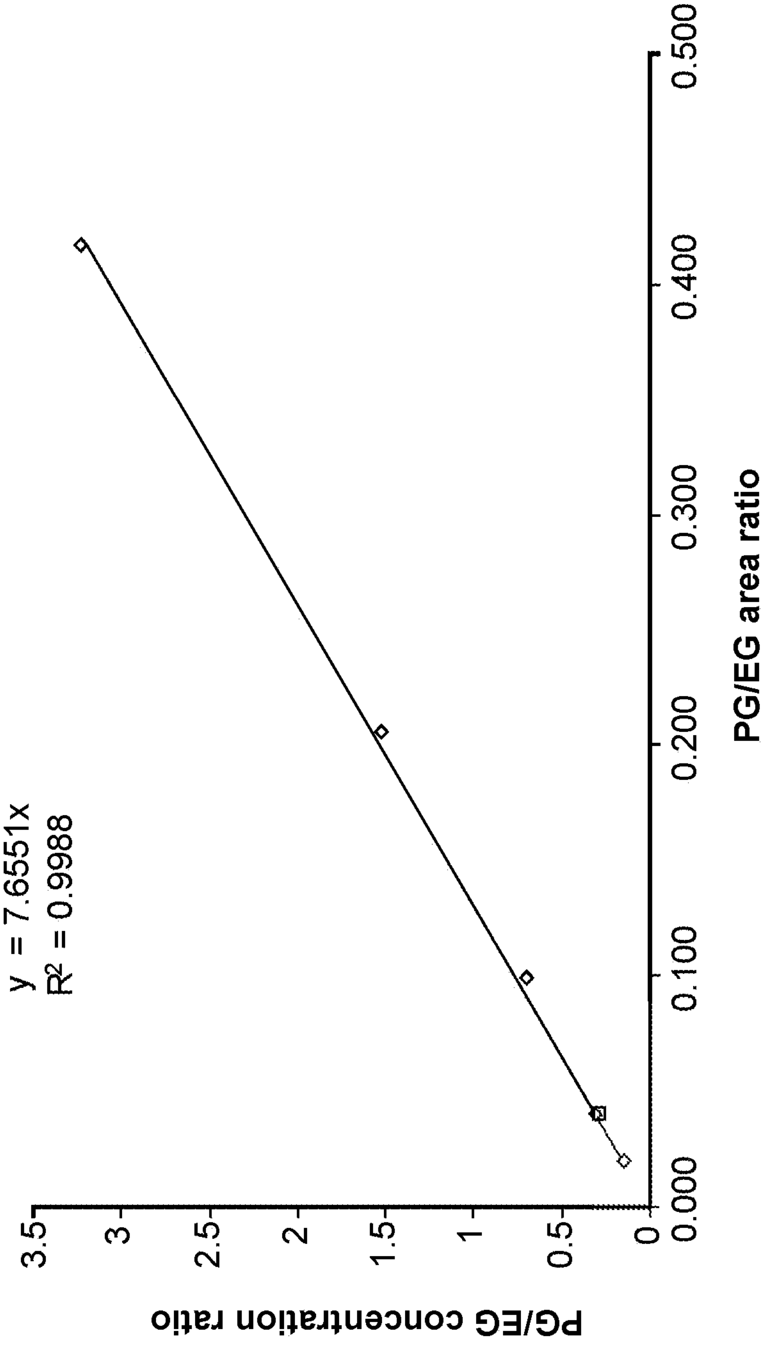

FIG. 27 depicts the calibration graph to determine propylene glycol concentrations in gas chromatography samples. PG/EG=ratio of propylene glycol to ethylene glycol as indicated.

Figure 28:
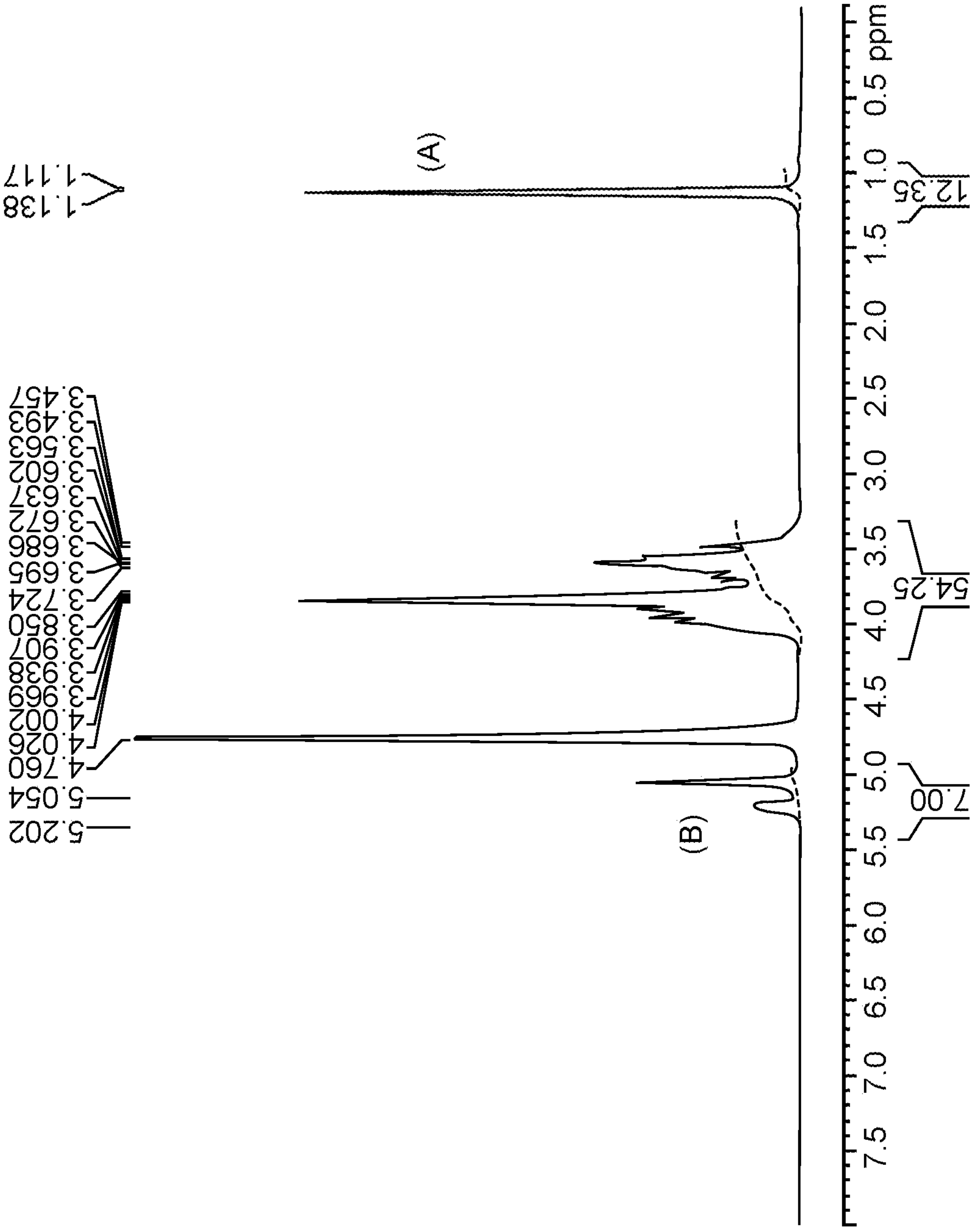

FIG. 28 depicts an exemplary $^{1}H$ NMR spectrum of Kleptose HPB® ($DS_a$ of 4.1) using the European Pharmacopeial method.

Figure 29A:
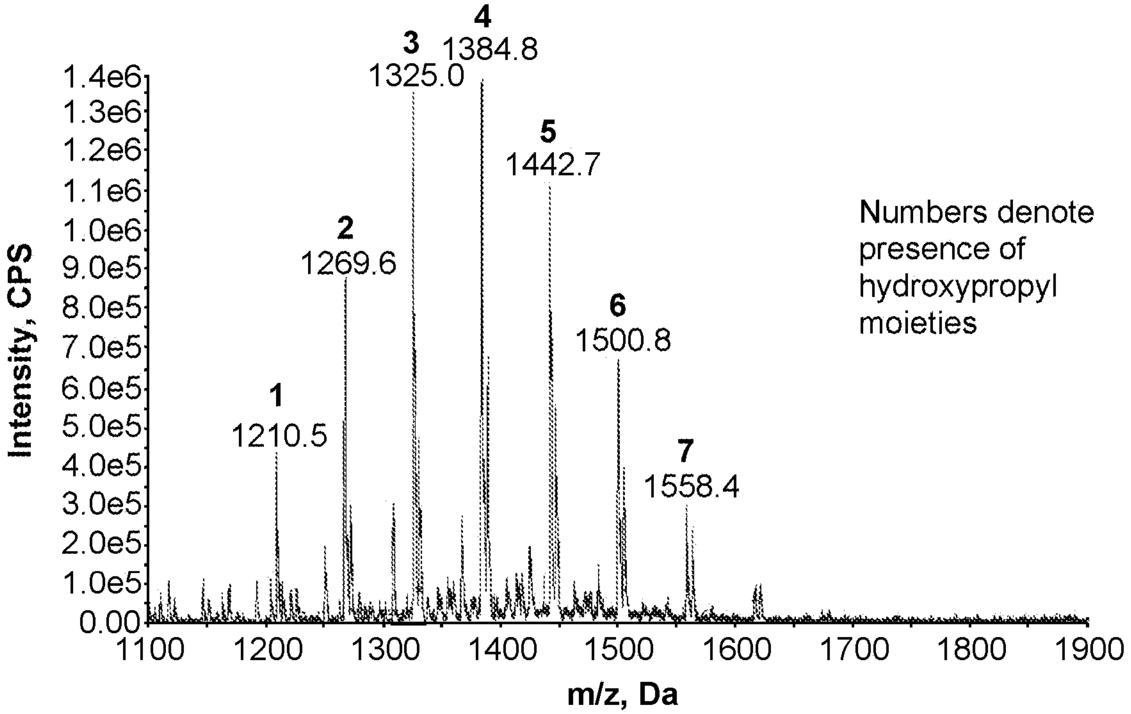
Figure 29B:
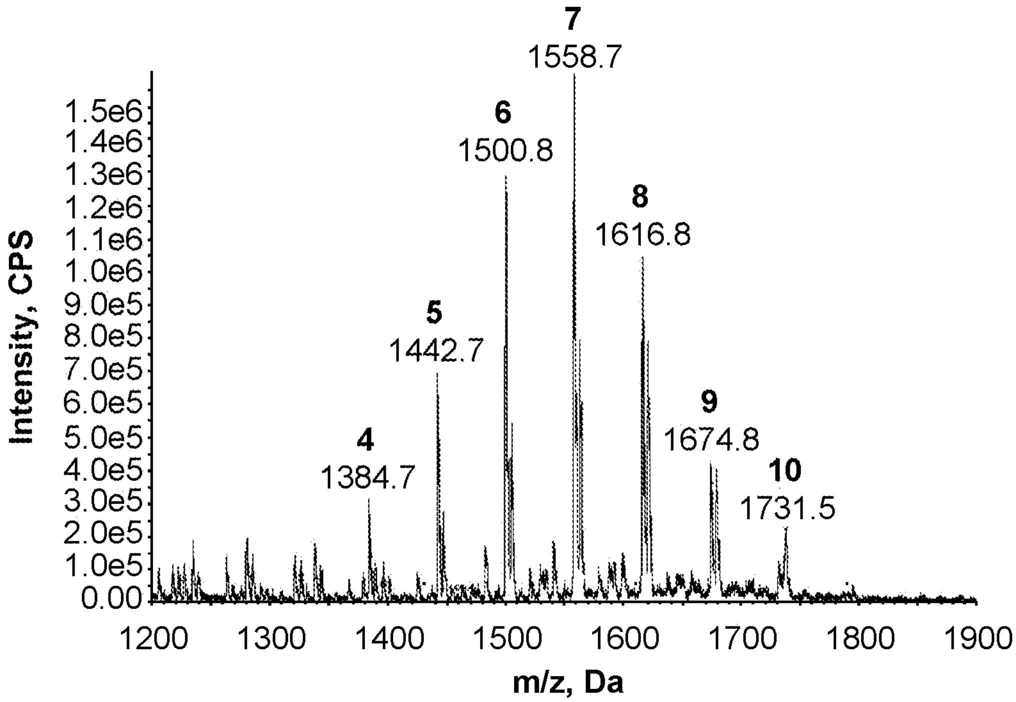

FIG. 29A and FIG. 29B present electrospray MS spectra data from a first laboratory, with FIG. 29A showing the Kleptose® HPB spectrum and FIG. 29B showing the spectrum of Trappsol® Cyclo™. Numbers have been added to the spectra to identify the number of hydroxypropyl moieties in each peak.

Figure 30A:
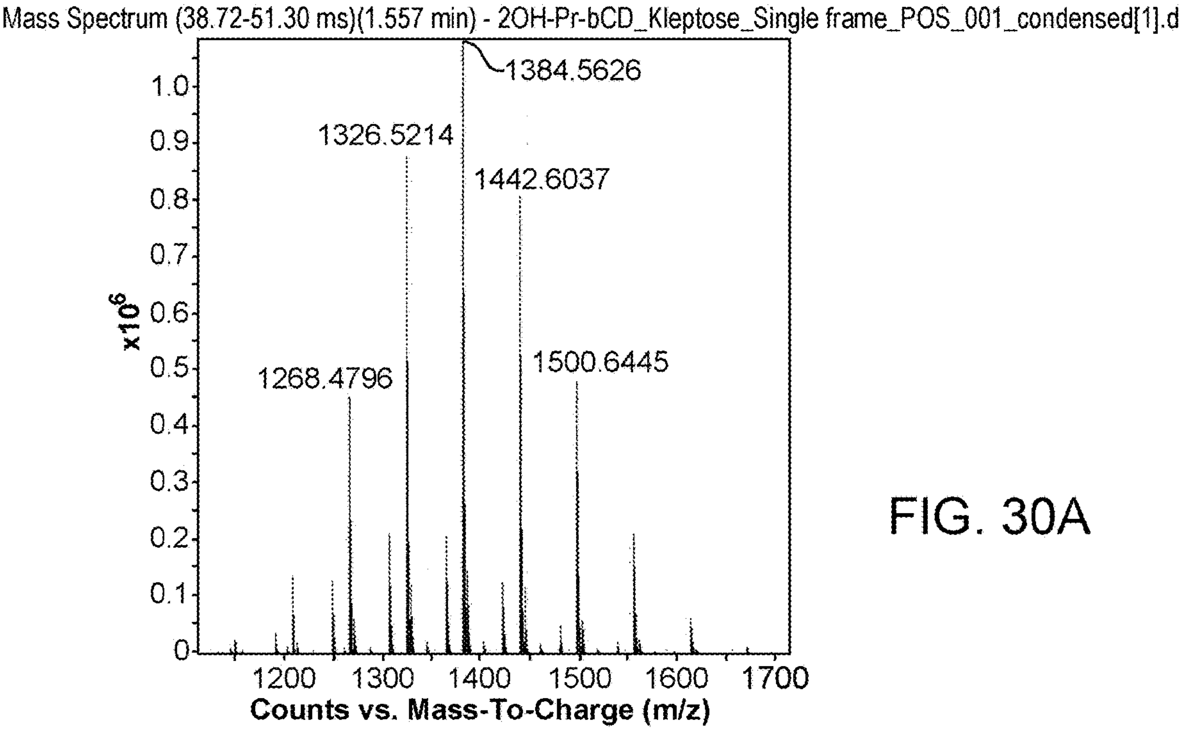
Figure 30B:
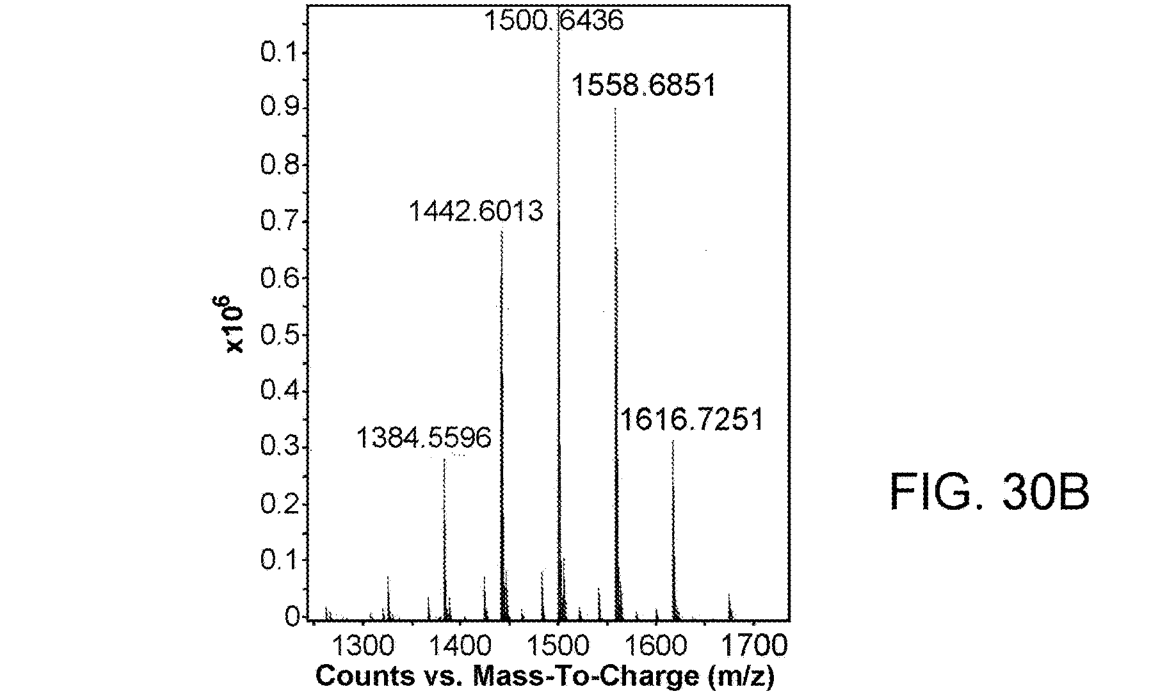

FIG. 30A and FIG. 30B IG. Present electrospray MS data from a second laboratory, with FIG. 30A showing the spectrum of Kleptose® HPB and FIG. 30B showing the spectrum of Trappsol® Cyclo™.

Figure 31A:
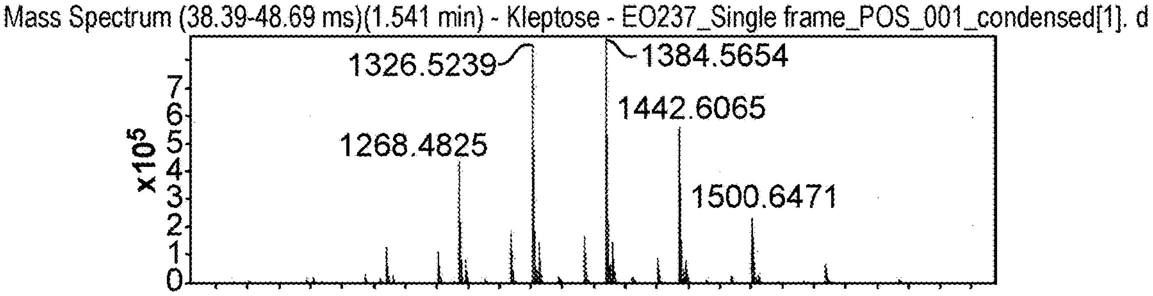
Figure 31B:
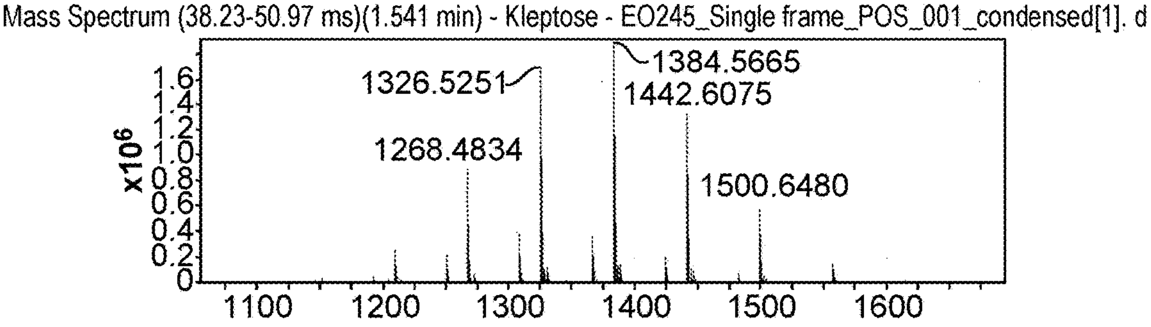
Figure 31C:
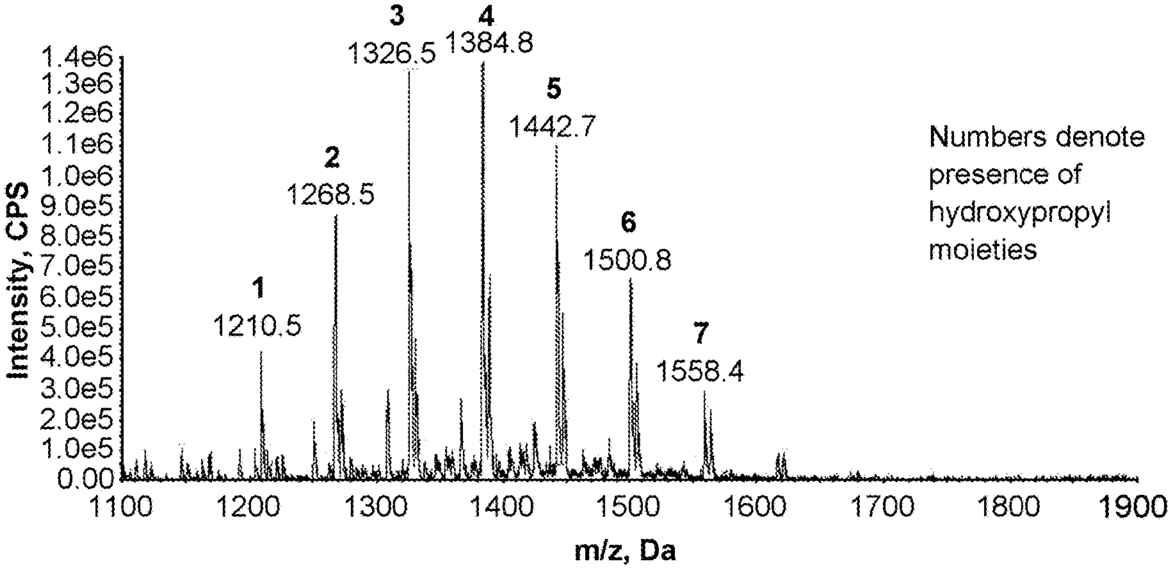

FIG. 31A, FIG. 31B, and FIG. 31C compare electrospray MS data from three different lots of Kleptose® HPB, performed by two different labs.

Figure 32A:
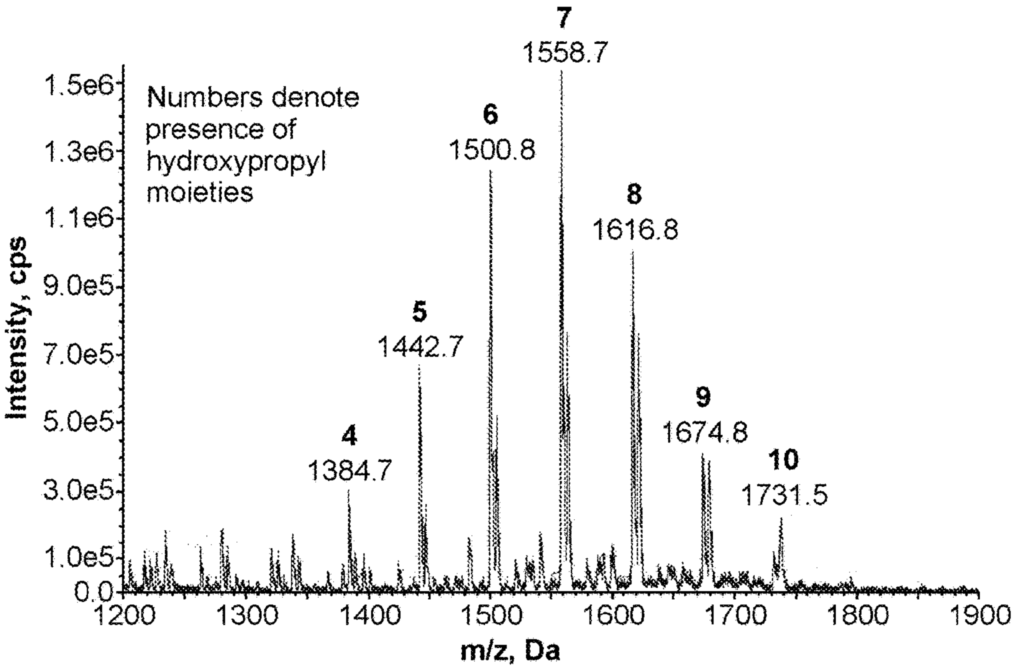
Figure 32B:
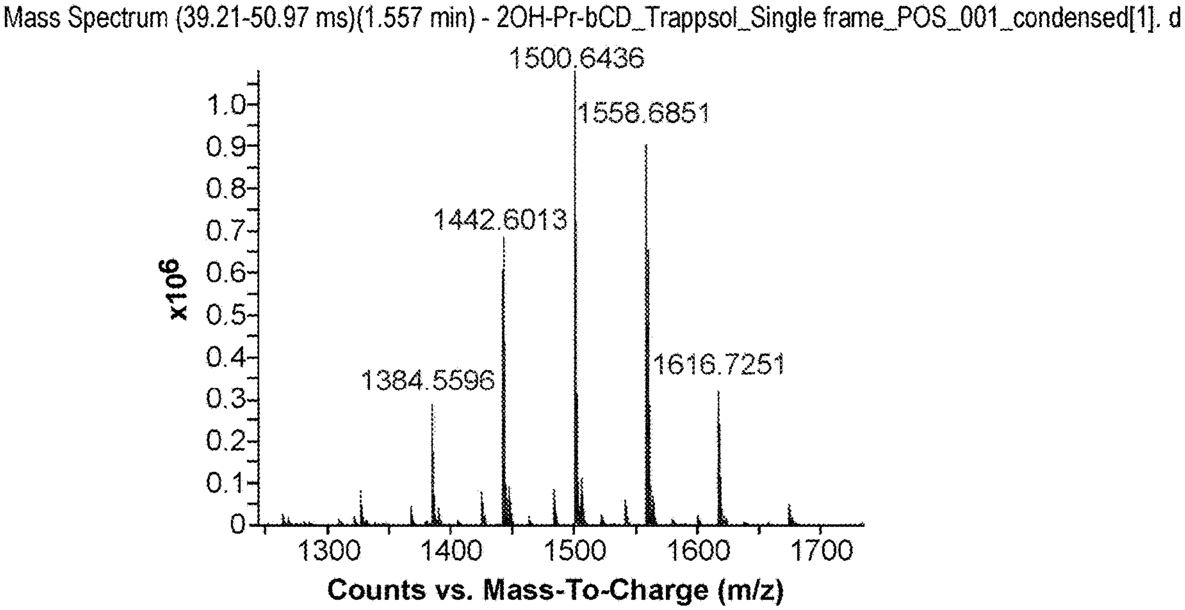

FIG. 32A and FIG. 32B present electrospray MS spectra from two different lots of Trappsol® Cyclo™, by two different laboratories, using the same conditions as were used to generate the Kleptose data shown in FIG. 31A, FIG. 31B, and FIG. 31C.

Figure 33A:
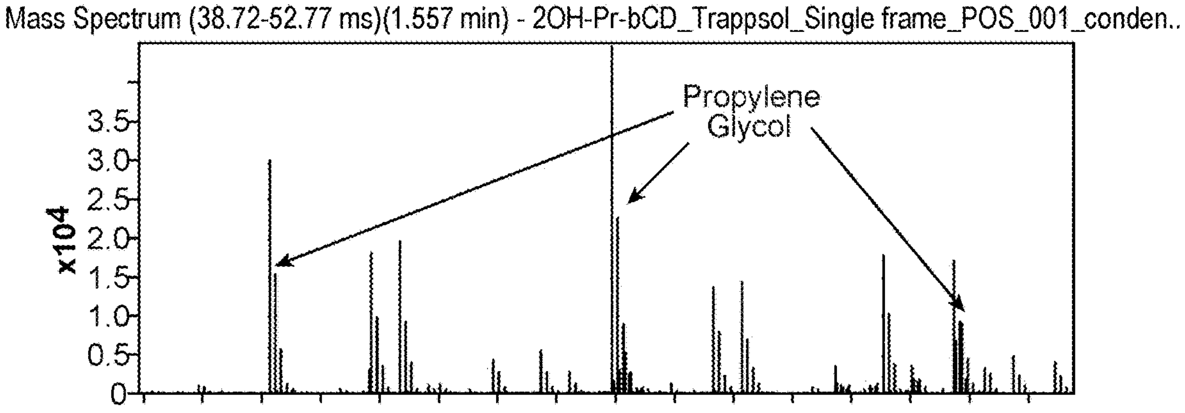
Figure 33B:
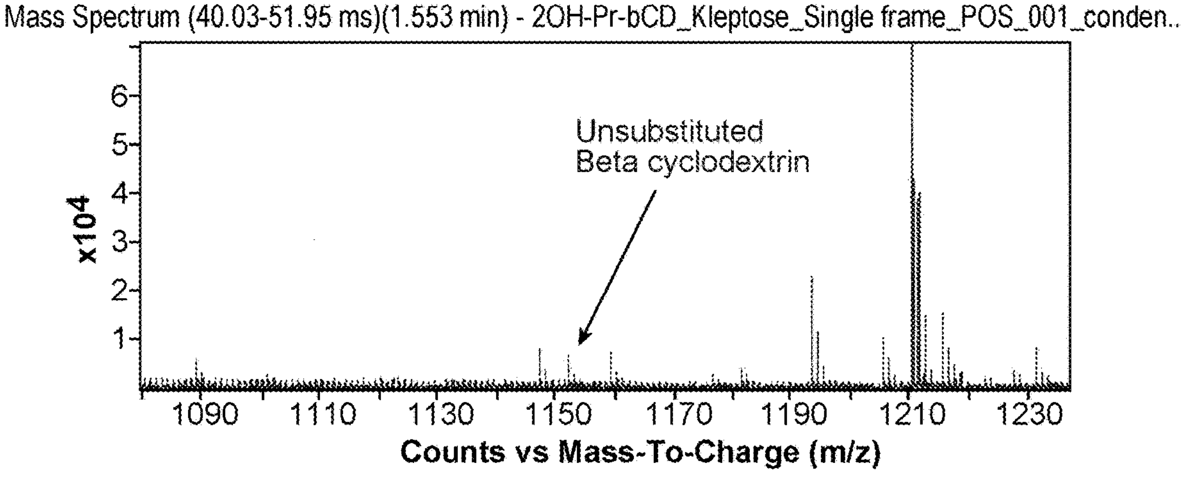

FIG. 33A and FIG. 33B show electrospray MS spectra in which the Y axis has been expanded as compared to FIG. 29A, FIG. 29B, FIG. 30A, FIG. 30B, FIG. 31A, FIG. 31B, FIG. 31C, FIG. 32A, and FIG. 32B to show peaks between 1090 and 1230 m/z. FIG. 33A is the spectrum obtained from Trappsol® Cyclo™. FIG. 33B is the spectrum obtained from Kleptose® HP.

Figure 34A:
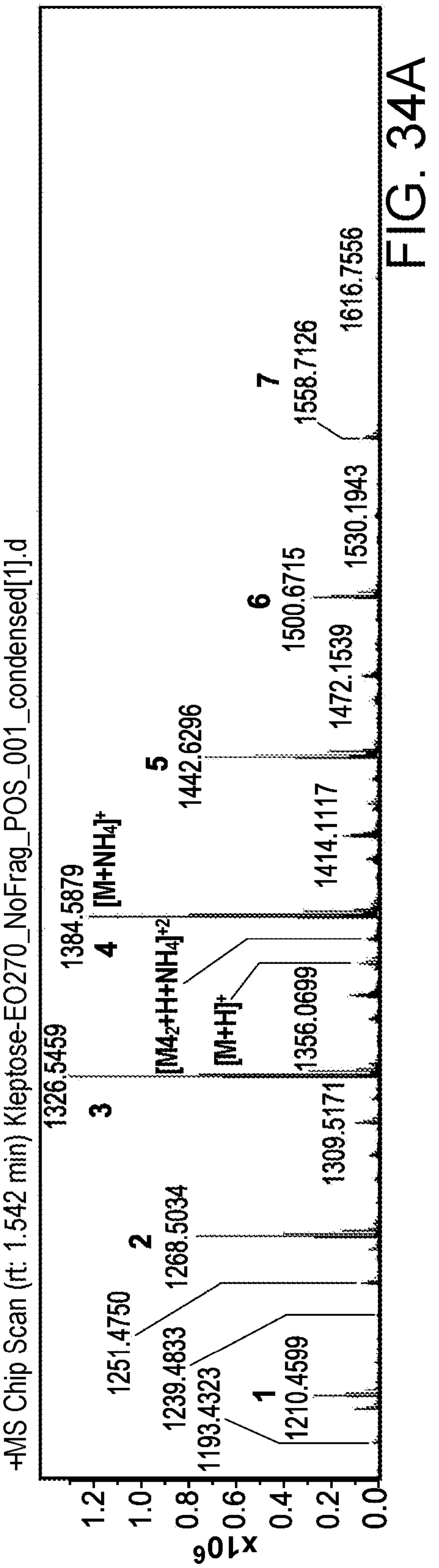
Figure 34B:
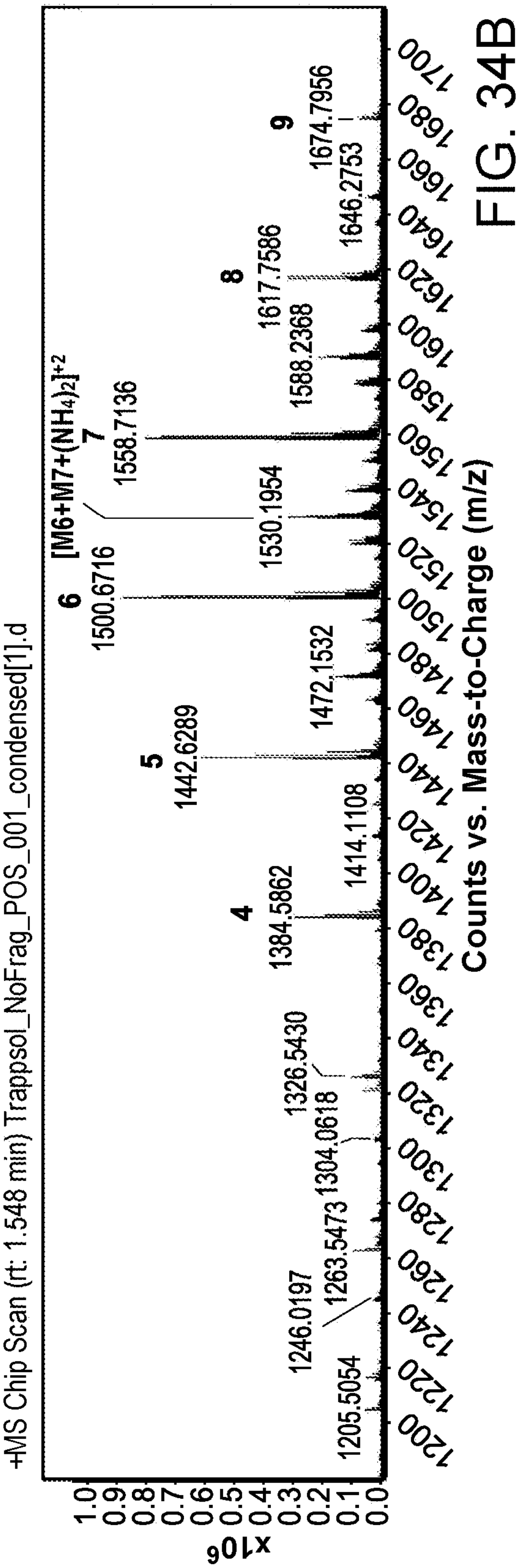

FIG. 34A and FIG. 34B present electrospray MS data further comparing the differences between Kleptose® HPB and Trappsol® Cyclo™, with FIG. 34A showing the Kleptose® HPB spectrum and FIG. 34B showing the spectrum of Trappsol® Cyclo™. Numbers have been added to the spectra to identify the number of hydroxypropyl moieties in each peak.

Figures 35A, 35B:
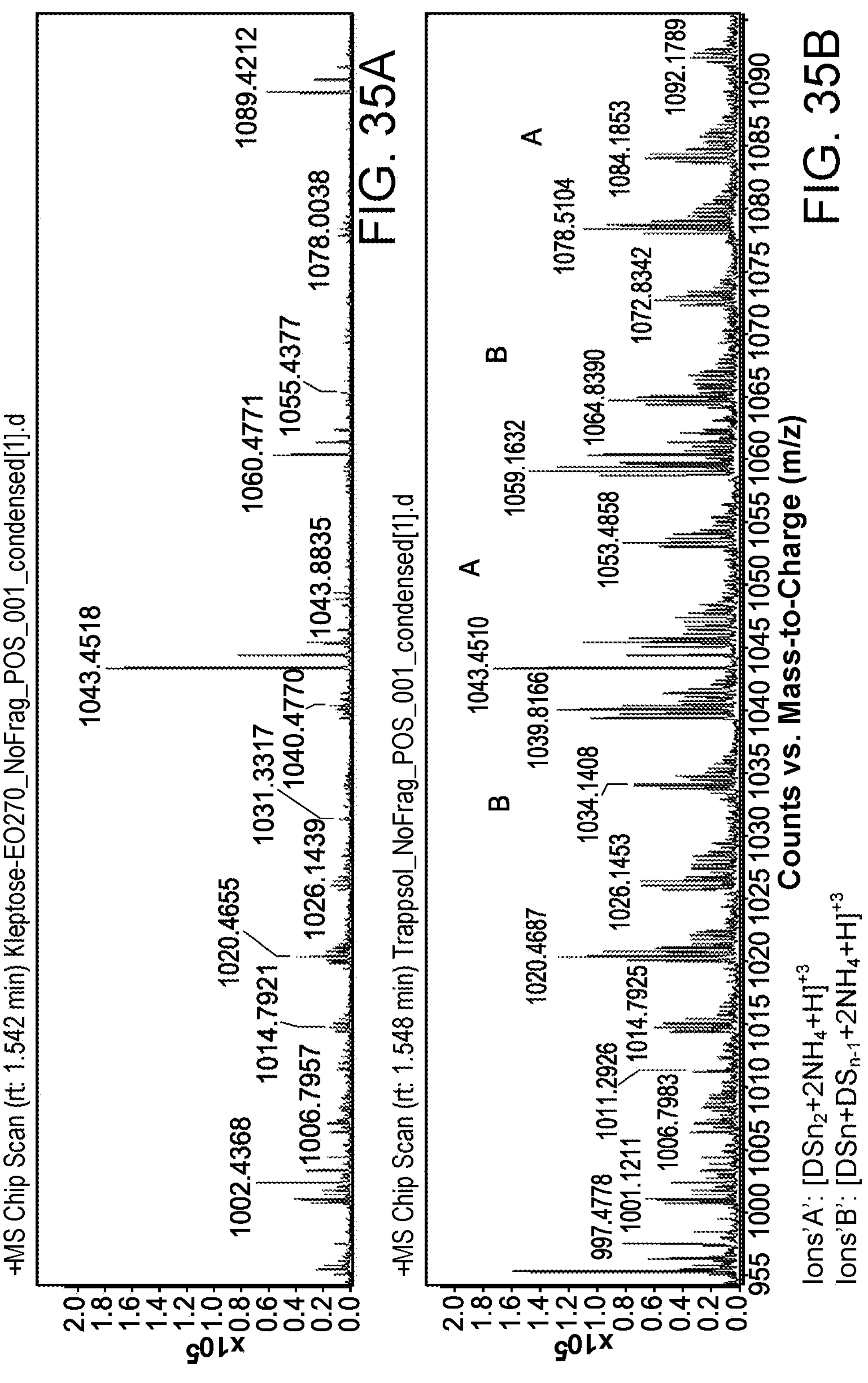

FIG. 35A and FIG. 35B present additional MS spectra differences between Kleptose® HPB and Trappsol® Cyclo™ between 995 and 1095 m/z, with FIG. 35A showing the Kleptose® HPB spectrum and FIG. 35B showing the spectrum of Trappsol® Cyclo™.

Figure 36A:
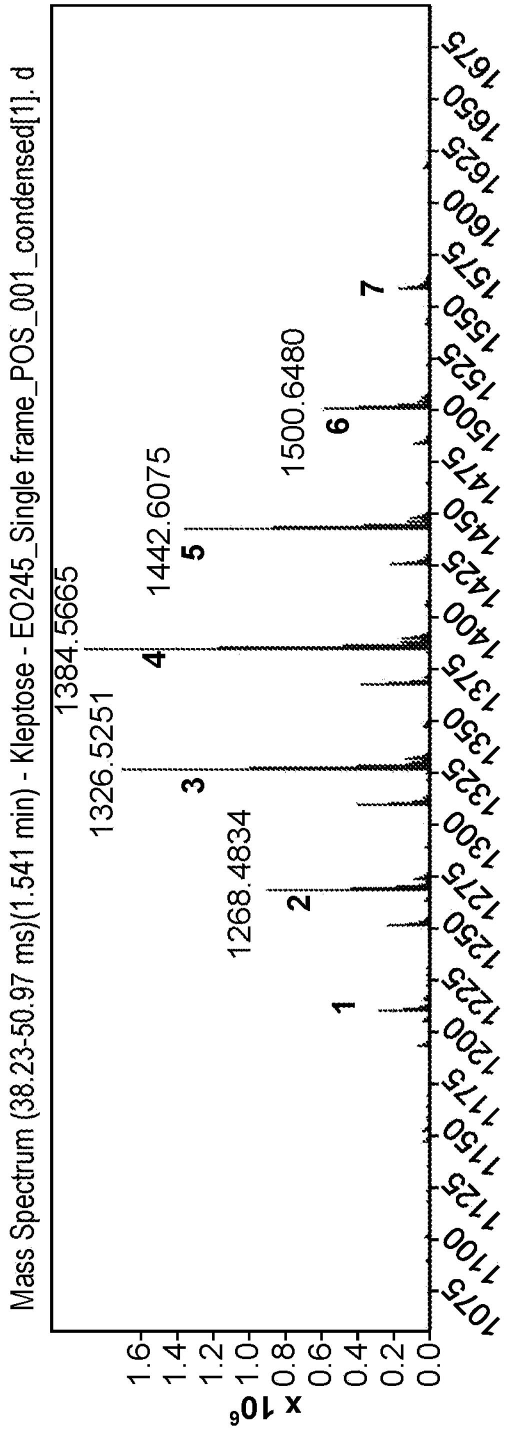
Figure 36B:
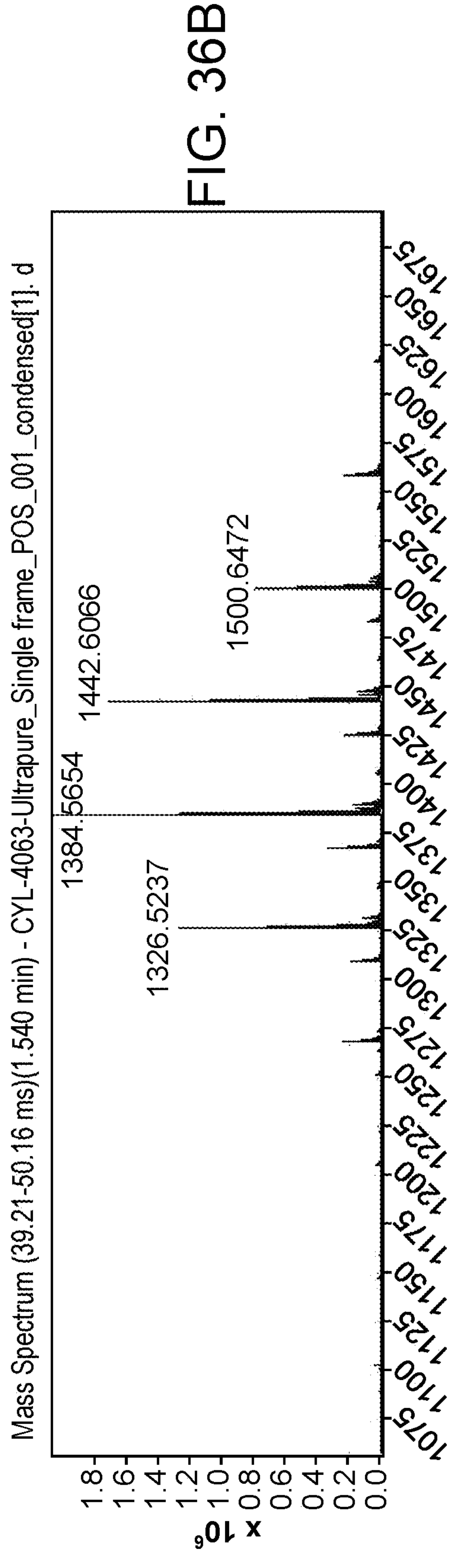

FIG. 36A and FIG. 36B present electrospray MS data showing the effect of purification with alumina adsorption on the substitution fingerprint. FIG. 36A shows the spectrum from the Kleptose® HPB starting material and FIG. 36B presents the spectrum from Batch CYL-4063, which was purified by combination of absorption chromatography on alumina and solvent precipitation (water-acetone).

Figure 37:
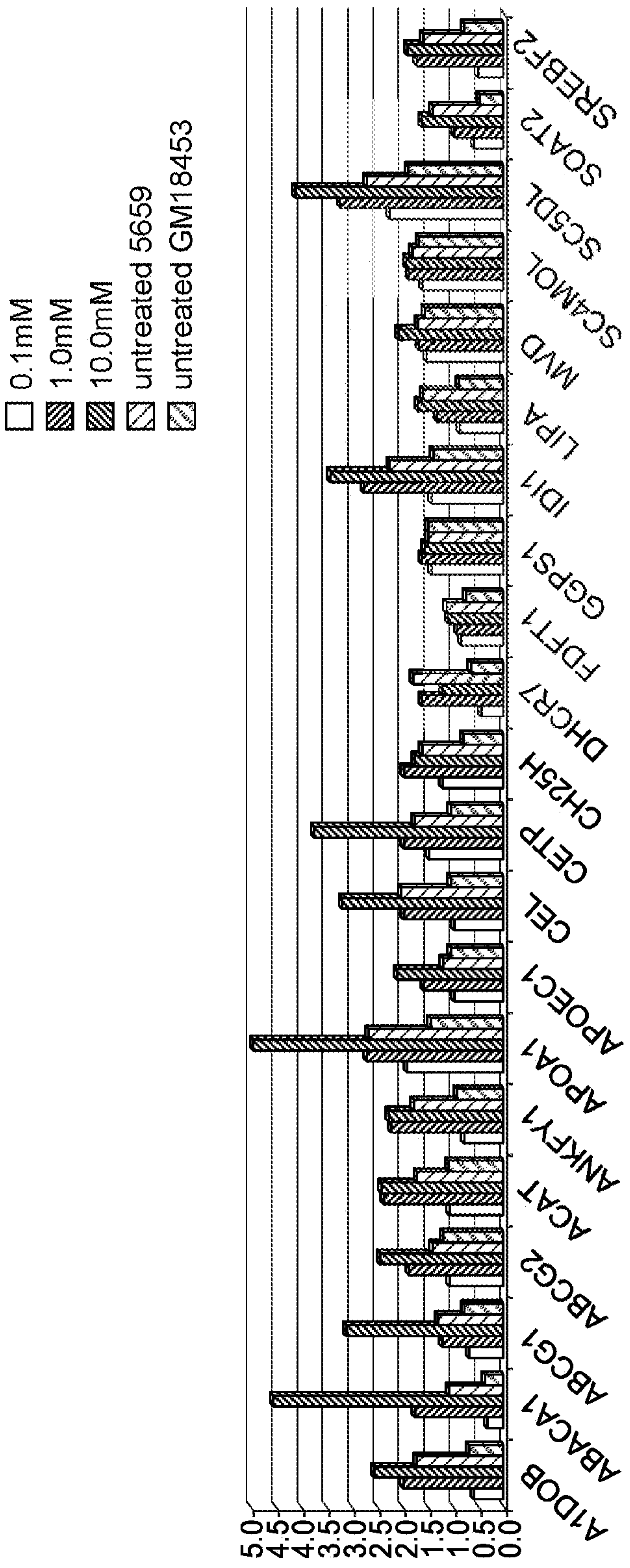

FIG. 37 shows fold changes in expression of selected cholesterol homeostasis-related genes in GM18453 and GM05659 cells treated with a range of Kleptose® HPB concentrations (0.1 mM to 10 mM).

Figure 38:
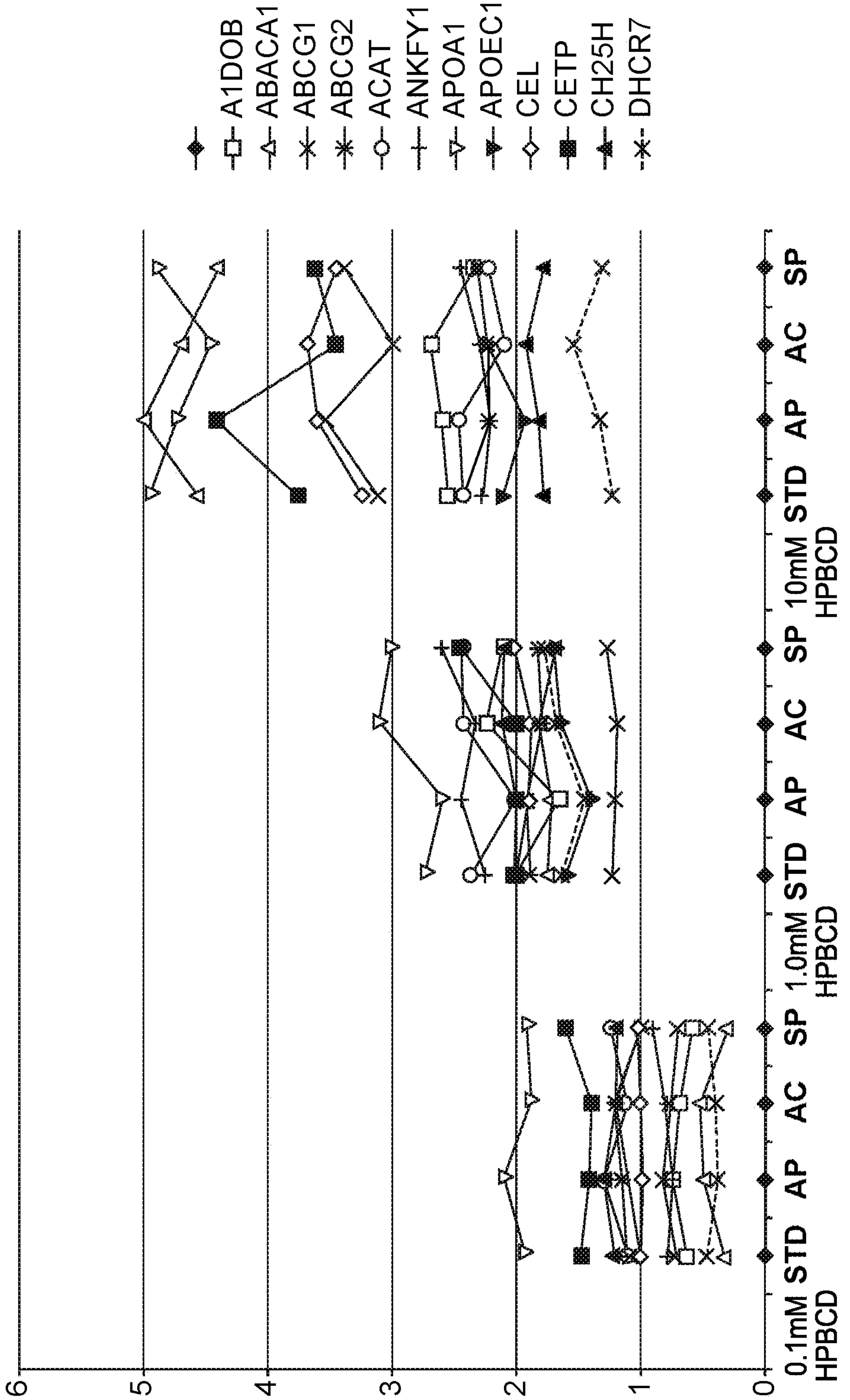

FIG. 38 shows fold changes in expression in GM18453 cells, which are homozygous for the NPC1 mutation, of the subset of cholesterol homeostasis genes that in which expression was statistically significantly different ($p<0.001$) upon treatment, for four different compositions: STD (Kleptose® HPB "standard"); AC (Kleptose® HPB purified by alumina chromatography); SP (Kleptose® HPB purified by solvent precipitation); and AP (Kleptose® HPB purified by alumina chromatography & solvent precipitation).

FIG. 39 shows the biological pathways that are most significantly affected, ranked by statistical significance, when GM18453 cells are respectively treated with Kleptose® HPB and with a batch of Kleptose® HPB purified by a process that includes adsorption to aluminum.

Figure 40:
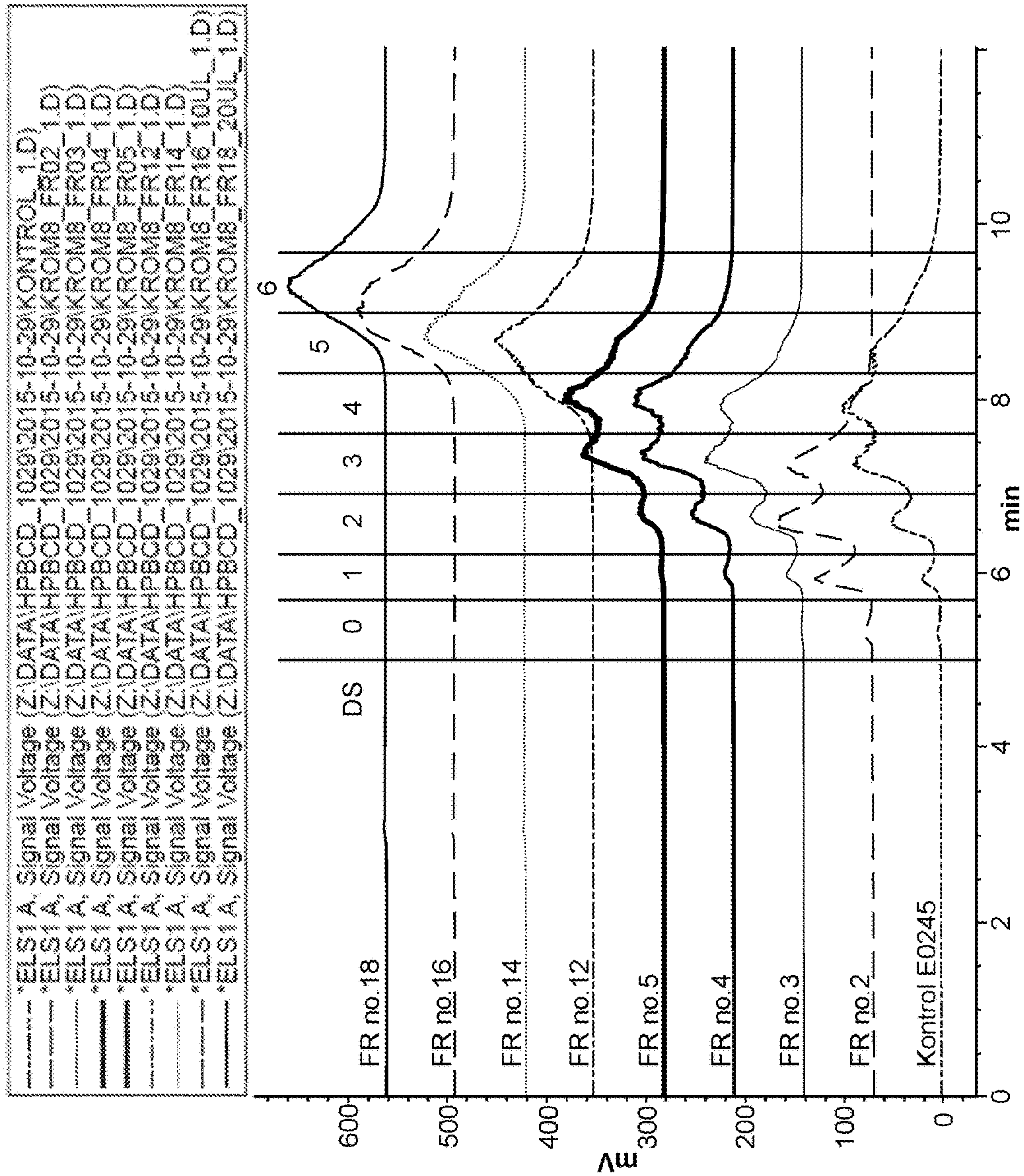

FIG. 40 shows chromatograms of various fractions obtained from preparative CD-Screen chromatographic separation of a batch of Kleptose® HPB, annotated to show the degree of substitution of the chromatographically separated hydroxypropyl beta-cyclodextrin species.

Figures 41A, 41B, 41C, 41D:
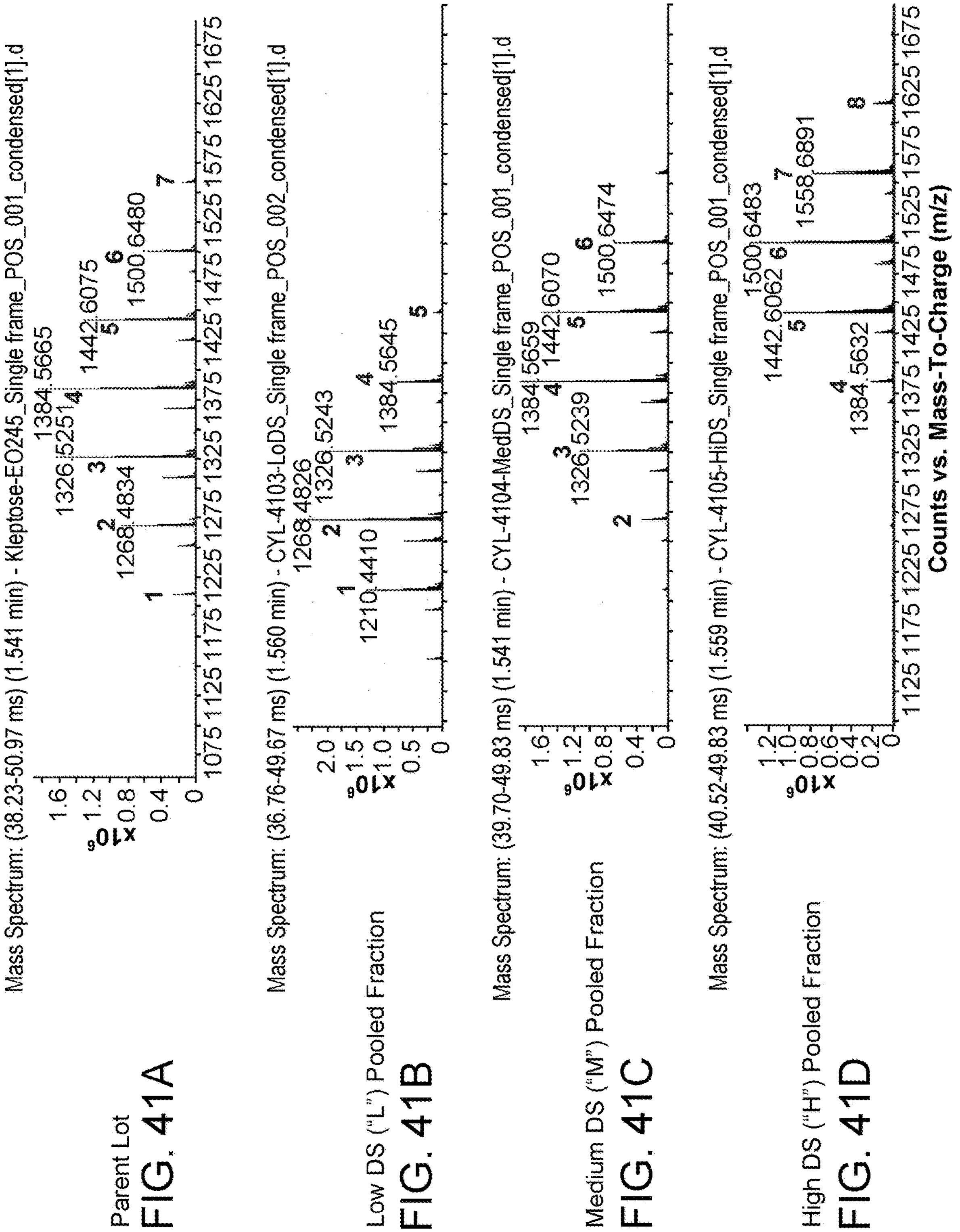

FIG. 41A, FIG. 41B, FIG. 41C, and FIG. 41D show electrospray MS spectra of Kleptose® HPB, the "L" fraction, the "M" fraction, and the "H" fraction, annotated to identify the signals by degree of hydroxypropyl substitution, with FIG. 41A showing Kleptose® HPB batch E0245; FIG. 41B showing the "L" fraction (Fraction 2 alone); FIG. 41C showing the "M" fraction (pool of Fractions 4-15); and FIG. 41D showing the "H" fraction (pool of Fractions 16-24).

FIG. 42 shows the 10 biological pathways most affected by treatment of the NPC cells with 1.0 mM of the "L", "M", and "H" fractions, ranked in descending order of statistical significance.

Figure 43:
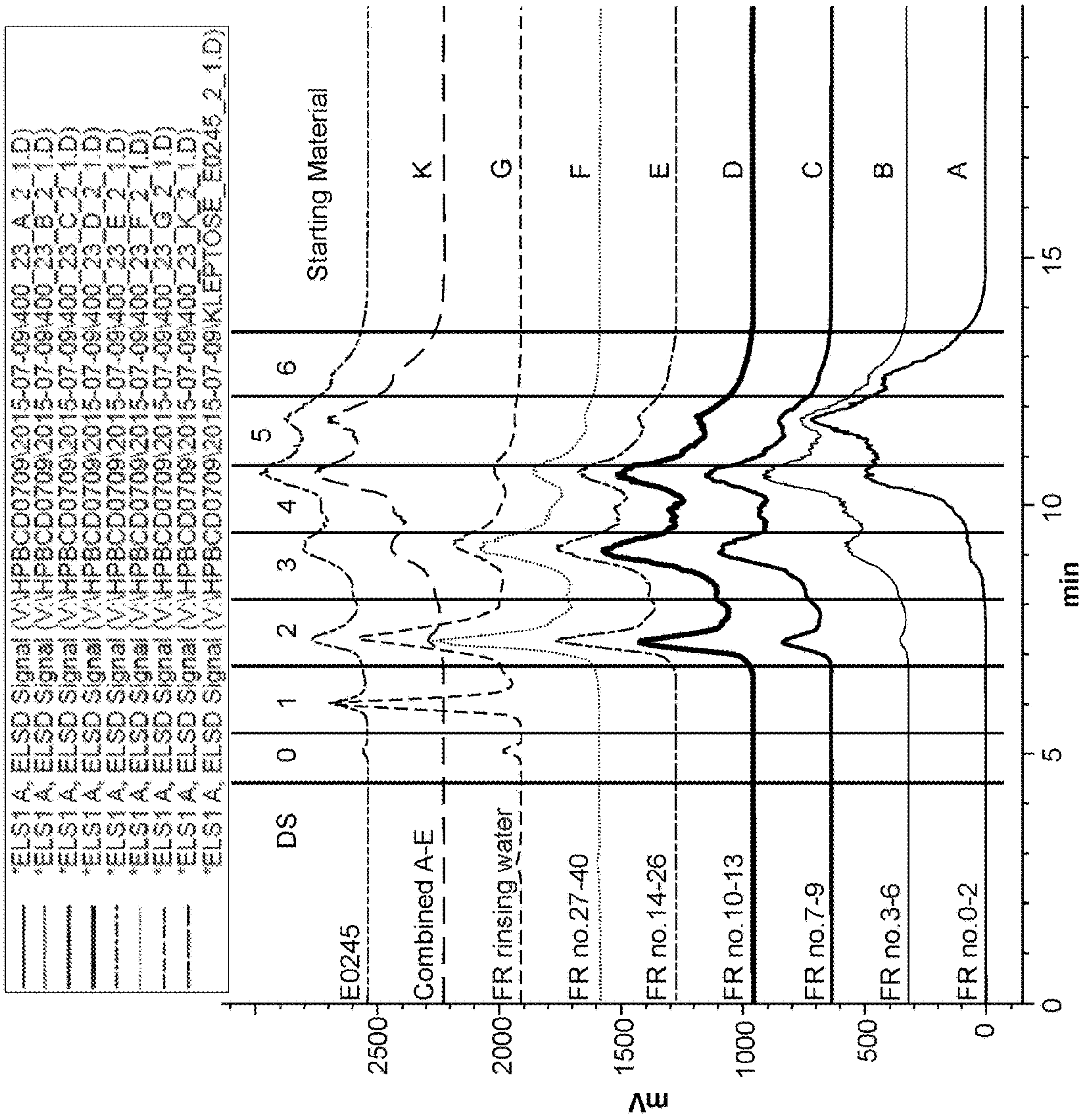

FIG. 43 shows chromatograms of various fractions obtained from preparative aluminum adsorption chromatographic separation of a batch of Kleptose® HPB (batch E0245), annotated to show the numerical fractions pooled to produce fractions "A"-"F" and "K", and annotated to show the degree of substitution of the chromatographically separated hydroxypropyl beta-cyclodextrin species.

Figure 44B:
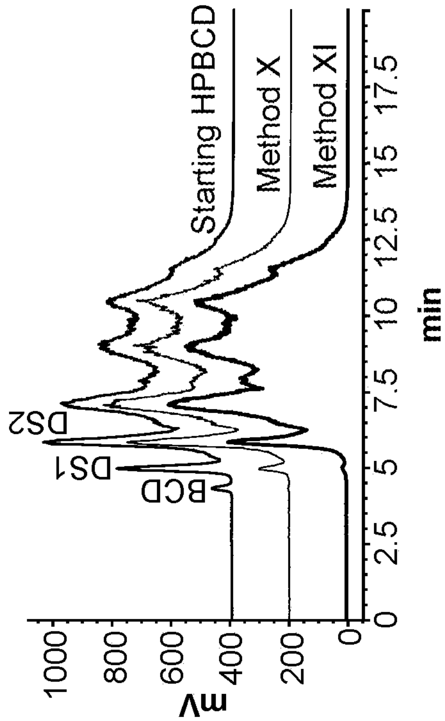
Figure 44A:
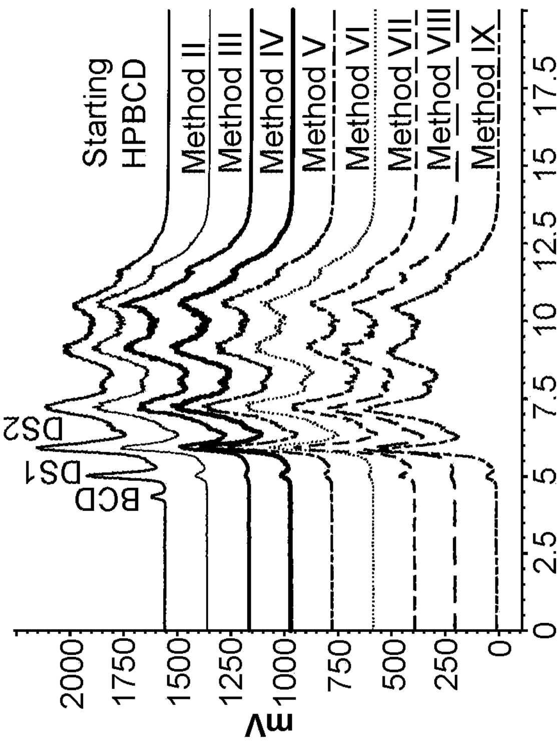

FIG. 44A and FIG. 44B show chromatograms of HPBCD mixture after different methods of purification, with FIG. 44A showing the chromatograms of purified HPBCD mixture after Methods II-IX, and FIG. 44B showing the chromatograms of purified HPBCD mixture after Methods X and XI.

Figure 45:
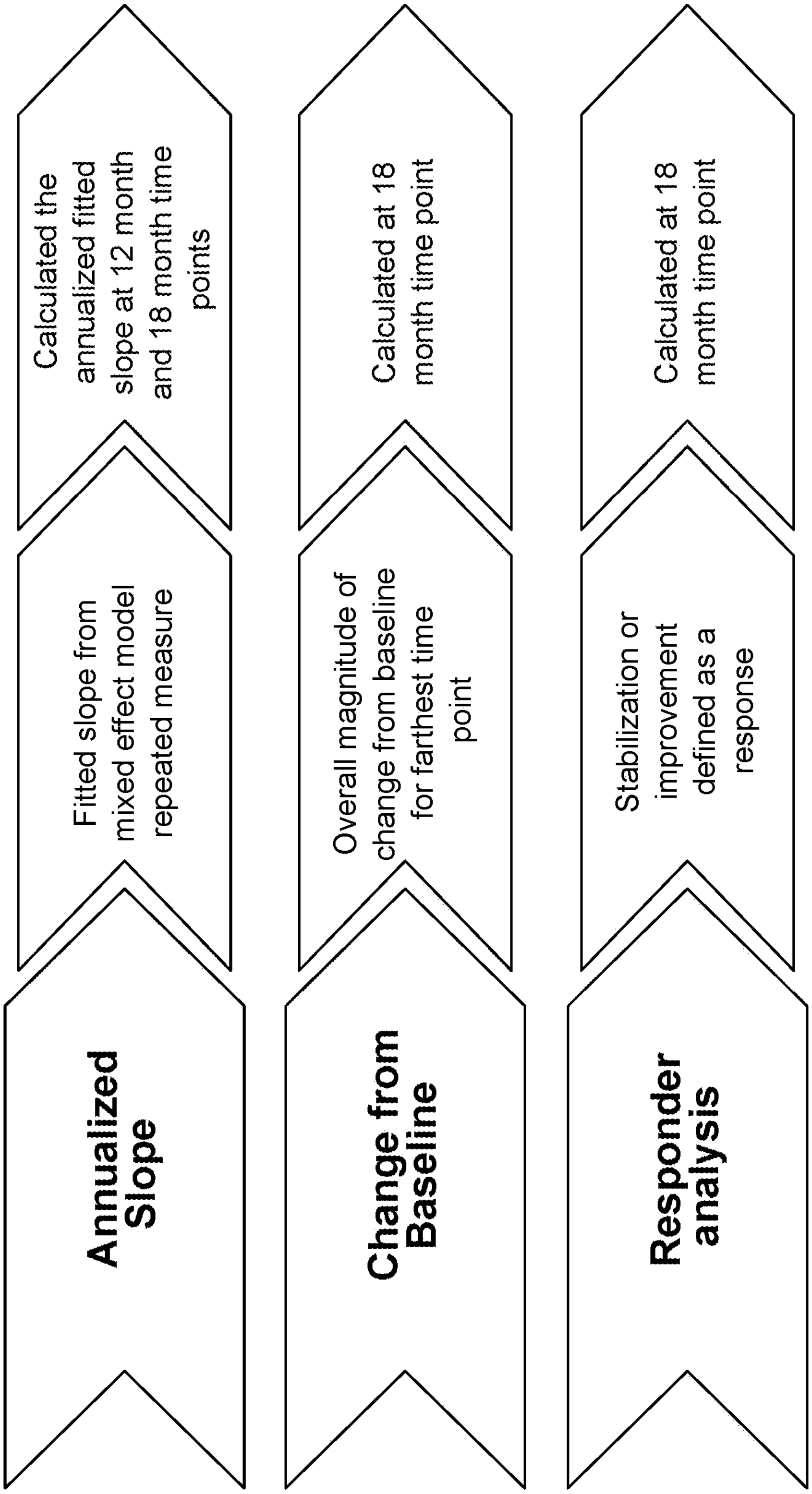

FIG. 45 summarizes the analyses conducted for the NPC phase I clinical trial data at 18 months.

Figure 46:
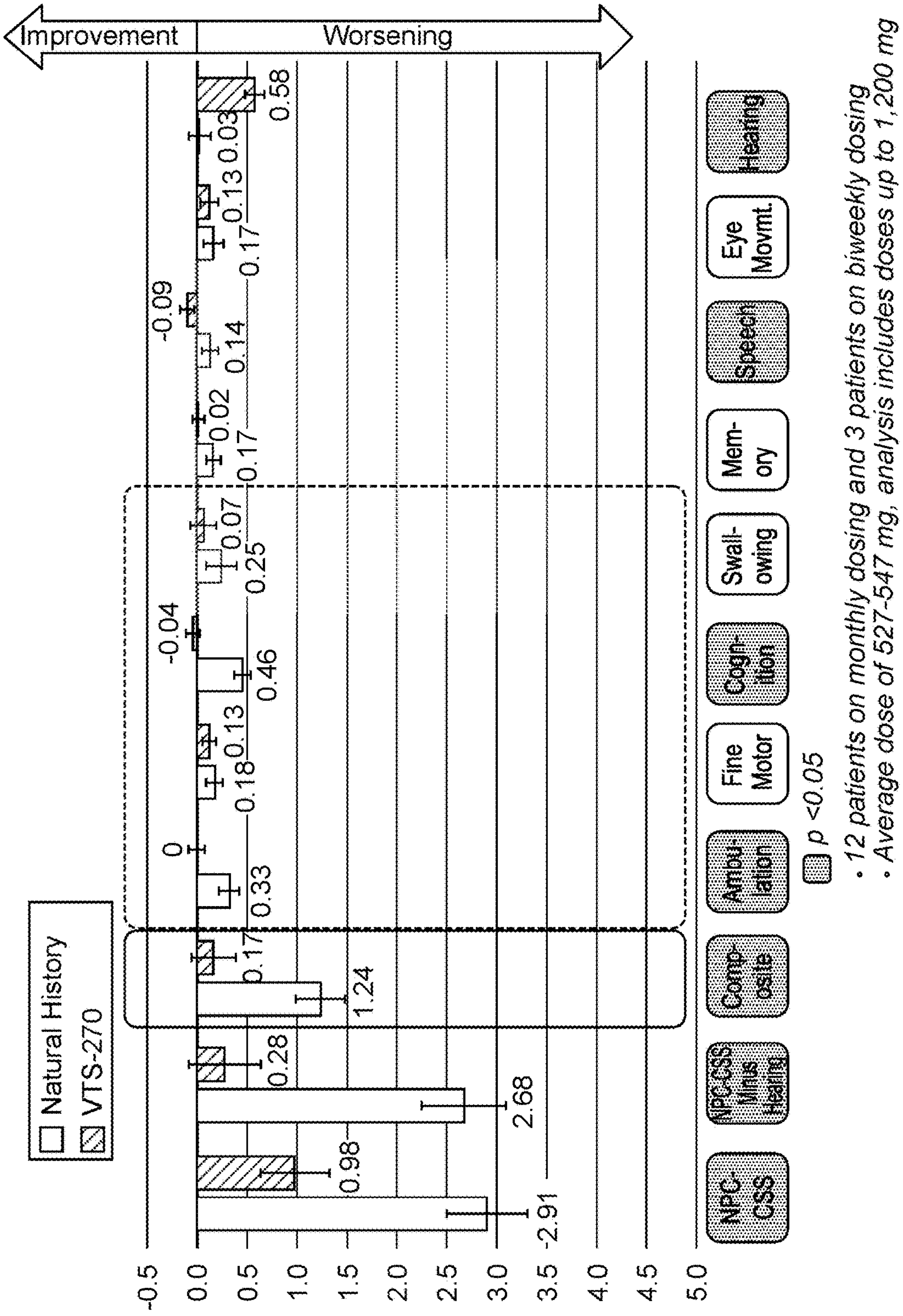

FIG. 46 shows the annualized rate of change of the Phase I clinical trial data at 18 months.

Figure 47:
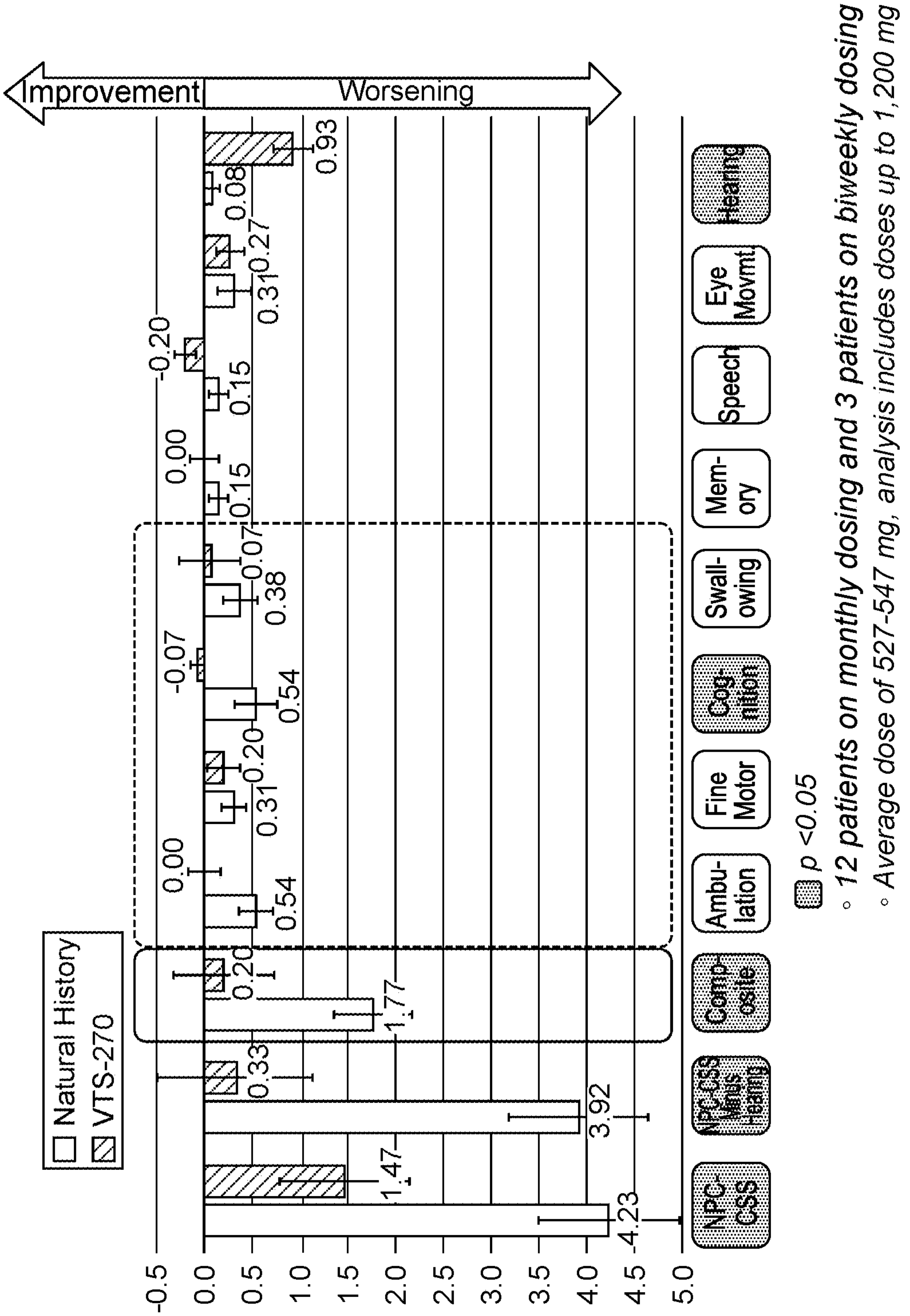

FIG. 47 shows the mean change from the baseline of the Phase I clinical trial data at 18 months.

Figure 48:
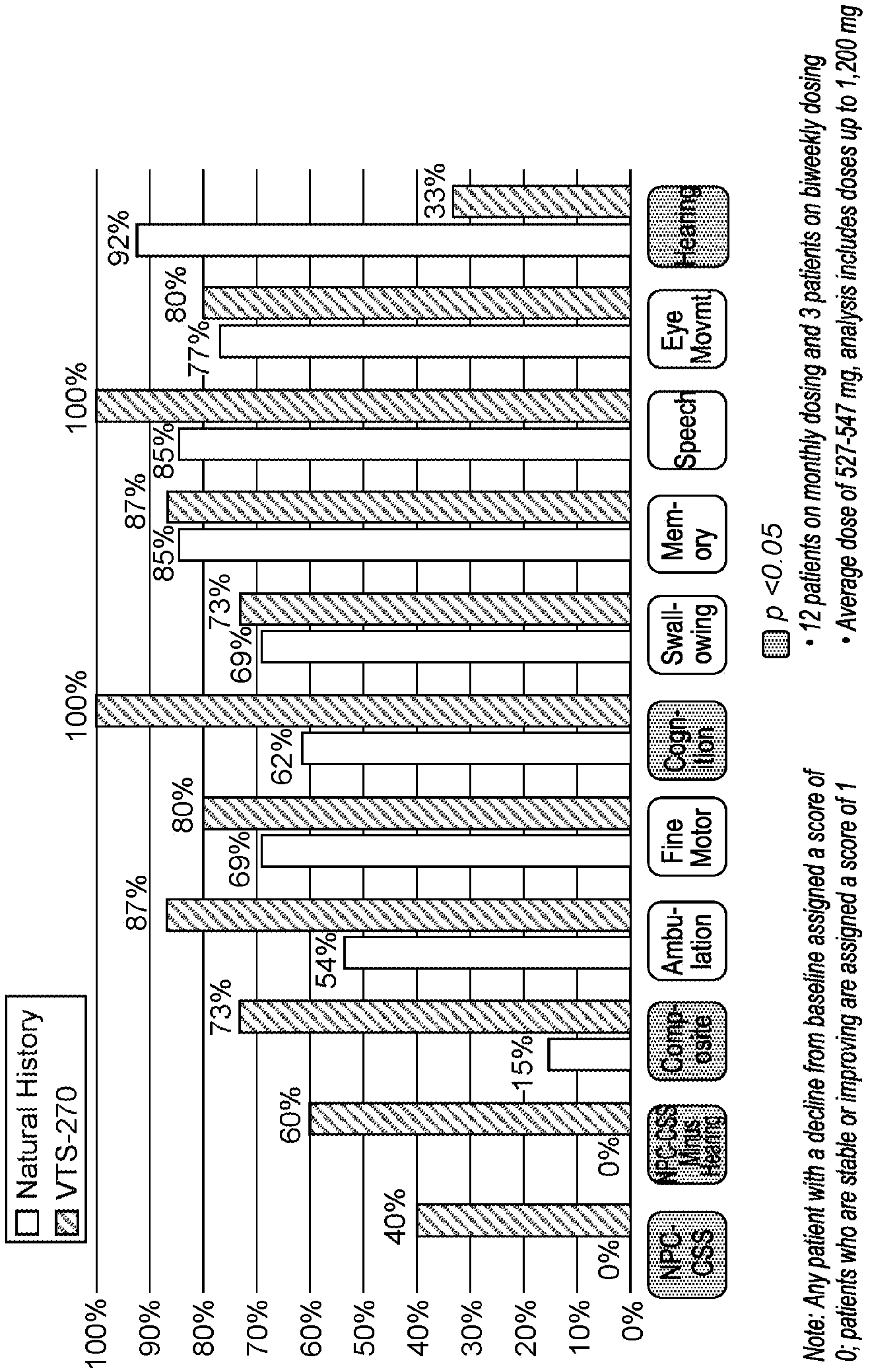

FIG. 48 shows the responder analysis of the Phase I clinical trial data at 18 months.

Figure 49:
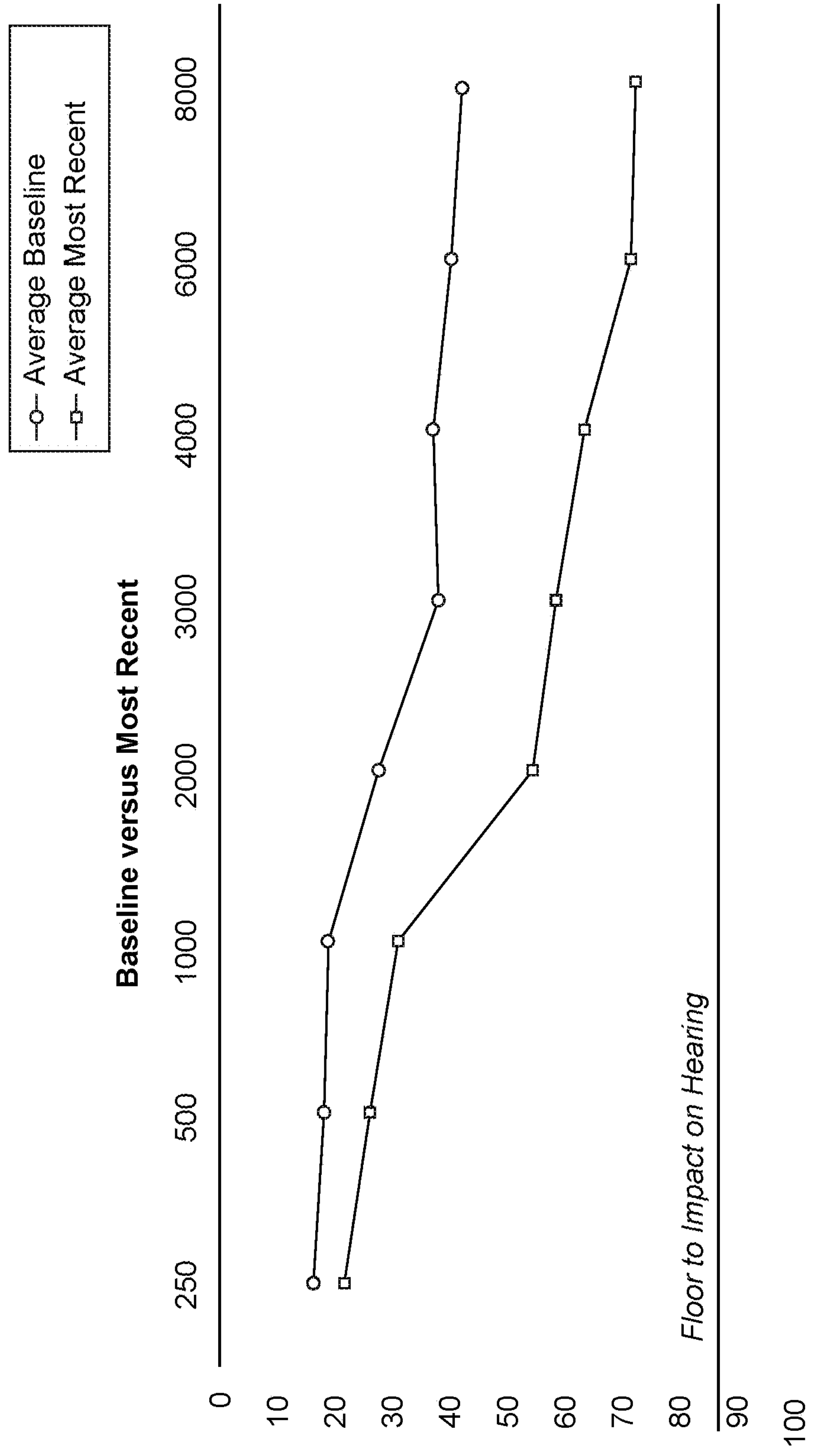

FIG. 49 shows the impact of treatment on hearing.

FIG. 50 summarizes the impact of treatment on hearing.

FIGS. 51A-51H show the results of standard analyses of two exemplary lots of Kleptose® HPB as performed by the manufacturer.

6. DETAILED DESCRIPTION

6.1. Experimental Observations

As described in detail below in Example 1, we analyzed initial data from a phase I clinical trial being conducted by the NIH in which patients with NPC type 1 disease are being treated by intrathecal administration of 2-hydroxypropyl beta-cyclodextrin ("HPBCD") using an existing parenteral grade composition, Kleptose® HPB (Roquette). In this non-randomized, open-label, single-center study, Kleptose® HPB is being administered via lumbar injection to drug-naive cohorts of patients at escalating doses. In certain of our analyses, we also included data from three patients being treated with intrathecal Kleptose® HPB at another institution under individual INDs.

Figure 1:
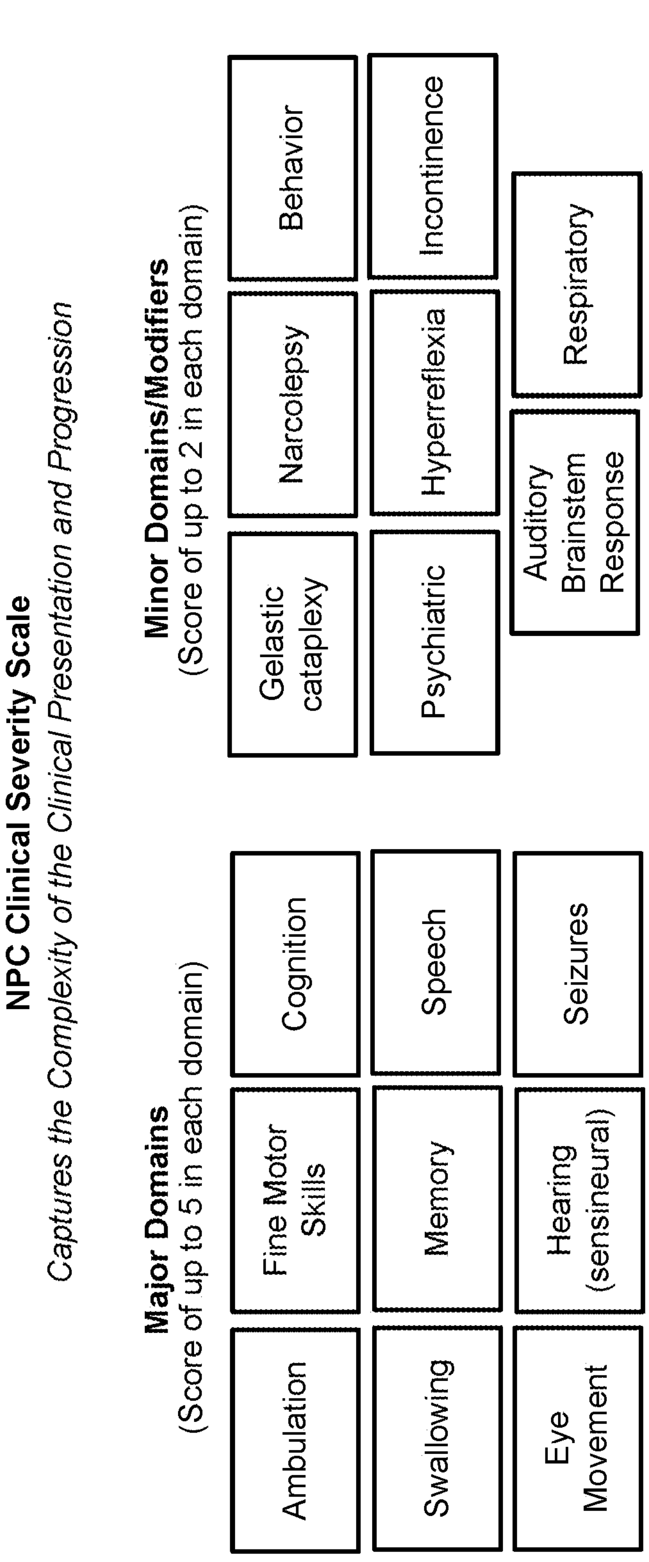
Figure 5:
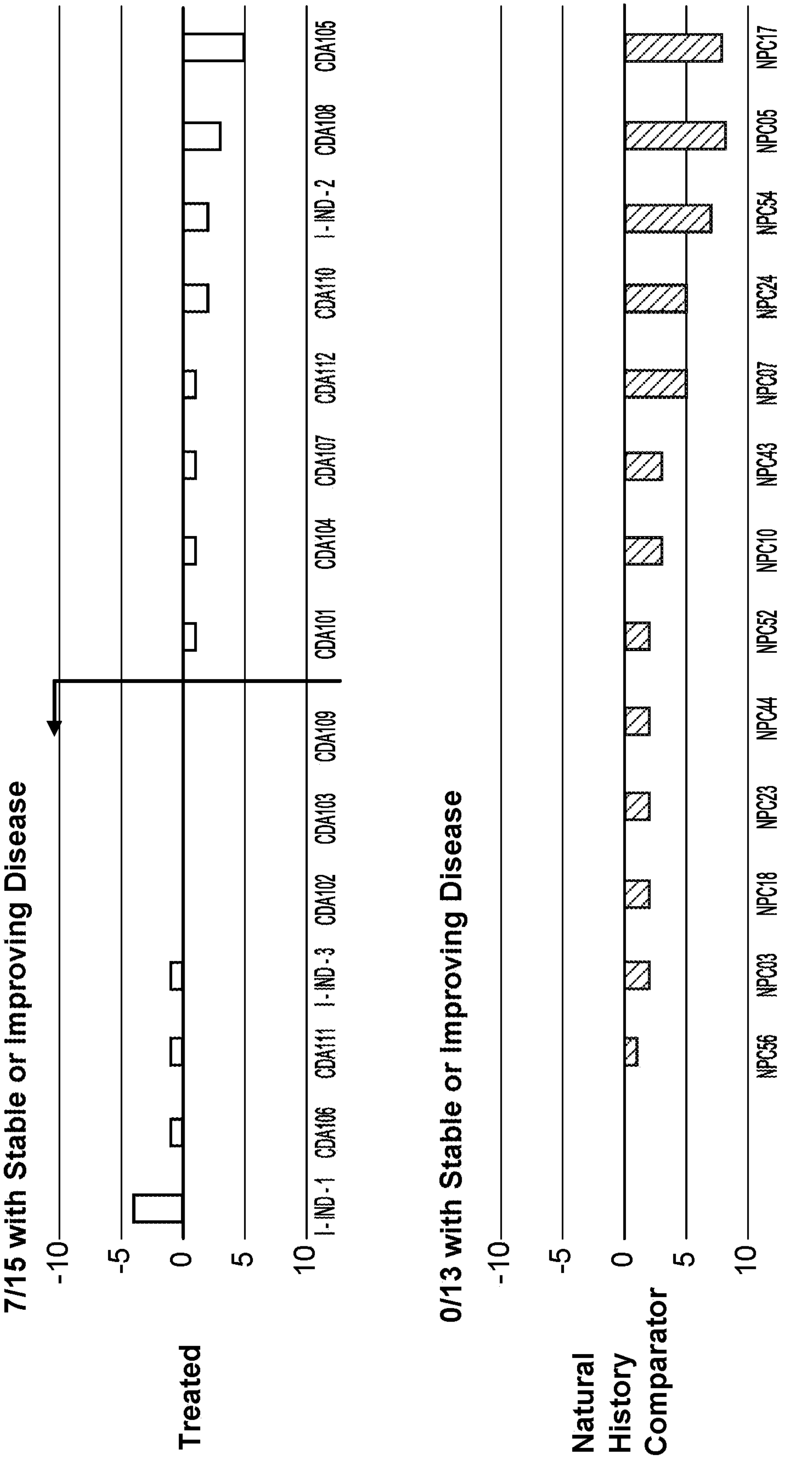
Figure 6:
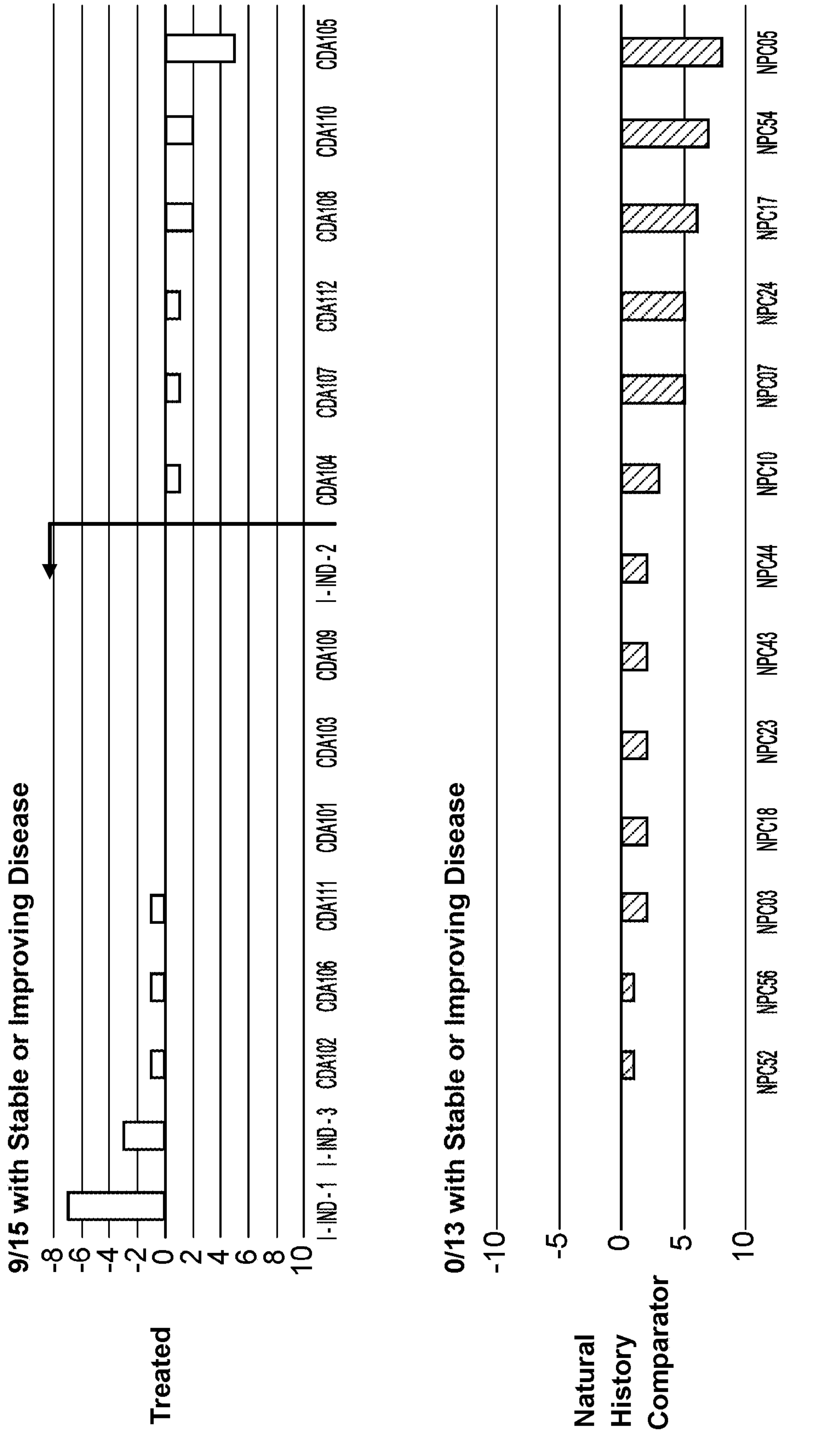
Figure 8:
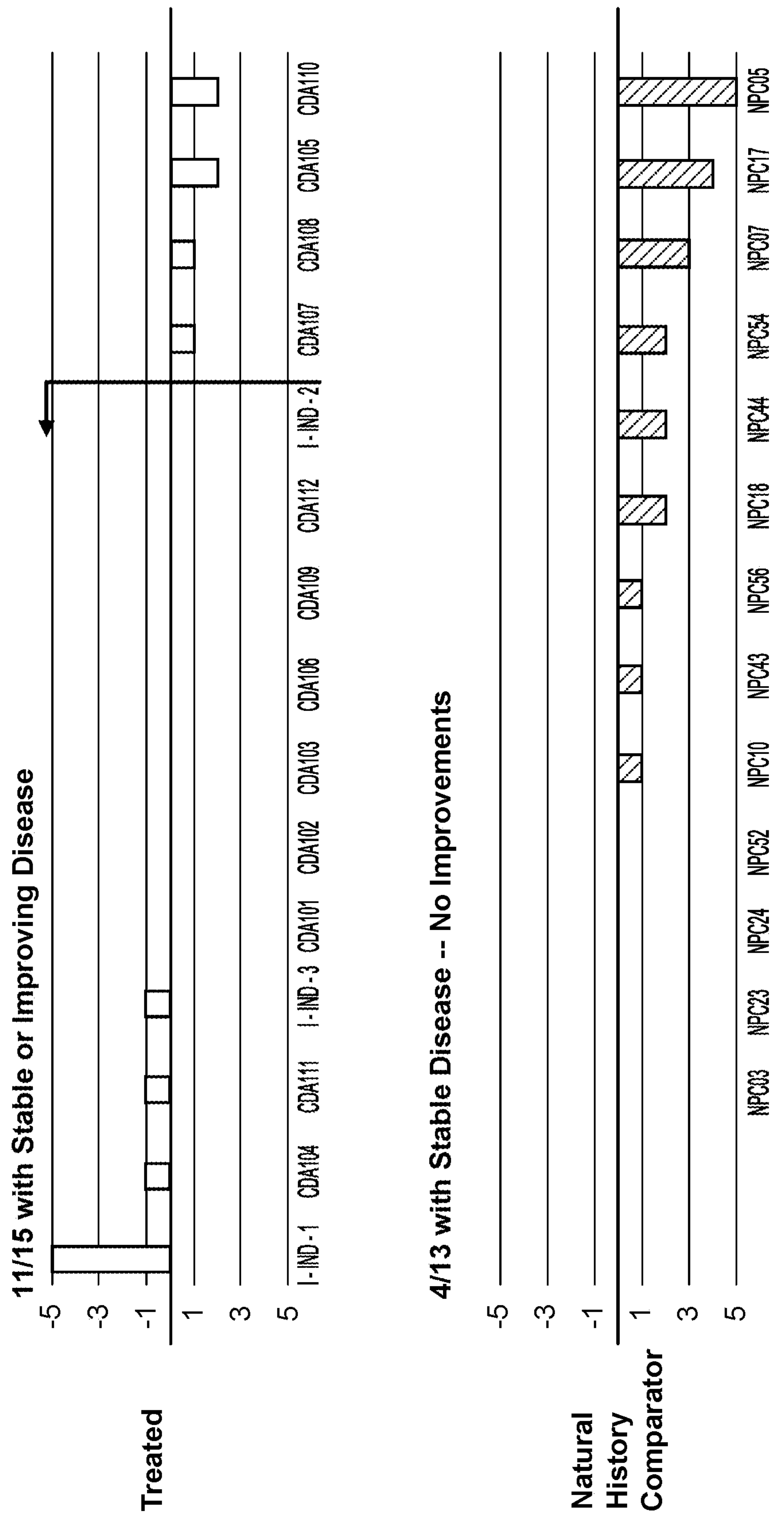

Our analyses confirmed that intrathecal administration of Kleptose® HPB provides therapeutic benefit in NPC type 1 disease. Using a standard aggregate outcome measure, the NPC Clinical Severity Scale (see Yanjanin et al., "Linear Clinical Progression, Independent of Age of Onset, in Niemann-Pick Disease, Type C," *Am. J. Med. Genet. Part B* 153B: 132-140 (2010); see also FIG. 1 and Table 1 herein), 7/15 patients were observed to have stable or improving disease, as compared to 0/13 in a cohort of patients in whom the natural history of untreated disease has been studied (see FIG. 5). Using a new composite endpoint informed by post-hoc analysis of the data (FIG. 7), we found that 11/15 study patients showed stable or improving disease versus only 4/13 with stable disease in the Natural History cohort (see FIG. 8). In certain of our analyses, we used the NPC Clinical Severity Score with hearing and auditory brainstem response (ABR) removed.

More detailed analyses, however, showed that while intrathecal administration of HPBCD improves certain signs and symptoms of NPC type 1 disease, it merely slows progression of others, and paradoxically appears to accelerate progression in other symptoms. In particular, hearing loss appears to have been accelerated in patients receiving intrathecal Kleptose® HPB (see, e.g., FIGS. 2, 3, 4).

As set forth below in detail in Example 3, we analyzed representative batches of Kleptose® HPB by various chromatographic methods. These analyses revealed that this parenteral grade product comprises a complex mixture of beta-cyclodextrin molecules having different degrees of substitution (see, e.g., FIGS. 11, 14, 16, 18); it is not known which of these species contributes to the observed improvement, the slowing of progression, and the acceleration in progression of the various clinical domains.

Further analyses using electrospray mass spectrometry, described in Example 5, demonstrated that there are significant differences in the substitution fingerprint of the hydroxypropyl beta-cyclodextrin composition used in the phase I clinical trial described in Example 1, Kleptose® HPB, as compared to the substitution fingerprint of a different commercially available hydroxypropyl beta-cyclodextrin composition, Trappsol® Cyclo™. We found that Kleptose® HPB has low lot-to-lot variability in the substitution fingerprint, and low levels of impurities, notably propylene glycol. In contrast, we found that Trappsol® Cyclo™ exhibits high lot-to-lot variability in its substitution fingerprint and significantly higher levels of propylene glycol, a presumed ototoxin.

To prepare for clinical trials in which HPBCD will be administered directly to the cerebrospinal fluid for longer periods of time, and possibly with more frequent dosing, we developed methods to reduce levels of propylene glycol, which is a presumed ototoxin; beta-cyclodextrin molecules having no hydroxypropyl substitutions, which are known to form precipitates; and bacterial endotoxin, which is highly inflammatory, as described in Examples 6 and 7. Although the methods were successful in reducing the specified impurities, we observed that absorption chromatography with alumina, whether used alone or in combination with solvent precipitation, also changed the compositional fingerprint, substantially reducing the amount of beta-cyclodextrin molecules having a single hydroxypropyl substitution (DS-1) and reducing the amount of beta-cyclodextrin molecules having two substitutions (DS-2) (see Example 7; Table 20). Reduction in the prevalence of molecules with low degrees of substitution (DS-0, as intended; and DS-1 and DS-2, unintended) increased the average degree of substitution ($DS_a$) of the mixture.

As detailed in Example 8 and summarized in FIGS. 35-38, gene expression profiling experiments using Kleptose® HPB and a batch of Kleptose® HPB further purified using adsorption to aluminum demonstrate that the activity of the hydroxypropyl beta-cyclodextrin mixtures on cells homozygous for the NPC1 mutation is a composite of the activities separately contributed by species having different degrees of hydroxypropyl substitution. Despite the change in compositional fingerprint as compared to Kleptose® HPB, there was, surprisingly, no change in the expression of genes known to be involved in cholesterol metabolism and transport. This discovery will allow the novel, more highly purified, and compositionally distinct HPBCD composition to be administered by intrathecal or intracerebroventricular route to the CSF of patients with NPC disease for longer periods, with therapeutic effect and increased safety.

6.2. Pharmaceutical Compositions

The present disclosure provides a pharmaceutical composition comprising, as a pharmaceutically active ingredient, a mixture of beta-cyclodextrin molecules substituted at one or more hydroxyl positions by hydroxypropyl groups, the mixture optionally including unsubstituted beta-cyclodextrin molecules.

6.2.1. Pharmaceutically Active Ingredient

The pharmaceutically active ingredient is a mixture of beta-cyclodextrin molecules substituted at one or more hydroxyl positions by hydroxypropyl groups, the mixture optionally including unsubstituted beta-cyclodextrin molecules. The term "pharmaceutically active ingredient" is used synonymously with "active pharmaceutical ingredient" in this disclosure.

6.2.1.1. Average Degree of Substitution

As used herein, "substituted at one or more hydroxyl positions by hydroxypropyl groups" refers to replacement of the hydrogen of one or more hydroxyl groups of a beta-cyclodextrin molecule with a hydroxypropyl group or a hydroxypropyl oligomer. For instance, "substituted at one or more hydroxyl positions by hydroxypropyl groups" can refer to an insertion of one or more—$CH_2CH(CH_3)O$— substituents within one or more O—H bonds on a beta-cyclodextrin molecule resulting in one or more ether linkages.

The number of hydroxypropyl groups per anhydroglucose unit in the mixture of beta-cyclodextrins is the "molar substitution", or "MS", and is determined according to the procedures set forth in the USP monograph on Hydroxypropyl Betadex (USP NF 2015) ("USP Hydroxypropyl Betadex monograph"), incorporated herein by reference in its entirety. In this disclosure, the term "average molar substitution", or "$MS_a$", is used synonymously with "MS" as that term is used in the USP Hydroxypropyl Betadex monograph, and the term "glucose unit" is used as a synonym for "anhydroglucose unit" as that term is used in the USP Hydroxypropyl Betadex monograph.

As used herein, the "degree of substitution" or "DS" refers to the total number of hydroxypropyl groups substituted directly or indirectly on a beta-cyclodextrin molecule. For example, a beta-cyclodextrin molecule containing glucose units, each of which is substituted with one hydroxypropyl group, has a DS=7. In another example, a beta-cyclodextrin molecule in which only one of the seven glucose units is substituted with a hydroxypropyl group, and that hydroxypropyl group is itself substituted with another hydroxypropyl group (e.g., a beta-cyclodextrin with a single occurrence of HP that comprises two hydroxypropyl groups), has a DS=2.

As used herein, the "average number of hydroxypropyl groups per beta-cyclodextrin," also known as an "average degree of substitution," "average DS," or "$DS_a$," refers to the total number of hydroxypropyl groups in a population of beta-cyclodextrins divided by the number of beta-cyclodextrin molecules. In an illustrative example, an equal parts mixture of beta-cyclodextrins containing glucose units that are each substituted with one hydroxypropyl group and beta-cyclodextrins containing glucose units that are each substituted with two hydroxypropyl groups has a $DS_a$=10.5 (average of equal parts beta-cyclodextrins with DS=7 and DS=14). In another illustrative example, a mixture of 33.3% beta-cyclodextrins in which only one of the seven glucose units is substituted with a hydroxypropyl group (i.e., DS=1) and 66.7% beta-cyclodextrins containing glucose units that are each substituted with one hydroxypropyl group (i.e., DS=7) has a $DS_a$=5.0.

The $DS_a$ is determined by multiplying the MS by 7. As used herein, $DS_a$ is used synonymously with "degree of substitution" as that term is defined in the USP Hydroxypropyl Betadex monograph.

In some embodiments, the beta-cyclodextrins in the mixture consist of glucose units of the structure:

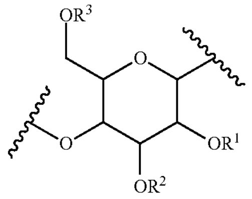

wherein $R^1$, $R^2$, and $R^3$, independently for each occurrence, are —H or —HP, wherein HP comprises one or more hydroxypropyl groups.

In some embodiments, HP comprises one hydroxypropyl group. In some embodiments, HP consists essentially of one hydroxypropyl group. In some embodiments, HP consists of one hydroxypropyl group.

In some embodiments, the average number of occurrences of HP per beta-cyclodextrin is about 3 to about 7, e.g., about 3 to about 6, about 3 to about 5, about 3 to about 4, about 4 to about 7, about 4 to about 6, about 4 to about 5, about 5 to about 7, about 5 to about 6, or about 6 to about 7.

In some embodiments, the total occurrences of $R^3$=HP are greater than the total occurrences of either $R^1$=HP or $R^2$=HP. In certain embodiments, the total occurrences of $R^3$=HP are greater than the total combined occurrences of $R^1$=HP and $R^2$=HP.

In some embodiments, at least about 5%, e.g., at least about 10%, at least about 15%, at least about 20%, at least about 25%, at least about 30%, at least about 35%, at least about 40%, or at least about 45% of total occurrences of $R^1$ and $R^2$ combined are HP.

In some embodiments, not more than about 95%, e.g., not more than about 90%, not more than about 85%, not more than about 80%, not more than about 75%, not more than about 70%, not more than about 65%, not more than about 60%, not more than about 55%, or not more than about 50% of total occurrences of $R^1$ and $R^2$ combined are HP.

In some embodiments, the percentage of $R^1$ and $R^2$ combined that are HP ranges from about 5% to about 95%, such as about 10% to about 95%, about 15% to about 95%, about 20% to about 95%, about 25% to about 95%, about 30% to about 95%, about 35% to about 95%, about 40% to about 95%, about 45% to about 95%, about 50% to about 95%, about 55% to about 95%, about 60% to about 95%, about 65% to about 95%, about 70% to about 95%, about 75% to about 95%, about 80% to about 95%, about 85% to about 95%, about 90% to about 95%; such as from about 5% to about 90%, about 10% to about 90%, about 15% to about 90%, about 20% to about 90%, about 25% to about 90%, about 30% to about 90%, about 35% to about 90%, about 40% to about 90%, about 45% to about 90%, about 50% to about 90%, about 55% to about 90%, about 60% to about 90%, about 65% to about 90%, about 70% to about 90%, about 75% to about 90%, about 80% to about 90%, about 85% to about 90%; such as from about 5% to about 85%, about 10% to about 85%, about 15% to about 85%, about 20% to about 85%, about 25% to about 85%, about 30% to about 85%, about 35% to about 85%, about 40% to about 85%, about 45% to about 85%, about 50% to about 85%, about 55% to about 85%, about 60% to about 85%, about 65% to about 85%, about 70% to about 85%, about 75% to about 85%, about 80% to about 85%; such as from about 5% to about 80%, about 10% to about 80%, about 15% to about 80%, about 20% to about 80%, about 25% to about 80%, about 30% to about 80%, about 35% to about 80%, about 40% to about 80%, about 45% to about 80%, about 50% to about 80%, about 55% to about 80%, about 60% to about 80%, about 65% to about 80%, about 70% to about 80%, about 75% to about 80%; such as from about 5% to about 75%, about 10% to about 75%, about 15% to about 75%, about 20% to about 75%, about 25% to about 75%, about 30% to about 75%, about 35% to about 75%, about 40% to about 75%, about 45% to about 75%, about 50% to about 75%, about 55% to about 75%, about 60% to about 75%, about 65% to about 75%, about 70% to about 75%; such as from about 5% to about 70%, about 10% to about 70%, about 15% to about 70%, about 20% to about 70%, about 25% to about 70%, about 30% to about 70%, about 35% to about 70%, about 40% to about 70%, about 45% to about 70%, about 50% to about 70%, about 55% to about 70%, about 60% to about 70%, about 65% to about 70%; such as from about 5% to about 65%, about 10% to about 65%, about 15% to about 65%, about 20% to about 65%, about 25% to about 65%, about 30% to about 65%, about 35% to about 65%, about 40% to about 65%, about 45% to about 65%, about 50% to about 65%, about 55% to about 65%, about 60% to about 65%; such as from about 5% to about 60%, about 10% to about 60%, about 15% to about 60%, about 20% to about 60%, about 25% to about 60%, about 30% to about 60%, about 35% to about 60%, about 40% to about 60%, about 45% to about 60%, about 50% to about 60%, about 55% to about 60%; such as from about 5% to about 55%, about 10% to about 55%, about 15% to about 55%, about 20% to about 55%, about 25% to about 55%, about 30% to about 55%, about 35% to about 55%, about 40% to about 55%, about 45% to about 55%, about 50% to about 55%; such as from about 5% to about 50%, about 10% to about 50%, about 15% to about 50%, about 20% to about 50%, about 25% to about 50%, about 30% to about 50%, about 35% to about 50%, about 40% to about 50%, about 45% to about 50%; such as from about 5% to about 45%, about 10% to about 45%, about 15% to about 45%, about 20% to about 45%, about 25% to about 45%, about 30% to about 45%, about 35% to about 45%, about 40% to about 45%; such as from about 5% to about 40%, about 10% to about 40%, about 15% to about 40%, about 20% to about 40%, about 25% to about 40%, about 30% to about 40%, about 35% to about 40%; such as from about 5% to about 35%, about 10% to about 35%, about 15% to about 35%, about 20% to about 35%, about 25% to about 35%, about 30% to about 35%; such as from about 5% to about 30%, about 10% to about 30%, about 15% to about 30%, about 20% to about 30%, about 25% to about 30%; such as from about 5% to about 25%, about 10% to about 25%, about 15% to about 25%, about 20% to about 25%; such as from about 5% to about 20%, about 10% to about 20%, about 15% to about 20%; such as from about 5% to about 15%, about 10% to about 15%; or about 5% to about 10%.

In some embodiments, at least about 5%, e.g., at least about 10%, at least about 15%, at least about 20%, at least about 25%, at least about 30%, at least about 35%, at least about 40%, at least about 45%, or at least about 50% of occurrences of $R^3$ are HP.

In some embodiments, not more than about 95%, e.g., not more than about 90%, not more than about 85%, not more than about 80%, not more than about 75%, not more than about 70%, not more than about 65%, not more than about 60%, or not more than about 55% of occurrences of $R^3$ are HP.

In some embodiments, the percentage of occurrence of $R^3$ that are HP ranges from about 20% to about 90%, e.g., about 25% to about 90%, about 30% to about 90%, about 35% to about 90%, about 40% to about 90%, about 45% to about 90%, about 50% to about 90%, about 55% to about 90%, about 60% to about 90%, about 65% to about 90%, about 70% to about 90%, about 75% to about 90%, about 80% to about 90%, about 85% to about 90%, about 20% to about 85%, about 25% to about 85%, about 30% to about 85%, about 35% to about 85%, about 40% to about 85%, about 45% to about 85%, about 50% to about 85%, about 55% to about 85%, about 60% to about 85%, about 65% to about 85%, about 70% to about 85%, about 75% to about 85%, about 80% to about 85%, about 20% to about 80%, about 25% to about 80%, about 30% to about 80%, about 35% to about 80%, about 40% to about 80%, about 45% to about 80%, about 50% to about 80%, about 55% to about 80%, about 60% to about 80%, about 65% to about 80%, about 70% to about 80%, about 75% to about 80%, about 20% to about 75%, about 25% to about 75%, about 30% to about 75%, about 35% to about 75%, about 40% to about 75%, about 45% to about 75%, about 50% to about 75%, about 55% to about 75%, about 60% to about 75%, about 65% to about 75%, about 70% to about 75%, about 20% to about 70%, about 25% to about 70%, about 30% to about 70%, about 35% to about 70%, about 40% to about 70%, about 45% to about 70%, about 50% to about 70%, about 55% to about 70%, about 60% to about 70%, about 65% to about 70%, about 20% to about 65%, about 25% to about 65%, about 30% to about 65%, about 35% to about 65%, about 40% to about 65%, about 45% to about 65%, about 50% to about 65%, about 55% to about 65%, about 60% to about 65%, about 20% to about 60%, about 25% to about 60%, about 30% to about 60%, about 35% to about 60%, about 40% to about 60%, about 45% to about 60%, about 50% to about 60%, about 55% to about 60%, about 20% to about 55%, about 25% to about 55%, about 30% to about 55%, about 35% to about 55%, about 40% to about 55%, about 45% to about 55%, about 50% to about 55%, about 20% to about 50%, about 25% to about 50%, about 30% to about 50%, about 35% to about 50%, about 40% to about 50%, about 45% to about 50%, about 20% to about 45%, about 25% to about 45%, about 30% to about 45%, about 35% to about 45%, about 40% to about 45%, about 5% to about 40%, about 10% to about 40%, about 15% to about 40%, about 20% to about 40%, about 25% to about 40%, about 30% to about 40%, about 35% to about 40%, about 20% to about 35%, about 25% to about 35%, about 30% to about 35%, about 20% to about 30%, about 25% to about 30%, or about 20% to about 25%.

In some embodiments, at least about 70%, e.g., at least about 75%, at least about 80%, at least about 85%, at least about 90%, or at least about 95%, of the beta-cyclodextrins collectively have an average number of occurrences of HP per beta-cyclodextrin of about 4 to about 7, e.g., about 4 to about 6, about 4 to about 5, about 5 to about 7, about 5 to about 6, or about 6 to about 7.

In some embodiments, the percentage of beta-cyclodextrins that collectively have an average number of occurrences of HP per beta-cyclodextrin of about 4 to about 7, e.g., about 4 to about 6, about 4 to about 5, about 5 to about 7, about 5 to about 6, or about 6 to about 7, ranges from about 50% to about 99%, such as about 55% to about 99%, about 60% to about 99%, about 65% to about 99%, about 70% to about 99%, about 75% to about 99%, about 80% to about 99%, about 85% to about 99%, about 90% to about 99%, about 95% to about 99%; such as from about 50% to about 97%, such as about 55% to about 97%, about 60% to about 97%, about 65% to about 97%, about 70% to about 97%, about 75% to about 97%, about 80% to about 97%, about 85% to about 97%, about 90% to about 97%, about 95% to about 97%; such as from about 50% to about 95%, about 55% to about 95%, about 60% to about 95%, about 65% to about 95%, about 70% to about 95%, about 75% to about 95%, about 80% to about 95%, about 85% to about 95%, about 90% to about 95%; such as from about 50% to about 90%, about 55% to about 90%, about 60% to about 90%, about 65% to about 90%, about 70% to about 90%, about 75% to about 90%, about 80% to about 90%, about 85% to about 90%; such as from about 50% to about 85%, about 55% to about 85%, about 60% to about 85%, about 65% to about 85%, about 70% to about 85%, about 75% to about 85%, about 80% to about 85%; such as from about 50% to about 80%, about 55% to about 80%, about 60% to about 80%, about 65% to about 80%, about 70% to about 80%, about 75% to about 80%; such as from about 50% to about 75%, about 55% to about 75%, about 60% to about 75%, about 65% to about 75%, about 70% to about 75%; such as from about 50% to about 70%, about 55% to about 70%, about 60% to about 70%, about 65% to about 70%; such as from about 50% to about 65%, about 55% to about 65%, about 60% to about 65%; such as from about 50% to about 60%, about 55% to about 60%; or such as from about 50% to about 55%.

In certain embodiments, the pharmaceutical compositions of the disclosure comprise, as a pharmaceutically active ingredient, a mixture of unsubstituted beta-cyclodextrin molecules and beta-cyclodextrin molecules substituted at one or more hydroxyl positions by hydroxypropyl groups, wherein the mixture has an average number of hydroxypropyl groups per beta-cyclodextrin molecule ($DS_a$) of about 3 to about 7.

In some embodiments, the $DS_a$ is about 3 to about 5, such as about 3 to about 4. In some embodiments, the $DS_a$ is 3.3±0.3, 3.5±0.3, or 3.7±0.3. In other embodiments, the $DS_a$ is 3.2±0.2, 3.3±0.2, 3.4±0.2, 3.5±0.2, 3.6±0.2, 3.7±0.2, or 3.8±0.2. In other embodiments, the $DS_a$ is 3.1±0.1, 3.2±0.1, 3.3±0.1, 3.4±0.1, 3.5±0.1, 3.6±0.1, 3.7±0.1, 3.8±0.1, or 3.9±0.1.

In some embodiments, the $DS_a$ is about 3.5 to about 5.5, such as about 3.5 to about 4.5. In some embodiments, the $DS_a$ is 3.8±0.3, 4.0±0.3, or 4.2±0.3. In other embodiments, the $DS_a$ is 3.7±0.2, 3.8±0.2, 3.9±0.2, 4.0±0.2, 4.1±0.2, 4.2±0.2, or 4.3±0.2. In other embodiments, the $DS_a$ is 3.6±0.1, 3.7±0.1, 3.8±0.1, 3.9±0.1, 4.0±0.1, 4.1±0.1, 4.2±0.1, 4.3±0.1, or 4.4±0.1.

In some embodiments, the $DS_a$ is about 4 to about 6, such as about 4 to about 5. In some embodiments, the $DS_a$ is 4.3±0.3, 4.5±0.3, or 4.7±0.3. In other embodiments, the $DS_a$ is 4.2±0.2, 4.3±0.2, 4.4±0.2, 4.5±0.2, 4.6±0.2, 4.7±0.2, or 4.8±0.2. In other embodiments, the $DS_a$ is 4.1±0.1, 4.2±0.1, 4.3±0.1, 4.4±0.1, 4.5±0.1, 4.6±0.1, 4.7±0.1, 4.8±0.1, or 4.9±0.1.

In some embodiments, the $DS_a$ is about 4.5 to about 6.5, such as about 4.5 to about 5.5. In some embodiments, the $DS_a$ is 4.8±0.3, 5.0±0.3, or 5.2±0.3. In other embodiments, the $DS_a$ is 4.7±0.2, 4.8±0.2, 4.9±0.2, 5.0±0.2, 5.1±0.2, 5.2±0.2, or 5.3±0.2. In other embodiments, the $DS_a$ is 4.6±0.1, 4.7±0.1, 4.8±0.1, 4.9±0.1, 5.0±0.1, 5.1±0.1, 5.2±0.1, 5.3±0.1, or 5.4±0.1.

In some embodiments, the $DS_a$ is about 5 to about 7, such as about 5 to about 6. In some embodiments, the $DS_a$ is 5.3±0.3, 5.5±0.3, or 5.7±0.3. In other embodiments, the $DS_a$ is 5.2±0.2, 5.3±0.2, 5.4±0.2, 5.5±0.2, 5.6±0.2, 5.7±0.2, or 5.8±0.2. In other embodiments, the $DS_a$ is 5.1±0.1, 5.2±0.1, 5.3±0.1, 5.4±0.1, 5.5±0.1, 5.6±0.1, 5.7±0.1, 5.8±0.1, or 5.9±0.1.

In some embodiments, the $DS_a$ is about 5.5 to about 6.5. In some embodiments, the $DS_a$ is 5.8±0.3, 6.0±0.3, or 6.2±0.3. In other embodiments, the $DS_a$ is 5.7±0.2, 5.8±0.2, 5.9±0.2, 6.0±0.2, 6.1±0.2, 6.2±0.2, or 6.3±0.2. In other embodiments, the $DS_a$ is 5.6±0.1, 5.7±0.1, 5.8±0.1, 5.9±0.1, 6.0±0.1, 6.1±0.1, 6.2±0.1, 6.3±0.1, or 6.4±0.1.

In some embodiments, the $DS_a$ is about 6 to about 7. In some embodiments, the $DS_a$ is 6.3±0.3, 6.5±0.3, or 6.7±0.3. In other embodiments, the $DS_a$ is 6.2±0.2, 6.3±0.2, 6.4±0.2, 6.5±0.2, 6.6±0.2, 6.7±0.2, or 6.8±0.2. In other embodiments, the $DS_a$ is 6.1±0.1, 6.2±0.1, 6.3±0.1, 6.4±0.1, 6.5±0.1, 6.6±0.1, 6.7±0.1, 6.8±0.1, or 6.9±0.1.

In some embodiments, the $DS_a$ is about 4.1±15%, about 4.2±15%, about 4.3±15%, about 4.4±15%, or about 4.5±15%, such as about 4.1±10%, about 4.2±10%, about 4.3±10%, about 4.4±10%, or about 4.5±10%, such as about 4.1±5%, about 4.2±5%, about 4.3±5%, about 4.4±5%, or about 4.5±5%. For example, in certain embodiments, the $DS_a$ is about 4.31±10%, about 4.32±10%, about 4.33±10%, about 4.34±10%, about 4.35±10%, about 4.36±10%, or about 4.37±10%, such as about 4.31±5%, about 4.32±5%, about 4.33±5%, about 4.34±5%, about 4.35±5%, about 4.36±5%, or about 4.37±5%. In particular embodiments, the $DS_a$ is about 4.34±10%, such as about 4.34±5%.

In some embodiments, the $DS_a$ is about 4.3±15%, about 4.4±15%, about 4.5±15%, about 4.6±15%, or about 4.7±15%, such as about 4.3±10%, about 4.4±10%, about 4.5±10%, about 4.6±10%, or about 4.7±10%, such as about 4.3±5%, about 4.4±5%, about 4.5±5%, about 4.6±5%, or about 4.7±5%. For example, in certain embodiments, the $DS_a$ is about 4.47±10%, about 4.48±10%, about 4.49±10%, about 4.50±10%, about 4.51±10%, about 4.52±10%, or about 4.53±10%, such as about 4.47±5%, about 4.48±5%, about 4.49±5%, about 4.50±5%, about 4.51±5%, about 4.52±5%, or about 4.53±5%. In particular embodiments, the $DS_a$ is about 4.50±10%, such as about 4.50±5%.

In some embodiments, the $DS_a$ is about 6.1±15%, about 6.2±15%, about 6.3±15%, about 6.4±15%, or about 6.5±15%, such as about 6.1±10%, about 6.2±10%, about 6.3±10%, about 6.4±10%, or about 6.5±10%, such as about 6.1±5%, about 6.2±5%, about 6.3±5%, about 6.4±5%, or about 6.5±5%. For example, in certain embodiments, the $DS_a$ is about 6.34±10%, about 6.35±10%, about 6.36±10%, about 6.37±10%, about 6.38±10%, about 6.39±10%, or about 6.40±10%, such as about 6.34±5%, about 6.35±5%, about 6.36±5%, about 6.37±5%, about 6.38±5%, about 6.39±5%, or about 6.40±5%. In particular embodiments, the $DS_a$ is about 6.37±10%, such as about 6.37±5%.

In some embodiments, the $DS_a$ is about 6.3±15%, about 6.4±15%, about 6.5±15%, about 6.6±15%, or about 6.7±15%, such as about 6.3±10%, about 6.4±10%, about 6.5±10%, about 6.6±10%, or about 6.7±10%, such as about 6.3±5%, about 6.4±5%, about 6.5±5%, about 6.6±5%, or about 6.7±5%. For example, in certain embodiments, the $DS_a$ is about 6.50±10%, about 6.51±10%, about 6.52±10%, about 6.53±10%, about 6.54±10%, about 6.55±10%, or about 6.56±10%, such as about 6.50±5%, about 6.51±5%, about 6.52±5%, about 6.53±5%, about 6.54±5%, about 6.55±5%, or about 6.56±5%. In particular embodiments, the $DS_a$ is about 6.53±10%, such as about 6.53±5%.

The distribution of the degree of substitution within a mixture of unsubstituted beta-cyclodextrin molecules and beta-cyclodextrin molecules substituted at one or more hydroxyl positions by hydroxypropyl groups can vary. For example, an equal parts mixture of beta-cyclodextrins containing glucose units each of which is substituted with one hydroxypropyl group and beta-cyclodextrins containing glucose units each of which is substituted with two hydroxypropyl groups has a $DS_a$=10.5 (average of equal parts beta-cyclodextrins with DS=7 and DS=14). Although $DS_a$=10.5, in this example there are no beta-cyclodextrins having DS=10 or DS=11 within the mixture. In other cases, the majority of beta-cyclodextrins within the mixture of beta-cyclodextrins have DS that are close to the $DS_a$.

In some embodiments of the disclosure, at least about 50%, e.g., at least about 55%, about 60%, about 65%, about 70%, about 75%, about 80%, about 85%, about 90%, about 95%, or about 97%, of the beta-cyclodextrins within the mixture have a DS within $DS_a \pm X\sigma$, wherein σ is the standard deviation, and X is 1, 2, or 3. For example, in some embodiments, at least about 50%, e.g., at least about 55%, about 60%, about 65%, about 70%, about 75%, about 80%, about 85%, about 90%, about 95%, or about 97%, of the beta-cyclodextrins within the mixture have a DS within $DS_a \pm 1\sigma$. In some embodiments, at least 70% of the beta-cyclodextrins have a DS within $DS_a \pm 1\sigma$. In some embodiments, at least 90% of the beta-cyclodextrins have a DS within $DS_a \pm 1\sigma$. In some embodiments, at least 95% of the beta-cyclodextrins have a DS within $DS_a \pm 1\sigma$.

In some embodiments, at least about 50%, e.g., at least about 55%, about 60%, about 65%, about 70%, about 75%, about 80%, about 85%, about 90%, about 95%, or about 97%, of the beta-cyclodextrins within the mixture have a DS within $DS_a \pm 2\sigma$. In some embodiments, at least 70% of the beta-cyclodextrins have a DS within $DS_a \pm 2\sigma$. In some embodiments, at least 90% of the beta-cyclodextrins have a DS within $DS_a \pm 2\sigma$. In some embodiments, at least 95% of the beta-cyclodextrins have a DS within $DS_a \pm 2\sigma$.

In some embodiments, at least about 50%, e.g., at least about 55%, about 60%, about 65%, about 70%, about 75%, about 80%, about 85%, about 90%, about 95%, or about 97%, of the beta-cyclodextrins within the mixture have a DS within $DS_a \pm 3\sigma$. In some embodiments, at least 70% of the beta-cyclodextrins have a DS within $DS_a \pm 3\sigma$. In some embodiments, at least 90% of the beta-cyclodextrins have a DS within $DS_a \pm 3\sigma$. In some embodiments, at least 95% of the beta-cyclodextrins have a DS within $DS_a \pm 3\sigma$.

In some embodiments, at least about 50%, e.g., at least about 55%, about 60%, about 65%, about 70%, about 75%, about 80%, about 85%, about 90%, about 95%, or about 97%, of the beta-cyclodextrins have a DS within $DS_a$±1. In some embodiments, at least 70% of the beta-cyclodextrins have a DS within $DS_a$±1. In some embodiments, at least 90% of the beta-cyclodextrins have a DS within $DS_a$±1. In some embodiments, at least 95% of the beta-cyclodextrins have a DS within $DS_a$±1.

In some embodiments, at least about 50%, e.g., at least about 55%, about 60%, about 65%, about 70%, about 75%, about 80%, about 85%, about 90%, about 95%, or about 97%, of the beta-cyclodextrins have a DS within $DS_a$±0.8.

In some embodiments, at least 70% of the beta-cyclodextrins have a DS within $DS_a$±0.8. In some embodiments, at least 90% of the beta-cyclodextrins have a DS within $DS_a$±0.8. In some embodiments, at least 95% of the beta-cyclodextrins have a DS within $DS_a$±0.8.

In some embodiments, at least about 50%, e.g., at least about 55%, about 60%, about 65%, about 70%, about 75%, about 80%, about 85%, about 90%, about 95%, or about 97%, of the beta-cyclodextrins have a DS within $DS_a$±0.6. In some embodiments, at least 70% of the beta-cyclodextrins have a DS within $DS_a$±0.6. In some embodiments, at least 90% of the beta-cyclodextrins have a DS within $DS_a$±0.6. In some embodiments, at least 95% of the beta-cyclodextrins have a DS within $DS_a$±0.6.

In some embodiments, at least about 50%, e.g., at least about 55%, about 60%, about 65%, about 70%, about 75%, about 80%, about 85%, about 90%, about 95%, or about 97%, of the beta-cyclodextrins have a DS within $DS_a$±0.5. In some embodiments, at least 70% of the beta-cyclodextrins have a DS within $DS_a$±0.5. In some embodiments, at least 90% of the beta-cyclodextrins have a DS within $DS_a$±0.5. In some embodiments, at least 95% of the beta-cyclodextrins have a DS within $DS_a$±0.5.

In some embodiments, at least about 50%, e.g., at least about 55%, about 60%, about 65%, about 70%, about 75%, about 80%, about 85%, about 90%, about 95%, or about 97%, of the beta-cyclodextrins have a DS within $DS_a$±0.4. In some embodiments, at least 70% of the beta-cyclodextrins have a DS within $DS_a$±0.4. In some embodiments, at least 90% of the beta-cyclodextrins have a DS within $DS_a$±0.4. In some embodiments, at least 95% of the beta-cyclodextrins have a DS within $DS_a$±0.4.

In some embodiments, at least about 50%, e.g., at least about 55%, about 60%, about 65%, about 70%, about 75%, about 80%, about 85%, about 90%, about 95%, or about 97%, of the beta-cyclodextrins have a DS within $DS_a$±0.3. In some embodiments, at least 70% of the beta-cyclodextrins have a DS within $DS_a$±0.3. In some embodiments, at least 90% of the beta-cyclodextrins have a DS within $DS_a$±0.3. In some embodiments, at least 95% of the beta-cyclodextrins have a DS within $DS_a$±0.3.

In some embodiments, at least about 50%, e.g., at least about 55%, about 60%, about 65%, about 70%, about 75%, about 80%, about 85%, about 90%, about 95%, or about 97%, of the beta-cyclodextrins have a DS within $DS_a$±0.2. In some embodiments, at least 70% of the beta-cyclodextrins have a DS within $DS_a$±0.2. In some embodiments, at least 90% of the beta-cyclodextrins have a DS within $DS_a$±0.2. In some embodiments, at least 95% of the beta-cyclodextrins have a DS within $DS_a$±0.2.

In some embodiments, at least about 50%, e.g., at least about 55%, about 60%, about 65%, about 70%, about 75%, about 80%, about 85%, about 90%, about 95%, or about 97%, of the beta-cyclodextrins have a DS within $DS_a$±0.1. In some embodiments, at least 70% of the beta-cyclodextrins have a DS within $DS_a$±0.1. In some embodiments, at least 90% of the beta-cyclodextrins have a DS within $DS_a$±0.1. In some embodiments, at least 95% of the beta-cyclodextrins have a DS within $DS_a$±0.1.

In some embodiments, the MS ranges from 0.40 to 0.80, such as 0.41 to 0.79, 0.42 to 0.78, 0.43 to 0.77, 0.44 to 0.76, 0.45 to 0.75, 0.46 to 0.74, 0.47 to 0.73, 0.48 to 0.72, 0.49 to 0.71, 0.50 to 0.70, 0.51 to 0.69, 0.52 to 0.68, 0.53 to 0.67, 0.54 to 0.66, 0.55 to 0.65, 0.56 to 0.64, 0.57 to 0.63, 0.58 to 0.62, or 0.59 to 0.61.

In certain embodiments, the MS is about 0.40, about 0.41, about 0.42, about 0.43, about 0.44, about 0.45, about 0.46, about 0.47, about 0.48, about 0.49, about 0.50, about 0.51, about 0.52, about 0.53, about 0.54, about 0.55, about 0.56, about 0.57, about 0.58, about 0.59, about 0.60, about 0.61, about 0.62, about 0.63, about 0.64, about 0.65, about 0.66, about 0.67, about 0.68, about 0.69, about 0.70, about 0.71, about 0.72, about 0.73, about 0.74, about 0.75, about 0.76, about 0.77, about 0.78, about 0.79, or about 0.80.

In certain embodiments, the MS is about 0.571-0.686 ($DS_a$ about 4.0 to about 4.8). In some of these embodiments, the MS is in the range of about 0.58 to about 0.68. In currently preferred embodiments, the MS is in the range of 0.58-0.68.

In various embodiments, the MS is at least about 0.55. In certain embodiments, the MS is at least about 0.56, 0.57, 0.58, 0.59, or 0.60. In certain embodiments, the MS is no more than about 0.70. In specific embodiments, the MS is no more than about 0.69, 0.68, 0.67, 0.66, or 0.65.

Hydroxypropyl groups can be bonded to the beta-cyclodextrins as monomers, or can themselves be sequentially bonded to one or more additional hydroxypropyl groups to form hydroxypropyl oligomers which are then bonded to the beta-cyclodextrins. In some embodiments, the hydroxypropyl groups are substituted at the hydroxyl positions of the beta-cyclodextrins as hydroxypropyl chains of the structure $—[CH_2CH(CH_3)O]_nH$, wherein n≥1 and the average number of hydroxypropyl chains per beta-cyclodextrin is about 3 to about 7, e.g., about 3 to about 6, about 3 to about 5, about 3 to about 4, about 4 to about 7, about 4 to about 6, about 4 to about 5, about 5 to about 7, about 5 to about 6, or about 6 to about 7. In some embodiments, n is 1, 2, 3 or 4.

In one illustrative example, a hydroxypropyl chain of the structure $—CH_2CH(CH_3)OH$ includes one hydroxypropyl group in the hydroxypropyl chain (i.e., n=1). In another illustrative example a hydroxypropyl chain of the structure $—[CH_2CH(CH_3)O]_3H$ includes three hydroxypropyl groups in the hydroxypropyl chain (i.e., n=3).

In certain embodiments, the average number of hydroxypropyl chains per beta-cyclodextrin is 3.3±0.3, 3.4±0.3, 3.6±0.3, or 3.8±0.3. In other embodiments, the average number of hydroxypropyl chains per beta-cyclodextrin is 4.0±0.3, 4.2±0.3, 4.4±0.3, 4.6±0.3, or 4.8±0.3. In other embodiments, the average number of hydroxypropyl chains per beta-cyclodextrin is 5.0±0.3, 5.2±0.3, 5.4±0.3, 5.6±0.3, or 5.8±0.3. And in other embodiments, the average number of hydroxypropyl chains per beta-cyclodextrin is 6.0±0.3, 6.2±0.3, 6.4±0.3, 6.6±0.3, or 6.7±0.3.

In some embodiments, the average number of hydroxypropyl chains per beta-cyclodextrin is 3.2±0.2, 3.3±0.2, 3.4±0.2, 3.5±0.2, 3.6±0.2, 3.7±0.2, or 3.8±0.2. In other embodiments, the average number of hydroxypropyl chains per beta-cyclodextrin is 4.0±0.2, 4.1±0.2, 4.2±0.2, 4.3±0.2, 4.4±0.2, 4.5±0.2, 4.6±0.2, 4.7±0.2, or 4.8±0.2. In other embodiments, the average number of hydroxypropyl chains per beta-cyclodextrin is 5.0±0.2, 5.1±0.2, 5.2±0.2, 5.3±0.2, 5.4±0.2, 5.5±0.2, 5.6±0.2, 5.7±0.2, or 5.8±0.2. And in other embodiments, the average number of hydroxypropyl chains per beta-cyclodextrin is 6.0±0.2, 6.1±0.2, 6.2±0.2, 6.3±0.2, 6.4±0.2, 6.5±0.2, 6.6±0.2, 6.7±0.2, or 6.8±0.2.

In some embodiments, the average number of hydroxypropyl chains per beta-cyclodextrin is 3.1±0.1, 3.2±0.1, 3.3±0.1, 3.4±0.1, 3.5±0.1, 3.6±0.1, 3.7±0.1, 3.8±0.1, or 3.9±0.1. In other embodiments, the average number of hydroxypropyl chains per beta-cyclodextrin is 4.0±0.1, 4.1±0.1, 4.2±0.1, 4.3±0.1, 4.4±0.1, 4.5±0.1, 4.6±0.1, 4.7±0.1, 4.8±0.1, or 4.9±0.1. In other embodiments, the average number of hydroxypropyl chains per beta-cyclodextrin is 5.0±0.1, 5.1±0.1, 5.2±0.1, 5.3±0.1, 5.4±0.1, 5.5±0.1, 5.6±0.1, 5.7±0.1, 5.8±0.1, or 5.9±0.1. And in other embodiments, the average number of hydroxypropyl chains per beta-cyclodextrin is 6.0±0.1, 6.1±0.1, 6.2±0.1, 6.3±0.1, 6.4±0.1, 6.5±0.1, 6.6±0.1, 6.7±0.1, 6.8±0.1, or 6.9±0.1.

In some embodiments, at least about 50%, e.g., about 55%, about 60%, about 65%, about 70%, about 75%, about 80%, about 85%, about 90%, about 95%, or about 97%, of the hydroxypropyl chains have n=1. In some embodiments, at least 70% of the hydroxypropyl chains have n=1. In some embodiments, at least 90% of the hydroxypropyl chains have n=1.

In some embodiments, percentage of the hydroxypropyl chains that have n=1 ranges from about 50% to about 99%, such as about 55% to about 99%, about 60% to about 99%, about 65% to about 99%, about 70% to about 99%, about 75% to about 99%, about 80% to about 99%, about 85% to about 99%, about 90% to about 99%, about 95% to about 99%; such as from about 50% to about 97%, such as about 55% to about 97%, about 60% to about 97%, about 65% to about 97%, about 70% to about 97%, about 75% to about 97%, about 80% to about 97%, about 85% to about 97%, about 90% to about 97%, about 95% to about 97%; such as from about 50% to about 95%, about 55% to about 95%, about 60% to about 95%, about 65% to about 95%, about 70% to about 95%, about 75% to about 95%, about 80% to about 95%, about 85% to about 95%, about 90% to about 95%; such as from about 50% to about 90%, about 55% to about 90%, about 60% to about 90%, about 65% to about 90%, about 70% to about 90%, about 75% to about 90%, about 80% to about 90%, about 85% to about 90%; such as from about 50% to about 85%, about 55% to about 85%, about 60% to about 85%, about 65% to about 85%, about 70% to about 85%, about 75% to about 85%, about 80% to about 85%; such as from about 50% to about 80%, about 55% to about 80%, about 60% to about 80%, about 65% to about 80%, about 70% to about 80%, about 75% to about 80%; such as from about 50% to about 75%, about 55% to about 75%, about 60% to about 75%, about 65% to about 75%, about 70% to about 75%; such as from about 50% to about 70%, about 55% to about 70%, about 60% to about 70%, about 65% to about 70%; such as from about 50% to about 65%, about 55% to about 65%, about 60% to about 65%; such as from about 50% to about 60%, about 55% to about 60%; or such as from about 50% to about 55%.

In some embodiments, less than about 50%, such as about 45%, about 40%, about 35%, about 30%, about 25%, about 20%, about 15%, about 10%, about 5%, or about 3%, of the hydroxypropyl chains have n=2. In some embodiments, less than 30% of the hydroxypropyl chains have n=2. In some embodiments, less than 10% of the hydroxypropyl chains have n=2.

In some embodiments, the percentage of the hydroxypropyl chains that have n=2 ranges from about 5% to about 50%, such as about 10% to about 50%, about 15% to about 50%, about 20% to about 50%, about 25% to about 50%, about 30% to about 50%, about 35% to about 50%, about 40% to about 50%, about 45% to about 50%; such as from about 5% to about 45%, about 10% to about 45%, about 15% to about 45%, about 20% to about 45%, about 25% to about 45%, about 30% to about 45%, about 35% to about 45%, about 40% to about 45%; such as from about 5% to about 40%, about 10% to about 40%, about 15% to about 40%, about 20% to about 40%, about 25% to about 40%, about 30% to about 40%, about 35% to about 40%; such as from about 5% to about 35%, about 10% to about 35%, about 15% to about 35%, about 20% to about 35%, about 25% to about 35%, about 30% to about 35%; such as from about 5% to about 30%, about 10% to about 30%, about 15% to about 30%, about 20% to about 30%, about 25% to about 30%; such as from about 5% to about 25%, about 10% to about 25%, about 15% to about 25%, about 20% to about 25%; such as from about 5% to about 20%, about 10% to about 20%, about 15% to about 20%; such as from about 5% to about 15%, about 10% to about 15%; or about 5% to about 10%.

In some embodiments, less than about 50%, such as about 45%, about 40%, about 35%, about 30%, about 25%, about 20%, about 15%, about 10%, about 5%, or about 3%, of the hydroxypropyl chains have n>2. In some embodiments, less than 10% of the hydroxypropyl chains have n>2.

In some embodiments, the percentage of the hydroxypropyl chains that have n>2 ranges from about 5% to about 50%, such as about 10% to about 50%, about 15% to about 50%, about 20% to about 50%, about 25% to about 50%, about 30% to about 50%, about 35% to about 50%, about 40% to about 50%, about 45% to about 50%; such as from about 5% to about 45%, about 10% to about 45%, about 15% to about 45%, about 20% to about 45%, about 25% to about 45%, about 30% to about 45%, about 35% to about 45%, about 40% to about 45%; such as from about 5% to about 40%, about 10% to about 40%, about 15% to about 40%, about 20% to about 40%, about 25% to about 40%, about 30% to about 40%, about 35% to about 40%; such as from about 5% to about 35%, about 10% to about 35%, about 15% to about 35%, about 20% to about 35%, about 25% to about 35%, about 30% to about 35%; such as from about 5% to about 30%, about 10% to about 30%, about 15% to about 30%, about 20% to about 30%, about 25% to about 30%; such as from about 5% to about 25%, about 10% to about 25%, about 15% to about 25%, about 20% to about 25%; such as from about 5% to about 20%, about 10% to about 20%, about 15% to about 20%; such as from about 5% to about 15%, about 10% to about 15%; or such as from about 5% to about 10%.

In some embodiments, the average number of hydroxypropyl chains per beta-cyclodextrin is about 4 to about 6. In some embodiments, at least about 60%, such as at least about 65%, at least about 70%, at least about 75%, at least about 80%, at least about 85%, at least about 90%, at least about 95%, or at least about 97%, of the beta-cyclodextrins collectively have an average number of hydroxypropyl chains per beta-cyclodextrin of about 4 to about 6. In some embodiments, the percentage of the beta-cyclodextrins that collectively have an average number of hydroxypropyl chains per beta-cyclodextrin of about 4 to about 6 ranges from about 60% to about 97%, such as about 65% to about 97%, about 70% to about 97%, about 75% to about 97%, about 80% to about 97%, about 85% to about 97%, about 90% to about 97%; such as from about 60% to about 95%, about 65% to about 95%, about 70% to about 95%, about 75% to about 95%, about 80% to about 95%, about 85% to about 95%, about 90% to about 95%; such as from about 60% to about 90%, about 65% to about 90%, about 70% to about 90%, about 75% to about 90%, about 80% to about 90%, about 85% to about 90%; such as from about 60% to about 85%, about 65% to about 85%, about 70% to about 85%, about 75% to about 85%, about 80% to about 85%; such as from about 60% to about 80%, about 65% to about 80%, about 70% to about 80%, about 75% to about 80%; such as from about 60% to about 75%, about 65% to about 75%, about 70% to about 75%; such as from about 60% to about 70%, about 65% to about 70%; or such as from about 60% to about 65%.

6.2.1.2. Substitution Fingerprint 6.2.1.2.1. DS-0

In typical embodiments, the pharmaceutically active ingredient contains less than about 2%, such as less than about 1.5%, less than about 1.4%, less than about 1.3%, less than about 1.2%, less than about 1.1%, less than about 1.0%, less than about 0.9%, less than about 0.8%, less than about 0.7%, less than about 0.6%, less than about 0.5%, less than about 0.4%, less than about 0.3%, less than about 0.2%, less than about 0.1%, less than about 0.09%, less than about 0.08%, less than about 0.07%, less than about 0.06%, or less than about 0.05% unsubstituted beta-cyclodextrin ("DS-0"; "BCD"), as determined by peak height of an electrospray MS spectrum.

In typical embodiments, no more than ("NMT") 1% of the beta-cyclodextrin mixture is unsubstituted with a hydroxypropyl group (BCD), as determined by peak height of an electrospray MS spectrum.

In some embodiments, the level of unsubstituted beta-cyclodextrins in the pharmaceutically active ingredient ranges from about 0.05% to about 2%, such as about 0.05% to about 1.5%, about 0.05% to about 1.4%, about 0.05% to about 1.3%, about 0.05% to about 1.2%, about 0.05% to about 1.1%, about 0.05% to about 1.0%, about 0.05% to about 0.8%, about 0.05% to about 0.6%, about 0.05% to about 0.5%, about 0.05% to about 0.4%, about 0.05% to about 0.3%, about 0.05% to about 0.2%, about 0.05% to about 0.1%, about 0.05% to about 0.07%, about 0.07% to about 1.5%, about 0.07% to about 1.4%, about 0.07% to about 1.3%, about 0.07% to about 1.2%, about 0.07% to about 1.1%, about 0.07% to about 1.0%, about 0.07% to about 0.8%, about 0.07% to about 0.6%, about 0.07% to about 0.5%, about 0.07% to about 0.4%, about 0.07% to about 0.3%, about 0.07% to about 0.2%, about 0.07% to about 0.1%, about 0.1% to about 1.5%, about 0.1% to about 1.4%, about 0.1% to about 1.3%, about 0.1% to about 1.2%, about 0.1% to about 1.1%, about 0.1% to about 1.0%, about 0.1% to about 0.8%, about 0.1% to about 0.6%, about 0.1% to about 0.5%, about 0.1% to about 0.4%, about 0.1% to about 0.3%, about 0.1% to about 0.2%, about 0.2% to about 1.5%, about 0.2% to about 1.4%, about 0.2% to about 1.3%, about 0.2% to about 1.2%, about 0.2% to about 1.1%, about 0.2% to about 1.0%, about 0.2% to about 0.8%, about 0.2% to about 0.6%, about 0.2% to about 0.5%, about 0.2% to about 0.4%, about 0.2% to about 0.3%, about 0.3% to about 1.5%, about 0.3% to about 1.4%, about 0.3% to about 1.3%, about 0.3% to about 1.2%, about 0.3% to about 1.1%, about 0.3% to about 1.0%, about 0.3% to about 0.8%, about 0.3% to about 0.6%, about 0.3% to about 0.5%, about 0.3% to about 0.4%, about 0.4% to about 1.5%, about 0.4% to about 1.4%, about 0.4% to about 1.3%, about 0.4% to about 1.2%, about 0.4% to about 1.1%, about 0.4% to about 1.0%, about 0.4% to about 0.8%, about 0.4% to about 0.6%, about 0.4% to about 0.5%, about 0.5% to about 1.5%, about 0.5% to about 1.4%, about 0.5% to about 1.3%, about 0.5% to about 1.2%, about 0.5% to about 1.1%, about 0.5% to about 1.0%, about 0.5% to about 0.8%, about 0.5% to about 0.6%, about 0.6% to about 1.5%, about 0.6% to about 1.4%, about 0.6% to about 1.3%, about 0.6% to about 1.2%, about 0.6% to about 1.1%, about 0.6% to about 1.0%, about 0.6% to about 0.8%, about 0.8% to about 1.5%, about 0.8% to about 1.4%, about 0.8% to about 1.3%, about 0.8% to about 1.2%, about 0.8% to about 1.1%, about 0.8% to about 1.0%, about 1.0% to about 1.5%, about 1.0% to about 1.4%, about 1.0% to about 1.3%, about 1.0% to about 1.2%, about 1.0% to about 1.1%, about 1.1% to about 1.5%, about 1.1% to about 1.4%, about 1.1% to about 1.3%, about 1.1% to about 1.2%, about 1.2% to about 1.5%, about 1.2% to about 1.4%, about 1.2% to about 1.3%, about 1.3% to about 1.5%, about 1.3% to about 1.4%, or about 1.4% to about 1.5%.

In various embodiments, the composition comprises no more than about 0.01% BCD, no more than about 0.02% BCD, no more than about 0.03% BCD, no more than about 0.04% BCD, or no more than about 0.05% BCD of the beta-cyclodextrin mixture.

6.2.1.2.2. Ds-1

In typical embodiments, less than 4% of the beta-cyclodextrin mixture is beta-cyclodextrin substituted with just one hydroxypropyl group ("DS-1"), as determined by peak height of an electrospray MS spectrum.

In various embodiments, less than 3.9%, less than 3.8%, less than 3.7%, less than 3.6%, or less than 3.5% of the beta-cyclodextrin mixture is DS-1. In certain embodiments, the pharmaceutically active ingredient comprises less than 3.5%, 3.4%, 3.3%, 3.2%, 3.1%, or 3.0% DS-1. In particular embodiments, the pharmaceutically active ingredient comprises less than 2.9%, 2.8%, 2.7%, 2.6%, 2.5%, 2.4%, 2.3%, 2.2%, 2.1%, or 2.0% DS-1. In some embodiments, the mixture of beta-cyclodextrin molecules comprises less than 1.9%, 1.8%, 1.7%, 1.6%, 1.5%, 1.4%, 1.3%, 1.2%, 1.1%, or 1.0% DS-1. In presently preferred embodiments, the pharmaceutically active ingredient comprises less than 0.9%, 0.8%, 0.7%, 0.6%, 0.5%, 0.4%, 0.3%, 0.2% or 0.1% DS-1, even less than about 0.09%, 0.08%, 0.07%, 0.06%, 0.05%, 0.04%, 0.03% DS-1. In certain preferred embodiments, the composition comprises less than 0.03%, even as low as 0.02% DS-1.

In currently preferred embodiments, the composition comprises less than about 0.05% BCD and less than about 0.03% DS-1.

6.2.1.2.3. DS-2

In various embodiments, the beta-cyclodextrin mixture has a low percentage of beta-cyclodextrin substituted with two hydroxypropyl groups ("DS-2"), as determined by peak height of an electrospray MS spectrum.

In various embodiments, less than 3.9%, less than 3.8%, less than 3.7%, less than 3.6%, or less than 3.5% of the beta-cyclodextrin mixture is DS-2. In certain embodiments, the pharmaceutically active ingredient comprises less than 3.5%, 3.4%, 3.3%, 3.2%, 3.1%, or 3.0% DS-2. In particular embodiments, the pharmaceutically active ingredient comprises less than 2.9%, 2.8%, 2.7%, 2.6%, 2.5%, 2.4%, 2.3%, 2.2%, 2.1%, or 2.0% DS-2. In some embodiments, the mixture of beta-cyclodextrin molecules comprises less than 1.9%, 1.8%, 1.7%, 1.6%, 1.5%, 1.4%, 1.3%, 1.2%, 1.1%, or 1.0% DS-2. In presently preferred embodiments, the pharmaceutically active ingredient comprises less than 0.9%, 0.8%, 0.7%, 0.6%, 0.5%, 0.4%, 0.3%, 0.2% or 0.1% DS-2, even less than about 0.09%, 0.08%, 0.07%, 0.06%, 0.05%, 0.04%, 0.03% DS-2. In certain preferred embodiments, the composition comprises less than 0.03%, even as low as 0.02% DS-2.

In typical embodiments, the mixture comprises at least 10% beta-cyclodextrin molecules having three hydroxypropyl substitutions ("DS-3") as a percentage of the total mixture, as determined by peak height of an electrospray MS spectrum. In various embodiments, at least 11%, at least 12%, at least 13%, at least 14%, at least 15%, at least 16%, at least 17%, at least 18%, at least 19%, at least 20%, at least 21%, at least 22%, at least 23%, at least 24%, or at least 25% of the beta-cyclodextrin mixture is DS-3.

In various embodiments, the mixture comprises no more than 30%, such as no more than 29%, no more than 28%, no more than 27%, no more than 26%, no more than 25%, no more than 24%, no more than 23%, no more than 22%, no more than 21%, no more than 20%, no more than 19%, no more than 18%, no more than 17%, no more than 16%, or no more than 15% of DS-3 as a percentage of the total mixture.

In certain embodiments, the percentage of DS-3 in the entire mixture ranges from 10% to 30%, such as 11% to 29%, 12% to 28%, 13% to 27%, 14% to 26%, 15% to 25%, 16% to 24%, 17% to 23%, 18% to 22%, or 19% to 21%.

In various embodiments, the mixture comprises about 15%, about 16%, about 17%, about 18%, about 19%, about 20%, about 21%, about 22%, about 23%, about 24%, or about 25% DS-3.

6.2.1.2.5. DS-4

In typical embodiments, the mixture comprises at least 20% beta-cyclodextrin molecules having four hydroxypropyl substitutions ("DS-4") as a percentage of the total mixture, as determined by peak height of an electrospray MS spectrum. In various embodiments, at least 21%, at least 22%, at least 23%, at least 24%, at least 25%, at least 26%, at least 27%, at least 28%, at least 29%, at least 30%, at least 31%, at least 32%, at least 33%, at least 34%, or at least 35% of the beta-cyclodextrin mixture is DS-4.

In various embodiments, the mixture comprises no more than 40%, such as no more than 39%, no more than 38%, no more than 37%, no more than 36%, no more than 35%, no more than 34%, no more than 33%, no more than 32%, no more than 31%, no more than 30%, no more than 29%, no more than 28%, no more than 27%, no more than 26%, or no more than 25% of DS-4 as a percentage of the total mixture.

In certain embodiments, the percentage of DS-4 in the entire mixture ranges from 20% to 40%, such as 21% to 39%, 22% to 38%, 23% to 37%, 24% to 36%, 25% to 35%, 26% to 34%, 27% to 33%, 28% to 32%, or 29% to 31%.

In various embodiments, the mixture comprises about 25%, about 26%, about 27%, about 28%, about 29%, about 30%, about 31%, about 32%, about 33%, about 34%, or about 35% DS-4.

In typical embodiments, the mixture comprises at least 15% beta-cyclodextrin molecules having five hydroxypropyl substitutions ("DS-5") as a percentage of the total mixture, as determined by peak height of an electrospray MS spectrum. In various embodiments, at least 16%, at least 17%, at least 18%, at least 19%, at least 20%, at least 21%, at least 22%, at least 23%, at least 24%, at least 25%, at least 26%, at least 27%, at least 28%, at least 29%, or at least 30% of the beta-cyclodextrin mixture is DS-5.

In various embodiments, the mixture comprises no more than 35%, such as no more than 34%, no more than 33%, no more than 32%, no more than 31%, no more than 30%, no more than 29%, no more than 28%, no more than 27%, no more than 26%, no more than 25%, no more than 24%, no more than 23%, no more than 22%, no more than 21%, or no more than 20% of DS-5 as a percentage of the total mixture.

In certain embodiments, the percentage of DS-5 in the entire mixture ranges from 15% to 35%, such as 16% to 34%, 17% to 33%, 18% to 32%, 19% to 31%, 20% to 30%, 21% to 29%, 22% to 28%, 23% to 27%, or 24% to 26%.

In various embodiments, the mixture comprises about 20%, about 21%, about 22%, about 23%, about 24%, about 25%, about 26%, about 27%, about 28%, about 29%, or about 30% DS-5.

6.2.1.2.7. DS-6

In typical embodiments, the mixture comprises at least 5% beta-cyclodextrin molecules having six hydroxypropyl substitutions ("DS-6") as a percentage of the total mixture, as determined by peak height of an electrospray MS spectrum. In various embodiments, at least 6%, at least 7%, at least 8%, at least 9%, at least 10%, at least 11%, at least 12%, at least 13%, at least 14%, at least 15%, at least 16%, at least 17%, at least 18%, at least 19%, or at least 20% of the beta-cyclodextrin mixture is DS-6.

In various embodiments, the mixture comprises no more than 25%, such as no more than 24%, no more than 23%, no more than 22%, no more than 21%, no more than 20%, no more than 19%, no more than 18%, no more than 17%, no more than 16%, no more than 15%, no more than 14%, no more than 13%, no more than 12%, no more than 11%, or no more than 10% of DS-6 as a percentage of the total mixture.

In certain embodiments, the percentage of DS-6 in the entire mixture ranges from 5% to 25%, such as 6% to 24%, 7% to 23%, 8% to 22%, 9% to 21%, 10% to 20%, 11% to 19%, 12% to 18%, 13% to 17%, or 14% to 16%.

In various embodiments, the mixture comprises about 7%, about 8%, about 9%, about 10%, about 11%, about 12%, about 13%, about 14%, about 15%, about 16%, or about 17% DS-6.

In typical embodiments, less than 10% of the beta-cyclodextrin mixture is beta-cyclodextrin substituted with seven hydroxypropyl groups ("DS-7") as a percentage of the total mixture, as determined by peak height of an electrospray MS spectrum. In various embodiments, less than 9%, less than 8%, less than 7%, less than 6%, less than 5%, less than 4%, less than 3%, less than 2%, or less than 1% of the beta-cyclodextrin mixture is DS-7.

In certain embodiments, the percentage of DS-7 in the entire mixture ranges from 1% to 10%, such as 2% to 9%, 3% to 8%, 4% to 7%, or 5% to 6%.

In various embodiments, the mixture comprises about 10%, about 9%, about 8%, about 7%, about 6%, about 5%, about 4%, about 3%, about 2%, or about 1% DS-7.

6.2.1.2.9. DS-8

In typical embodiments, the beta-cyclodextrin mixture comprises less than 2% of beta-cyclodextrin substituted with eight hydroxypropyl groups ("DS-8") as a percentage of the total mixture, as determined by peak height of an electrospray MS spectrum. In various embodiments, less than 1.5%, less than 1.4%, less than 1.3%, less than 1.2%, less than 1.1%, less than 1%, less than 0.9%, less than 0.8%, less than 0.7%, less than 0.6%, less than 0.5%, less than 0.4%, less than 0.3%, less than 0.2%, less than 0.1%, less than 0.09%, less than 0.08%, less than 0.07%, less than 0.06%, less than 0.05%, less than 0.04%, less than 0.03%, less than 0.02%, or less than 0.01% of beta-cyclodextrin is DS-8.

In certain embodiments, the percentage of DS-8 in the entire mixture ranges from 0.01% to 2%, such as 0.02% to 1.9%, 0.03% to 1.8%, 0.04% to 1.7%, 0.05% to 1.6%, 0.06% to 1.5%, 0.07% to 1.4%, 0.08% to 1.3%, 0.09% to 1.2%, 0.1% to 1.1%, 0.2% to 1%, 0.3% to 0.9%, 0.4% to 0.8%, or 0.5% to 0.7%.

In various embodiments, the mixture comprises about 1.5%, about 1.4%, about 1.3%, about 1.2%, about 1.1%, about 1%, about 0.9%, about 0.8%, about 0.7%, about 0.6%, about 0.5%, about 0.4%, about 0.3%, about 0.2%, about 0.1%, about 0.09%, about 0.08%, about 0.07%, about 0.06%, about 0.05%, about 0.04%, about 0.03%, about 0.02%, or about 0.01% DS-8.

6.2.1.2.10. DS-9

In typical embodiments, no more than 1% of the beta-cyclodextrin mixture is beta-cyclodextrin substituted with nine hydroxypropyl groups ("DS-9") as a percentage of the total mixture, as determined by peak height of an electrospray MS spectrum. In various embodiments, no more than 0.9%, no more than 0.8%, no more than 0.7%, no more than 0.6%, no more than 0.5%, no more than 0.4%, no more than 0.3%, no more than 0.2%, no more than 0.1%, no more than 0.09%, no more than 0.08%, no more than 0.07%, no more than 0.06%, no more than 0.05%, no more than 0.04%, no more than 0.03%, no more than 0.02%, or no more than 0.01% of beta-cyclodextrin is DS-10.

6.2.1.2.11. DS-10

In typical embodiments, no more than 1% of the beta-cyclodextrin mixture is beta-cyclodextrin substituted with ten hydroxypropyl groups ("DS-10") as a percentage of the total mixture, as determined by peak height of an electrospray MS spectrum. In various embodiments, no more than 0.9%, no more than 0.8%, no more than 0.7%, no more than 0.6%, no more than 0.5%, no more than 0.4%, no more than 0.3%, no more than 0.2%, no more than 0.1%, no more than 0.09%, no more than 0.08%, no more than 0.07%, no more than 0.06%, no more than 0.05%, no more than 0.04%, no more than 0.03%, no more than 0.02%, or no more than 0.01% of beta-cyclodextrin is DS-10.

6.2.1.2.12. Profile

In various embodiments, the beta-cyclodextrin mixture contains at least 75% of DS-3, DS-4, DS-5, and DS-6, collectively, as a percentage of the entire mixture. In certain embodiments, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, or at least 98% of beta-cyclodextrin in the mixture is DS-3, DS-4, DS-5, and DS-6, collectively.

In various embodiments, the beta-cyclodextrin mixture comprises DS-3, DS-4, DS-5, and DS-6, collectively, as a percentage of the entire mixture in the range from about 75% to about 98%, such as about 76% to about 97%, about 77% to about 96%, about 78% to about 95%, about 79% to about 94%, about 80% to about 93%, about 81% to about 92%, about 82% to about 91%, about 83% to about 90%, about 84% to about 89%, about 85% to about 88%, or about 86% to about 87%.

In typical embodiments, the beta-cyclodextrin mixture comprises at least 25% of DS-5 and DS-6, collectively, as a percentage of the entire mixture. In certain embodiments, at least 26%, at least 27%, at least 28%, at least 29%, at least 30%, at least 31%, at least 32%, at least 33%, at least 34%, at least 35%, at least 36%, at least 37%, at least 38%, at least 39%, at least 40%, at least 41%, at least 42%, at least 43%, at least 44%, at least 45%, at least 46%, at least 47%, at least 48%, at least 49%, or at least 50% of beta-cyclodextrin in the mixture is DS-5 and DS-6, collectively.

In various embodiments, the beta-cyclodextrin mixture comprises DS-5 and DS-6, collectively, as a percentage of the entire mixture in the range from about 25% to about 50%, such as about 26% to about 49%, about 27% to about 48%, about 28% to about 47%, about 29% to about 46%, about 30% to about 45%, about 31% to about 44%, about 32% to about 43%, about 33% to about 42%, about 34% to about 41%, about 35% to about 40%, about 36% to about 39%, or about 37% to about 38%.

In various embodiments, the beta-cyclodextrin species with the greatest prevalence as a percentage of the entire mixture is DS-4.

6.2.1.3. Starting Material

In certain embodiments, the present disclosure describes a pharmaceutical composition wherein the sole pharmaceutically active ingredient is obtained by purifying one or more hydroxypropyl beta-cyclodextrin products selected from Kleptose® HBP, Kleptose® HP, Trappsol® Cyclo, and Cavasol® W7 HP Pharma.

Kleptose® HBP and Kleptose® HP are hydroxypropyl beta-cyclodextrin products available from Roquette Pharma, Lestrem, France. Kleptose® HBP is a parenteral grade endotoxin-controlled composition of hydroxypropyl beta-cyclodextrins with a $DS_a$ of about 4.3. Kleptose® HP is an endotoxin-controlled composition of hydroxypropyl beta-cyclodextrins with a higher $DS_a$ than Kleptose® HBP. Trappsol® Cyclo is a parenteral grade of hydroxypropyl beta cyclodextrin with a $DS_a$ of about 6.37, and is available in a powdered or sterile liquid form from Sphingo Biotechnology, Inc., a division of CTD Holdings, Inc., Alachua, Florida, USA. Cavasol® W7 HP Pharma is a pharmaceutical grade hydroxypropyl-beta-cyclodextrin with a $DS_a$ from about 4.1 to about 5.1, e.g., a $DS_a$ of about 4.5, available from Wacker Chemie A G, München, Germany.

In an illustrative example, the pharmaceutical composition is one wherein the sole pharmaceutically active ingredient is obtained by purifying Kleptose® HBP. In certain embodiments, the pharmaceutical composition is one in which the sole pharmaceutically active ingredient is obtained by purifying Kleptose® HBP (Roquette) by hydrophilic interaction, e.g., by HPLC purification, or by affinity purification, e.g., affinity chromatography. In various embodiments, the pharmaceutically active ingredient is obtained by purifying Kleptose® HBP (Roquette) by one or more of the procedures described in Examples 6, 7 and 9 herein.

In a variety of embodiments, the purification provides a portion or fraction of the Kleptose® HBP having increased activity, e.g., increased affinity for unesterified cholesterol.

In other embodiments, the pharmaceutical composition is one in which the sole pharmaceutically active ingredient is obtained by purifying Trappsol® Cyclo (CTD) by hydrophilic interaction, e.g., by HPLC purification, or by affinity purification, e.g., affinity chromatography. In various embodiments, the pharmaceutically active ingredient is obtained by purifying Trappsol® Cyclo with absorption chromatography on alumina using one or more of the procedures described in Examples 6, 7 and 9 herein.

In some embodiments, the pharmaceutical composition purified from Trappsol® Cyclo (CTD) comprises a mixture of beta-cyclodextrin molecules substituted at one or more hydroxyl positions by hydroxypropyl groups, the mixture optionally including unsubstituted beta-cyclodextrin molecules, and a diluent that is pharmaceutically acceptable for intrathecal, intracerebroventricular, or intravenous administration. The composition comprises no more than ("NMT") 5 EU of endotoxins per gram of beta-cyclodextrin mixture, no more than 0.5% propylene glycol, as measured by the HPLC method set forth in the USP Hydroxypropyl Betadex monograph, and no more than 1 ppm propylene oxide, determined according to the USP Hydroxypropyl Betadex monograph.

In some embodiments, the pharmaceutical composition purified from Trappsol® Cyclo (CTD) comprises NMT 1.5 EU of endotoxins per gram of beta-cyclodextrin mixture. In some embodiments, the composition comprises no more than 0.01% propylene glycol, as measured by the HPLC method set forth in the USP Hydroxypropyl Betadex monograph.

In certain embodiments, the pharmaceutically active ingredient purified from Trappsol® Cyclo (CTD) comprises less than 5%, such as less than 4.5%, less than 4%, less than 3.5%, less than 3%, less than 2.5%, less than 2%, less than 1.5%, less than 1%, less than 0.5%, or less than 0.1% unsubstituted beta-cyclodextrin ("DS-0"), beta-cyclodextrin substituted with one hydroxypropyl group ("DS-1"), and beta-cyclodextrin substituted with two hydroxypropyl groups ("DS-2"), collectively, as determined by peak heights of an electrospray MS spectrum.

In certain embodiments, the pharmaceutically active ingredient purified from Trappsol® Cyclo (CTD) comprises at least 50%, such as at least 55%, at least 60%, at least 65%, at least 70%, at least 75%, at least 80%, at least 85%, or at least 90% beta-cyclodextrin substituted with five hydroxypropyl groups ("DS-5"), beta-cyclodextrin substituted with six hydroxypropyl groups ('DS-6"), and beta-cyclodextrin substituted with seven hydroxypropyl groups ('DS-7"), collectively, as determined by peak heights of an electrospray MS spectrum.

In certain embodiments, the pharmaceutically active ingredient purified from Trappsol® Cyclo (CTD) comprises less than 5%, such as less than 4.5%, less than 4%, less than 3.5%, less than 3%, less than 2.5%, less than 2%, less than 1.5%, less than 1%, less than 0.5%, or less than 0.1% beta-cyclodextrin substituted with nine hydroxypropyl groups ("DS-9") and beta-cyclodextrin substituted with ten hydroxypropyl groups ("DS-10"), collectively, as determined by peak heights of an electrospray MS spectrum.

In still other embodiments, the pharmaceutical composition is one in which the sole pharmaceutically active ingredient is obtained by purifying Cavasol® W7 HP by hydrophilic interaction, e.g., by HPLC purification, or by affinity purification, e.g., affinity chromatography. In various embodiments, the pharmaceutically active ingredient is obtained by purifying Cavasol® W7 HP by one or more of the procedures described in Examples 6, 7 and 9 herein.

In certain embodiments, purifying one or more hydroxypropyl beta-cyclodextrin products selected from Kleptose® HBP, Kleptose® HP, Trappsol® Cyclo, and Cavasol® W7 HP Pharma comprises one or more of complex formation, precipitation, and adsorption chromatography. In some embodiments, the purification comprises one method, e.g., adsorption chromatography. In some embodiments, the purification comprises two or more methods, e.g., precipitation in combination with adsorption chromatography. In cases where the purification comprises two or more methods used in combination, the methods can be combined in any order to purify a hydroxypropyl beta-cyclodextrin product. In an illustrative example, Kleptose® HBP or Trappsol® Cyclo can first be subjected to adsorption chromatography, then one or more selected fractions from the chromatographic step can be subjected to solvent precipitation from a precipitation solvent system to effect further purification. In an alternative example, Kleptose® HBP can first be subjected to solvent precipitation from a precipitation solvent system, then the precipitate can be subjected to adsorption chromatography to effect further purification.

In some embodiments, the purification of one or more hydroxypropyl beta-cyclodextrin products, e.g., Kleptose® HBP or Trappsol® Cyclo, results in an increase in $DS_a$ due to removal of unsubstituted (DS=0) and/or monosubstituted (DS=1) beta-cyclodextrins. In an illustrative example, a commercial sample of Kleptose® HBP having $DS_a$=4.34 contains 0.6% unsubstituted beta-cyclodextrins (DS=0) and 3.68% monosubstituted beta-cyclodextrins (DS=1). The $DS_a$ after removal of the DS=0 and DS=1 species can be calculated using the following equations:

$$x(0)+y(1)+z(DS_a)=4.34$$

$$x+y+z=1$$

wherein x=fraction of unsubstituted beta-cyclodextrins; y=fraction of monosubstituted beta-cyclodextrins; z=fraction of beta-cyclodextrins with DS≥2. In this instance, the $DS_a$ of the resulting sample after removal of beta-cyclodextrins having DS=0 and DS=1 is 4.5.

Accordingly, in certain embodiments the present disclosure provides a method for purifying one or more hydroxypropyl beta-cyclodextrin products selected from Kleptose® HBP, Kleptose® HP, Trappsol® Cyclo, and Cavasol® W7 HP Pharma, particularly Kleptose® HBP or Trappsol® Cyclo, wherein the purification method reduces in the product the amount of propylene glycol or propylene glycol oligomers (e.g., by solvent precipitation) and/or the amount of unsubstituted beta-cyclodextrin (DS=0) and/or the amount of monosubstituted beta-cyclodextrin (DS=1) (e.g., by adsorption chromatography). In certain of such embodiments, wherein the amount of unsubstituted beta-cyclodextrin (DS=0) and/or the amount of monosubstituted beta-cyclodextrin (DS=1) in the product is reduced, the purified product exhibits an increased $DS_a$. Hence, in certain embodiments the present disclosure provides a method for increasing the $DS_a$ of one or more hydroxypropyl beta-cyclodextrin products selected from Kleptose® HBP, Kleptose® HP, Trappsol® Cyclo, and Cavasol® W7 HP Pharma, particularly Kleptose® HBP or Trappsol® Cyclo, the method comprising reducing the amount of unsubstituted beta-cyclodextrin (DS=0) and/or monosubstituted beta-cyclodextrin (DS=1) in the product, for example, according one or more purification steps described herein, such as adsorption chromatography.

Although Kleptose® HBP, Kleptose® HP, Trappsol® Cyclo, and Cavasol® W7 HP Pharma each have a reported $DS_a$, as discussed above, $DS_a$ is an average measure, and therefore each of these hydroxypropyl beta-cyclodextrin products is comprised of hydroxypropyl beta-cyclodextrins with varying DS values. In some embodiments, the pharmaceutically active ingredient described herein is obtained by isolating from one or more of these products one or more hydroxypropyl beta-cyclodextrin fractions with a $DS_a$ described herein.

6.2.2. Endotoxin Levels

In certain embodiments, the pharmaceutical compositions of the disclosure contain a low level of bacterial endotoxins. The low level of bacterial endotoxins allows for the disclosed pharmaceutical compositions to be administered by certain routes, e.g., via intrathecal or intracerebroventricular administration, for longer periods and at higher levels than can safely be done with other compositions having higher levels of endotoxins.

As used herein, "IU" refers to an International Unit of bacterial endotoxin, also known as a United States Pharmacopeial (USP) Endotoxin Unit ("EU"). The level of bacterial endotoxins (IU; synonymously, EU) in the composition is determined by Limulus amoebocyte lysate test, according to the procedures set forth in "<85> Bacterial Endotoxins Test," the United States Pharmacopeial Convention, Interim Revision Announcement dated Apr. 1, 2011 ("USP Endotoxin Monograph"), incorporated herein by reference in its entirety.

In some embodiments, the pharmaceutical composition contains less than about 10 IU, such as less than about 6, about 5, about 4, about 3, about 2, about 1.5, about 1.2, about 1 IU, about 0.8 IU, about 0.6 IU, about 0.5 IU, about 0.4 IU, about 0.3 IU, about 0.2 IU, about 0.1 IU, about 0.07 IU, or about 0.05 IU endotoxin per gram of pharmaceutically active ingredient. In some embodiments, the pharmaceutical composition contains a level of bacterial endotoxin in a range of from about 0.05 IU to about 10 IU, e.g., about 0.05 IU to about 6 IU, about 0.05 IU to about 5 IU, about 0.05 IU to about 4 IU, about 0.05 IU to about 3 IU, about 0.05 IU to about 2 IU, about 0.05 IU to about 1.5 IU, about 0.05 IU to about 1.2 IU, about 0.05 IU to about 1 IU, about 0.05 IU to about 0.8 IU, about 0.05 IU to about 0.6 IU, about 0.05 IU to about 0.5 IU, about 0.05 IU to about 0.4 IU, about 0.05 IU to about 0.3 IU, about 0.05 IU to about 0.2 IU, or about 0.05 IU to about 0.1 IU endotoxin per gram of the beta-cyclodextrin mixture.

In certain embodiments, the pharmaceutical composition comprises no more than ("NMT") 5 EU/g beta-cyclodextrin mixture, NMT 4 EU/g beta-cyclodextrin mixture, NMT 3 EU/g beta-cyclodextrin mixture, or no more than 2 EU/g beta-cyclodextrin mixture. In preferred embodiments, the pharmaceutical composition comprises NMT 1.5 EU/g beta-cyclodextrin mixture. In certain embodiments, the pharmaceutical composition comprises NMT 1.4 EU/g beta-cyclodextrin mixture, NMT 1.3 EU/g beta-cyclodextrin mixture, NMT 1.2 EU/g beta-cyclodextrin mixture, NMT 1.1 EU/g beta-cyclodextrin mixture, or NMT 1.0 EU/g beta-cyclodextrin mixture.

6.2.3. Process Impurities

Pharmaceutical compositions comprising mixtures of hydroxypropyl beta-cyclodextrins may contain impurities arising from the synthesis of hydroxypropyl beta-cyclodextrins. Such impurities may include unreacted starting materials such as unsubstituted beta-cyclodextrins and propylene oxide, and reaction by-products such as propylene glycol and propylene glycol oligomers. In certain embodiments, the pharmaceutical compositions described herein exhibit reduced levels of one or more of such impurities.

6.2.3.1. Propylene Glycol

In some embodiments, the pharmaceutically active ingredient comprises less than about 1%, such as less than about 0.9%, 0.8%, 0.7%, 0.6%, or 0.5%, propylene glycol, determined according to the USP Hydroxypropyl Betadex monograph. In various embodiments, the pharmaceutically active ingredient comprises less than about 0.4%, 0.3%, 0.2% or 0.1% propylene glycol, determined according to the USP Hydroxypropyl Betadex monograph. In certain embodiments, the pharmaceutical composition comprises less than about 0.09%, 0.08%, 0.07%, or less than about 0.05% propylene glycol, determined according to the USP Hydroxypropyl Betadex monograph. In currently preferred embodiments, the pharmaceutically active ingredient comprises no more than 0.5% propylene glycol, determined according to the USP Hydroxypropyl Betadex monograph.

In some embodiments, the pharmaceutically active ingredient comprises from about 0.05% to about 1% propylene glycol, such as about 0.05% to about 0.8%, about 0.05% to about 0.6%, about 0.05% to about 0.5%, about 0.05% to about 0.4%, about 0.05% to about 0.3%, about 0.05% to about 0.2%, about 0.05% to about 0.1%, about 0.05% to about 0.07%, about 0.07% to about 1%, about 0.07% to about 0.8%, about 0.07% to about 0.6%, about 0.07% to about 0.5%, about 0.07% to about 0.4%, about 0.07% to about 0.3%, about 0.07% to about 0.2%, about 0.07% to about 0.1%, about 0.1% to about 1%, about 0.1% to about 0.8%, about 0.1% to about 0.6%, about 0.1% to about 0.5%, about 0.1% to about 0.4%, about 0.1% to about 0.3%, about 0.1% to about 0.2%, about 0.2% to about 1%, about 0.2% to about 0.8%, about 0.2% to about 0.6%, about 0.2% to about 0.5%, about 0.2% to about 0.4%, about 0.2% to about 0.3%, about 0.3% to about 1%, about 0.3% to about 0.8%, about 0.3% to about 0.6%, about 0.3% to about 0.5%, about 0.3% to about 0.4%, about 0.4% to about 1%, about 0.4% to about 0.8%, about 0.4% to about 0.6%, about 0.4% to about 0.5%, about 0.5% to about 1%, about 0.5% to about 0.8%, about 0.5% to about 0.6%, about 0.6% to about 1%, about 0.6% to about 0.8%, or about 0.8% to about 1.0%, determined according to the USP Hydroxypropyl Betadex monograph.

In some embodiments, the pharmaceutically active ingredient comprises less than about 0.01% propylene glycol monomers, determined according to the USP Hydroxypropyl Betadex monograph. In some embodiments, the pharmaceutically active ingredient comprises less than about 0.2% propylene glycol dimers, determined according to the USP Hydroxypropyl Betadex monograph. In some embodiments, the pharmaceutically active ingredient comprises less than about 0.2% propylene glycol trimers, determined according to the USP Hydroxypropyl Betadex monograph.

6.2.3.2. Propylene Oxide

In some embodiments, the pharmaceutically active ingredient contains less than about 1 ppm, such as less than about 0.8 ppm, less than about 0.6 ppm, less than about 0.5 ppm, less than about 0.4 ppm, less than about 0.3 ppm, less than about 0.2 ppm, less than about 0.1 ppm, less than about 0.07 ppm, or less than about 0.05 ppm, propylene oxide, determined according to the USP Hydroxypropyl Betadex monograph. For example, the pharmaceutically active ingredient can have about 1, about 0.8, about 0.6, about 0.5, about 0.4, about 0.3, about 0.2, about 0.1, about 0.07, or about 0.05 ppm propylene oxide, determined according to the USP Hydroxypropyl Betadex monograph.

In some embodiments, the pharmaceutically active ingredient has an amount of propylene oxide in a range of from about 0.05 to about 1 ppm, such as about 0.05 to about 0.8, about 0.05 to about 0.6, about 0.05 to about 0.5, about 0.05 to about 0.4, about 0.05 to about 0.3, about 0.05 to about 0.2, about 0.05 to about 0.1, about 0.1 to about 1, about 0.1 to about 0.8, about 0.1 to about 0.6, about 0.1 to about 0.5, about 0.1 to about 0.4, about 0.1 to about 0.3, about 0.1 to about 0.2, about 0.2 to about 1, about 0.2 to about 0.8, about 0.2 to about 0.6, about 0.2 to about 0.5, about 0.2 to about 0.4, about 0.2 to about 0.3, about 0.3 to about 1, about 0.3 to about 0.8, about 0.3 to about 0.6, about 0.3 to about 0.5, about 0.3 to about 0.4, about 0.4 to about 1, about 0.4 to about 0.8, about 0.4 to about 0.6, about 0.4 to about 0.5, about 0.5 to about 1, about 0.5 to about 0.8, about 0.5 to about 0.6, about 0.6 to about 1, about 0.6 to about 0.8, or about 0.8 to about 1 ppm, determined according to the USP Hydroxypropyl Betadex monograph.

6.2.4. Other Compositional Characteristics

Hydroxypropyl beta-cyclodextrin compositions comprising a pharmaceutically active ingredient of the disclosure and, optionally, one or more additional therapeutic agents, such as the combination therapeutic agents described in Section 6.3.3., are provided herein.

In certain embodiments, the pharmaceutical composition comprises about 100 mg to about 2000 mg, such as about 100 to about 1800, about 100 to about 1600, about 100 to about 1500, about 100 to about 1200, about 100 to about 1000, about 100 to about 800, about 100 to about 600, about 100 to about 500, about 100 to about 400, about 100 to about 300, about 100 to about 200, about 200 to about 2000, about 200 to about 1800, about 200 to about 1600, about 200 to about 1500, about 200 to about 1200, about 200 to about 1000, about 200 to about 800, about 200 to about 600, about 200 to about 500, about 200 to about 400, about 200 to about 300, about 300 to about 2000, about 300 to about 1800, about 300 to about 1600, about 300 to about 1500, about 300 to about 1200, about 300 to about 1000, about 300 to about 800, about 300 to about 600, about 300 to about 500, about 300 to about 400, about 400 to about 2000, about 400 to about 1800, about 400 to about 1600, about 400 to about 1500, about 400 to about 1200, about 400 to about 1000, about 400 to about 800, about 400 to about 600, about 400 to about 500, about 500 to about 2000, about 500 to about 1800, about 500 to about 1600, about 500 to about 1500, about 500 to about 1200, about 500 to about 1000, about 500 to about 800, about 500 to about 600, about 600 to about 2000, about 600 to about 1800, about 600 to about 1600, about 600 to about 1500, about 600 to about 1200, about 600 to about 1000, about 600 to about 800, about 800 to about 2000, about 800 to about 1800, about 800 to about 1600, about 800 to about 1500, about 800 to about 1200, or about 800 to about 1000 mg of the pharmaceutically active ingredient. For example, the pharmaceutical composition can comprise about 100, about 200, about 300, about 400, about 500, about 600, about 800, about 1000, about 1200, about 1400, about 1500, about 1600, about 1800, or about 2000 mg of the pharmaceutically active ingredient.

In some embodiments, the pharmaceutical composition for administration, for example, a pharmaceutical composition suitable for intrathecal administration, has a concentration of about 10 mg/mL to about 200 mg/mL, such as about 10 to about 180, about 10 to about 150, about 10 to about 120, about 10 to about 100, about 10 to about 80, about 10 to about 60, about 10 to about 50, about 10 to about 40, about 10 to about 30, about 10 to about 20, about 20 to about 200, about 20 to about 180, about 20 to about 150, about 20 to about 120, about 20 to about 100, about 20 to about 80, about 20 to about 60, about 20 to about 50, about 20 to about 40, about 20 to about 30, about 30 to about 200, about 30 to about 180, about 30 to about 150, about 30 to about 120, about 30 to about 100, about 30 to about 80, about 30 to about 60, about 30 to about 50, about 30 to about 40, about 40 to about 200, about 40 to about 180, about 40 to about 150, about 40 to about 120, about 40 to about 100, about 40 to about 80, about 40 to about 60, about 40 to about 50, about 50 to about 200, about 50 to about 180, about 50 to about 150, about 50 to about 120, about 50 to about 100, about 50 to about 80, about 50 to about 60, about 60 to about 200, about 60 to about 180, about 60 to about 150, about 60 to about 120, about 60 to about 100, about 60 to about 80, about 80 to about 200, about 80 to about 180, about 80 to about 150, about 80 to about 120, about 80 to about 100, about 100 to about 200, about 100 to about 180, about 100 to about 150, about 100 to about 120, about 120 to about 200, about 120 to about 180, about 120 to about 150, about 150 to about 200, about 150 to about 180, or about 180 to about 200 mg/mL of the pharmaceutically active ingredient. For example, the pharmaceutical composition can have a concentration of about 10, about 20, about 30, about 40, about 50, about 60, about 70, about 80, about 90, about 100, about 110, about 120, about 130, about 140, about 150, about 160, about 170, about 180, about 190, or about 200 mg/mL of the pharmaceutically active ingredient. In certain embodiments, the pharmaceutical composition for intrathecal administration has a concentration of about 200 mg/mL of the pharmaceutically active ingredient.

In certain embodiments, the pharmaceutical compositions described herein exhibit a low level of ototoxicity when administered to an animal. In some embodiments, the pharmaceutical composition exhibits a lower ototoxicity than Trappsol® Cyclo. The ototoxicity can be assessed in vitro by toxicity in a House Ear Institute-organ of *Corti* 1 (HEI-OC1) cell or in vivo by a brainstem auditory evoked response (BAER) test in an animal, such as a mouse, a rat, a cat, a dog, a monkey, a chimpanzee, or a human. See, for example, Leigh-Paffenroth, E. et al. "Objective Measures of Ototoxicity," September 2005, vol. 9, No. 1, pages 10-16, in Perspectives on Hearing and Hearing Disorders: Research and Diagnostics, Special Interest Division 6 of the American Speech-Language-Hearing Association, incorporated herein by reference in its entirety.

In some embodiments, the pharmaceutical composition, e.g., a pharmaceutical composition suitable for intrathecal administration, has an osmolality in a range of from about 300 to about 450 mOsm/kg, e.g., about 300 to about 400, about 300 to about 350, about 350 to about 450, or about 350 to about 400 mOsm/kg. In some embodiments, the composition has an osmolality of about 300, about 320, about 350, about 380, about 400, about 420, or about 450 mOsm/kg.

Suitable diluents for pharmaceutical compositions as described herein, e.g., pharmaceutical compositions suitable for intrathecal or intracerebroventricular administration, include isotonic saline solutions. Compositions, such as pharmaceutical composition suitable for intrathecal administration, may also be diluted with Elliotts B® solution (buffered intrathecal electrolyte/dextrose injection from Lukare Medical, LLC, Scotch Plains, New Jersey, USA).

In some embodiments, the pharmaceutical composition for injection is made by dissolving the Active Pharmaceutical Ingredient (the mixture of beta-cyclodextrin molecules) in water, adding sodium chloride to 0.9% w/v, and adjusting pH to 6.0-8.0 as necessary with 0.01N sodium hydroxide. The pharmaceutical composition is then sterile filtered into vials and autoclaved. The product is stable and can be stored at 15-25° C.

The compositions will usually be supplied as part of a sterile, pharmaceutical composition that will normally include a pharmaceutically acceptable carrier. This composition can be in any suitable form (depending upon the desired method of administration). For example, the pharmaceutical composition can be formulated as an aqueous solution and administered by intrathecal injection or intrathecal infusion.

In some embodiments, pharmaceutical compositions comprise unit dose forms that contain an amount of a pharmaceutically active ingredient of the disclosure per dose. Such a unit can contain for example but without limitation about 5 mg to about 5 g, for example 5 mg to about 4 g, 5 mg to about 3 g, 5 mg to about 2 g, 5 mg to about 1 g, about 50 mg to about 5 g, about 50 mg to about 4 g, about 50 mg to about 3 g, about 50 mg to about 2 g, about 50 mg to about 1 g, about 200 mg to about 5 g, about 200 mg to about 4 g, about 200 mg to about 3 g, about 200 mg to about 2 g, about 200 mg to about 1 g, about 400 mg to about 5 g, about 400 mg to about 4 g, about 400 mg to about 3 g, about 400 mg to about 2 g, about 400 mg to about 1 g, about 500 mg to about 5 g, about 500 mg to about 4 g, about 500 mg to about 3 g, about 500 mg to about 2 g, about 500 mg to about 1 g, about 600 mg to about 5 g, about 600 mg to about 4 g, about 600 mg to about 3 g, about 600 mg to about 2 g, about 600 mg to about 1 g, about 800 mg to about 5 g, about 800 mg to about 4 g, about 800 mg to about 3 g, about 800 mg to about 2 g, about 800 mg to about 1 g, about 1 g to about 5 g, about 1 g to about 4 g, about 1 g to about 3 g, about 1 g to about 2 g, about 1200 mg to about 5 g, about 1200 mg to about 4 g, about 1200 mg to about 3 g, about 1200 mg to about 2 g, about 1400 mg to about 5 g, about 1400 mg to about 4 g, about 1400 mg to about 3 g, about 1400 mg to about 2 g, about 1600 mg to about 5 g, about 1600 mg to about 4 g, about 1600 mg to about 3 g, about 1600 mg to about 2 g, about 1800 mg to about 5 g, about 1800 mg to about 4 g, about 1800 mg to about 3 g, or about 1800 mg to about 2 g of the pharmaceutically active ingredient. Certain embodiments include unit doses that contain about 900 mg, about 1200 mg, and about 1800 mg of the pharmaceutically active ingredient.

In certain embodiments, the unit dose can contain between about 200 mg and about 900 mg of the pharmaceutically active ingredient of the disclosure, such as about 200 mg, about 250 mg, about 300 mg, about 350 mg, about 400 mg, about 450 mg, about 500 mg, about 550 mg, about 600 mg, about 650 mg, about 700 mg, about 750 mg, about 800 mg, about 850 mg, or about 900 mg of the pharmaceutically active ingredient.

Pharmaceutical compositions of the hydroxypropyl beta-cyclodextrin mixtures of the disclosure can be prepared for storage as lyophilized formulations or aqueous solutions by mixing the pharmaceutically active ingredient having the desired degree of purity with optional pharmaceutically-acceptable carriers, excipients or stabilizers typically employed in the art (all of which are referred to herein as "carriers"), i.e., buffering agents, stabilizing agents, preservatives, isotonifiers, non-ionic detergents, antioxidants, and other miscellaneous additives. See, Remington's Pharmaceutical Sciences, 16th edition (Osol, ed. 1980).

In some embodiments, buffering agents are used to help to maintain the pH in the range that approximates physiological conditions from about 2 mM to about 50 mM, such as about 2 to about 40, about 2 to about 30, about 2 to about 20, about 2 to about 10, about 10 to about 50, about 10 to about 40, about 10 to about 30, about 10 to about 20, about 20 to about 50, about 20 to about 40, about 20 to about 30, or about 40 to about 50 mM. For example, one or more buffering agents can be present at a concentration of about 2, about 5, about 10, about 15, about 20, about 25, about 30, about 35, about 40, about 45, or about 50 mM. Suitable buffering agents for use with the present disclosure include both organic and inorganic acids and salts thereof, such as citrate buffers (e.g., monosodium citrate-disodium citrate mixture, citric acid-trisodium citrate mixture, citric acid-monosodium citrate mixture, etc.), succinate buffers (e.g., succinic acid-monosodium succinate mixture, succinic acid-sodium hydroxide mixture, succinic acid-disodium succinate mixture, etc.), tartrate buffers (e.g., tartaric acid-sodium tartrate mixture, tartaric acid-potassium tartrate mixture, tartaric acid-sodium hydroxide mixture, etc.), fumarate buffers (e.g., fumaric acid-monosodium fumarate mixture, fumaric acid-disodium fumarate mixture, monosodium fumarate-disodium fumarate mixture, etc.), gluconate buffers (e.g., gluconic acid-sodium glyconate mixture, gluconic acid-sodium hydroxide mixture, gluconic acid-potassium glyuconate mixture, etc.), oxalate buffer (e.g., oxalic acid-sodium oxalate mixture, oxalic acid-sodium hydroxide mixture, oxalic acid-potassium oxalate mixture, etc.), lactate buffers (e.g., lactic acid-sodium lactate mixture, lactic acid-sodium hydroxide mixture, lactic acid-potassium lactate mixture, etc.) and acetate buffers (e.g., acetic acid-sodium acetate mixture, acetic acid-sodium hydroxide mixture, etc.). Additionally, phosphate buffers, histidine buffers and trimethylamine salts such as Tris can be used.

In some embodiments, preservatives are added to retard microbial growth, in amounts ranging from 0.01%-1% (w/v), such as 0.1%-1%, 0.2%-1%, 0.3%-1%, 0.5%-1%, 0.01%-0.5%, 0.02%-0.5%, 0.05%-0.5%, 0.1%-0.5%, 0.2%-0.5%, or 0.05%-0.2% (w/v). For example, a preservative in an amount of about 0.02%, about 0.05%, about 0.1%, about 0.2%, about 0.5%, about 0.8% (w/v) can be added. Suitable preservatives for use with the present disclosure include phenol, benzyl alcohol, meta-cresol, methyl paraben, propyl paraben, octadecyldimethylbenzyl ammonium chloride, benzalconium halides (e.g., chloride, bromide, and iodide), hexamethonium chloride, and alkyl parabens such as methyl or propyl paraben, catechol, resorcinol, cyclohexanol, and 3-pentanol.

In some embodiments, isotonifiers sometimes known as "stabilizers" are added to ensure isotonicity of liquid compositions of the present disclosure and include polyhydric sugar alcohols, for example trihydric or higher sugar alcohols, such as glycerin, erythritol, arabitol, xylitol, sorbitol and mannitol. Stabilizers refer to a broad category of excipients which can range in function from a bulking agent to an additive which solubilizes the therapeutic agent or helps to prevent denaturation or adherence to the container wall. Typical stabilizers can be polyhydric sugar alcohols (enumerated above); amino acids such as arginine, lysine, glycine, glutamine, asparagine, histidine, alanine, ornithine, L-leucine, 2-phenylalanine, glutamic acid, threonine, etc., organic sugars or sugar alcohols, such as lactose, trehalose, stachyose, mannitol, sorbitol, xylitol, ribitol, myoinisitol, galactitol, glycerol and the like, including cyclitols such as inositol; polyethylene glycol; amino acid polymers; sulfur containing reducing agents, such as urea, glutathione, thioctic acid, sodium thioglycolate, thioglycerol, α-monothioglycerol and sodium thio sulfate; low molecular weight polypeptides (e.g., peptides of 10 residues or fewer); proteins such as human serum albumin, bovine serum albumin, gelatin or immunoglobulins; hydrophylic polymers, such as polyvinylpyrrolidone monosaccharides, such as xylose, mannose, fructose, glucose; disaccharides such as lactose, maltose, sucrose and trisaccharides such as raffinose; and polysaccharides such as dextran. In some embodiments, stabilizers are present in the range from 0.1 to 10,000 weights per part of weight of pharmaceutically active ingredient, such as 0.1 to 1,000, 0.2 to 2,000, 0.5 to 5,000, 1 to 10,000, or 1 to 1,000 weights per part of weight of pharmaceutically active ingredient. For example, stabilizers can be present in about 0.2, about 0.5, about 1, about 5, about 10, about 20, about 50, about 100, about 200, about 500, about 1,000, about 2,000, about 5,000, or about 8,000 weights per part of weight of pharmaceutically active ingredient.

In some embodiments, ionic surfactants are added to help solubilize the therapeutic agent as well as to protect the active ingredient against agitation-induced aggregation. In some embodiments, non-ionic surfactants or detergents (also known as "wetting agents") are added to help solubilize the therapeutic agent as well as to protect the active ingredient against agitation-induced aggregation. Suitable non-ionic surfactants include polysorbates (20, 80, etc.), polyoxamers (184, 188 etc.), Pluronic polyols, polyoxyethylene sorbitan monoethers (TWEEN®-20, TWEEN®-80, etc.). In some embodiments, non-ionic surfactants are present in a range of from about 0.05 mg/mL to about 1.0 mg/mL, such as about 0.05 mg/mL to about 0.2 mg/mL, about 0.07 mg/mL to about 0.2 mg/mL, about 0.1 mg/mL to about 0.3 mg/mL, or about 0.1 mg/mL to about 0.5 mg/mL. For instance, non-ionic surfactants can be present in about 0.05, about 0.07, about 0.08, about 0.1, about 0.2, about 0.3, about 0.4, about 0.5, about 0.6, about 0.8, or about 1.0 mg/mL.

Additional miscellaneous excipients include bulking agents (e.g., starch), chelating agents (e.g., EDTA), antioxidants (e.g., ascorbic acid, methionine, vitamin E), and cosolvents.

In some embodiments, the pharmaceutical composition herein also contains a combination of therapeutic agents, e.g., a second therapeutic agent in addition to the pharmaceutically active ingredient of the disclosure (the mixture of beta-cyclodextrins described herein). Examples of suitable combination therapeutic agents are provided in Section 6.3.3. below.

In some embodiments, the pharmaceutical compositions described herein solubilize lipids in an aqueous medium. The aqueous medium can be, for example, distilled water or deionized water, or can be an aqueous environment, e.g., blood, cerebrospinal fluid, or lymphatic fluid, in the body of a subject. The solubilizing ability of the compositions can be typically measured by UV transmission properties of the solution, e.g., as monitored by UV spectrometry or by HPLC, with a decrease in transmission correlating with formation of a suspension within the solution. In some embodiments, the lipids that are solubilized comprise unesterified or esterified cholesterol; cholesterol metabolites, e.g., 7-ketocholesterol, 7β-hydroxycholesterol, 24S-hydroxycholesterol, 25-hydroxycholesterol, 27-hydroxycholesterol, and cholestane-3β,5α,6β-triol; sphingolipids; glycolipids; ceramides; gangliosides, e.g., GM2 ((2S,3R,4E)-3-Hydroxy-2-(octadecanoylamino) octadec-4-en-1-yl 2-acetamido-2-deoxy-β-D-galactopyranosyl-(1→4)-[5-acetamido-3,5-dideoxy-D-glycero-α-D-galacto-non-2-ulopyranonosyl-(2→3)]-β-D-galactopyranosyl-(1→4)-β-D-glucopyranoside) or GM3 (monosialodihexosylganglioside); or any combination thereof.

As used herein, a weight per volume ("weight/volume" or "w/v") solution refers to the weight of a solute dissolved in a volume of water. In an illustrative example, a 10% (w/v) solution of hydroxypropyl beta-cyclodextrins has 1 g of the solute in 10 mL of the aqueous solution. In another example, a 20% (w/v) solution of hydroxypropyl beta-cyclodextrins has 200 mg of the solute in 1 mL of the aqueous solution.

In some embodiments, 1 mL of a 20% (w/v) solution of the pharmaceutically active ingredient described herein solubilizes at least 2 mg, such as at least 3 mg, at least 4 mg, at least 5 mg, at least 6 mg, at least 7 mg, at least 8 mg, or at least 10 mg, of unesterified cholesterol in distilled water at room temperature when measured, e.g., by UV spectrometry, after about 24 hours. In some embodiments, about 200 mg of the pharmaceutically active ingredient solubilizes at least 2 mg, such as at least 3 mg, at least 4 mg, at least 5 mg, at least 6 mg, at least 7 mg, at least 8 mg, or at least 10 mg of unesterified cholesterol in distilled water at room temperature when measured after about 24 hours.

6.3. Methods of Treatment

The disclosure provides a method of treating Niemann-Pick disease Type C (NPC), such as Niemann-Pick disease Type C1 (NPC1) or Niemann-Pick disease Type C2 (NPC2), comprising administering to a subject having Niemann-Pick disease a therapeutically effective amount of a pharmaceutical composition as described herein.

As used herein, a "subject" is a mammal, such as a mouse, a rat, a cat, a dog, a cow, a pig, a horse. In some embodiments, the mammal is a primate, such as a monkey, a chimpanzee, or a human. For example, a subject can be a human subject, i.e., a human patient. In certain embodiments, the patient is a pediatric patient or an adult patient. Pediatric human patients include pediatric patients with disease characterized at early-infantile onset (less than 2 years of age), late-infantile onset (2 to less than 6 years of age), juvenile onset (6 to less than 15 years of age) and adolescent onset (15 years of age or greater).

The terms "treat", "treating" or "treatment" refer to administration of a pharmaceutical composition described herein so as to modulate beneficially a level of one or more lipid biomarkers or therapeutic effects as described in Section 6.3.4. compared to a baseline level. An exemplary treatment phase involves a repeat administration of a pharmaceutical composition described herein where the score of one or more domains of the NPC Severity Scale as defined in Section 6.3.4.2 is reduced compared to a prior baseline value.

The terms "maintain", "maintaining" or "maintenance" refer to administration of a pharmaceutical composition described herein to hold constant a baseline level of one or more biological effects as described in Section 6.3.4. A maintenance phase of administration may prevent progression of NPC as compared with no administration or administration of a placebo. An illustrative example of a maintenance phase is a repeat administration of a pharmaceutical composition described herein where the score of one or more domains of the NPC Severity Scale as defined in Section 6.3.4.2 is held at the same level as a baseline value.

6.3.1. Administration of the Hydroxypropyl Beta-Cyclodextrin Pharmaceutical Compositions In some embodiments, the method comprises administering about 200 mg to about 3000 mg, such as about 200 to about 2800, about 200 to about 2600, about 200 to about 2500, about 200 to about 2400, about 200 to about 2200, about 200 to about 2000, about 200 to about 1800, about 200 to about 1600, about 200 to about 1500, about 200 to about 1200, about 200 to about 1100, about 200 to about 1000, about 200 to about 800, about 200 to about 700, about 200 to about 600, about 200 to about 500, about 200 to about 400, about 200 to about 300; about 300 to about 3000, about 300 to about 2800, about 300 to about 2600, about 300 to about 2500, about 300 to about 2400, about 300 to about 2200, about 300 to about 2000, about 300 to about 1800, about 300 to about 1600, about 300 to about 1500, about 300 to about 1200, about 300 to about 1100, about 300 to about 1000, about 300 to about 800, about 300 to about 700, about 300 to about 600, about 300 to about 500, about 300 to about 400; such as from about 400 to about 3000, about 400 to about 2800, about 400 to about 2600, about 400 to about 2500, about 400 to about 2400, about 400 to about 2200, about 400 to about 2000, about 400 to about 1800, about 400 to about 1600, about 400 to about 1500, about 400 to about 1200, about 400 to about 1100, about 400 to about 1000, about 400 to about 800, about 400 to about 700, about 400 to about 600, about 400 to about 500; such as from about 500 to about 3000, about 500 to about 2800, about 500 to about 2600, about 500 to about 2500, about 500 to about 2400, about 500 to about 2200, about 500 to about 2000, about 500 to about 1800, about 500 to about 1600, about 500 to about 1500, about 500 to about 1200, about 500 to about 1100, about 500 to about 1000, about 500 to about 800, about 500 to about 700, about 500 to about 600; such as from about 600 to about 3000, about 600 to about 2800, about 600 to about 2600, about 600 to about 2500, about 600 to about 2400, about 600 to about 2200, about 600 to about 2000, about 600 to about 1800, about 600 to about 1600, about 600 to about 1500, about 600 to about 1200, about 600 to about 1100, about 600 to about 1000, about 600 to about 800, about 600 to about 700; such as from about 700 to about 3000, about 700 to about 2800, about 700 to about 2600, about 700 to about 2500, about 700 to about 2400, about 700 to about 2200, about 700 to about 2000, about 700 to about 1800, about 700 to about 1600, about 700 to about 1500, about 700 to about 1200, about 700 to about 1100, about 700 to about 1000, about 700 to about 800; such as from about 800 to about 3000, about 800 to about 2800, about 800 to about 2600, about 800 to about 2500, about 800 to about 2400, about 800 to about 2200, about 800 to about 2000, about 800 to about 1800, about 800 to about 1600, about 800 to about 1500, about 800 to about 1200, about 800 to about 1100, about 800 to about 1000; such as from about 1000 to about 3000, about 1000 to about 2800, about 1000 to about 2600, about 1000 to about 2500, about 1000 to about 2400, about 1000 to about 2200, about 1000 to about 2000, about 1000 to about 1800, about 1000 to about 1600, about 1000 to about 1500, about 1000 to about 1200, about 1000 to about 1100; such as from about 1100 to about 3000, about 1100 to about 2800, about 1100 to about 2600, about 1100 to about 2500, about 1100 to about 2400, about 1100 to about 2200, about 1100 to about 2000, about 1100 to about 1800, about 1100 to about 1600, about 1100 to about 1500, about 1100 to about 1200; such as from about 1200 to about 3000, about 1200 to about 2800, about 1200 to about 2600, about 1200 to about 2500, about 1200 to about 2400, about 1200 to about 2200, about 1200 to about 2000, about 1200 to about 1800, about 1200 to about 1600, about 1200 to about 1500; such as from about 1500 to about 3000, about 1500 to about 2800, about 1500 to about 2600, about 1500 to about 2500, about 1500 to about 2400, about 1500 to about 2200, about 1500 to about 2000, about 1500 to about 1800, about 1500 to about 1600; such as from about 1600 to about 3000, about 1600 to about 2800, about 1600 to about 2600, about 1600 to about 2500, about 1600 to about 2400, about 1600 to about 2200, about 1600 to about 2000, about 1600 to about 1800; such as from about 1800 to about 3000, about 1800 to about 2800, about 1800 to about 2600, about 1800 to about 2500, about 1800 to about 2400, about 1800 to about 2200, about 1800 to about 2000; such as from about 2000 to about 3000, about 2000 to about 2800, about 2000 to about 2600, about 2000 to about 2500, about 2000 to about 2400, about 2000 to about 2200; such as from about 2200 to about 3000, about 2200 to about 2800, about 2200 to about 2600, about 2200 to about 2500, about 2200 to about 2400; such as from about 2400 to about 3000, about 2400 to about 2800, about 2400 to about 2600, about 2400 to about 2500; such as from about 2500 to about 3000, about 2500 to about 2800, about 2500 to about 2600; such as from about 2600 to about 3000, about 2600 to about 2800; or about 2800 to about 3000 mg, of the pharmaceutically active ingredient to the subject per administration.

In some embodiments, the dosage schedule consists of administration once every week, once every two weeks, once every three weeks, once a month, once every two months, or once every three months. For example, the method can comprise administering about 200, about 300, about 400, about 500, about 600, about 700, about 800, about 900, about 1000, about 1200, about 1400, about 1500, about 1600, about 1800, about 2000, about 2200, about 2400, about 2500, or about 3000 mg of the pharmaceutically active ingredient to the subject per administration.

In some embodiments, the administering occurs in a single dose per administration. In other embodiments, the pharmaceutical composition is administered in divided doses, with the overall dose divided into two doses, three doses, or even four doses, per administration, e.g., over a week, two weeks, a month, two months, etc., specifically over two weeks. The composition may also be administered continuously, or in any effective range or value therein depending on the condition being treated, the route of administration and the age, weight and condition of the subject.

In some embodiments, the pharmaceutical compositions of the disclosure are suitable for intrathecal or intracerebroventricular administration. In certain embodiments, intrathecal administration of the pharmaceutical composition is through an intrathecal port. In certain of these embodiments, the port is a Celsite® port (B. Braun Medical, France). In certain embodiments, the intrathecal administration comprises administering as an intrathecal slow bolus (1-2 minute, depending on the volume administered) lumbar puncture injection (maximum rate of administration=4.5 mL/minute). In certain embodiments, the techniques of lumbar puncture include use of a non-cutting needle, such as a Whiteacre or Sprotte needle, insertion parallel to dural fibers, and replacing stylet prior to needle removal. In certain embodiments, prior to injection, a volume of CSF fluid equal to the volume to be administered is removed.

In another illustrative example, intracerebroventricular administration can be through an Ommaya reservoir.

For treatment of NPC described herein, an effective dose of the pharmaceutically active ingredient, the hydroxypropyl beta-cyclodextrin mixture, can range from about 0.001 to about 1000 mg/kg, such as about 0.1 to about 1000, about 1 to about 1000, about 10 to about 1000, about 20 to about 1000, about 50 to about 1000, about 100 to about 1000, about 200 to about 1000, about 300 to about 1000, about 400 to about 1000, about 500 to about 1000, about 600 to about 1000, about 800 to about 1000; such as from about 0.1 to about 800, about 1 to about 800, about 10 to about 800, about 20 to about 800, about 50 to about 800, about 100 to about 800, about 200 to about 800, about 300 to about 800, about 400 to about 800, about 500 to about 800, about 600 to about 800; such as from about 0.1 to about 600, about 1 to about 600, about 10 to about 600, about 20 to about 600, about 50 to about 600, about 100 to about 600, about 200 to about 600, about 300 to about 600, about 400 to about 600, about 500 to about 600; such as from about 0.1 to about 500, about 1 to about 500, about 10 to about 500, about 20 to about 500, about 50 to about 500, about 100 to about 500, about 200 to about 500, about 300 to about 500, about 400 to about 500; such as from about 0.1 to about 400, about 1 to about 400, about 10 to about 400, about 20 to about 400, about 50 to about 400, about 100 to about 400, about 200 to about 400, about 300 to about 400; such as from about 0.1 to about 300, about 1 to about 300, about 10 to about 300, about 20 to about 300, about 50 to about 300, about 100 to about 300, about 200 to about 300; such as from about 0.1 to about 200, about 1 to about 200, about 10 to about 200, about 20 to about 200, about 50 to about 200, about 100 to about 200; such as from about 0.1 to about 100, about 1 to about 100, about 10 to about 100, about 20 to about 100, about 50 to about 100; such as from about 0.1 to about 50, about 1 to about 50, about 10 to about 50, about 20 to about 50; such as from about 0.1 to about 20, about 1 to about 20, about 10 to about 20; such as from about 0.1 to about 10, about 1 to about 10; or about 0.1 to about 1 mg/kg.

In some embodiments, the method comprises a treatment phase wherein the administering occurs every week, every two weeks, every three weeks, or every month, in order to reduce symptoms of NPC.

In some embodiments, the method comprises a maintenance phase wherein the administering occurs every three weeks, every month, every two months, or every three months, in order to maintain a steady state of the disease.

In some embodiments, the pharmaceutical composition is administered as a bolus, followed by a continuous maintenance dose.

In certain embodiments, the pharmaceutical composition is administered monthly through intrathecal or intracerebroventricular administration. In certain embodiments, the pharmaceutical composition is administered continuously through intrathecal or intracerebroventricular administration.

In some embodiments, the method comprises a treatment phase wherein 900 mg of the pharmaceutically active ingredient is administered to the patient as initial doses and a maintenance phase wherein less than 900 mg of the pharmaceutically active ingredient is administered every other week by intrathecal administration.

6.3.2. Multiple Routes of Administration

In some embodiments, the method comprises administering the pharmaceutically active ingredient using multiple routes of administration. In certain embodiments, the method comprises administering the pharmaceutically active ingredient (i) intrathecally or by intracerebroventricular administration, and (ii) intravenously. These embodiments usefully allow reduction of cholesterol accumulation in both the central nervous system and peripheral organs.

In some embodiments, the intravenous administration comprises administering about 200 mg/kg to about 4000 mg/kg of the beta-cyclodextrin mixture by intravenous infusion over 6 to 8 hours to the patient. In some embodiments, the intravenous administration comprises administering about 500 mg/kg to about 4000 mg/kg of the beta-cyclodextrin mixture by intravenous infusion over 6 to 8 hours to the patient.

In typical embodiments, the pharmaceutical composition comprises about 200 mg/mL of the beta-cyclodextrin mixture. In certain other embodiments, the pharmaceutical composition comprises about 250 mg/mL of the beta-cyclodextrin mixture. In some embodiments, the pharmaceutical composition is administered once every three days, once every week, once every two weeks, once every three weeks, once every month, once every two months, or once every three months. In certain embodiments, intravenous administration is started shortly after birth. In certain other embodiments, intravenous administration is started after intrathecal (or intracerebroventricular) administration is initiated. In some embodiments, the liver volume, the spleen volume, and/or liver enzyme activity of the patient are monitored to determine the efficacy of the treatment, and for adjustment of dosage schedule.

6.3.3. Combination Therapy

Described below are combination therapy methods in which the hydroxypropyl beta-cyclodextrin pharmaceutical compositions of the disclosure can optionally be utilized. In some embodiments, the combination methods of the disclosure involve the administration of at least two agents to a subject, the first of which is the hydroxypropyl beta-cyclodextrin mixture described herein (for example, in a pharmaceutical composition described herein), and the additional agent(s) is a combination therapeutic agent. The hydroxypropyl beta-cyclodextrin mixture and the combination therapeutic agent(s) can be administered simultaneously (e.g., in a pharmaceutical composition as described herein), sequentially, or separately.

The combination therapy methods of the present disclosure can result in a greater than additive effect, i.e., a synergistic effect, for example, providing therapeutic benefits greater than the expected sum of the benefit from the hydroxypropyl beta-cyclodextrin mixture and the combination therapeutic agent when each is administered individually.

In some embodiments, the hydroxypropyl beta-cyclodextrin mixture and the combination therapeutic agent are administered concurrently, either simultaneously or successively. As used herein, the hydroxypropyl beta-cyclodextrin mixture and the combination therapeutic agent are said to be administered successively if they are administered to the subject on the same day, for example, during the same subject visit. Successive administration can occur 1, 2, 3, 4, 5, 6, 7, or 8 hours apart. In contrast, the hydroxypropyl beta-cyclodextrin mixture and the combination therapeutic agent are said to be administered separately if they are administered to the subject on different days, for example, the hydroxypropyl beta-cyclodextrin mixture and the combination therapeutic agent can be administered at a 1-day, 2-day or 3-day, 1-week, 2-week or monthly intervals. In the methods of the present disclosure, administration of the hydroxypropyl beta-cyclodextrin mixture can precede or follow administration of the combination therapeutic agent.

As a non-limiting example, the hydroxypropyl beta-cyclodextrin mixture and the combination therapeutic agent can be administered concurrently for a period of time, followed by a second period of time in which the administration of the hydroxypropyl beta-cyclodextrin mixture and the combination therapeutic agent is alternated.

Because of the potentially synergistic effects of administering the hydroxypropyl beta-cyclodextrin mixture and the combination therapeutic agent, such agents can be administered as a therapeutically effective combination in amounts that are not therapeutically effective if one or both of the agents were administered alone.

In certain embodiments, the combination therapeutic agent is a vitamin E or a derivative thereof, an enzyme replacement therapy, a steroid, a glucosyl transferase enzyme inhibitor, a histone deacetylase (HDAC) inhibitor, or a molecular chaperone activator.

Vitamin E or vitamin E derivatives include but are not limited to alpha-tocopherol, delta-tocopherol, and tocopherol derivatives. In some embodiments, vitamin E derivatives include esterified tocopherols, e.g., tocopheryl acetate, and chemically related tocopherol derivatives such as those described in PCT Publication No. WO 2014/078573, incorporated herein by reference in its entirety.

Enzyme replacement therapies include but are not limited to agalsidase beta (Fabrazyme®), imiglucerase (Cerezyme®), verlaglucerase alfa (VPRIV™), taliglucerase (Elelyso™), alglucosidase alfa (Myozyme® or Lumizyme®), laronidase (Aldurazyme®), idursulfase intravenous (Elaprase®), and galsulfase (Naglazyme™).

Steroids include but are not limited to neurosteroids, such as allopregnanolone and ganaxolone.

Glucosyl transferase enzyme inhibitors include but are not limited to glucoceramide synthase inhibitors, such as miglustat (Zavesca®).

HDAC inhibitors include but are not limited to vironostat, romidepsin, trichostatin A, valproate, butyrate, trapoxins, and apicidin.

The molecular chaperone activators include but are not limited to arimoclomol.

6.3.4. Biological Effects of the Methods 6.3.4.1. Effect on Biomarkers

In some embodiments, the methods of treating NPC comprise maintaining or modulating levels of one or more lipids, such as unesterified cholesterol or gangliosides, that have accumulated in one or more body organs, e.g., in the brain, and that lead to disease symptoms. In certain embodiments, modulating levels of one or more lipids includes lowering levels of one or more lipids. In some embodiments, the efficacy of the methods is determined by measuring the level of storage of one or more lipids before (baseline level) and after the start of treatment. For example, in some embodiments, the subject methods lower levels of one or more lipids by about 20%, about 25%, about 30%, about 35%, about 40%, about 45%, about 50%, about 55%, about 60, about 65%, about 70%, about 75%, about 80%, about 85%, about 90%, about 95%, or about 97% relative to a baseline level.

In some embodiments, the subject methods lower levels of one or more lipids by 20%+5%, 25%+5%, 30%+5%, 35%+5%, 40%+5%, 45%+5%, 50%+5%, 55%+5%, 60%+5%, 65%+5%, 70%+5%, 75%+5%, 80%+5%, 85%+5%, 90%+5%, or 95%+5%, relative to a baseline level.

In some embodiments, the subject methods lower levels of one or more lipids by 20%+3%, 25%±3%, 30%±3%, 35%±3%, 40%±3%, 45%±3%, 50%±3%, 55%±3%, 60%±3%, 65%±3%, 70%±3%, 75%±3%, 80%±3%, 85%±3%, 90%±3%, 95%±3%, or 97%±3%, relative to a baseline level.

In some embodiments, the subject methods lower levels of one or more lipids by 20%±2%, 25%±2%, 30%±2%, 35%±2%, 40%±2%, 45%±2%, 50%±2%, 55%±2%, 60%±2%, 65%±2%, 70%±2%, 75%±2%, 80%±2%, 85%±2%, 90%±2%, 95%±2%, or 97%±2%, relative to a baseline level.

In some embodiments, the subject methods lower levels of one or more lipids by at least about 20%, such as at least about 25%, about 30%, about 35%, about 40%, about 45%, about 50%, about 55%, about 60%, about 65%, about 70%, about 75%, about 80%, about 85%, about 90%, about 95%, or about 97%, relative to a baseline level.

In some embodiments, the subject methods lower levels of one or more lipids in a range of from about 20% to about 97%, such as about 20% to about 95%, about 20% to about 90%, about 20% to about 85%, about 20% to about 80%, about 20% to about 75%, about 20% to about 70%, about 20% to about 65%, about 20% to about 60%, about 20% to about 55%, about 20% to about 50%, about 20% to about 45%, about 20% to about 40%, about 20% to about 35%, about 20% to about 30%, about 20% to about 25%; such as from about 25% to about 97%, about 25% to about 95%, about 25% to about 90%, about 25% to about 85%, about 25% to about 80%, about 25% to about 75%, about 25% to about 70%, about 25% to about 65%, about 25% to about 60%, about 25% to about 55%, about 25% to about 50%, about 25% to about 45%, about 25% to about 40%, about 25% to about 35%, about 25% to about 30%; such as from about 30% to about 97%, about 30% to about 95%, about 30% to about 90%, about 30% to about 85%, about 30% to about 80%, about 30% to about 75%, about 30% to about 70%, about 30% to about 65%, about 30% to about 60%, about 30% to about 55%, about 30% to about 50%, about 30% to about 45%, about 30% to about 40%, about 30% to about 35%; such as from about 35% to about 97%, about 35% to about 95%, about 35% to about 90%, about 35% to about 85%, about 35% to about 80%, about 35% to about 75%, about 35% to about 70%, about 35% to about 65%, about 35% to about 60%, about 35% to about 55%, about 35% to about 50%, about 35% to about 45%, about 35% to about 40%; such as from about 40% to about 97%, about 40% to about 95%, about 40% to about 90%, about 40% to about 85%, about 40% to about 80%, about 40% to about 75%, about 40% to about 70%, about 40% to about 65%, about 40% to about 60%, about 40% to about 55%, about 40% to about 50%, about 40% to about 45%; such as from about 45% to about 97%, about 45% to about 95%, about 45% to about 90%, about 45% to about 85%, about 45% to about 80%, about 45% to about 75%, about 45% to about 70%, about 45% to about 65%, about 45% to about 60%, about 45% to about 55%, about 45% to about 50%; such as from about 50% to about 97%, about 50% to about 95%, about 50% to about 90%, about 50% to about 85%, about 50% to about 80%, about 50% to about 75%, about 50% to about 70%, about 50% to about 65%, about 50% to about 60%, about 50% to about 55%; such as from about 55% to about 97%, about 55% to about 95%, about 55% to about 90%, about 55% to about 85%, about 55% to about 80%, about 55% to about 75%, about 55% to about 70%, about 55% to about 65%, about 55% to about 60%; such as from about 60% to about 97%, about 60% to about 95%, about 60% to about 90%, about 60% to about 85%, about 60% to about 80%, about 60% to about 75%, about 60% to about 70%, about 60% to about 65%; such as from about 65% to about 97%, about 65% to about 95%, about 65% to about 90%, about 65% to about 85%, about 65% to about 80%, about 65% to about 75%, about 65% to about 70%; such as from about 70% to about 97%, about 70% to about 95%, about 70% to about 90%, about 70% to about 85%, about 70% to about 80%, about 70% to about 75%; such as from about 75% to about 97%, about 75% to about 95%, about 75% to about 90%, about 75% to about 85%, about 75% to about 80%; such as from about 80% to about 97%, about 80% to about 95%, about 80% to about 90%, about 80% to about 85%; such as from about 85% to about 97%, about 85% to about 95%, about 85% to about 90%; such as from about 90% to about 97%, about 90% to about 95%, or about 95% to about 97%, relative to a baseline level.

In an NPC patient, measuring the level of storage of one or more lipids can be performed by monitoring one or more biomarkers in a sample of cerebrospinal fluid (CSF), plasma, or urine. In some embodiments, CSF is used to determine the excretion levels of the one or more lipids directly. In some embodiments, a downstream protein biomarker that has been modulated by the change in the levels of one or more lipids is monitored. In some embodiments, the method comprises administering an amount of the pharmaceutically active ingredient sufficient to modulate, e.g., lower relative to a baseline level, the level in cerebrospinal fluid of one or more of: tau protein, amyloid peptide, neurofilament light protein (NFL), glial fibrillary acidic protein (GFAP), sterol, oxysterol, chitotriosidase activity, calbindin, lysosomal-associated membrane protein 1 (LAMP-1), GM2 or GM3 ganglioside, sphingosine, and sphingosine-1-phosphate (S1P).

In some embodiments, plasma samples are used to determine the levels of one or more lipids, e.g., cholesterol or cholesterol metabolites, present in the blood before and after the start of treatment. In some embodiments, the method comprises administering an amount of the pharmaceutically active ingredient sufficient to modulate, e.g., lower relative to a baseline level, the level in plasma of one or more of: 7-ketocholesterol, 7β-hydroxycholesterol, 24S-hydroxycholesterol, 25-hydroxycholesterol, 27-hydroxycholesterol, and cholestane-3β,5α, 6β-triol.

Monitoring other lipids, such as metabolites like 3β-sulfoxy-7β-N-acetylglucosaminyl-5-cholen-24-oic acid (SNAG-$\Delta^5$-CA), glycine-conjugated 3β-sulfoxy-7β-N-acetylglucosaminyl-5-cholen-24-oic acid (SNAG-$\Delta^5$-CG), and taurine-conjugated 3β-sulfoxy-7β-N-acetylglucosaminyl-5-cholen-24-oic acid (SNAG-$\Delta^5$-CT), that have been reported in the urine of NPC1 patients may provide useful biomarkers (Maekawa, M. et al. "Focused metabolomics using liquid chromatography/electrospray ionization tandem mass spectrometry for analysis of urinary conjugated cholesterol metabolites from patients with Niemann-Pick disease type C and 3β-hydroxysteroid dehydrogenase deficiency." Annals of Clinical Biochemistry OnlineFirst, published Mar. 2, 2015). In some embodiments, the method comprises administering an amount of the pharmaceutically active ingredient sufficient to modulate, e.g., lower relative to a baseline level, the level in urine of one or more of: 3β-sulfoxy-7β-N-acetylglucosaminyl-5-cholen-24-oic acid (SNAG-$\Delta^5$-CA), glycine-conjugated 3β-sulfoxy-7β-N-acetylglucosaminyl-5-cholen-24-oic acid (SNAG-$\Delta^5$-CG), and taurine-conjugated 3β-sulfoxy-7β-N-acetylglucosaminyl-5-cholen-24-oic acid (SNAG-$\Delta^5$-CT).

6.3.4.2. Therapeutic Effects

In some embodiments, the methods of the disclosure have a beneficial effect on one or more symptoms of NPC.

One measure to characterize and quantify NPC disease progression is through the use of the NPC Severity Scale, which determines clinical signs and symptoms in nine major domains (ambulation, cognition, eye movement, fine motor skills, hearing, memory, seizures, speech, and swallowing) and eight minor domains (auditory brainstem response, behavior, gelastic cataplexy, hyperreflexia, incontinence, narcolepsy, psychiatric, and respiratory problems) (Yanjanin et al., "Linear Clinical Progression, Independent of Age of Onset, in Niemann-Pick Disease, Type C," *Am. J. Med. Genet. Part B* 153B: 132-140 (2010)) ("Yanjanin 2010"). The overall clinical severity score (or "overall score") is the aggregate of all the assessments in each of the major and minor domains, and is determined by the sum of all the individual domain scores See Table 1, below; see also FIG. 1.

TABLE 1

NPC Clinical Severity Scale (from Yanjanin, 2010)

| Eye Movement | Score | Ambulation | Score |
|---|---|---|---|
| Normal eye movement | 0 | Normal | 0 |
| Mild vertical supranuclear gaze palsy (VSGP) detected by physician only | 1 | Clumsy | 1 |
| Functional VSGP, noted by family or compensation with head movements | 2 | Ataxic unassisted gait or not walking by 18 months | 2 |
| Total VSGP, abnormal horizontal saccades may be present | 3 | Assisted ambulation or not walking by 24 months | 4 |
| Total ophthalmoplegia (vertical and horizontal saccades absent) | 5 | Wheelchair dependent | 5 |
| **Speech** | **Score** | **Swallow** | **Score** |
| Normal speech | 0 | Normal, no dysphagia | 0 |
| Mild dysarthria (easily understood) | 1 | Cough while eating | 1 |
| | | Intermittent dysphagia* w/Liquids | +1 |
| | | w/Solids | +1 |
| Severe dysarthria (difficult to understand) | 2 | Dysphagia* w/Liquids | +2 |
| | | w/Solids | +2 |
| Non-verbal/functional communication skills for needs | 3 | Nasogastric tube or gastric tube for supplemental feeding | 4 |
| Minimal communication | 5 | Nasogastric tube or gastric tube feeding only | 5 |
| **Fine Motor Skills** | **Score** | **Cognition** | **Score** |
| Normal | 0 | Normal | 0 |
| Slight dysmetria/dystonia (independent manipulation) | 1 | Mild learning delay, grade appropriate for age | 1 |
| Mild dysmetria/Dystonia (requires little to no assistance, able to feed self without difficulty) | 2 | Moderate learning delay, individualized curriculum or modified work setting | 3 |
| Moderate dysmetria/dystonia (limited fine motor skills, difficulty feeding self) | 4 | Severe delay/plateau, no longer in school or no longer able to work, some loss of cognitive function | 4 |
| Severe Dysmetria/Dystonia (gross motor limitation, requires assistance for self-care activities) | 5 | Minimal cognitive function | 5 |
| **Hearing (sensineural)** | **Score** | **Memory** | **Score** |
| Normal hearing (all tones ≤15 dB HL) | 0 | Normal | 0 |
| High frequency hearing loss (PTA** ≤15 dB HL, >15 dB HL in high frequencies) | 1 | Mild short-term or long-term memory loss | 1 |
| | | Moderate short-term or long-term memory loss (gets lost) | 2 |
| Slight-mild hearing loss (PTA 16-44 dB HL) | 2 | Difficulty following commands | 3 |

TABLE 1-continued

| NPC Clinical Severity Scale (from Yanjanin, 2010) | | | |
|---|---|---|---|
| Moderate hearing loss (PTA 45-70 dB HL) | 3 | Unable to follow commands or short-and long- term memory loss | 4 |
| Severe hearing loss (PTA 71-90 dB HL) | 4 | | |
| Profound hearing loss (PTA >90 dB HL) | 5 | Minimal memory | 5 |
| **Seizures** | **Score** | | |
| No history of seizures | 0 | | |
| Hx of single seizure | 1 | | |
| Rare seizures | 2 | | |
| Seizures, well controlled with meds | 3 | | |
| Seizures, difficult to control with meds | 5 | | |
| **Modifiers** | **Score** | **Modifiers** | **Score** |
| Gelastic cataplexy | | Hyperreflexia | |
| No history | 0 | None | 0 |
| Definitive history | +1 | Mild (3+) | +1 |
| Frequent (every month) | +2 | Severe (+clonus) | +2 |
| Narcolepsy | | Incontinence | |
| No history | 0 | No problems | 0 |
| Definitive history | +1 | Occasional | +1 |
| Frequent (every month) | +2 | Frequent | +2 |
| Behavior | | Auditory Brainstem Response (ABR) | |
| No problems | 0 | Normal | 0 |
| Hx of ADHD, aggressive | +1 | Abnormal | +1 |
| Harmful to self/others | +2 | Absent | +2 |
| Psychiatric | | Respiratory | |
| No problems | 0 | No problems | 0 |
| Hx of mild depression | +1 | Hx pneumonia | +1 |
| Hx of major depression, hallucinations, or psychotic episodes | +2 | Pneumonia >2x/year or active therapeutic intervention | +2 |

*Score is additive within these two subsections

**PTA = pure tone average-reported on the audiogram

In some embodiments, the method comprises maintaining or reducing one or more domain scores of the NPC Severity Scale selected from: ambulation, fine motor skills, cognition, speech, swallowing, eye movement, memory, hearing, seizures, auditory brainstem response, behavior, gelastic cataplexy, hyperreflexia, incontinence, narcolepsy, psychiatric, and respiratory problems. In some embodiments, the method comprises maintaining or reducing one or more domain scores of the NPC Severity Scale selected from: ambulation, fine motor skills, cognition, speech, swallowing, eye movement, memory, hearing, and seizures. In some embodiments, the method comprises maintaining or reducing one or more domain scores of NPC Severity Scale selected from: ambulation, fine motor skills, cognition, speech, swallowing, memory, and seizures. In some embodiments, the method comprises maintaining or reducing one or more domain scores of the NPC Severity Scale selected from: ambulation, fine motor skills, cognition, and swallowing.

In some embodiments, treatment that improves the condition of a patient comprises reducing the score of one or more domains of the NPC Severity Scale compared to a baseline score. In some embodiments, the reduction in the score ranges from about 20% to about 95%, such as about 30% to about 95%, about 40% to about 95%, about 50% to about 95%, about 60% to about 95%, about 70% to about 95%, about 80% to about 95%, about 90% to about 95%; such as from about 30% to about 90%, about 40% to about 90%, about 50% to about 90%, about 60% to about 90%, about 70% to about 90%, about 80% to about 90%; such as from about 20% to about 80%, about 30% to about 80%, about 40% to about 80%, about 50% to about 80%, about 60% to about 80%, about 70% to about 80%; such as from about 20% to about 70%, about 30% to about 70%, about 40% to about 70%, about 50% to about 70%, about 60% to about 70%; such as from about 20% to about 60%, about 30% to about 60%, about 40% to about 60%, about 50% to about 60%; such as from about 20% to about 50%, about 30% to about 50%, about 40% to about 50%; such as from about 20% to about 40%, about 30% to about 40%; or about 20% to about 30%, compared to a baseline score. For example, the reduction in the score can be about 20%, about 30%, about 40%, about 50%, about 60%, about 70%, about 80%, about 90%, or about 95%, compared to a baseline score.

In some embodiments, the subject methods reduce the score of one or more domains by 20%±5%, 25%±5%, 30%±5%, 35%±5%, 40%±5%, 45%±5%, 50%±5%, 55%±5%, 60%±5%, 65%±5%, 70%±5%, 75%±5%, 80%±5%, 85%±5%, 90%±5%, or 95%±5%, relative to a baseline level.

In some embodiments, the subject methods reduce the score of one or more domains by 20%±3%, 25%±3%, 30%±3%, 35%±3%, 40%±3%, 45%±3%, 50%±3%, 55%±3%, 60%±3%, 65%±3%, 70%±3%, 75%±3%, 80%±3%, 85%±3%, 90%±3%, 95%±3%, or 97%±3%, relative to a baseline level.

In some embodiments, the subject methods reduce the score of one or more domains by 20%±2%, 25%±2%, 30%±2%, 35%±2%, 40%±2%, 45%±2%, 50%±2%, 55%±2%, 60%±2%, 65%±2%, 70%±2%, 75%±2%, 80%±2%, 85%±2%, 90%±2%, 95%±2%, or 97%±2%, relative to a baseline level.

In some embodiments, treatment that improves the condition of a patient comprises reducing the overall score of the NPC Severity Scale as compared to a baseline overall score. In some embodiments, the reduction in the overall score ranges from about 20% to about 97%, such as about 25% to about 97%, about 30% to about 97%, about 35% to about 97%, about 40% to about 97%, about 45% to about 97%, about 50% to about 97%, about 55% to about 97%, about 60% to about 97%, about 65% to about 97%, about 70% to about 97%, about 75% to about 97%, about 80% to about 97%, about 85% to about 97%, about 90% to about 97%; such as from about 20% to about 95%, about 25% to about 95%, about 30% to about 95%, about 35% to about 95%, about 40% to about 95%, about 45% to about 95%, about 50% to about 95%, about 55% to about 95%, about 60% to about 95%, about 65% to about 95%, about 70% to about 95%, about 75% to about 95%, about 80% to about 95%, about 85% to about 95%, about 90% to about 95%; such as from about 20% to about 90%, about 25% to about 90%, about 30% to about 90%, about 35% to about 90%, about 40% to about 90%, about 45% to about 90%, about 50% to about 90%, about 55% to about 90%, about 60% to about 90%, about 65% to about 90%, about 70% to about 90%, about 75% to about 90%, about 80% to about 90%, about 85% to about 90%; such as from about 20% to about 85%, about 25% to about 85%, about 30% to about 85%, about 35% to about 85%, about 40% to about 85%, about 45% to about 85%, about 50% to about 85%, about 55% to about 85%, about 60% to about 85%, about 65% to about 85%, about 70% to about 85%, about 75% to about 85%, about 80% to about 85%; such as from about 20% to about 80%, about 25% to about 80%, about 30% to about 80%, about 35% to about 80%, about 40% to about 80%, about 45% to about 80%, about 50% to about 80%, about 55% to about 80%, about 60% to about 80%, about 65% to about 80%, about 70% to about 80%, about 75% to about 80%; such as from about 20% to about 75%, about 25% to about 75%, about 30% to about 75%, about 35% to about 75%, about 40% to about 75%, about 45% to about 75%, about 50% to about 75%, about 55% to about 75%, about 60% to about 75%, about 65% to about 75%, about 70% to about 75%; such as from about 20% to about 70%, about 25% to about 70%, about 30% to about 70%, about 35% to about 70%, about 40% to about 70%, about 45% to about 70%, about 50% to about 70%, about 55% to about 70%, about 60% to about 70%, about 65% to about 70%; such as from about 20% to about 65%, about 25% to about 65%, about 30% to about 65%, about 35% to about 65%, about 40% to about 65%, about 45% to about 65%, about 50% to about 65%, about 55% to about 65%, about 60% to about 65%; such as from about 20% to about 60%, about 25% to about 60%, about 30% to about 60%, about 35% to about 60%, about 40% to about 60%, about 45% to about 60%, about 50% to about 60%, about 55% to about 60%; such as from about 20% to about 55%, about 25% to about 55%, about 30% to about 55%, about 35% to about 55%, about 40% to about 55%, about 45% to about 55%, about 50% to about 55%; such as from about 20% to about 50%, about 25% to about 50%, about 30% to about 50%, about 35% to about 50%, about 40% to about 50%, about 45% to about 50%; such as from about 20% to about 45%, about 25% to about 45%, about 30% to about 45%, about 35% to about 45%, about 40% to about 45%; such as from about 20% to about 40%, about 25% to about 40%, about 30% to about 40%, about 35% to about 40%; such as from about 20% to about 35%, about 25% to about 35%, about 30% to about 35%; such as from about 20% to about 30%, about 25% to about 30%; or such as from about 20% to about 25%, compared to a baseline overall score. For example, the reduction in overall score of the NPC Severity Scale can be about 20%, about 25%, about 30%, about 35%, about 40%, about 45%, about 50%, about 55%, about 60%, about 65%, about 70%, about 75%, about 80%, about 85%, about 90%, about 95%, or about 97%, compared to a baseline overall score.

In some embodiments, the subject methods reduce the overall score by 20%±5%, 25%±5%, 30%±5%, 35%±5%, 40%±5%, 45%±5%, 50%±5%, 55%±5%, 60%±5%, 65%±5%, 70%±5%, 75%±5%, 80%±5%, 85%±5%, 90%±5%, or 95%±5%, relative to a baseline overall level.

In some embodiments, the subject methods reduce the overall score by 20%±3%, 25%±3%, 30%±3%, 35%±3%, 40%±3%, 45%±3%, 50%±3%, 55%±3%, 60%±3%, 65%±3%, 70%±3%, 75%±3%, 80%±3%, 85%±3%, 90%±3%, 95%±3%, or 97%±3%, relative to a baseline overall level.

In some embodiments, the subject methods reduce the overall score by 20%±2%, 25%±2%, 30%±2%, 35%±2%, 40%±2%, 45%±2%, 50%±2%, 55%±2%, 60%±2%, 65%±2%, 70%±2%, 75%±2%, 80%±2%, 85%±2%, 90%±2%, 95%±2%, or 97%±2%, relative to a baseline overall level.

In some embodiments, a maintenance phase that holds constant the condition of a patient comprises holding a score of a domain of the NPC Severity Scale within a range compared to a baseline score. In some embodiments, the maintenance in the score refers to a score within about 15%, such as within about 10% or about 5% of the score at a baseline level.

In some embodiments, the subject methods result in a score that is within 5%±3%, 10%±3%, or 15%±3%, relative to a baseline score. In some embodiments, the subject methods result in a score that is within 5%±2%, 10%±2%, or 15%±2%, relative to a baseline score.

In some embodiments, a maintenance phase that holds constant the condition of a patient comprises holding an overall score of NPC Severity Scale within a range compared to a baseline overall score. In some embodiments, the maintenance in the overall score refers to an overall score within about 15%, such as within about 10% or about 5% of an overall score at a baseline level.

In some embodiments, the subject methods result in an overall score that is within 5%±3%, 10%±3%, or 15%±3%, relative to a baseline overall score. In some embodiments, the subject methods result in an overall score that is within 5%±2%, 10%±2%, or 15%±2%, relative to a baseline overall score.

Other measures that can be used to characterize the efficacy of the methods of the disclosure include a global domain comprising a blinded Clinician clinical global impression of change (CGI-Clinician) or a Caregiver clinical global impression of change (CGI-Caregiver) following treatment, a Timed Up and Go (TUG) test, 9-hole peg test (9-HPT), and quality-of-life measures, such as a United States National Institutes of Health PROMIS-PRO (Patient Reported Outcomes Measurement Information System-Patient Reported Outcomes) Caregiver Quality of Life rating.

The methods of the disclosure can be characterized by clinical safety measures, which includes one or more of:

characterization and severity of clinical adverse events; audiologic testing, e.g., by BAER testing; clinical laboratory tests, e.g., hematology, clinical chemistry, coagulation, urinalysis, CSF analysis; vital signs; physical and neurological exam findings; and electrocardiograms.

6.3.5. Treatment of Other Lysosomal Storage Disorders

As demonstrated in Example 8 (see Section 7.8.2.5), the hydroxypropyl beta-cyclodextrin mixtures described herein have significant effects on genes related to autophagy, demonstrating that the pharmaceutically active ingredient and pharmaceutical compositions described herein will be effective in ameliorating certain consequences of the defects in other lysosomal storage disorders.

Accordingly, in another aspect, methods are presented for treating lysosomal storage disorders other than Niemann-Pick Disease Type C (NPC), comprising administering to a subject having a lysosomal storage disorder other than NPC a therapeutically effective amount of a pharmaceutical composition as described herein.

In various embodiments, the lysosomal storage disorder is selected from Aspartylglucosaminuria, Wolman disease, Cystinosis, Danon disease, Fabry disease, Farber disease, Fucosidosis, Gaucher disease, GM1-Gangliosidosis types I/II/III, GM2-Gangliosidosis, alpha-Mannosidosis types I/II, beta-Mannosidosis, Metachromatic leukodystrophy, Sialidosis types I/II, Mucolipidosis type IV, Scheie syndrome, Hunter syndrome, Sanfilippo syndrome A, Sanfilippo syndrome B, Sanfilippo syndrome C, Sanfilippo syndrome D, Galactosialidosis types I/II, Krabbe disease, Sandhoff disease, Vogt-Spielmeyer disease, Hurler syndrome, Niemann-Pick disease other than Niemann-Pick Type C, I-cell disease (mucolipidosis II), pseudo-Hurler polydystrophy, Morquio syndrome, Maroteaux-Lamy syndrome, Sly syndrome, Mucopolysaccharidosis type IX, Multiple sulfatase deficiency, Batten disease, Tay-Sachs disease, Pompe disease, Batten disease, Batten disease, late infantile, Northern Epilepsy, Pycnodysostosis, Schindler disease, Sialuria, and Salla disease.

In certain embodiments, the lysosomal storage disorder is Tay-Sachs disease, Sphingolipidoses, Gaucher disease, Mucolipidosis, Galactosialidosis, Salla disorder, Cystinosis, Danon disease, Fabry disease, Farber disease, Lipofuscinoses, Pompe disease, Gangliodisosis, ISSD, Krabbe disease, Niemann-Pick disease other than NPC, leukodystrophy, Hurler disease, Scheie disease, Hunter disease, San Filippo disease, Sandhoff disease, Schinder disease, Batten disorder, or Wolman disease.

In a further embodiment, the lysosomal storage disorder is Niemann-Pick disease other than NPC, Tay-Sachs disease, Fabry disease, Farber disease, San Filippo disease, Batten disorder, or Wolman disease.

7. EXAMPLES

The following examples are provided by way of exemplification and illustration, not limitation.

7.1. Example 1: Phase I Clinical Trial for Niemann-Pick Disease Type C

A Phase 1 clinical trial was initiated by NIH using a commercially available parenteral grade hydroxypropyl beta-cyclodextrin mixture according to the following protocol.

7.1.1. Protocol

In this Phase 1, non-randomized, open-label, single-center study conducted by the NIH, hydroxypropyl beta-cyclodextrin (Kleptose® HPB, Roquette) is administered intrathecally via lumbar injection to drug-naive cohorts of 3 patients each at initial doses of 200 mg, followed by escalation to 300, 400 mg, and 900 mg. All patients in the cohort (three patients per cohort) receive HP-Beta-CD once monthly for at least two doses, and the decision to dose-escalate is based on safety and on biochemical data. Subsequent dose escalations are effected in increments of up to 300 mg. Safety is assessed by adverse events (AEs), audiologic evaluation, clinical laboratory tests, vital signs, physical examinations, chest X-rays and electrocardiograms (ECGs). Biochemical efficacy is measured by change from baseline in plasma 24 (S)-HC. PK is assessed for plasma HP-Beta-CD.

7.1.2. Drug Product (Kleptose® HPB)

The hydroxypropyl beta-cyclodextrin product used in this Phase I Clinical Trial was Kleptose® HPB (Roquette, France) with a $DS_a$ of about 4.34±10%.

7.1.3. Inclusion Criteria

Patient eligibility inclusion criteria were:

1) Aged greater than or equal to 2 and less than or equal to 25 years old at time of enrollment, either gender and any ethnicity.
2) Diagnosis of NPC1 based upon one of the following:
a) Two NPC1 mutations;
b) Positive filipin staining and at least one NPC1 mutation;
c) Vertical supranuclear gaze palsy (VSNGP) in combination with either:
i) One NPC1 mutation, or
ii) Positive filipin staining and no NPC2 mutations.
3) Patients with at least one neurological manifestation of NPC1. For example, but not limited to, hearing loss, vertical supranuclear gaze palsy, ataxia, dementia, dystonia, seizures, dysarthria, or dysphagia.
4) Ability to travel to the NIH CC repeatedly for evaluation and follow-up.
5) If taking miglustat, the patient must have been taking a constant dose of the medication for no less than 3 months prior to baseline evaluation and must be willing to maintain that dose level for the duration of the trial.
6) Willing to discontinue all non-prescription supplements, with the exception of an age-appropriate multivitamin.
7) Women of reproductive age must be willing to use an effective method of contraception for the duration of the trial.
8) Willing to participate in all aspects of trial design including serial blood and CSF collections.

7.1.4. Exclusion Criteria

Patient eligibility exclusion criteria were:

1) Aged below 2 or above 25 years of age at enrollment in the trial.
2) Subjects will be excluded if their weight would result in an endotoxin level that would exceed 0.2 EU/kg for either the saline or drug dosing.
3) Severe manifestations of NPC1 that would interfere with the patient s ability to comply with the requirements of this protocol.
4) Neurologically asymptomatic patients.
5) Patients who have received any form of cyclodextrin in an attempt to treat NPC1. Treatment with another drug preparation for another medical indication that contains cyclodextrin as an excipient, will not exclude a patient.
6) History of hypersensitivity reactions to cyclodextrin or components of the formulation.
7) Pregnancy or breastfeeding at any time during the study.

8) Patients with suspected infection of the CNS or any systemic infection.

9) Spinal deformity that would impact the ability to perform a lumbar puncture.

10) Skin infection in the lumbar region.

11) Neutropenia, defined as an absolute neutrophil count (ANC) of less than 1,500.

12) Thrombocytopenia (a platelet count of less than 75,000 per cubic millimeter).

13) Evidence of disturbed circulation of CSF.

14) Contraindication for anesthesia.

15) Prior use of anticoagulants or history/presence of a bleeding disorder with increased risk of clinical bleeding or an INR greater than 2.

16) Patients with clinical evidence of acute liver disease having symptoms of jaundice or right upper quadrant pain.

17) Presence of anemia defined as two standard deviations below normal for age and gender.

18) For subjects 18 years of age and older, the eGFR is automatically calculated and reported by the NIH CC laboratory utilizing the CKD-EPI Creatinine 2009 equation. Subjects greater than or equal to 18 years of age if eGFR is less than or equal to 60 mL/min/1.73 m2 are excluded. For subjects <18 years of age, the NKDEP calculator is utilized (http://www.nkdep.nih-.gov/lab-evaluation/gfr-calculators/children-conventional-unit.shtml). Results are reported as >75 mL/min/1.73 m2 or lower. Subjects <18 years of age if eGFR is less than or equal to 75 15 mL/min/1.73 m2 are excluded.

19) Hematuria on a single urinalysis, as defined by the American Urological Association (AUA) as five or more red blood cells per high-power field (or >25/micro L) on microscopic evaluation of urinary sediment from a properly collected urinalysis specimen. The patient will not be excluded if 2 subsequent urine specimens are negative for hematuria as defined by the AUA.

20) Proteinuria (1+ protein on urinalysis) unless evaluated and classified as benign by patient s primary medical provider or by NIH nephrology consult or in the context of normal urine protein creatinine ratio and in the absence of clinical symptoms (edema, hypertension).

21) Active pulmonary disease, oxygen requirement or clinically significant history of decreased blood oxygen saturation, pulmonary therapy, or requiring active suction.

22) Patients unable to complete a behavioral audiologic evaluation including pure-tone threshold assessment (500 Hz to 8000 Hz) to monitor for ototoxicity and for whom OAEs cannot be reliably obtained at baseline.

23) Patients with ongoing seizures, that are not stable in frequency, type or duration over a 2 month period prior to enrollment, requiring change in dose of antiepileptic medication (other than adjustment for weight) over a 2 month period prior to enrollment, or requiring 3 or more antiepileptic medications to control seizures.

24) Patients, who in the opinion of the investigators are unable to comply with the protocol or have specific health concerns that would potentially increase the risk of participation.

7.1.5. Initial Analysis of Clinical Data

Initial data from this study, with additional data from Individual INDs at another institution also using intrathecal administration of Kleptose® HPB ("I-IND"), were analyzed as follows:

7.1.5.1. Summary of Analysis of Initial Data

We performed an analysis to examine the rate of change in the NPC clinical severity score and its major domains in a data set that included both the NIH subjects and three subjects from an I-IND study at another institution. The major findings are listed below:

When comparing Table 2 and Table 3 (see below), the drug dose impacts the rate of change in the NPC clinical severity score and its domains, with the most profound change observed in hearing.

Cyclodextrin generally decreases the rate of decline in the NPC clinical severity score and its components (Table 4) (below). This is true for all components with the exception of eye movement, hearing, and seizures.

When limiting the comparison of cyclodextrin to the NIH Natural History study to NIH subjects (Table 5), the pattern is also consistent with the Cyclodextrin group declining at a slower rate, with the exception of eye movement.

Figure 3:
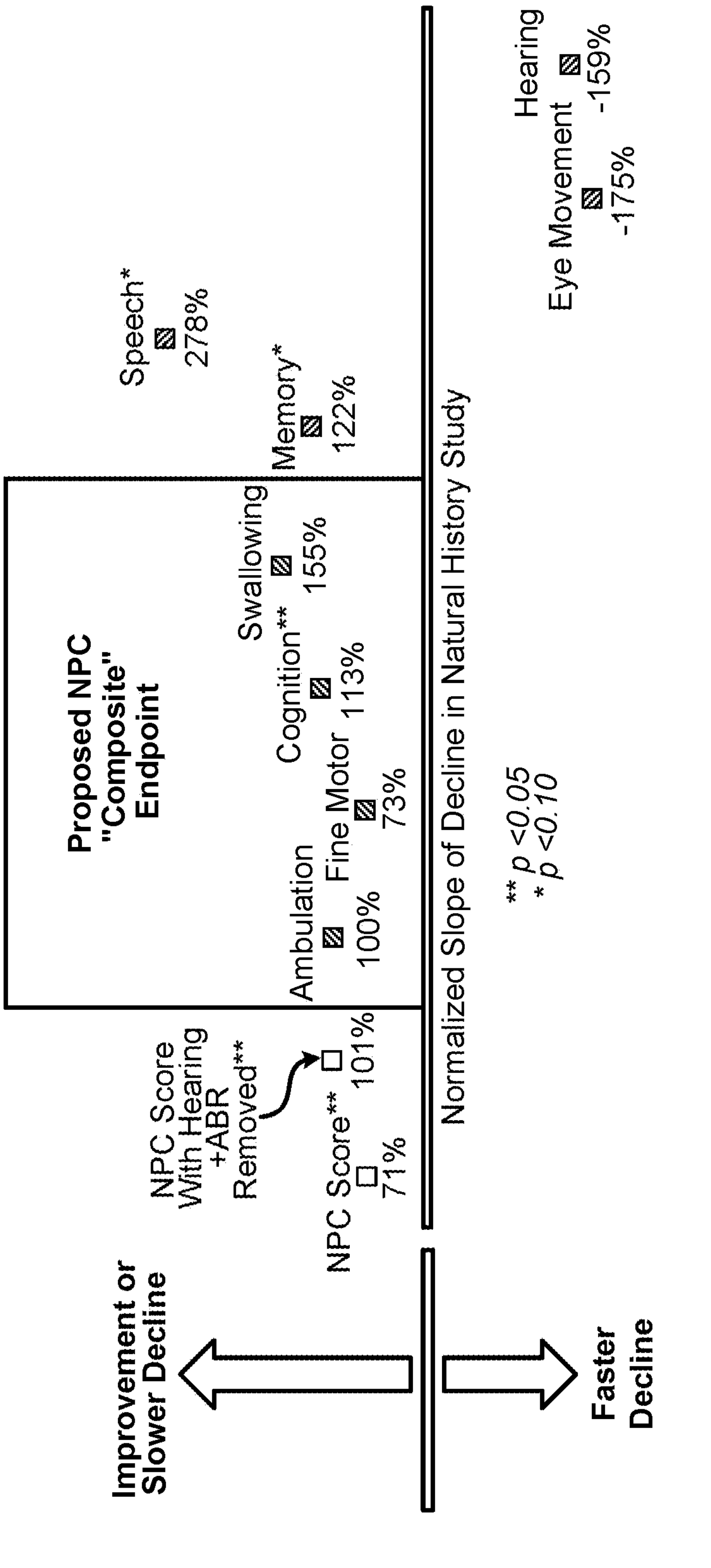
Figure 4:
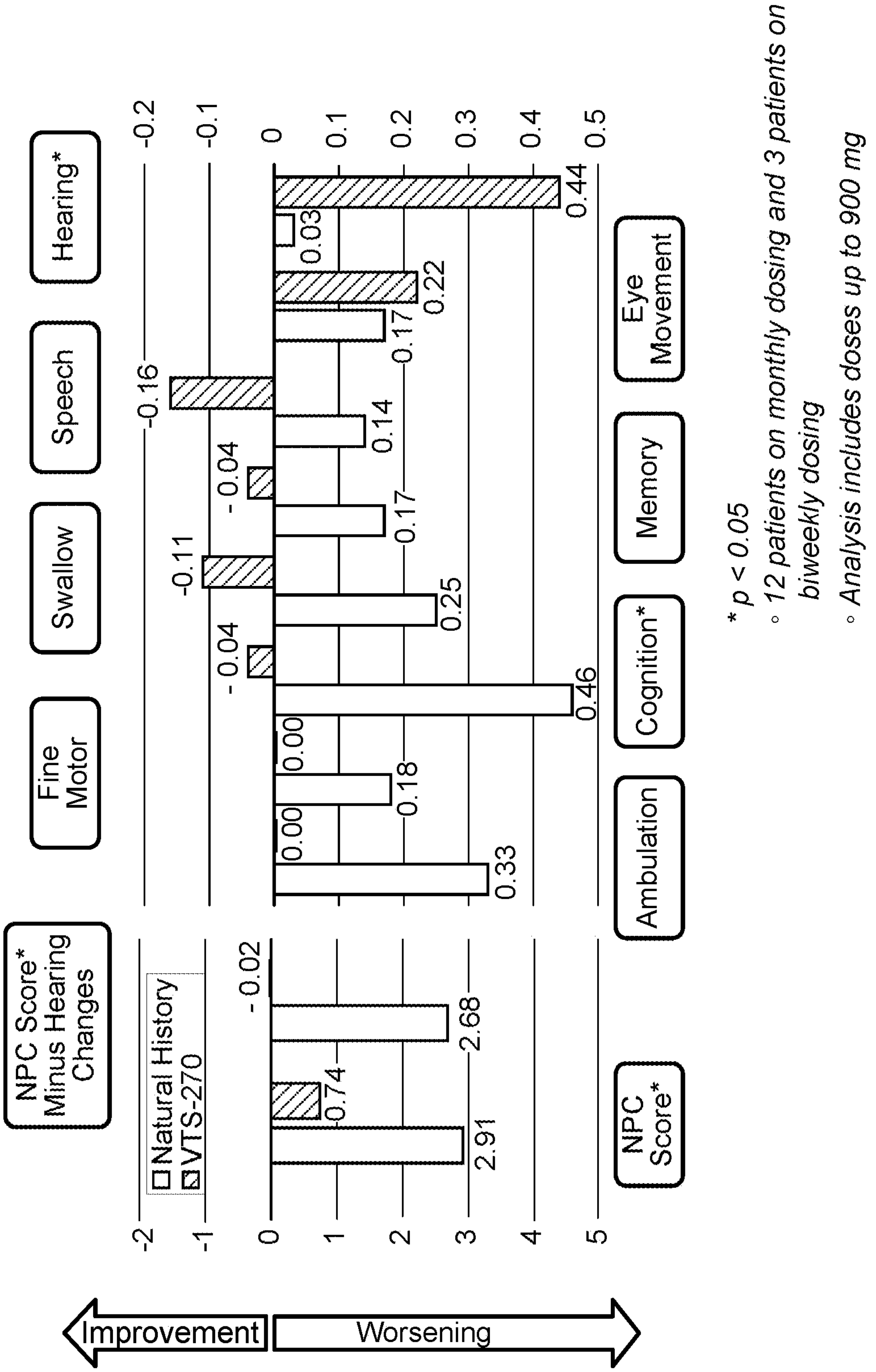

The results from the initial analysis of Phase I clinical trial data are summarized in FIGS. 2-3.

7.1.5.2. Analysis Methods

The goal of the analyses below was to understand the changes over time in the twelve NIH Phase 1 study subjects (identification beginning with "CDA") and three subjects from another site who are also receiving intrathecal treatment with Kleptose® HPB (identification beginning with "I-IND"). The following results are based on 15 subjects who received hydroxypropyl beta-cyclodextrin. Subjects CDA113 and CDA114 are not included in the following analyses because they have not yet received a dose of hydroxypropyl beta-cyclodextrin. Four (4) out of the 15 subjects have available data at baseline and 6 months (subjects CDA110, CDA111, CDA112, and I-IND-3); the remaining 11 subjects have available data at baseline, 6 months, and 12 months (CDA101-CDA109, I-IND-1).

We used a linear mixed model to obtain the estimated slope of changes over time. The word mixed in "linear mixed model" is used to denote the fact that the model includes both "fixed" and "random" effects. The "random" portion of the model accounts for the repeated measures on each subject, or longitudinal nature of the data. The "fixed" portion of the model provides an estimate of the average change over time, that is, the slope of the change. This approach is advantageous because it utilizes all collected data and the interaction term allows for the exploration of different rates of change in groups. This model is fit assuming an unstructured correlation matrix, which means that no assumptions were made about the correlation between the multiple measurements and each correlation is estimated. In future analyses, covariates may be added to the models below to explore the effects of covariates such as dose.

We computed regression diagnostics for each model presented in this analysis and used Cook's D to identify potential outlier/influential observations, refitting models where outliers/influential observations were identified (Note: an outlier/influential observation is defined as an observation with a Cook's D value of 0.4 or greater). We chose Cook's D as the diagnostic of interest because it includes both the outcome and any covariates to identify potential outliers. When outliers are identified, two sets of models are presented; the first model presented is based on the full data set, while a second set of models is based on the data with the outliers removed. For this analysis we removed all of the I-IND-1 subject's values rather than just the baseline value. These values are present in the last two columns of Table 2 and Table 3. Note that the results obtained from these two analyses can be quite different due to the relatively small sample size of 15 subjects in the Phase 1 study and the total of 41 observations included in the models (when the full data set is included).

We also used the same approach for the comparison of the Phase 1 subjects to the NIH Natural History data set. The NIH Natural History data set is described in Yanjanin et al., "Linear Clinical Progression, Independent of Age of Onset, in Niemann-Pick Disease, Type C," *Am. J. Med. Genet. Part B* 153B: 132-140 (2010).

For the analyses presented here, we fit basic models to the subjects who received cyclodextrin (presented in Table 2). For this analysis, we present the estimated change in the corresponding NPC outcome over a period of one year. In Table 3, we present results for the average change over time while controlling for the dose received. Table 4 and Table 5 present models that compare Cyclodextrin subjects to subjects in a comparable age range in the NIH Natural History study. The results presented are the estimated slope in each of the two groups and the p-value for testing the equality of the slopes between the two groups.

7.1.5.3. Changes Over Time in Subjects Receiving Cyclodextrin

Table 2 presents the average slope for the overall NPC score and each of its components for the 15 subjects who received at least one dose of cyclodextrin. These results provide information on the rate of change in the outcome over one year. These rates are smaller than those observed in the full Natural History population that was presented in prior analyses. Note: we removed the baseline data for one I-IND subject who had a total score of 31, a total score of 31 with hearing removed, ambulation of 4, swallow of 3, fine motor of 4, and cognition of 4. Overall, this subject improved over time. Additionally, one NIH subject was an outlier in the eye movement analysis due to a high value of 5 in this domain. The analyses for the full data set are presented in columns 2 and 3 and the results obtained when outliers were removed are presented in columns 4 and 5.

TABLE 2

Average change over time (in years) for the NPC score and its components fit to subjects in the Phase 1 studies

| NPC score | Avg change over time in yrs (std. error) | | p-value | Avg change over time in yrs with I-IND-1 subject removed (std error) | | p-value |
|---|---|---|---|---|---|---|
| Total Score | 0.74 | (0.59) | 0.22 | 1.16 | (0.42) | 0.01 |
| Total Score with hearing removed | 0.31 | (0.62) | 0.62 | 0.89 | (0.44) | 0.06 |
| Total Score with hearing and ABR removed[a] | −0.02 | (0.64) | 0.97 | 0.61 | (0.46) | 0.19 |
| Ambulation | 0.001 | (0.16) | 0.99 | 0.19 | (0.10) | 0.07 |
| Fine Motor | 0.002 | (0.08) | 0.98 | 0.002 | (0.09) | 0.98 |
| Cognition | −0.04 | (0.06) | 0.47 | −0.05 | (0.06) | 0.47 |
| Swallowing | −0.10 | (0.27) | 0.71 | 0.15 | (0.19) | 0.43 |
| Eye Movement[b] | 0.24 | (0.17) | 0.18 | 0.26 | (0.12) | 0.66 |
| Speech | −0.16 | (0.15) | 0.29 | −0.08 | (0.15) | 0.57 |
| Hearing | 0.44 | (0.18) | 0.02 | −0.29 | (0.15) | 0.07 |
| Memory | −0.04 | (0.13) | 0.77 | 0.05 | (0.12) | 0.69 |
| Seizures | Model not stable | | — | — | | — |

Notes:

[a]One additional outlier removed yielding 0.20 (0.35) and p-value of 0.57.

[b]Eye movement score of 5 removed yielding 0.05 (0.13) and p-value of 0.67 (CDA105).

Table 3 contains analysis results that include dose as part of the model. These models provide information about the effect of dose of drug. Note the effect of this when looking at hearing. When dose is included in the model, the slope for the change over time is no longer significant.

TABLE 3

Average change over time (in years) for the NPC score and its components adjusted for dose fit to subjects in the Phase 1 studies

| NPC score | Avg change over time in yrs (std. error) | | p-value | Avg change over time in yrs with I-IND-1 removed (std error) | | p-value |
|---|---|---|---|---|---|---|
| Total Score[a] | 1.79 | (1.59) | 0.27 | 0.81 | (1.12) | 0.48 |
| Total Score with hearing removed[b] | 1.50 | (1.67) | 0.38 | 0.61 | (1.18) | 0.61 |
| Total Score with hearing and ABR removed[c] | 0.93 | (1.73) | 0.60 | 0.07 | (1.21) | 0.95 |
| Ambulation | 0.41 | (0.43) | 0.35 | 0.19 | (0.26) | 0.47 |
| Fine Motor | −0.10 | (0.22) | 0.65 | −0.10 | (0.24) | 0.69 |
| Cognition[d] | 0.13 | (0.15) | 0.41 | 0.14 | (0.16) | 0.38 |
| Swallowing | 0.49 | (0.70) | 0.49 | 0.10 | (0.50) | 0.85 |
| Eye Movement[e] | 0.16 | (0.45) | 0.73 | 0.20 | (0.47) | 0.68 |
| Speech | −0.09 | (0.39) | 0.83 | −0.16 | (0.38) | 0.68 |
| Hearing | 0.40 | (0.49) | 0.43 | 0.27 | (0.40) | 0.52 |
| Memory | −0.22 | (0.35) | 0.59 | −0.33 | (0.31) | 0.30 |
| Seizures | Model not stable | | — | — | | — |

Notes:

[a]One additional outlier removed yielding 1.09 (0.85) with p-value of 0.22.

[b]One additional outlier removed yielding 0.91 (0.90) with p-value of 0.32.

[c]One additional outlier removed yielding 0.38 (0.92) with p-value of 0.42.

[d]Additional outliers when I-IND-1 removed; however, model does not converge when these outliers are removed.

[e]CDA105 subject 1 year value of eye movement score of 5 also removed yielding 0.30 (0.32) with p-value of 0.37.

7.1.5.4. Comparison of Phase 1 and I-IND Subjects with Corresponding Subjects in the Natural History Study To better understand the effect of cyclodextrin, we compared the subjects in the Phase 1 and I-IND studies with subjects of comparable age in the NIH Natural History study. For this comparison, we limited the data set to subjects who had more than a single time point of data and were between 6 and 26 years of age. We fit a mixed model with time, treatment group and a time by treatment group interaction term in the model. Table 4 below presents the results from this analysis.

The results presented in Table 4 are consistent with the slower rate of change in the Cyclodextrin group compared to the Natural History population, with the exception of the eye movement, and hearing subdomains.

TABLE 4

Average change over time separated out by Cyclodextrin use for both NIH Phase 1, NIH Natural History, and I-IND subjects

| NPC score | Avg change over time in yrs (std. error) for Cyclodextrin group | Avg change over time in yrs (std. error) for Natural History study | p-value for difference in slopes between the two groups |
|---|---|---|---|
| Total Score | 0.74 (0.67) | 2.53 (0.27) | 0.02 |
| Total Score with hearing removed | 0.31 (0.68) | 2.36 (0.27) | 0.01 |
| Total Score with hearing and ABR removed | −0.02 (0.69) | 2.23 (0.28) | 0.004 |
| Ambulation | 0.001 (0.18) | 0.27 (0.07) | 0.18 |
| Fine Motor | 0.03 (0.10) | 0.11 (0.04) | 0.34 |
| Cognition | −0.04 (0.16) | 0.31 (0.06) | 0.04 |
| Speech | −0.16 (0.13) | 0.09 (0.05) | 0.09 |
| Eye Movement | 0.22 (0.16) | 0.08 (0.06) | 0.42 |
| Swallowing | −0.11 (0.23) | 0.20 (0.09) | 0.22 |
| Hearing | 0.44 (0.16) | 0.17 (0.06) | 0.13 |
| Memory | −0.04 (0.12) | 0.18 (0.05) | 0.10 |
| Seizures | NA | NA | NA |

7.1.5.5. Comparison of Phase 1 Subjects with Corresponding Subjects in the Natural History Study To better understand the effect of cyclodextrin within the NIH population, we compared the subjects in the Phase 1 study with subjects of comparable age in the Natural History Study. For this comparison, we limited the data set to subjects who had more than one time point of data and were between 6 and 26 years of age. We fit a mixed model with time, treatment group, and a time by treatment group interaction term in the model. The table below presents the results from these analyses, which are similar to those in Table 4. Note that the seizures outcome is somewhat unstable with several outliers. Only the full data set results are presented. With the exception of eye movement, all rates in the Cyclodextrin group are smaller than those observed in the Natural History study.

TABLE 5

Average change over time separated out by Cyclodextrin use for NIH Phase 1 and NIH Natural History subjects

| NPC score | Avg change over time in yrs (std. error) for Cyclodextrin group | Avg change over time in yrs (std. error) for Natural History study | p-value for difference in slopes between the two groups |
|---|---|---|---|
| Total Score | 1.16 (0.68) | 2.53 (0.24) | 0.06 |
| Total Score with hearing removed | 1.06 (0.66) | 2.36 (0.24) | 0.08 |
| Total Score with hearing and ABR removed | 0.86 (0.68) | 2.23 (0.24) | 0.06 |
| Ambulation | 0.21 (0.18) | 0.27 (0.06) | 0.78 |
| Fine Motor | 0.06 (0.11) | 0.11 (0.04) | 0.66 |
| Cognition | −0.05 (0.18) | 0.31 (0.07) | 0.07 |
| Speech | −0.10 (0.14) | 0.09 (0.05) | 0.24 |
| Eye Movement | 0.32 (0.18) | 0.08 (0.06) | 0.21 |
| Swallowing | 0.17 (0.21) | 0.20 (0.08) | 0.88 |
| Hearing[a] | 0.11 (0.12) | 0.17 (0.04) | 0.66 |
| Memory | 0.06 (0.13) | 0.18 (0.05) | 0.38 |
| Seizures | NA | NA | NA |

Notes:
[a]Outliers were detected in this model and removed to create smaller slope values in the Natural history group.

7.1.5.6. Analyses that Compare Only Subjects Who have Ever Used Miglustat

The results presented below include subjects who used miglustat during the time period. This includes eight subjects from the Natural history study and 14 subjects from the Phase 1 study. We then reran the analyses presented in Table 4 for this population. These results are presented in Table 6 below.

TABLE 6

Average change over time separated out by Cyclodextrin use for NIH Phase 1 and NIH Natural History subjects who reported Miglustat use

| NPC score | Avg change over time in yrs (std. error) for Cyclodextrin group | Avg change over time in yrs (std. error) for Natural History study | p-value for difference in slopes between the two groups |
|---|---|---|---|
| Total Score | 0.71 (0.67) | 2.58 (0.24) | 0.01 |
| Total Score with hearing removed | 0.59 (0.66) | 2.39 (0.23) | 0.01 |
| Total Score with hearing and ABR removed | 0.37 (0.67) | 2.25 (0.24) | 0.01 |
| Ambulation | 0.12 (0.16) | 0.26 (0.06) | 0.38 |
| Fine Motor | 0.06 (0.10) | 0.08 (0.04) | 0.89 |
| Cognition | −0.07 (0.21) | 0.33 (0.07) | 0.09 |
| Speech | −0.23 (0.14) | 0.08 (0.05) | 0.05 |
| Eye Movement | 0.12 (0.11) | 0.05 (0.04) | 0.55 |
| Swallowing | 0.07 (0.22) | 0.20 (0.08) | 0.58 |
| Hearing | 0.13 (0.14) | 0.19 (0.05) | 0.68 |
| Memory | 0.06 (0.15) | 0.21 (0.05) | 0.38 |
| Seizures | NA | NA | NA |

Table 7 below presents the results that include only NIH subjects. The three subjects from I-IND are removed for this comparison. The results presented here presented here are similar to those presented in Table 5 above. The difference between the two populations is that the five NIH subjects in the Natural History study and one NIH subject in the Phase 1 study have been removed from the population as these subjects reported no miglustat use at any point in time.

TABLE 7

Average change over time separated out by Cyclodextrin use for both NIH Phase 1 and I-IND subjects who reported Miglustat use

| NPC score | Avg change over time in yrs (std. error) for Cyclodextrin group | Avg change over time in yrs (std. error) for Natural History study | p-value for difference in slopes between the two groups |
|---|---|---|---|
| Total Score | 0.34 (0.67) | 2.58 (0.27) | 0.004 |
| Total Score with hearing removed | −0.13 (0.68) | 2.39 (0.27) | 0.001 |
| Total Score with hearing and ABR removed | −0.49 (0.69) | 2.25 (0.28) | 0.001 |
| Ambulation | −0.10 (0.17) | 0.26 (0.07) | 0.06 |
| Fine Motor | 0.002 (0.10) | 0.08 (0.04) | 0.48 |
| Cognition | −0.04 (0.17) | 0.33 (0.07) | 0.06 |
| Speech | −0.27 (0.13) | 0.08 (0.05) | 0.01 |
| Eye Movement | 0.05 (0.11) | 0.05 (0.04) | 0.97 |
| Swallowing | −0.21 (0.24) | 0.20 (0.10) | 0.13 |
| Hearing | 0.48 (0.18) | 0.19 (0.07) | 0.15 |
| Memory | −0.04 (0.14) | 0.21 (0.06) | 0.10 |
| Seizures | NA | NA | NA |

7.1.6. Further Analysis of Clinical Data

Further analyses were performed on the same NIH clinical trial dataset, but with 4 data points included in the control data set that were not included in the analyses described above. These analyses are summarized in FIGS. 4, 5, 6 and 8.

7.2. Example 2: Standard Analysis of Drug Product

The hydroxypropyl beta-cyclodextrin product used in the Phase I Clinical Trial described in Example 1 was Kleptose® HPB (Roquette, France) with a DSa of about 4.34±10%. Standard analyses of two exemplary lots of Kleptose® HPB, as performed by the manufacturer, are shown in FIGS. 51A-51H.

7.3. Example 3: HPLC Separation of Hydroxypropyl Beta-Cyclodextrin Mixtures

Various chromatographic methods were used to assess the complexity of the cyclodextrin mixture in a commercially available parenteral grade hydroxypropyl beta-cyclodextrin pharmaceutical composition, Kleptose® HPB, batches of which were used in a phase I clinical trial.

7.3.1. CD-Screen Column

The HPLC method from European Pharmacopeia monograph number 1804 (Hydroxypropylbetadex) (revised Jan. 1, 2009) was used to separate components in commercial Kleptose HBP® (Roquette).

HPLC conditions: Stationary phase: CD-Screen, particle size 5 μm (ChiroQuest), Column: 1=250 mm, Ø=4.0 mm; temperature: 30° C. Mobile phase: mobile phase A: water; mobile phase B: water:methanol (10:90 V/V). Flow rate: 1.0 mL/min; Detection: Alltech 3300 evaporative light-scattering detector; carrier gas: nitrogen; flow rate: 1.5 L/min; evaporator temperature: 70° C.; Injection: 20 μL.

Gradient Program (European Pharmacopeial Method):

TABLE 8

| Time (min) | Mobile phase A (% V/V) | Mobile phase B (% V/V) |
|---|---|---|
| 0-5 | 52 | 48 |
| 5-15 | 52 → 0 | 48 → 100 |
| 15-20 | 0 | 100 |

Figure 9:
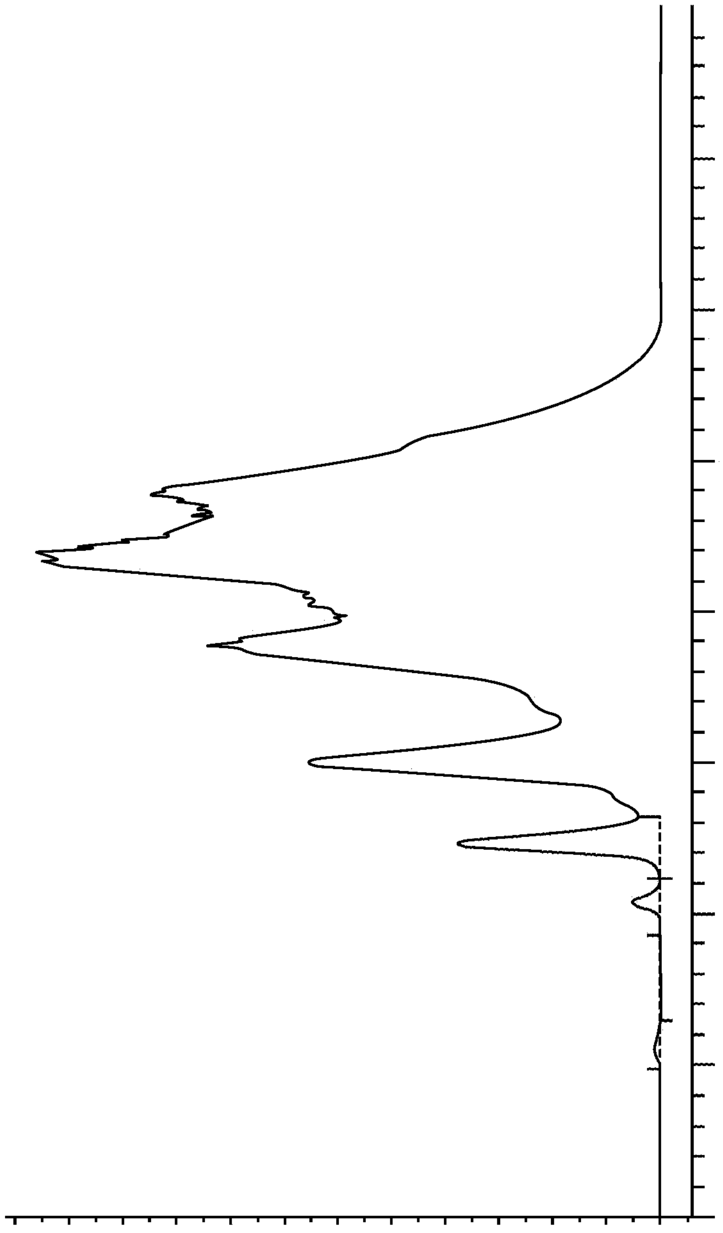
FIG. 9 depicts a representative HPLC chromatogram using a CD-screen method.
Figure 10:
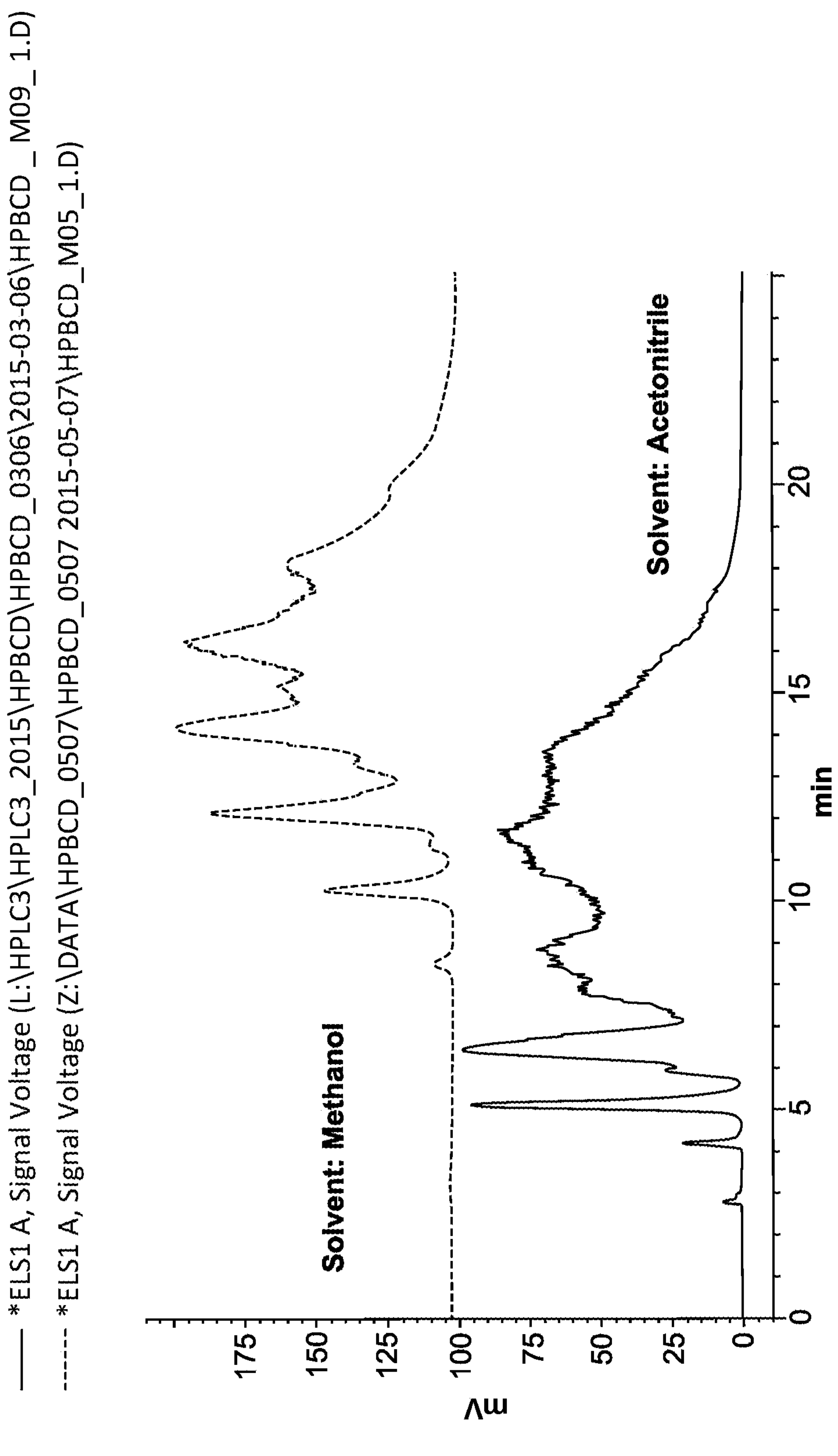
FIG. 10 depicts the comparative HPLC chromatograms using different solvents in a CD-screen method. Upper trace: methanol; lower trace: acetonitrile.

FIG. 9 depicts the results of Kleptose® HBP ($DS_a$=4.2) hydroxypropyl beta-cyclodextrin in the CD-Screen HPLC method. Species eluted in the order of increasing DS. Unsubstituted beta-cyclodextrin eluted at about 5 min, with monosubstituted hydroxypropyl beta-cyclodextrin eluting at about 6 min. FIG. 10 depicts comparative chromatograms of hydroxypropyl beta-cyclodextrins using CD-Screen column with methanol and acetonitrile solvent gradients (Gradient with methanol: 0 min 30% B, 40 min 100% B; Gradient with acetonitrile: 0-5 min 18% B, 25 min 40% B. Other method parameters remained unchanged). The retention times varied depending on the solvent strength and polarity of the mobile phase.

Mass spectrometry detection method: Agilent 1260 HPLC with 6460 Triple Quadrupole mass spectrometer. Agilent Jet Stream electrospray ionization (ESI) source, negative mode, m/z 500-3000; fragmentor voltage: 35 V, Source parameters: gas temperature: 300° C., gas flow: 13 L/min, nebulizer: 60 psi, sheath gas flow: 11 L/min, sheath gas temperature (heater): 400° C., capillary voltage: 3500 V. Ammonium formate buffer (0.1 M, pH=6.0) was applied instead of water in the mobile phases for the HPLC-MS measurements.

Figure 11:
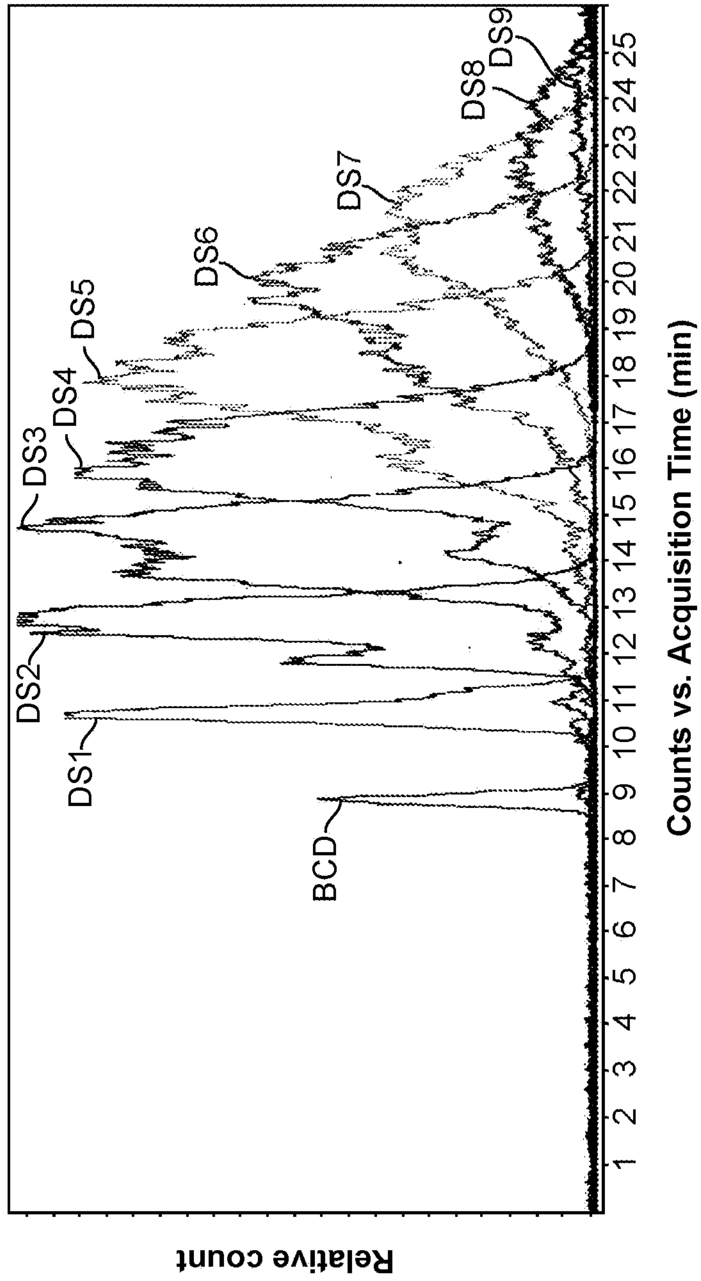
FIG. 11 depicts the mass spectrometry extracted ion chromatograms of hydroxypropyl beta-cyclodextrins having a different degree of substitution (DS) using a CD-screen column.

FIG. 11 shows the extracted ion chromatogram of the sample from the HPLC-MS analysis. BCD=unsubstituted beta-cyclodextrin; DSx=hydroxypropyl beta-cyclodextrins with DS of x. For example, "DS3" refers to hydroxypropyl beta-cyclodextrins having DS=3.

7.3.2. Reversed Phase C18 Chromatography

Kleptose® HBP (Roquette) (same batch as used in Section 7.3.1) was analyzed. An analytical column (4 mm×250 mm) was filled with LiChroprep RP18 silica gel. One set of conditions tested included the following: Stationary phase: LiChroprep RP18 silica gel, particle size 25-40 μm (Merck), Column: 1=250 mm, Ø=4.0 mm; temperature: 30° C. Mobile phase: mobile phase A: water; mobile phase B: water:methanol R (10:90 V/V). The gradient program used the following conditions: 0 min at 10% mobile phase B gradient to 20 min at 100% mobile phase B. Flow rate: 1.0 mL/min; Detection: Alltech 3300 evaporative light-scattering detector; carrier gas: nitrogen; flow rate: 1.5 L/min; evaporator temperature: 70° C.

Figure 12:
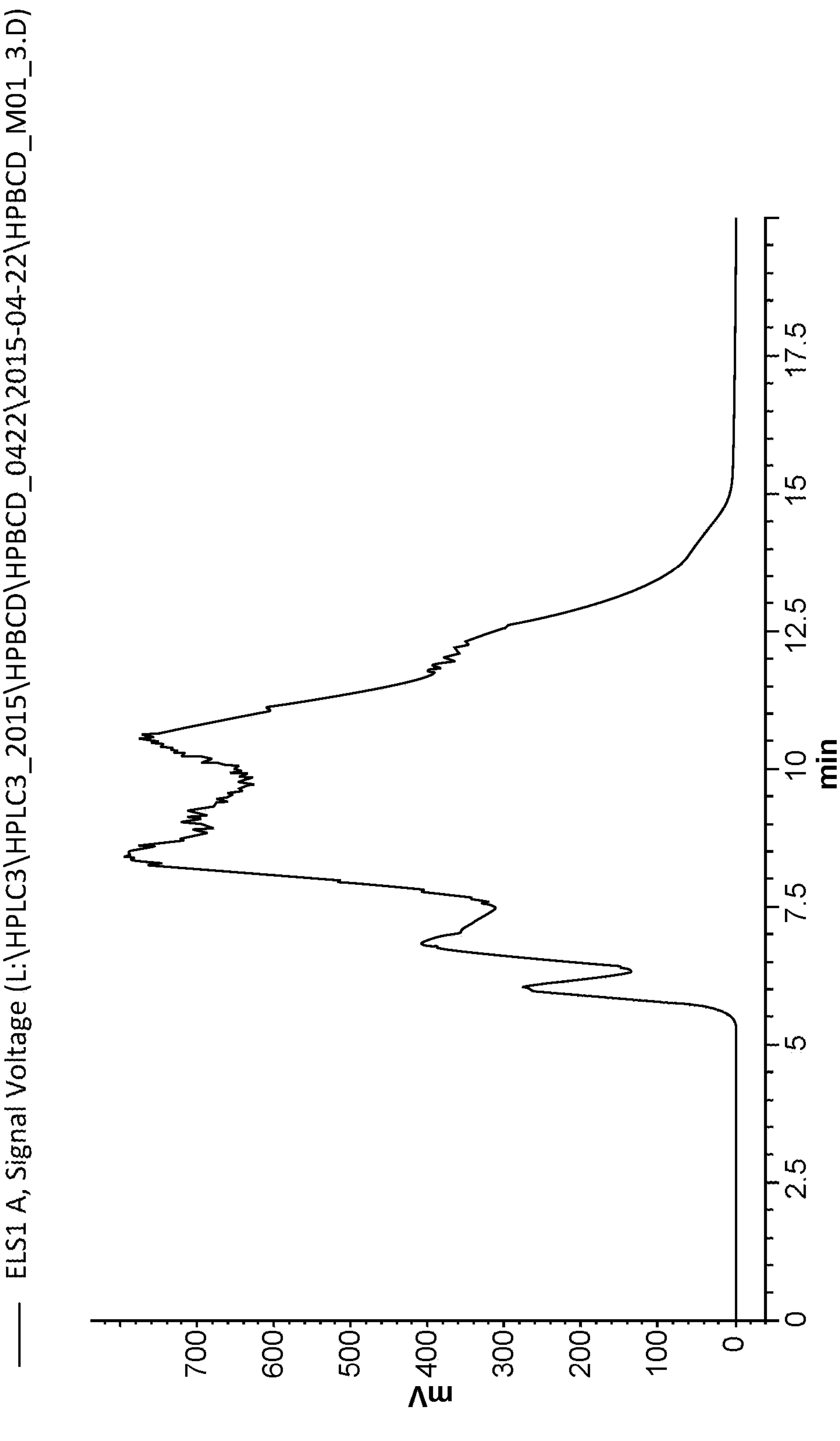
FIG. 12 depicts a representative HPLC chromatogram using a LiChrosphere C18 reverse phase column.
Figure 13:
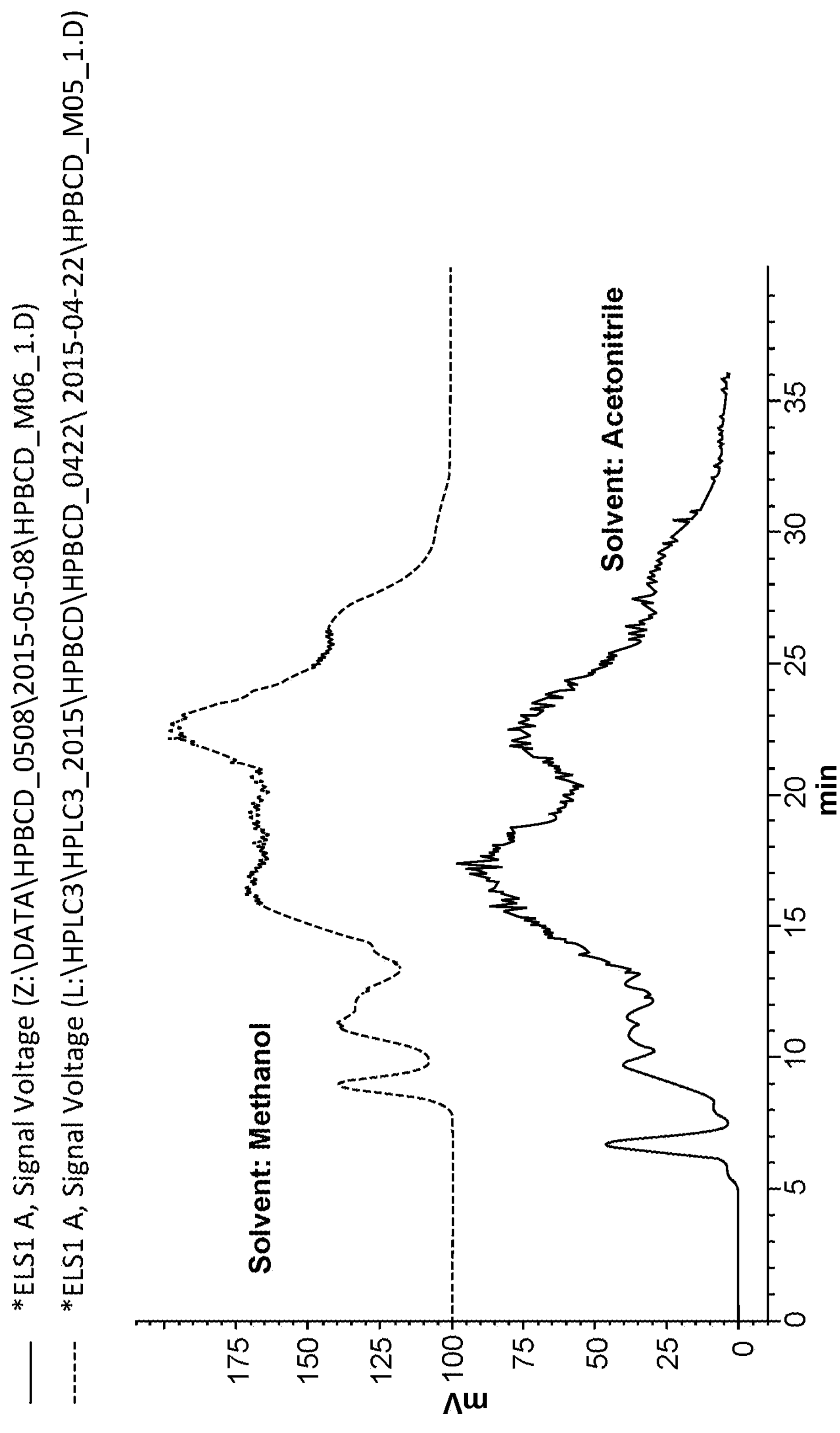
FIG. 13 depicts the comparative HPLC chromatograms using different solvents in a LiChrosphere C18 reverse phase chromatography method. Upper trace: methanol; lower trace: acetonitrile.

FIG. 12 shows a typical HPLC chromatogram of Kleptose® HPB ($DS_a$=4.2) on LiChrosphere C18 stationary phase. FIG. 13 shows comparative chromatograms of hydroxypropyl beta-cyclodextrins using LiChrosphere C18 column with methanol and acetonitrile solvent gradients. (Gradient with methanol: 0 min 10% B, 15 min 30% B, 40 min 80% B. Gradient with acetonitrile: 0 min 5% B, 40 min 80% B. The other parameters of the method were not changed.)

Figure 14:
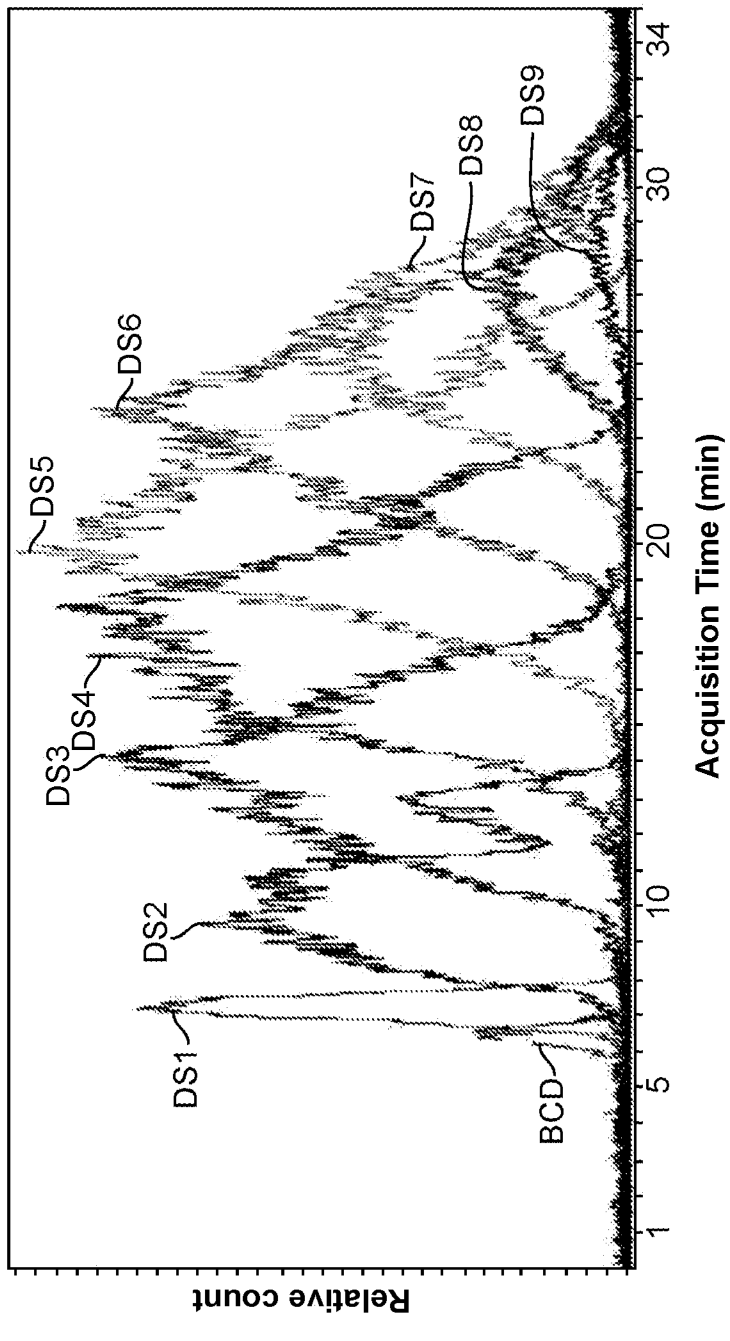
FIG. 14 depicts the mass spectrometry extracted ion chromatograms of hydroxypropyl beta-cyclodextrins having a different degree of substitution (DS) using the LiChrosphere C18 column.

Mass spectrometry conditions as described in Section 7.3.1 were used. FIG. 14 shows the extracted ion chromatogram of hydroxypropyl beta-cyclodextrins having different DS from the HPLC-MS analysis.

7.3.3. Hydrophilic Interaction Liquid Chromatography (HILIC)

Hydrophilic interaction liquid chromatography (HILIC) uses hydrophilic stationary phases with eluents typically used in reverse phase chromatography. The approach uses liquid-liquid partition chromatography principles such that analytes may elute in order of increasing polarity. The method described herein used an amino column which contained aminopropyl groups bound to the surface of the silica gel.

Kleptose® HBP (Roquette) (same batch as used in Section 7.3.1) was analyzed. HPLC conditions: Stationary phase: Nucleosil NH2, particle size 5 μm (Macherey Nagel), Column: 1=250 mm, Ø=4.0 mm; temperature: 30° C. Mobile phase: mobile phase A: acetonitrile-water (80:20 V/V); mobile phase B: water. Flow rate: 1.0 mL/min; Detection: Agilent 385 evaporative light-scattering detector; carrier gas: nitrogen; flow rate: 1.2 L/min; evaporator temperature: 50° C.; nebuliser temperature: 30° C.

Figure 15:
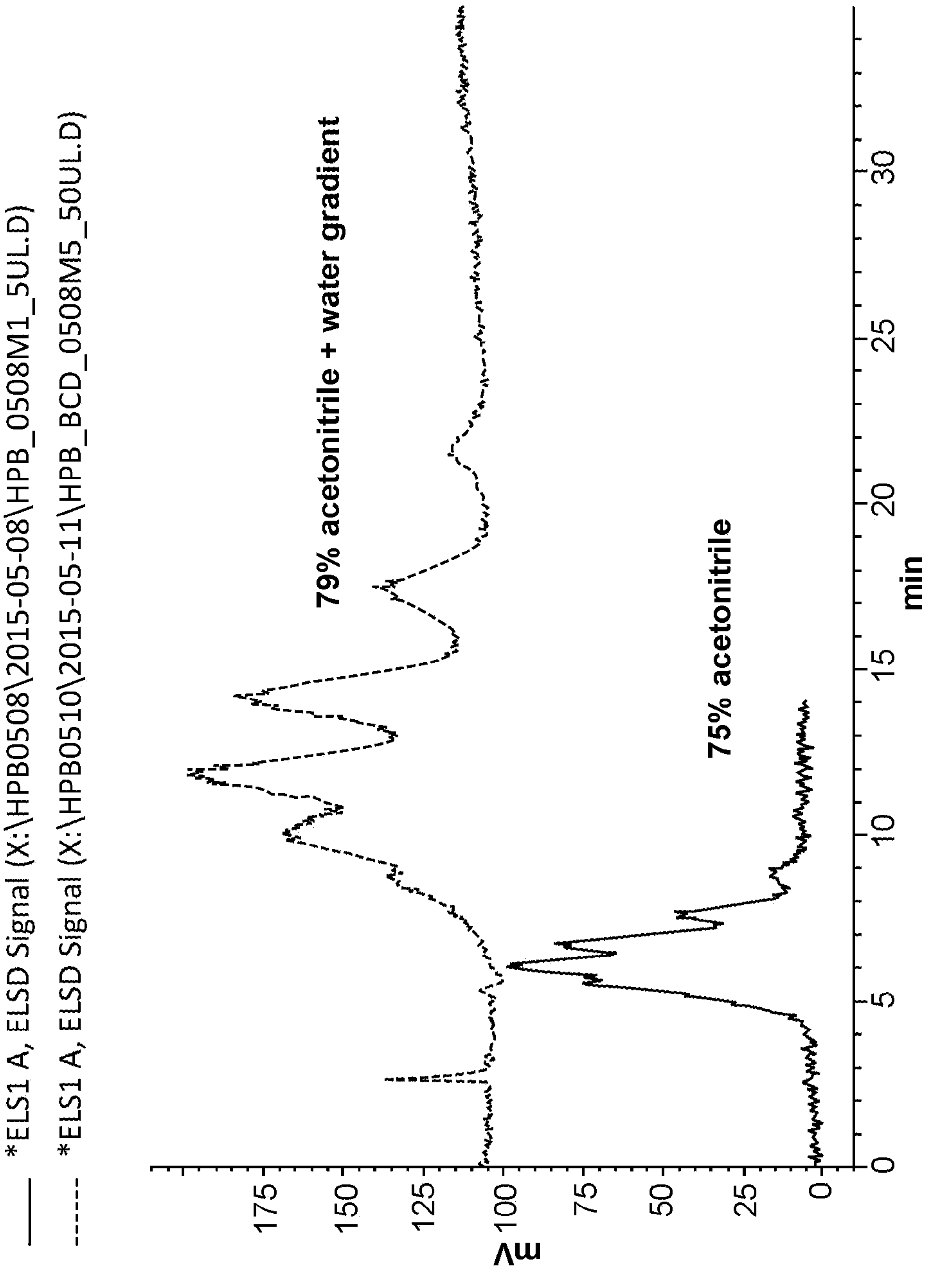
FIG. 15 depicts the comparative HPLC chromatograms using different solvents in a HILIC column. Upper trace: 79% acetonitrile in water gradient; lower trace: 75% acetonitrile.

FIG. 15 shows the separation of hydroxypropyl beta-cyclodextrins using the HILIC method on a Nucleosil NH2 column.

Figure 16:
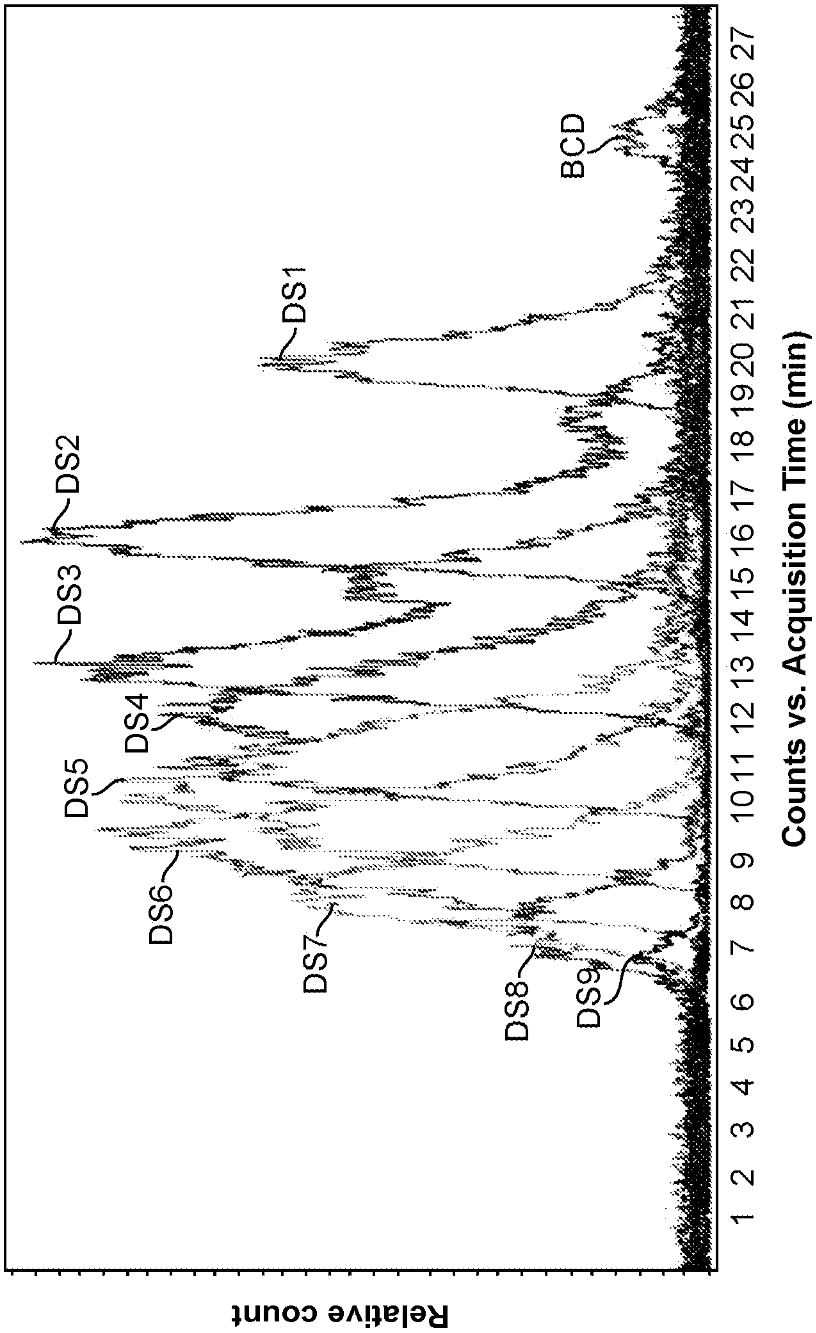
FIG. 16 depicts the mass spectrometry extracted ion chromatograms of hydroxypropyl beta-cyclodextrins having a different degree of substitution (DS) using a HILIC column.

Mass spectrometry conditions were the same as those described in Section 7.3.1. FIG. 16 shows the extracted ion chromatogram of hydroxypropyl beta-cyclodextrins having different DS from the HPLC-MS analysis. BCD=unsubstituted beta-cyclodextrin; DSx=hydroxypropyl beta-cyclodextrins with DS of x. For example, "DS3" refers to hydroxypropyl beta-cyclodextrins having DS=3. On this HPLC method, the higher DS substituted hydroxypropyl beta-cyclodextrins eluted first.

7.3.4. Silica Gel Chromatography

Kleptose HBP® (Roquette) (same batch as used in Section 7.3.1) was analyzed. HPLC method: Stationary phase: LiChrosphere Si-60, particle size 5 μm (Merck), Column: 1=250 mm, Ø=4.0 mm; temperature: 30° C. Mobile phase: mobile phase A: acetonitrile-0.1 M ammonium formate pH=7.5 (80:20 V/V); mobile phase B: 0.1 M ammonium formate pH=7.5. Flow rate: 1.0 mL/min; Detection: Agilent 385 evaporative light-scattering detector; carrier gas: nitrogen; flow rate: 1.2 L/min; evaporator temperature: 50° C.; nebulizer temperature: 30° C.

Figure 17:
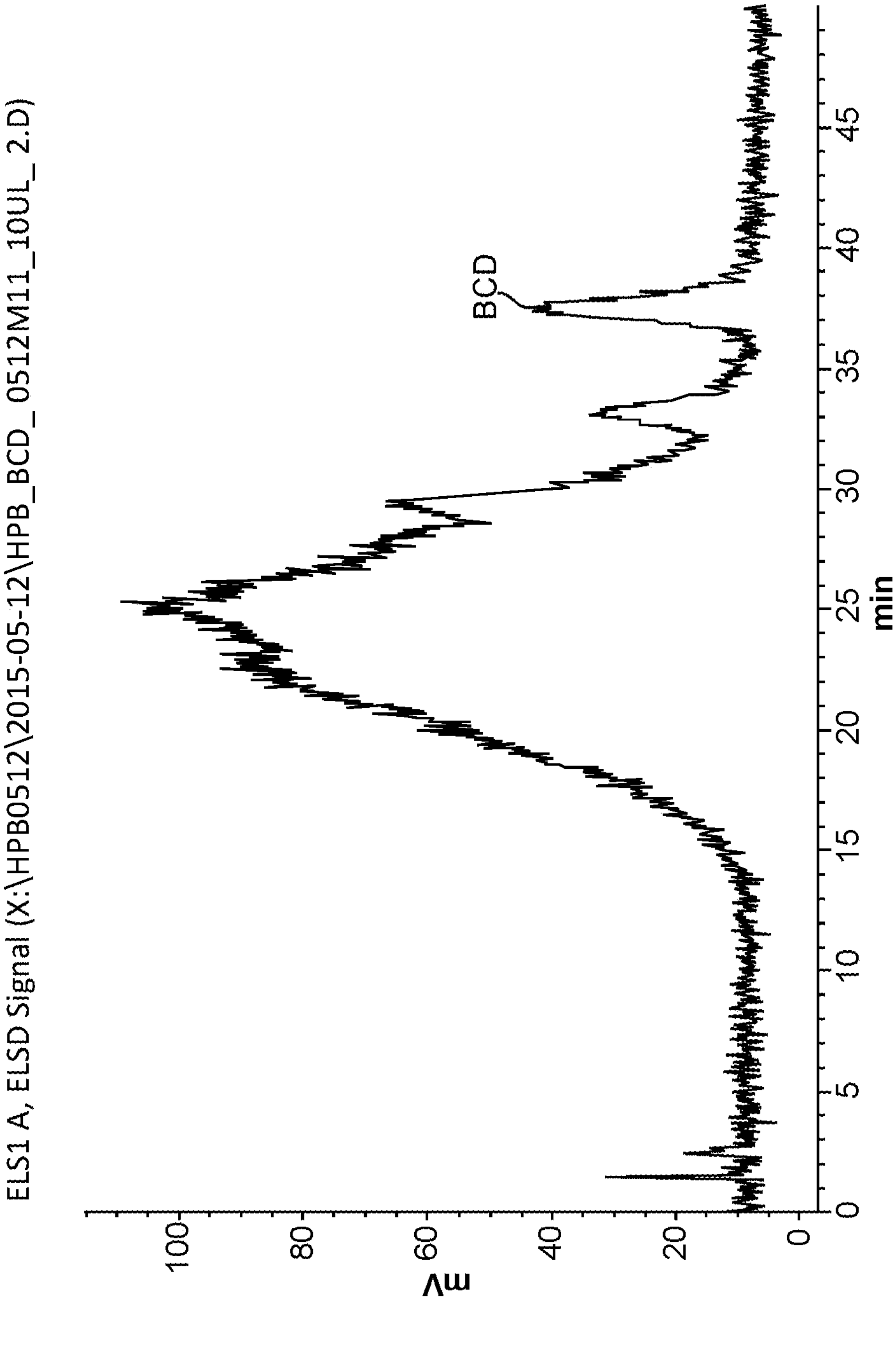
FIG. 17 depicts a representative HPLC chromatogram using a silica gel column.

FIG. 17 shows the separation of the components of hydroxypropyl beta-cyclodextrins using LiChrosphere Si 60 column. In this instance, the sample was spiked with beta-cyclodextrin to facilitate detection.

Figure 18:
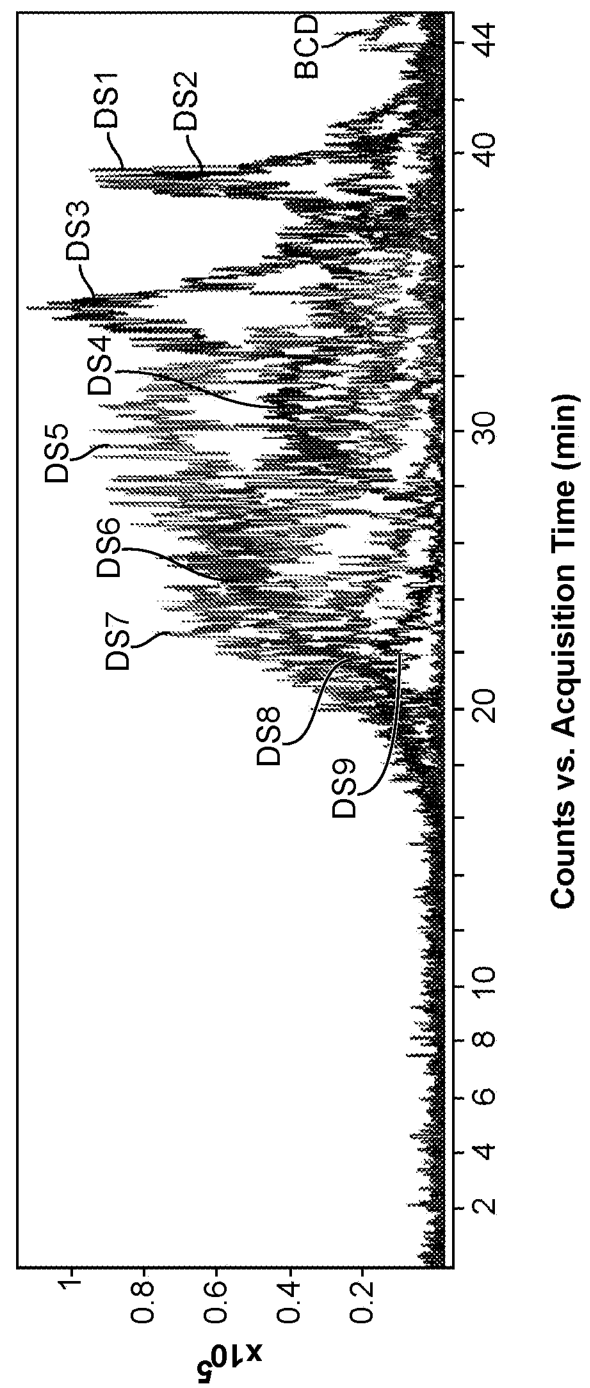
FIG. 18 depicts the mass spectrometry extracted ion chromatograms of hydroxypropyl beta-cyclodextrins having a different degree of substitution (DS) using a silica gel column.

Mass spectrometry conditions were the same as those described in Section 7.3.1. FIG. 18 shows the extracted ion chromatogram of hydroxypropyl beta-cyclodextrins having different DS. BCD=unsubstituted beta-cyclodextrin; DSx=hydroxypropyl beta-cyclodextrins with DS of x. For example, "DS3" refers to hydroxypropyl beta-cyclodextrins having DS=3. On this HPLC method, the higher DS substituted hydroxypropyl beta-cyclodextrins eluted first.

7.4. Example 4: Improved Analytical Methods 7.4.1. Gas Chromatography

The official European Pharmacopeia monograph method for the determination of propylene glycol (PG) content in Hydroxypropylbetadex has a limit of quantification of only approximately 0.5% relative to HPBCD. Accordingly, a more sensitive analytical method was needed, and an improved method with modified sample preparation (compared to the European Pharmacopeia Hydroxypropylbetadex analysis, monograph number: 1804, revised Jan. 1, 2009) was developed. This method was used to quantify PG at 0.01% level (relative to HPBCD), a much greater sensitivity than the limit of detection in the European Pharmacopeial method.

The conditions of the method were as follows: Apparatus: Gas chromatograph: Shimadzu GC-17A; Detector: Flame ionization detector (FID); Injector: Shimadzu AOC-5000 auto injector; Software: Shimadzu Class-VP 7.4 Version; Gases: Carrier gas: Helium (99.999%), Other gases: Nitrogen (99.999%), Synthetic air (99.999%), Hydrogen (from Whatman Hydrogen generator).

| Column: Supelco Supercowax-10 (30 m × 0.32 mm × 1.0 μm) | | |
|---|---|---|
| Rate (° C./min) | Temperature (° C.): | time (min): |
| — | 150 | 0 |
| | 200 | 10 |
| 40 | 240 | 1 |

Propylene glycol retention time ~6.35 min; internal standard ethylene glycol retention time ~7.15 min.

Five calibration points: between 0.1 and 2 mg/mL corresponding to 0.01%, 0.02%, 0.05%, 0.1%, 0.2% PG related to HPBCD.

The calibration stock solutions were prepared from solutions of approximately 200 mg of propylene glycol, accurately weighed into 10 mL graduated glass flask and filled up to the mark with purified water (Table 14). To obtain the concentrations listed in the table below an adequate dilution was performed. Once the target concentration (see Table 14 below) was achieved, 1 mL from this solution, 100 μL internal standard solution (IST), 500 mg NaCl and 1 mL water were added in a crew cap vial and the solution was extracted with 1 mL dichloromethane (DCM). The samples were harvested from the organic phase and injected directly.

TABLE 14

| Preparation of GC calibration samples | | | | |
|---|---|---|---|---|
| Sample | Stock solution | Dilution | Sample preparation | Extraction with |
| IST Target concentration: 50 mg/mL | 250 mg ethylene glycol (EG)/5 mL water | Not applicable | Not applicable | Not applicable |
| KAL1 Target PG concentration: 0.1 mg/mL | 200 mg PG/10 mL water | 50 µL/10 mL water | 100 µL IST + 1 mL KAL 1 + 500 mg NaCl + 1 mL water | 1 mL DCM |
| KAL2 Target PG concentration: 0.2 mg/mL | 200 mg PG/10 mL water | 100 µL/10 mL water | 100 µL IST + 1 mL KAL 2 + 500 mg NaCl + 1 mL water | 1 mL DCM |
| KAL3 Target PG concentration: 0.5 mg/mL | 200 mg PG/10 mL water | 250 µL/10 mL water | 100 pL IST + 1 mL KAL 3 + 500 mg NaCl + 1 mL water | 1 mL DCM |
| KAL4 Target PG concentration: 1.0 mg/mL | 200 mg PG/10 mL water | 500 µL/10 mL water | 100 µL IST + 1 mL KAL 4 + 500 mg NaCl + 1 mL water | 1 mL DCM |
| KAL5 Target PG concentration: 2.0 mg/mL | 200 mg PG/10 mL water | 1 mL/10 mL water | 100 µL IST + 1 mL KAL 5 + 500 mg NaCl + 1 mL water | 1 mL DCM |

The calibration solution KAL2 was used to determine system suitability by performing five parallel measurements (Requirements: RSD <5%—RSD of the area ratio of PG and EG).

Extraction blank sample: 1 mL DCM was added to 0.1 mL IST solution, 500 mg NaCl and 2 mL distilled water then stirred vigorously for 0.5 min, and left to stay. After the phases were separated, about 0.2 mL of the DCM phase was put into the vial.

Sample preparation: 1 mL DCM was added to 1.0 g of the HPBCD sample, 0.1 mL IST solution, 500 mg NaCl and 2 mL distilled water in a crew cap vial and stirred vigorously for 0.5 min, and left to stay. After the phases were separated, about 0.2 mL of the DCM phase is put into the vial. Representative chromatogram of Kleptose HPB® (Roquette) sample containing ~0.18% PG is depicted in FIG. 25.

Propylene glycol (PG) content of HPBCD samples was calculated by plotting a calibration curve displaying the propylene glycol/ethylene glycol (PG/EG) weigh-in concentration ratios (in mg/mL) as a function of PG/EG peak areas. In the HPBCD samples, an unknown parameter was the PG content that was derived from the other three factors and equation of the calibration curve.

The suitability of the method to separate monopropylene glycol from its di- and tri-substituted derivatives is shown in FIG. 26. The oversubstituted glycols showed several peaks and eluted later due to the higher boiling points. Di- and tripropylene glycol content was tested in the starting material and in the final samples.

The linearity of the method was proven by testing five samples of PG concentration between 0.1 and 2 mg/mL corresponding to 0.01%, 0.02%, 0.05%, 0.1%, 0.2% PG related to HPBCD as described in Table 14. Each sample was analyzed in triplicate to assess the precision of the method. Table 15 summarizes experimental data of the precision and linearity analysis. Linearity curve of the calibration set is depicted in FIG. 27.

TABLE 15

| Experimental and statistical evaluation of method precision and linearity | | | | | | |
|---|---|---|---|---|---|---|
| Sample | KAL1 PG/EG (area) | KAL2 PG/EG (area) | KAL3 PG/EG (area) | KAL4 PG/EG (area) | KAL5 PG/EG (area) | Slope regression |
| I | 0.1372 | 0.3252 | 0.7359 | 1.6351 | 2.9511 | 7.6382 0.9966 |
| II | 0.1520 | 0.3168 | 0.7052 | 1.5245 | 3.2239 | 7.6551 0.9988 |
| III | 0.1688 | 0.2839 | 0.6601 | 1.4519 | 2.9009 | 7.2976 0.9986 |
| average | 0.153 | 0.309 | 0.700 | 1.537 | 3.029 | |
| stdev | 0.016 | 0.022 | 0.038 | 0.092 | 0.180 | |
| RSD | 10.4 | 7.1 | 5.4 | 6.0 | 5.9 | |

PG = propylene glycol; EG = ethylene glycol; RSD = relative standard deviation.

The data in Table 15 showed that the method was linear in the 0.01-0.2% PG content range.

7.4.2. Analytical HPLC

Residual BCD (unsubstituted beta-cyclodextrin) content, HPBCD fraction with degree of substitution of 1, and sum of cyclodextrin (CD) related impurities other than BCD were determined with the HPLC method in European Pharmacopeia 7.8 (Hydroxypropylbetadex, monograph number: 1804, revised Jan. 1, 2009) and as described in Section 7.3.1. The distribution fingerprints of the substances were recorded with the same method as well.

7.4.3. NMR

The average degree of substitution ($DS_a$) was calculated from the ratio of the signal from the three protons of the methyl group in the hydroxypropyl group and the signal from the proton attached to the C1 carbon (anomeric proton) of the anhydroglucose units from $^1$H-NMR spectrum.

The peak areas of the doublet from the methyl groups at ~1.2 ppm (A) and of the signals of the anomeric protons between +5 ppm and +5.4 ppm (B) were measured from the $^1$H NMR. An exemplary spectrum is shown in FIG. 28. As a reference, the peak area of the anomeric protons was set to 7.0 because 7 protons provide this peak in beta-cyclodextrin derivatives. Following assignment of the reference peak, the average degree of substitution was calculated using the expression: $DS_a=A/3$.

7.4.4. Cholesterol Solubilization Assay

In vitro cholesterol solubilization assays were performed as follows. A hydroxypropyl beta-cyclodextrin mixture test solution in distilled water is stirred at room temperature, whereupon an excess amount of unesterified cholesterol is added, such that an amount of the cholesterol remains undissolved. After 24 hours, the solids are filtered away, and the cholesterol present in solution is measured by HPLC method.

HPLC conditions: Analytical column: Nucleosil 120, C8, 5 μm, 100 mm×4.0 mm (Macherey Nagel); Column temperature: 40° C.; Mobile phase: Acetonitrile:water=78:22; Flow rate: 1.5 mL/min; Injection volume: 20 μL; Detector: UV 210 nm; Stop time: 5 min.

A stock solution of cholesterol is prepared by weighing and transferring 10 mg cholesterol in to 10 mL of acetonitrile/isopropanol (75:25). A reference solution of cholesterol is prepared by diluting the stock solution by ten-fold with the HPLC mobile phase (to give a concentration of 0.1 mg/mL).

The samples for the solubility experiments are diluted after filtration two-fold with acetonitrile, and additional HPLC mobile phase is used for further dilution, if needed.

The concentration of dissolved cholesterol is determined with the following equations:

$$\text{Cholesterol concentration (mg/mL)}=(\text{Area}_S/\text{Area}_R)\times\text{Conc}_R$$

$\text{Area}_S$=peak area of Cholesterol from the chromatogram of Sample Solution $\text{Area}_R$=peak area of Cholesterol from the chromatogram of Reference Solution $\text{Conc}_R$=concentration of SBECD-WS in the Calibration Standard solution (mg/mL).

7.5. Example 5: Electrospray MS Analysis

As discussed in Example 2 above, Kleptose® HPB has an average molar substitution of 0.58-0.68 ($DS_a$ 4.06-4.76), with two representative batches having an average molar substitution of 0.62 ($DS_a$ 4.34). Trappsol® Cyclo™, a hydroxypropyl beta-cyclodextrin composition available from a different manufacturer, has a higher reported average molar substitution of about 0.91 ($DS_a$ 6.37).

Electrospray mass spectrometry analysis was performed on commercially available samples of Kleptose® HPB and Trappsol® Cyclo™ (CTD Holdings, Inc.) ("Trappsol®") by two different laboratories.

The methods used by the first laboratory were as follows. About 50 μg of hydroxypropyl beta-cyclodextrin ("HPBCD") sample was dissolved in 1 mL of 1% formic acid in 80% methanol in water. This HPBCD solution was infused into an API-4000 mass spectrometer (Applied Biosystems). Positive ion electrospray mode was applied for MS scanning from m/z 1100 to 2000. The MS spectra (10-15 average scans) were recorded. Each signal height of propylene oxide addition products of β-cyclodextrin was measured and the propylene oxide adduct population of HPBCD was calculated from the sum of individual signal heights. Analyst 1.51 software (Applied Biosystems) was used for the MS operation. As shown in FIG. 29A-B, electrospray MS data from the first lab demonstrates that the differences in average molar substitution are caused by markedly different degrees and distributions of hydroxypropyl substitutions in Kleptose® HPB (FIG. 29A) and Trappsol® (FIG. 29B). Numbers have been added to the spectra to identify the number of hydroxypropyl moieties in each peak.

The methods used by the second laboratory were as follows. Samples were prepared at 1 mg/mL in water and diluted to ~5 μM in 1:1 water:acetonitrile for electrospraying. Ions were formed using an Agilent Nanospray source with a direct infusion rate of 600 nL/min (sheath gas at 150° C. and flow rate of 5 L/min with a Vcap potential of 1500 V). Potentials in the interface between the ESI source and ion mobility drift tube were adjusted for optimal signal intensities. Spectra were accumulated for 3 min at a single potential across the drift tube and clearly show ion mobility separations between multiple classes of ions in the electrospray plume. The analyzer used was the Agilent 6560, a linear, low field ion mobility mass spectrometer, and can be considered a substantially modified version of an Agilent Q-TOF accommodating an IM drift tube at the MS sampling orifice employing ion funnel technology. Electrospray MS data from the second laboratory, shown in FIG. 30A-B, confirms the difference in substitution fingerprint (compare FIGS. 30A (Kleptose® HPB) and 30B (Trappsol®)). The data also confirm that electrospray MS is sufficiently robust an analytical tool that it can be used routinely by different labs to reproducibly fingerprint hydroxypropyl beta-cyclodextrin compositions.

FIG. 31A-C compare electrospray MS data from three different lots of Kleptose® HPB, performed by two different labs (FIGS. 31A and 31B, second laboratory; FIG. 31C, first laboratory), and demonstrates that the substitution fingerprint is nearly identical between lots. The low lot-to-lot variability in substitution fingerprint is consistent with the observation that the average molar substitution was identical between two exemplary lots of Kleptose® HPB, as discussed in Example 2 above. FIG. 32A-B present electrospray MS spectra from two different lots of Trappsol®, by two different laboratories (FIG. 32A, first laboratory; FIG. 32B, second laboratory) using the same conditions as were used to generate the Kleptose data shown in FIGS. 31A and 31B, and demonstrate that there is significant lot-to-lot variability in the Trappsol® substitution fingerprint.

FIG. 33A-B show electrospray MS spectra from the second laboratory in which the Y axis has been expanded as compared to FIGS. 29-32 to show peaks between 1090 and 1230 m/z. FIG. 33A is the spectrum obtained from Trappsol®. FIG. 33B is the spectrum obtained from Kleptose® HPB. The spectra show that there are significant levels of propylene glycol in Trappsol® (propylene glycol peaks are labeled in FIG. 33A), but not in Kleptose® HPB. Kleptose® HPB has a small but detectable amount of unsubstituted cyclodextrin, shown by the peak labeled in FIG. 33B.

FIG. 34A-B show the further differences between Kleptose® HPB and Trappsol® samples: 1) DS are significantly different between the two samples. Trappsol® shows condensation reactions that must include both axial and equatorial hydroxyls; 2) Principal ions of both samples are $NH_4^+$ adduction from ammonia present in the solids. $MH^+$ ions are also present for each DS; 3) Isotope clusters for each of the major ions shows doubly charged homo-dimers of the ammonium adducts. In the case of Trappsol® doubly charged dimers of the protonated ions are seen as well; 4) Both materials show doubly charged homo-dimers from adduction of both a proton and ammonium; 5) Doubly charged hetero-dimers, noted for the case of DS6-DS7 at m/z 1530, are formed in both materials but are far more intense in Trappsol® than in Kleptose® HPB; 6) All of these differences were maintained at 2.5 μM concentrations in 80% ACN. This indicates the dimers have strong intermolecular associations.

FIG. 35A-B show additional differences between Kleptose® HPB and Trappsol® samples are in the form of triply charged dimers of both homo and hetero-origin. These show greater intensity in Trappsol® and are virtually absent in Kleptose® HPB.

In summary, electrospray MS analysis demonstrates significant differences in the substitution fingerprint of the hydroxypropyl beta-cyclodextrin composition used in the phase I clinical trial described in Example 1, Kleptose® HPB, as compared to the substitution fingerprint of a different hydroxypropyl beta-cyclodextrin composition that is commercially available, Trappsol® Cyclo™. Kleptose® HPB has low lot-to-lot variability in the substitution fingerprint, and low levels of impurities, notably propylene glycol. In contrast, Trappsol® exhibits high lot-to-lot variability in its substitution fingerprint and significantly higher levels of propylene glycol, a presumed ototoxin. Trappsol® also exhibits triply charged cyclodextrin dimers of both homo and hetero-origin, which are absent in Kleptose® HPB.

7.6. Example 6: Purification of Hydroxypropyl Beta-Cyclodextrin Compositions

Three purification methods (complexation, precipitation, and adsorption) were investigated for their ability to further reduce propylene glycol (PG) and unsubstituted beta-cyclodextrin (DS=0) impurities in Kleptose® HBP.

7.6.1. Complexation/Association with Organic Compounds

Experiment 5.6.1A: 1.0 g HPBCD (Kleptose HBP® (Roquette)) was dissolved in water (10 mL). p-Xylene (Trial #5.6.1.1) or toluene (Trial #5.6.1.2) (1.0 mL) was added to the solutions and the mixtures were stirred for 24 hrs at room temperature and 1 hr at 5-7° C. The opalescent solutions were filtered through 0.45 μm cellulose acetate membrane filter and the filtrates were evaporated at 40° C. to dryness.

Trial #5.6.1.1:0.7 g; yield: 70%.

Trial #5.6.1.2:0.8 g; yield: 80%.

Experiment 5.6.1B: 2.0 g HPBCD (Kleptose HBP® (Roquette)) was dissolved in water (4 mL). D-Limonene (Trial #5.6.1.3, 0.04 mL, ~10 equivalents) or L-menthol (Trial #5.6.1.4, 0.04 g, ~10 equivalents) or benzyl alcohol (Trial #5.6.1.5, 0.03 mL, ~10 equivalents) or cholesterol (Trial #5.6.1.6, 0.1 g, ~10 equivalents) was added to the solution and the mixture was stirred for 72 hrs at room temperature. The solutions were kept at 5° C. for 4 hrs.

Trial #5.6.1.4 and Trial #5.6.1.5 remained clear solutions, no precipitate was formed.

Trial #5.6.1.3 and Trial #5.6.1.6 formed precipitate. The solutions from Trial #5.6.1.3 and Trial #5.6.1.6 were each filtered through 0.45 μm cellulose acetate membrane filter and the filtrates were evaporated at 40° C. until dryness.

Trial #5.6.1.3:2.1 g; yield: 105%.

Trial #5.6.1.6:1.4 g; yield: 70%.

Results for the samples derived from selective complex formation or association with small molecules are summarized in Table 9.

TABLE 9

Analysis of HPBCD samples after selective complexation or association

| Test | Kleptose ® HPB | Trial #5.6.1.1 (p-Xylene) | Trial #5.6.1.2 (toluene) | Trial #5.6.1.3 (D-Limonene) | Trial #5.6.1.6 (L-menthol) |
|---|---|---|---|---|---|
| Propylene glycol content | 0.18% | ND | ND | ND | ND |
| Unsubstituted β-cyclodextrin content | 0.60% | 0.38% | 0.54% | 0.21% | 0.60% |
| HPBCD DS = 1 content | 3.68% | 3.14% | 3.25% | 2.61% | 3.42% |
| Other cyclodextrin related impurities | 0.23% | 0.23% | 0.19% | 0.14% | 0.24% |

ND = not determined.

Figure 19:
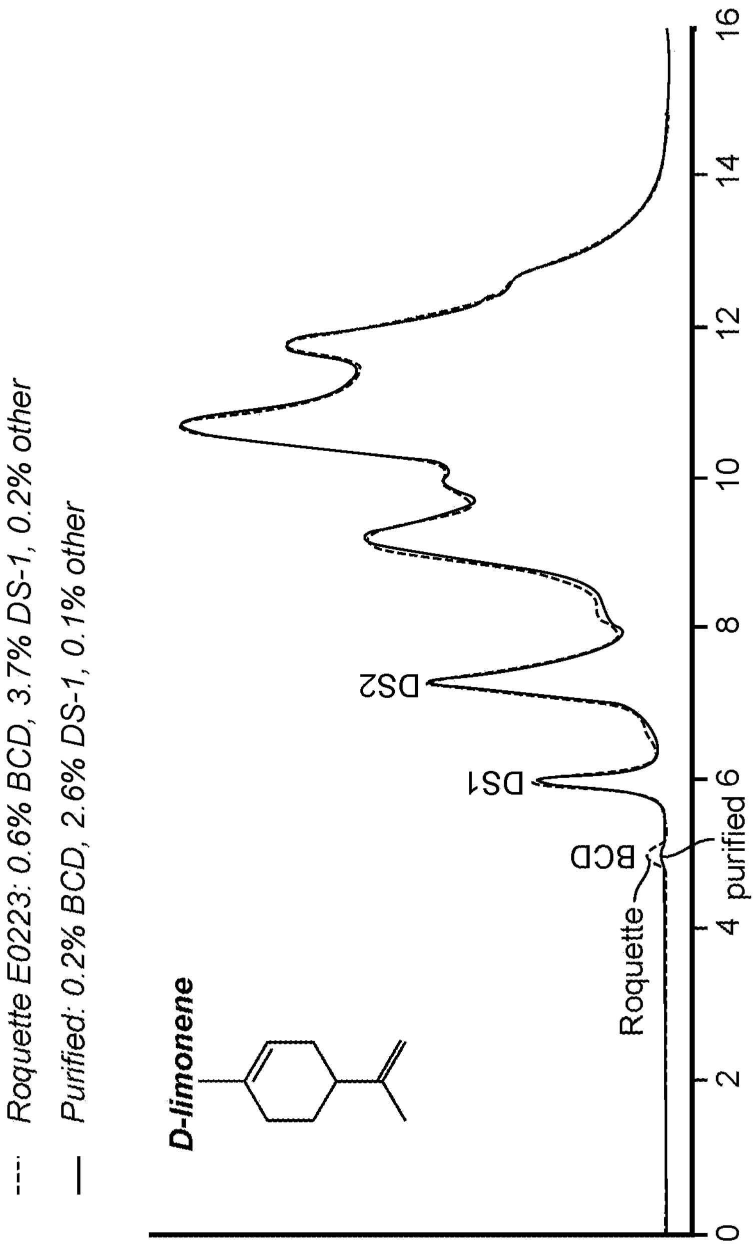
FIG. 19 shows overlay HPLC traces for the commercial Kleptose HPB® (Roquette, batch E0223) (upper trace), and after purification by complexation with D-limonene (lower trace). X-axis shows retention time in minutes.

Trials #5.6.1.1, #5.6.1.2, and #5.6.1.3 showed a decrease in unsubstituted beta-cyclodextrin content compared to commercial Kleptose® HBP. In addition, D-limonene in Trial #5.6.1.3 showed a decrease in the levels of monosubstituted hydroxypropyl beta-cyclodextrin ("HPBCD DS=1"), and other cyclodextrin-related impurities (see FIG. 19). FIG. 19 shows the impurities unsubstituted beta-cyclodextrin (BCD) at retention time ~5 min, monosubstituted hydroxypropyl beta-cyclodextrins (DS-1) at retention time ~6 min, and hydroxypropyl beta-cyclodextrins having DS=2 (DS-2) at retention time ~7.4 min.

7.6.2. Precipitation

General method: 1.0 g HPBCD (Kleptose HBP® (Roquette)) was dissolved in 5 mL or 2 mL solvent(S), and precipitated in 50 mL or 20 mL precipitating agent (PA). The filtered solid material was rinsed 3 times with 3 mL PA. The exception was with Trial #5.6.2.11:1.0 g HPBCD was dissolved in water (2 mL) and extracted with chloroform (3×10 mL). The organic phases were combined, dried on $Na_2SO_4$, decanted, and evaporated at 40° C. until dryness. The preparations for each Trial are summarized in Table 10.

TABLE 10

| Preparation of precipitation samples | | | | | | |
|---|---|---|---|---|---|---|
| Trial # | Solvent (S) | Amount S (mL) | Precipitating agent (PA) | Amount PA (mL) | Yield (%) | Comments |
| 5.6.2.1 | methanol | 5 | acetone | 50 | 92 | Solvents and |
| 5.6.2.2 | | | acetonitrile | | 96 | precipitating agents |
| 5.6.2.3 | | | chloroform | | 78 | were of technical |
| 5.6.2.4 | | 2 | acetone | | 95 | grade; the filtered |
| 5.6.2.5 | | | acetonitrile | | 98 | solids were dried in |
| 5.6.2.6 | | | chloroform | | 98 | air, at room |
| 5.6.2.7 | water | | acetone | | 99 | temperature |
| 5.6.2.8 | | | acetonitrile | | 99 | |
| 5.6.2.9 | | | chloroform | 3 × 10 | 96 | extraction |
| 5.6.2.4.2 | methanol | | acetone | 50 | 90 | Solvents and |
| 5.6.2.5.2 | | | acetonitrile | | 94 | precipitating agents |
| 5.6.2.7.2 | water | | acetone | | 84 | were of HPLC or GC |
| 5.6.2.8.2 | | | acetonitrile | | 91 | quality; the filtered |
| 5.6.2.10 | methanol | | acetone | 20 | 92 | solids were dried |
| 5.6.2.11 | water | | chloroform | | ND | under vacuum, at room temperature |

ND = not determined.

Analytical results of solvent precipitation experiments are summarized in Table 11.

TABLE 11

| Comparative analysis of the HPBCD samples purified by precipitation | | | | | | | |
|---|---|---|---|---|---|---|---|
| Test | Kleptose ® HPB | Trial 5.6.2.10 | Trial 5.6.2.2 | Trial 5.6.2.3 | Trial 5.6.2.7.2 | Trial 5.6.2.8.2 | Trial 5.6.2.11 |
| Propylene glycol | 0.18% | 0.015% | 0.035% | 0.14% | <0.01% | <0.01% | 0.18% |
| β-cyclodextrin | 0.60% | ND | ND | ND | ND | ND | ND |
| HPBCD DS = 1 | 3.68% | ND | ND | ND | ND | ND | ND |
| Total other cyclodextrin related impurities | 0.23% | ND | ND | ND | ND | ND | ND |

ND = not determined.

Figure 20:
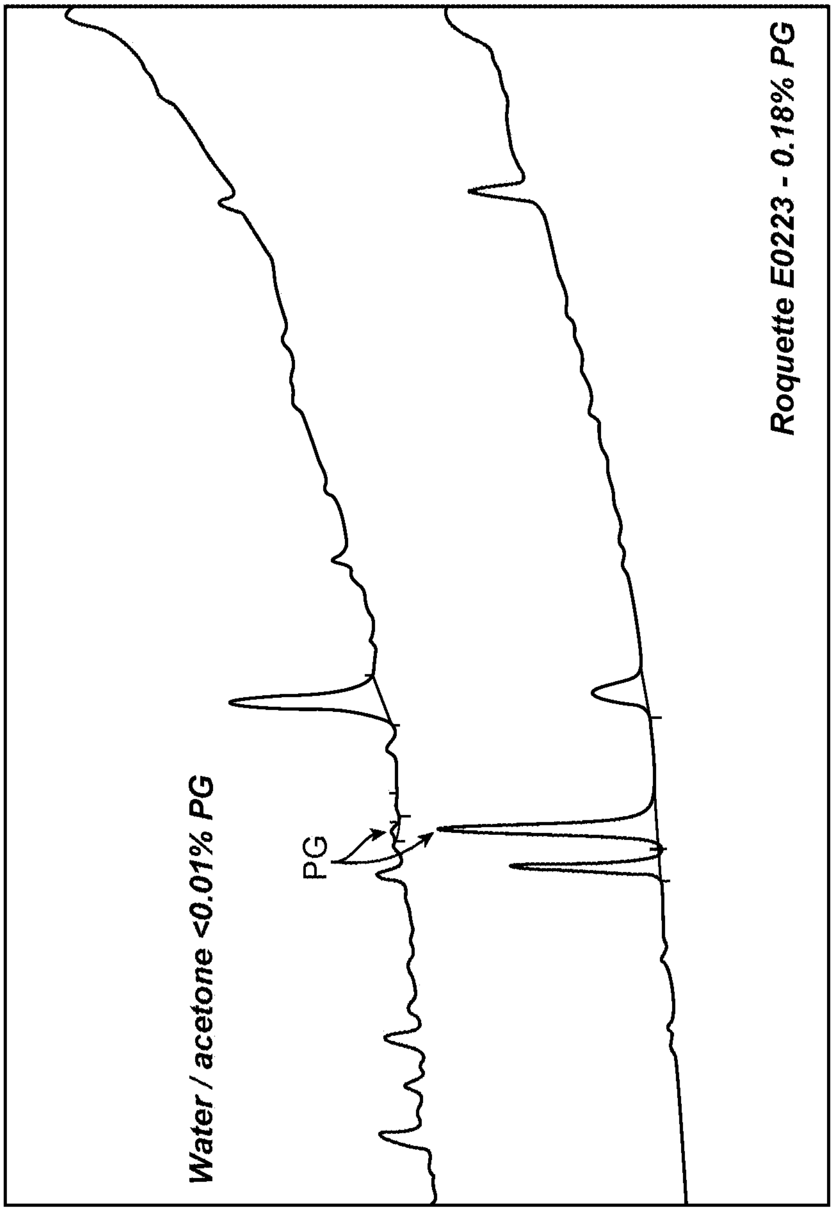
FIG. 20 shows HPLC traces for a sample obtained after solvent precipitation using water/acetone mixture (upper trace) in comparison to the commercial Kleptose HPB® (Roquette, batch E0223).

As shown in Table 11, precipitation reduced the level of propylene glycol in the hydroxypropyl beta-cyclodextrin samples. Trials #5.6.2.10, 5.6.2.2, and 5.6.2.3 using methanol in combination with acetone, acetonitrile, or chloroform, respectively, as precipitating agents were able to reduce the propylene glycol levels by 92%, 81%, and 22%, respectively. Trials #5.6.2.7.2 and 5.6.2.8.2 using water in combination with acetone or acetonitrile, respectively, as precipitating agents reduced the propylene glycol levels by >95% (see FIG. 20, comparing Trial #5.6.2.7.2 versus Kleptose HPB®). In comparison, Trial #5.6.2.11 using water and chloroform did not significantly change the propylene glycol levels as compared with the commercial Kleptose HPB®.

7.6.3. Adsorption 7.6.3.1. Clarification with Alumina 2.0 g HPBCD (Kleptose HBP® (Roquette)) was dissolved in methanol (8 mL, Trial #5.6.3.1.1) or ethanol (8 mL, Trial #5.6.3.1.2), and stirred for half an hour with alumina (2.0 g, aluminum oxide 90 standardized, Merck) at room temperature. The alumina was filtered out, washed with methanol or ethanol (3×2 mL), and water (3×2 mL). The filtrates (SZ) and the first rinsing solvents (M1 [methanol] or E1 [ethanol]) were evaporated at 40° C. until dryness.

Trial #5.6.3.1.1: Sample 5.6.3.1.1-SZ: 1.6 g; yield: 80%.

Trial #5.6.3.1.1: Sample 5.6.3.1.1-M1: 0.2 g; yield: 10%.

Trial #5.6.3.1.2: Sample 5.6.3.1.2-SZ: 1.5 g; yield: 75%.

Trial #5.6.3.1.2: Sample 5.6.3.1.2-E1: 0.2 g; yield: 10%.

7.6.3.2. Chromatography on Alumina

Trial #5.6.3.2.1:2.0 g HPBCD (Kleptose HBP® (Roquette)) was dissolved in methanol (2 mL), and chromatographed through alumina (10 g, aluminum oxide 90 standardized, Merck) with methanol, flow rate: 3 mL/min, 1 min/fraction, 30 fractions. The column was washed with water, flow rate: 10 mL/min, 20 mins (W). The following fractions were combined and evaporated at 40° C. until dryness:

Sample 5.6.3.2.1A: 2nd fraction: 0.5 g, yield: 25%.

Sample 5.6.3.2.1B: 3-8th fractions: 1.1 g, yield: 55%.

Sample 5.6.3.2.1C: 9-14th fractions: 0.2 g, yield: 10%.

Sample 5.6.3.2.1D: 15th-W fractions: 0.2 g, yield: 10%.

Trial #5.6.3.2.2:5.0 g HPBCD (Kleptose HBP® (Roquette)) was dissolved in methanol (10 mL), and chromatographed through alumina (200 g, aluminum oxide 90 standardized, Merck) with the following solvent gradient: 100% methanol, flow rate: 5 mL/min, 3 min/fraction, 1-30th fractions; 80% methanol, 20% water, 5 mL/min, 3 min/fraction, 31-43rd fractions; 50% methanol-water, 5 mL/min, 3 min/fraction, 44-60th fractions; 100% water, 5 mL/min, 3 min/fraction, 61-70th fractions; washing (W): 100% water, 10 mL/min, 30 min.

The following fractions were combined and evaporated at 40° C. until dryness:

Sample 5.6.3.2.2A: 0-5th fractions: 0.1 g, yield: 2%.

Sample 5.6.3.2.2B: 6-10th fractions: 0.6 g, yield: 12%.

Sample 5.6.3.2.2C: 11-16th fractions: 0.5 g, yield: 10%.

Sample 5.6.3.2.2D: 17-45th fractions: 1.1 g, yield: 22%.

Sample 5.6.3.2.2E: 46-51st fractions: 0.5 g, yield: 10%.

Sample 5.6.3.2.2F: 52-56th fractions: 0.9 g, yield: 18%.

Sample 5.6.3.2.2G: 57-66th fractions: 0.5 g, yield: 10%.

Sample 5.6.3.2.2H: 67-W fractions: 1.3 g, yield: 26%.

7.6.4. Anion Exchange Resin

Trial #5.6.3.3:1.0 g HPBCD was dissolved in water (10 mL), and the pH was set between 10-12 (measured by universal pH paper, Merck pH1-14) with 0.1 N NaOH. The solution was stirred with 5.0 g of anion exchange resin (Purolite, product code: 47111) for 14 hrs. The resin was filtered out, the filtrate was neutralized with cation exchange resin (Purolite, product code: 15131) and treated with charcoal. The solid sample was isolated by evaporation at 40° C. until dryness to give Sample 5.6.3.3, Yield: 0.9 g, 90%.

Characterization of Samples from Adsorption

TABLE 12

Comparative analysis of the HPBCD samples purified by selective adsorption

| Sample | Kleptose ® HPB | 5.6.3.1.1-SZ | 5.6.3.1.2-SZ | 5.6.3.2.1A | 5.6.3.2.1B | 5.6.3.2.1C | 5.6.3.3 |
|---|---|---|---|---|---|---|---|
| Propylene glycol | 0.18% | ND | ND | 0.10% | 0.18% | ND | 0.15% |
| β-cyclodextrin | 0.60% | 0.13% | 0.33% | 0.14% | 0.12% | 0.23% | 0.36% |
| HPBCD DS = 1 | 3.68% | 2.11% | 2.45% | 1.74% | 2.16% | 4.74% | 2.69% |
| Total other cyclodextrin related impurities | 0.23% | 0.1% | 0.15% | 0.06% | 0.06% | 0.12% | 0.19% |

ND = not determined.

TABLE 13

Comparative analysis of the HPBCD samples purified by selective adsorption (chromatography)

| | Kleptose ® | 5.6.3.2.2 | | | | | | | |
|---|---|---|---|---|---|---|---|---|---|
| Sample | HPB | A | B | C | D | E | F | G | H |
| Propylene glycol | 0.18% | ND | 0.26% | 0.06% | 0.31% | 0.16% | 0.05% | 0.05% | 0.03% |
| beta-cyclodextrin | 0.60% | <0.05% | <0.05% | <0.05% | <0.05% | <0.05% | <0.05% | <0.05% | 1.53% |

TABLE 13-continued

| Comparative analysis of the HPBCD samples purified by selective adsorption (chromatography) | | | | | | | | | |
|---|---|---|---|---|---|---|---|---|---|
| | Kleptose ® | 5.6.3.2.2 | | | | | | | |
| Sample | HPB | A | B | C | D | E | F | G | H |
| HPBCD DS = 1 | 3.68% | <0.05% | 0.05% | <0.05% | <0.05% | 0.07% | 0.14 % | 0.49% | 10.79% |
| Total other cyclo-dextrin related impur-ities | 0.23% | 0.38% | <0.05% | <0.05% | 0.08% | 0.23% | 0.20% | 0.51% | 1.18% |

ND = not determined.

Figure 21:
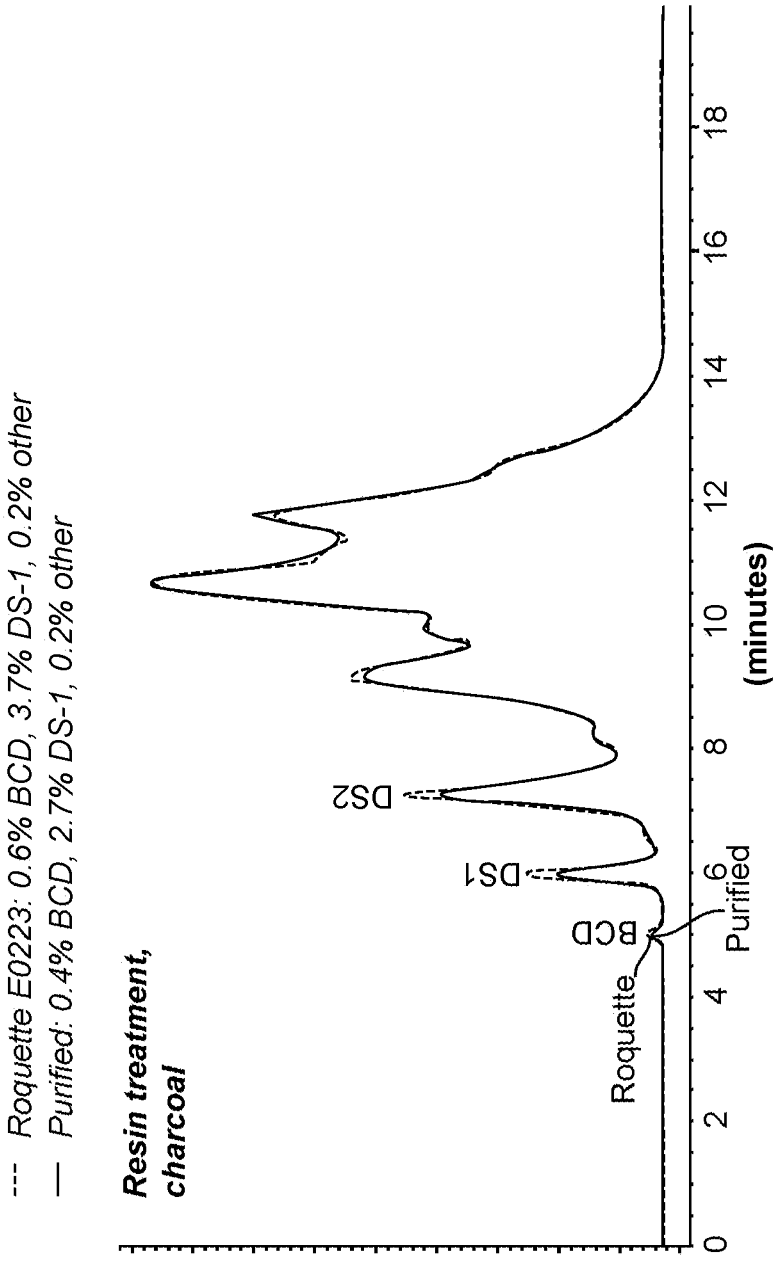
FIG. 21 shows overlay HPLC traces for the commercial Kleptose HPB® (Roquette, batch E0223) (upper trace), and after purification by resin and charcoal treatment (lower trace). X-axis shows retention time in minutes.

A graphical representation of the data in Tables 12 and 13 is depicted in FIGS. 21-24. Fractions A through H correspond to Samples 5.6.3.2.2A through 5.6.3.2.2H, respectively. While anion exchange resin followed by charcoal treatment served to reduce some of the impurities (Trial #5.6.3.3, FIG. 21), aluminum oxide adsorption was found to be effective in reducing CD related impurity levels (Trial #5.6.3.1, FIG. 22), even more so when applied in chromatography (FIG. 23). FIGS. 21-23 show the impurity unsubstituted beta-cyclodextrin (BCD) at retention time ~5 min, as well as monosubstituted hydroxypropyl beta-cyclodextrins (DS-1) at retention time ~6 min, and hydroxypropyl beta-cyclodextrins having DS=2 (DS-2) at retention time ~7.4 min. The eight fractions (A to H) collected in Trial #5.6.3.2.2 are depicted in FIG. 24. Fractions B-D contained the target impurities, propylene glycol and BCD, in extremely low concentrations. BCD was reduced below the quantification limit in fractions A-G. Concomitantly, DS-1 HPBCD content was below 0.15% in fractions A-F (96% or greater reduction); and CD-related other impurities decreased significantly in fractions B-D. Based on these findings, $Al_2O_3$ based chromatography was deemed suitable to efficiently remove CD related impurities from HPBCD.

7.7. Example 7: Purification on Larger Scale

To prepare for a phase II clinical trial, three purification methods (precipitation, adsorption on alumina, and a combination of precipitation and alumina absorption) were investigated for their ability to reduce propylene glycol (PG) and unsubstituted beta-cyclodextrin (DS=0) impurities in Kleptose® HBP on a larger scale. Purification was performed on 10 g batches of HPBCD (Kleptose® HBP (Roquette)); precipitation was also performed on a 30 g batch. Results obtained from the 10 g batches are set forth in the Tables 16, 17 and 18. Results obtained from the 30 g batch is set forth in the Table 19.

7.7.1. Solvent Precipitation

During preparation of 10 g HPBCD, the precipitation was done from water with acetone. HPBCD was dissolved in half equivalent water (20 g HPBCD in 10 ml water), poured into five times volume (100 ml) of acetone and washed thrice with double volume (40 ml) of acetone after decanting. The dissolution takes 30-60 minutes using ultrasound and stirring. The gluey nature of the precipitate was reduced by thrice washing with acetone prior to filtering. The yield was 87-93%.

At the 30 g scale methanol was used instead water for the dissolution of HPBCD. 43 g HPBCD was dissolved in 43 ml methanol, and then poured into 430 ml acetone. The precipitate was easy to filter after thrice washing with acetone (43 ml). The yield was 99%. Based on the GC results, using methanol during purification was faster and resulted in a better yield than using water.

7.7.2. Chromatography on Alumina

The HPBCD was dissolved in methanol to obtain approximately 1 mg/ml solutions. For example, 10.0 g HPBCD was dissolved in methanol (10 mL), and chromatographed through alumina (180 $cm^3$ column of 220 g alumina packing) with methanol, flow rate of 5 mL/min, fractions were harvested every 10 minutes with 8-20 fractions in total. The eluent was 100% methanol. To manufacture 10 g of purified HPBCD 20-22 g of starting materials were used with a 70-75% yield for the pure product.

7.7.3. Combination of Chromatography on Alumina and Solvent Precipitation

For the combination protocol the solvent precipitation as described above was followed by above described chromatography on alumina for 10.0 g HPBCD batches.

TABLE 16

| Analysis of the HPBCD samples purified by solvent precipitation (Batch ID: CYL-4061) | | |
|---|---|---|
| Test | Analysis | Result |
| Identification | HPLC, NMR | conforms |
| Average degree of substitution | NMR | 4.2 |
| Unsubstituted β-cyclodextrin content | HPLC | 0.6% |
| HPBCD DS-1 | HPLC | 3.7% |
| Total other cyclodextrin related impurities | HPLC | 0.08% |
| Propylene glycol content | GC | 0.01% |
| Di-propylene glycol content | GC | <0.2% |
| Tri-propylene glycol content | GC | <0.2% |
| Cholesterol solubilizing potency (at 50 mg/ml CD concentration) | HPLC | 23 mg/ml |
| Solubility (in 100 $cm^3$ solvent, at 25° Celsius) | | Methanol: >60 g<br>Ethanol: >60 g |

TABLE 17

| Analysis of the HPBCD samples purified by absorption chromatography on alumina (Batch ID: CYL-4062) | | |
|---|---|---|
| Test | Analysis | Result |
| Identification | HPLC, NMR | conforms |
| Average degree of substitution | NMR | ND |
| Unsubstituted ⌋-cyclodextrin content | HPLC | <0.05% |
| HPBCD DS-1 | HPLC | 0.1% |
| Total other cyclodextrin related impurities | HPLC | 0.05% |
| Propylene glycol content | GC | 0.05% |
| Di-propylene glycol content | GC | <0.2% |
| Tri-propylene glycol content | GC | <0.2% |
| Cholesterol solubilizing potency (at 50 mg/ml CD concentration) | HPLC | 27 mg/ml |
| Solubility (in 100 $cm^3$ solvent, at 25° Celsius) | | Methanol: >60 g<br>Ethanol: >60 g |

TABLE 18

| Analysis of the HPBCD samples purified by combination of absorption chromatography on alumina and solvent precipitation (Batch ID: CYL-4063) | | |
|---|---|---|
| Test | Analysis | Result |
| Identification | HPLC, NMR | conforms |
| Average degree of substitution | NMR | 4.6 |
| Unsubstituted β-cyclodextrin content | HPLC | <0.05% |
| HPBCD DS-1 | HPLC | 0.02% |
| Total other cyclodextrin related impurities | HPLC | <0.05% |
| Propylene glycol content | GC | <0.01% |
| Di-propylene glycol content | GC | <0.2% |
| Tri-propylene glycol content | GC | <0.2% |
| Cholesterol solubilizing potency (at 50 mg/ml CD concentration) | HPLC | 22 mg/ml |
| Solubility (in 100 $cm^3$ solvent, at 25° Celsius) | | Methanol: >60 g<br>Ethanol: >60 g |

TABLE 19

| Analysis of the HPBCD (30 g) samples purified by combination of absorption chromatography on alumina and solvent precipitation (Batch ID: CYL-4077) | | |
|---|---|---|
| Test | Analysis | Result |
| Identification | HPLC, NMR | conforms |
| Average degree of substitution | NMR | 4.7 |
| Unsubstituted β-cyclodextrin content | HPLC | <0.02% |
| HPBCD DS-1 | HPLC | 0.12% |
| Total other cyclodextrin related impurities | HPLC | <0.02% |
| Propylene glycol content | GC | <0.02% |
| Cholesterol solubilizing potency (at 50 mg/ml CD concentration) | HPLC | 22 mg/ml |
| Solubility (in 100 $cm^3$ solvent, at 25° Celsius) | | Methanol: >60 g<br>Ethanol: >60 g |

Table 20 compares results from the 3 purification methods.

TABLE 20

Comparison of purification methods

| Test | Kleptose ® HPB | solvent precipitation Batch ID: (CYL-4061) | absorption chromatography on alumina Batch ID: (CYL-4062) | combination of absorption chromatography on alumina and solvent precipitation (water-acetone) (10 g) Batch ID: (CYL-4063) | combination of absorption chromatography on alumina and solvent precipitation (methanol-acetone) (30 g) Batch ID: (CYL-4077) |
|---|---|---|---|---|---|
| Identification | | conforms | conforms | conforms | conforms |
| Average degree of substitution | 4.34 | 4.2 | ND | 4.6 | 4.7 |
| Unsubstituted β-cyclodextrin content | 0.60% | 0.6% | <0.05% | <0.05% | <0.02% |
| HPBCD DS-1 | 3.68% | 3.7% | 0.1% | 0.02% | 0.12% |
| Total other cyclodextrin related impurities | 0.23% | 0.08% | 0.05% | <0.05% | <0.02% |
| Propylene glycol content | 0.18% | 0.01% | 0.05% | <0.01% | <0.02% |
| Di-propylene glycol content | | <0.2% | <0.2% | <0.2% | |
| Tri-propylene glycol content | | <0.2% | <0.2% | <0.2% | |

TABLE 20-continued

Comparison of purification methods

| Test | Kleptose ® HPB | solvent precipitation Batch ID: (CYL-4061) | absorption chromatography on alumina Batch ID: (CYL-4062) | combination of absorption chromatography on alumina and solvent precipitation (water-acetone) (10 g) Batch ID: (CYL-4063) | combination of absorption chromatography on alumina and solvent precipitation (methanol-acetone) (30 g) Batch ID: (CYL-4077) |
|---|---|---|---|---|---|
| Cholesterol solubilizing potency (at 50 mg/ml CD concentration) | | 23 mg/ml | 27 mg/ml | 22 mg/ml | 22 mg/ml |
| Solubility (in 100 $cm^3$ solvent, at 25° Celsius) | | Methanol: >60 g Ethanol: >60 g | Methanol: >60 g Ethanol: >60 g | Methanol: >60 g Ethanol: >60 g | Methanol: >60 g Ethanol: >60 g |

7.7.4. Effect of Purification on Substitution Fingerprint

Electrospray MS analysis was performed essentially as described in Example 5 (second laboratory) on an aliquot of Batch CYL-4063, the batch purified by combination of absorption chromatography on alumina and solvent precipitation (water-acetone), and on an aliquot of the parent lot of Kleptose® HPB. The spectra are compared in FIG. 36A-B, with FIG. 36A showing the spectrum from the starting material and FIG. 36B showing the spectrum from the purified batch. As can be seen, the purification eliminates unsubstituted beta-cyclodextrin molecules ("DS-0"), nearly all cyclodextrin molecules with a single hydroxypropyl substitution ("DS-1"), and reduces the concentration of cyclodextrin molecules having two hydroxypropyl substitutions ("DS-2"). The spectra also suggest little change in the relative proportions and thus distribution of the more highly substituted hydroxypropyl beta-cyclodextrin species, DS3, DS4, DS5, DS6 and DS7.

We quantified the peak distribution of 14 batches of Kleptose® HPB ("EOxxx") and the purified Batch CYL-4063. The signal of each peak and the percentage each peak contributes to the total signal are summarized in Table 21.

TABLE 21

Quantification of peak distribution

| Batch ID | m/z 1152 (DS-0) | m/z 1210 (DS-1) | m/z 1268 (DS-2) | m/z 1326 (DS3) | m/z 1384 (DS4) | m/z 1442 (DS5) | m/z 1500 (DS6) | m/z 1558 (DS7) | m/z 1618 (DS8) | Total Signal | DS-2/ DS-1 |
|---|---|---|---|---|---|---|---|---|---|---|---|
| EO190 | 8271 | 40791 | 139700 | 321271 | 418999 | 312241 | 154341 | 50521 | 0 | 1446134 | 3.4 |
| | 0.6% | 2.8% | 9.7% | 22.2% | 29.0% | 21.6% | 10.7% | 3.5% | 0.0% | 100.0% | |
| EO194 | 0 | 74463 | 261482 | 581280 | 683474 | 493534 | 235243 | 78741 | 0 | 2408217 | 3.5 |
| | 0.0% | 3.1% | 10.9% | 24.1% | 28.4% | 20.5% | 9.8% | 3.3% | 0.0% | 100.0% | |
| EO197 | 14510 | 67730 | 211808 | 438806 | 488923 | 334509 | 155845 | 52450 | 0 | 1764582 | 3.1 |
| | 0.8% | 3.8% | 12.0% | 24.9% | 27.7% | 19.0% | 8.8% | 3.0% | 0.0% | 100.0% | |
| EO199 | 14595 | 80072 | 258738 | 547035 | 604472 | 417563 | 202219 | 67725 | 8196 | 2200613 | 3.2 |
| | 0.7% | 3.6% | 11.8% | 24.9% | 27.5% | 19.0% | 9.2% | 3.1% | 0.4% | 100.0% | |
| EO230 | 9783 | 51565 | 178426 | 349066 | 380442 | 264898 | 125560 | 41141 | 0 | 1400879 | 3.5 |
| | 0.7% | 3.7% | 12.7% | 24.9% | 27.2% | 18.9% | 9.0% | 2.9% | 0.0% | 100.0% | |
| EO234 | 12101 | 64237 | 210693 | 427987 | 486218 | 329743 | 152141 | 49506 | 0 | 1732625 | 3.3 |
| | 0.7% | 3.7% | 12.2% | 24.7% | 28.1% | 19.0% | 8.8% | 2.9% | 0.0% | 100.0% | |
| EO240 | 10871 | 55903 | 187803 | 365483 | 390189 | 270539 | 127936 | 42957 | 0 | 1451681 | 3.4 |
| | 0.7% | 3.9% | 12.9% | 25.2% | 26.9% | 18.6% | 8.8% | 3.0% | 0.0% | 100.0% | |
| EO242 | 7678 | 31064 | 101220 | 192348 | 192221 | 128433 | 60981 | 23856 | 0 | 737801 | 3.3 |
| | 1.0% | 4.2% | 13.7% | 26.1% | 26.1% | 17.4% | 8.3% | 3.2% | 0.0% | 100.0% | |
| EO253 | 11527 | 53739 | 174134 | 335106 | 358419 | 254261 | 119699 | 44125 | 0 | 1351010 | 3.2 |
| | 0.9% | 4.0% | 12.9% | 24.8% | 26.5% | 18.8% | 8.9% | 3.3% | 0.0% | 100.0% | |
| EO265 | 0 | 40533 | 128930 | 263039 | 296342 | 203297 | 98477 | 32960 | 0 | 1063578 | 3.2 |
| | 0.0% | 3.8% | 12.1% | 24.7% | 27.9% | 19.1% | 9.3% | 3.1% | 0.0% | 100.0% | |
| EO270 | 18518 | 101531 | 340195 | 681274 | 764792 | 530914 | 241841 | 82688 | 0 | 2761754 | 3.4 |
| | 0.7% | 3.7% | 12.3% | 24.7% | 27.7% | 19.2% | 8.8% | 3.0% | 0.0% | 100.0% | |
| EO277 | 15144 | 69571 | 229585 | 488128 | 540927 | 377689 | 178205 | 59435 | 8755 | 1967438 | 3.3 |
| | 0.8% | 3.5% | 11.7% | 24.8% | 27.5% | 19.2% | 9.1% | 3.0% | 0.4% | 100.0% | |
| EO237 | 27395 | 143476 | 478761 | 988885 | 1124832 | 769561 | 363246 | 123518 | 0 | 4019673 | 3.3 |
| | 0.7% | 3.6% | 11.9% | 24.6% | 28.0% | 19.1% | 9.0% | 3.1% | 0.0% | 100.0% | |
| EO245 | 0 | 295840 | 965902 | 1907408 | 2345018 | 1807732 | 880668 | 285778 | 0 | 8488345 | 3.3 |
| | 0.0% | 3.5% | 11.4% | 22.5% | 27.6% | 21.3% | 10.4% | 3.4% | 0.0% | 100.0% | |

TABLE 21-continued

| Quantification of peak distribution | | | | | | | | | | | |
|---|---|---|---|---|---|---|---|---|---|---|---|
| Batch ID | m/z 1152 (DS-0) | m/z 1210 (DS-1) | m/z 1268 (DS-2) | m/z 1326 (DS3) | m/z 1384 (DS4) | m/z 1442 (DS5) | m/z 1500 (DS6) | m/z 1558 (DS7) | m/z 1618 (DS8) | Total Signal | DS-2/ DS-1 |
| Mean | 0.6% | 3.6% | 12.0% | 24.5% | 27.6% | 19.3% | 9.2% | 3.1% | 0.1% | 100.0% | 3.3 |
| SD | 0.3% | 0.3% | 1.0% | 1.0% | 0.7% | 1.1% | 0.7% | 0.2% | 0.1% | | 0.1 |
| CYL- | 0 | 0 | 258436 | 1401875 | 2525377 | 2328043 | 1223567 | 409420 | 35622 | 8182339 | N/D |
| 4063 | 0.0% | 0.0% | 3.2% | 17.1% | 30.9% | 28.5% | 15.0% | 5.0% | 0.4% | 100.0% | |

7.8. Example 8: Effects of Purification on Gene Expression Profiles

As discussed in Example 7, purification efforts at large scale were successful in reducing propylene glycol, which is a presumed ototoxin; beta-cyclodextrin molecules having no hydroxypropyl substitutions (DS-0), which are known to form precipitates; and bacterial endotoxin, which is highly inflammatory. However, we observed that absorption chromatography with alumina, whether used alone or in combination with solvent precipitation, also effected significant alteration in the compositional profile, or fingerprint, substantially reducing the amount of DS-1 hydroxypropyl beta-cyclodextrin, and—in the batch analyzed by electrospray MS, which had been purified by a combination of absorption chromatography with alumina and solvent precipitation—reducing the amount of DS-2 hydroxypropyl beta-cyclodextrin, with little apparent effect on the presence and ratios of the more highly substituted species present in Kleptose® HPB (DS3, DS4, DS5, DS6, DS7).

In order to assess the potential pharmacological effects of this substantial alteration in compositional fingerprint, we performed gene expression profiling.

7.8.1. Materials & Methods

7.8.1.1. Cells

GM18453 cells (homozygous for NPC1 mutation) and wild type GM05659 cells were obtained from Coriell Medical Institute. Cell lines were cultured in 10% FBS, DMEM, and 100 units/ml of penicillin and streptomycin. 500,000 cells/well were synchronized with 10 ug/ml mitomycin prior to cyclodextrin treatment. Hydroxypropyl cyclodextrins (HPCDs) were dissolved in PBS at the range of concentrations used in the study (0.1 mM to 10 mM).

7.8.1.2. RNA Preparation and Whole Transcriptome Analysis

NPC1 (GM18453) and wild type cells (GM05659) were lysed and RNA extracted using Trizol® reagent (Invitrogen). The cells were then subjected to DNAse I (Qiagen) treatment. The purity and concentration of samples was checked with both Qubit spectrophotometer and Nano Drop ND-1000 and the RNA integrity (RIN) was evaluated using Agilent 2100 Bioanalyzer. Extracted mRNA was enriched using RiboMinus™ Eukaryote kit (Invitrogen) according to manufacturer's instructions. The final quantity of RNA was 10 µg per reaction. cDNA libraries generated using the Clontech SMARTer Stranded RNA-Seq Kit were size-selected in the range of 150-250 bp and sequenced in accordance to the protocol provided by Illumina. Samples were sequenced using the HiSeq 2000 platform with 75 bp forward and 35 reverse primers.

7.8.1.3. RNA-Seq Data Analysis

Sequencing of cDNA libraries resulted in 20941134 to 42375128 paired reads per sample. For greater mapping quality, base reads were trimmed to 50 base pairs. All color-spaced reads were aligned to human reference genome (Ensembl, release 73) using TopHat v2.1.0 that used Bowtie version 1.0.0. Values for RPKM (reads per kilobase of transcript per million mapped reads) for assessing gene expression levels were calculated with Cufflinks v2.0.2 and raw counts were retrieved with Illumina BaseSpace Core Apps using gene annotations of protein coding genes downloaded from Ensembl (release 73). Differential expression/fold changes was estimated on raw counts with edgeR. All programs were used with their default parameters with TopHat set to not to find novel junctions.

Fold changes for each gene was visualized using TIBCO Spotfire (version 6.5). A combination of treemap and bar graphs were used to display differential gene expression changes. To view full transcriptome changes for 10 mM HPCD treatments, bar graph views were found to be most optimal.

7.8.1.4. RNA Seq Assay Validation Analysis

Raw RNA Seq base reads were subjected to directed computational analysis of a selected set of cholesterol homeostatic genes to establish responsiveness to Kleptose® HPB treatment. The selected genes are listed in Table 22 below.

TABLE 22

| Selected Cholesterol Genes for Gene Response Analysis in GM18453 and GM05659 Cells | |
|---|---|
| Gene ID | Classification |
| A1DOB | cholesterol transport |
| ABACA1 | cholesterol transport |
| ABCG1 | cholesterol transport |
| ABCG2 | cholesterol transport |
| ACAT | cholesterol esterification |
| ANKFY1 | lysosomal |
| APOA1 | lipid metabolism |
| APOEC1 | lipid metabolism |
| CEL | lipid transport |
| CETP | cholesterol ester transfer |
| CH25H | lipid transport |
| DHCR7 | lipoprotein assembly |
| FDFT1 | cholesterol synthesis |
| GGPS1 | cholesterol synthesis |
| IDI1 | cholesterol synthesis |
| LIPA | lipid metabolism |
| MVD | cholesterol synthesis |
| SC4MOL | cholesterol synthesis |
| SC5DL | cholesterol synthesis |
| SOAT2 | lipoprotein assembly |
| SREBF2 | cholesterol synthesis |

7.8.1.5. Metabolic Pathway Analysis

All cyclodextrin cell treatments were analyzed to determine key metabolic pathways affected in the 18453 NPC1 cell line. Using Ingenuity Pathway Analysis software, Gene ID, fold change and p-value per gene was used to generate Volcano scatter plots. These plots reveal upregulated and down regulated genes for the various treatments. Groups of genes are then probability weighted for their ability to perturb particular metabolic pathways (−log 10 (pACCC)) versus their differential expression levels (−Dlog10(pORA). The probabilistic mapping of gene members likely to perturb pathways does not necessarily exclude other gene members' involvement in perturbing other pathways.

These data were analyzed in the context of pathways obtained from the Kyoto Encyclopedia of Genes and Genomes (KEGG) database (Release 73.0+/03-16, March 15) (Kanehisa et al., 2000; Kanehisa et al., 2002), the gene ontology from the Gene Ontology Consortium database (2014-September 19) (Ashburner et al., 2000; Gene Ontology Consortium, 2001), miRNAs from the miRBase (Release 21) and TARGETSCAN (TargetScan Release 6.2 (updated March 2015)) databases (Griffiths-Jones et al., 2008; Kozomara and Griffiths-Jones, 2014; Friedman et al., 2009; Grimson et al., 2007), and diseases from the KEGG database (Release 73.0+/03-16, March 15) (Kanehisa et al., 2000; Kanehisa et al., 2002).

Ingenuity Pathway Analysis (Qiagen) scores the pathways using the impact analysis proposed by (Draghici et al., 2007; Tarca et al., 2009, Khatri et al., 2007). Impact analysis uses two types of evidence: i) the over-representation of differentially expressed (DE) genes in a given pathway and ii) the perturbation of that pathway computed by propagating the measured expression changes across the pathway topology. These aspects are captured by two independent probability values, pORA and pAcc, that are then combined in a unique global p-value. The pathway topologies, comprised of genes and their interactions, are obtained from the KEGG database (Kanehisa et al., 2000; Kanehisa et al., 2010; Kanehisa et al., 2012; Kanehisa et al., 2014).

The first probability, pORA, represents the probability of obtaining a number of DE genes on the given pathway greater or equal to the one observed just by chance (Draghici et al., 2003; Draghici 2011). Let us consider there are N genes measured in the experiment, with M of theses on the given pathway. Based on a priori selection of DE genes, K out of M genes were found to be differentially expressed. The probability of observing exactly x differentially expressed genes on the given pathway is computed based on the hypergeometric distribution: Because hypergeometric is a discrete distribution, the probability of observing fewer than x genes on the given pathway just by chance can be calculated by summing the probabilities of having 1 or 2 or . . . or x−1 genes on the pathway:

$$P(X=x|N,M,K)=\frac{\binom{M}{x}\binom{N-M}{K-x}}{\binom{N}{K}} \tag{1}$$

To compute the over-representation p-value of obtaining a number of DE genes on the given pathway greater or equal to the one observed the Ingenuity Pathway tool calculates pORA=p (x)=1−p(x−1):

$$p_u(x-1)= P(X=1)+P(X=2)+\ \ldots\ +P(X=x-1)=\sum_{i=0}^{x-1}\frac{\binom{M}{i}\binom{N-M}{K-i}}{\binom{N}{K}} \tag{2}$$

The second probability, pAcc, is calculated based on the amount of perturbation measured in each pathway. A perturbation factor is computed for each gene on the pathway using:

$$p_0(x)=1-\sum_{i=0}^{x-1}\frac{\binom{M}{i}\binom{N-M}{K-i}}{\binom{N}{K}}$$

In the equation shown, the term ΔE(g) represents the signed normalized measured expression change of gene g, and a (g) is an a priori weight based on the type of the gene. The second term is the sum of the perturbation factors of all genes u, directly upstream of the target gene g, normalized by the number of downstream genes of each such gene N (u). The value of 8 quantifies the strength of the interaction between genes g and u. The sign of β represents the type of interaction: plus for activation like signals, and minus for inhibition like signals. Subsequently, Ingenuity Pathway Analysis calculates the net perturbation accumulation at the level of each gene Acc(g), as the difference between the perturbation factor PF(g) and the observed log fold-change:

$$PF(g)=\alpha(g)\cdot\Delta E(g)+\sum_{u\in US_g}\beta_{ug}\frac{PF(u)}{N_{ds}(u)} \tag{4}$$

$$Acc(g_i)=PF(g_i)-\Delta E(g_i) \tag{5}$$

All perturbation accumulations are computed at the same time by solving the system of linear equations resulting from combining the above equation (see above) for all genes on the pathway. Once all gene perturbation accumulations are computed, Ingenuity Pathway computes the total accumulation of the pathway as the sum of all absolute accumulations of the genes. The significance of obtaining a larger total accumulation (pAcc) just by chance is assessed through bootstrap.

The two types of evidence, pORA and pAcc, are combined into one final p-value using Fisher's method. This p-value is then corrected for multiple comparisons using FDR and Bonferroni. Bonferroni is the simplest and more conservative of the two (Bonferroni, 1935; Bonferroni, 1936). It reduces the false discovery rate by imposing a more stringent threshold on each comparison weighed by the total number of comparisons. FDR is more powerful at the extent of discovering more false positives (Benjamini and Hochberg, 1995; Benjamini and Yekutieli, 2001). It ensures that the overall percentage of false positives is below the chosen threshold.

7.8.2. Results 7.8.2.1. Assay Validation

Prior to performing full transcriptome analyses, GM18453 and GM05659 cells were treated with a range of Kleptose® HPB concentrations (0.1 mM to 10 mM) and effects on selected cholesterol homeostasis-related genes were assessed.

The results are tabulated in Table 23 below, and graphed in FIG. 37. Results are expressed as fold changes (log (FC)).

TABLE 23

| Kleptose ® HPB treatment of GM05659 and GM18453 cells | | | | | | |
|---|---|---|---|---|---|---|
| Gene ID | Gene Classification | untreated GM05659 (wild type) cells | untreated GM18453 | 0.1 mM GM18453 | 1.0 mM GM18453 | 10.0 mM GM18453 |
| A1DOB | cholesterol transport | 1.723 | 0.721 | 0.6332 | 2.016 | 2.558 |
| ABACA1 | cholesterol transport | 1.115 | 0.403 | 0.345 | 1.7634 | 4.569 |
| ABCG1 | cholesterol transport | 1.316 | 0.805 | 0.717 | 1.23 | 3.109 |
| ABCG2 | cholesterol transport | 1.432 | 1.222 | 1.101 | 1.893 | 2.467 |
| ACAT | cholesterol esterification | 1.742 | 1.124 | 1.112 | 2.371 | 2.4322 |
| ANKFY1 | lysosomal | 1.823 | 0.957 | 0.786 | 2.254 | 2.279 |
| APOA1 | lipid metabolism | 2.672 | 1.459 | 1.93447 | 2.7346 | 4.9437 |
| APOEC1 | lipid metabolism | 1.217 | 1.081 | 0.9996 | 1.5988 | 2.1115 |
| CEL | lipid transport | 2.045 | 1.038 | 1.006 | 1.989 | 3.229 |
| CETP | cholesterol ester transfer | 1.789 | 1.106 | 1.4803 | 2.005 | 3.7633 |
| CHOLES-TEROL 25H | lipid transport | 1.643 | 0.845 | 1.2246 | 2.007 | 1.788 |
| DHCR7 | lipoprotein assembly | 1.821 | 0.677 | 0.4668 | 1.634 | 1.228 |
| FDFT1 | cholesterol synthesis | 1.145 | 0.781 | 0.8491 | 0.9572 | 1.117 |
| GGPS1 | cholesterol synthesis | 1.509 | 1.512 | 1.432 | 1.648 | 1.589 |
| IDI1 | cholesterol synthesis | 2.28 | 1.402 | 1.227 | 2.766 | 3.444 |
| LIPA | lipid metabolism | 1.607 | 0.917 | 0.893 | 1.339 | 1.7232 |
| MVD | cholesterol synthesis | 1.7224 | 1.593 | 1.5423 | 1.6772 | 2.1077 |
| SC4MOL | cholesterol synthesis | 1.837 | 1.71 | 1.6632 | 1.8905 | 1.9436 |
| SC5DL | cholesterol synthesis | 2.734 | 1.893 | 2.2911 | 3.244 | 4.131 |
| SOAT2 | lipoprotein assembly | 1.436 | 0.533 | 0.6021 | 0.9978 | 1.639 |
| SREBF2 | cholesterol synthesis | 1.6044 | 0.821 | 0.5299 | 1.7541 | 1.9444 |

The results demonstrate dose-dependent effects of Kleptose® HPB on the homozygous NPC1 cells, and further demonstrate that of the three concentrations tested, 1.0 mM Kleptose® HPB is suitable to provide meaningful data.

7.8.2.2. Analysis of Purified Compositions 7.8.2.2.1. Effect on Expression of Pre-Selected Cholesterol Homeostasis Genes As discussed in Example 7, we found that purification protocols that include adsorption to alumina significantly change the substitution fingerprint of the hydroxypropyl beta-cyclodextrin mixture. In order to assess how these changes alter the pharmacological effects of the composition, we compared the effects on expression of cholesterol homeostasis genes of (i) the variously purified compositions and (ii) Kleptose® HPB in GM18453 cells, which are homozygous for the NPC1 mutation.

To our surprise, we found no difference.

FIG. 38 shows fold changes in expression in GM18453 cells, which are homozygous for the NPC1 mutation, of the subset of cholesterol homeostasis genes in which expression was statistically significantly different ($p<0.001$) upon treatment, for four different compositions: STD (Kleptose® HPB “standard”); AC (Kleptose® HPB purified by alumina chromatography); SP (Kleptose® HPB purified by solvent precipitation); and AP (Kleptose® HPB purified by alumina chromatography & solvent precipitation). See Example 7 for details on the purification protocols and respective compositions.

None of the purified compositions, at any of the tested concentrations, differed in effect from the parent composition, Kleptose® HPB (“STD”), despite the removal of low DS species in the alumina-purified compositions. It would appear, therefore, that a relevant pharmacological activity of the composition-its effects on cholesterol homeostasis-resides in the more highly substituted species present in Kleptose® HPB, since removal of the unsubstituted beta-cyclodextrin molecules (DS-0), monosubstituted hydroxypropyl beta-cyclodextrins (DS-1), and substantial reduction in the di-substituted hydroxypropyl beta-cyclodextrins (DS-2) had no discernible effect on the composition’s ability to alter expression of cholesterol homeostasis genes in NPC1 cells.

7.8.2.2.2. Whole Genome Analysis

In the analysis described above, we assessed changes in expression of genes that had been pre-selected for relevance to the primary defect caused by the NPC1 mutation, and compared effects on expression of only that subset of the pre-selected genes whose expression was statistically significantly different upon treatment with hydroxypropyl beta-cyclodextrin. To confirm the observation that removal of low DS species has no appreciable effect on relevant pharmacologic activities, and to further explore possible differences between the compositions, we performed whole genome analyses to identify the biological pathways most affected, on a statistical basis, by treatment.

We performed whole genome pathway analyses of NPC1 cells treated with 1.0 mM Kleptose® HPB and 1.0 mM of purified batch CYL-4063. As described in detail in Example 7, CYL-4063 was prepared from Kleptose® HPB by a combination of absorption chromatography on alumina and solvent precipitation. As shown in Table 21 in Example 7, purification significantly reduced the prevalence of low DS species, with only 3.2% of the cyclodextrin species in CYL-4063 having 0, 1, and 2 substitutions, collectively, as compared to an average collective content of DS-0, DS-1, and DS-2 of 16.2% in Kleptose® HPB.

As shown in FIG. 39, of the top four pathways identified as statistically most significantly affected by treatment with 1.0 mM Kleptose® HPB, three are also among the top four pathways most statistically affected by treatment with 1.0 mM CYL-4063: the erbB signaling pathway, the MAPK signaling pathway, and the GnRH signaling pathway. These results confirm that there is little perturbation in the overall activity of the hydroxypropyl beta-cyclodextrin mixture on GM 18453 cells, despite removal of the low DS species from CYL-4063.

Moreover, we also observed that the steroid biosynthesis pathway, a pathway directly affected by the primary defect caused by the NPC1 mutation in these cells, is the second most significantly affected pathway upon treatment with 1.0 mM CYL-4063, but only sixth most statistically significant pathway affected by treatment with 1.0 mM Kleptose® HPB. These results are consistent with the hypothesis that the composition's effects on cholesterol homeostasis resides in the more highly substituted cyclodextrin species, which are present in greater concentration in the purified composition.

7.8.2.3. Activity of Fractions Having Different Degrees of Substitution

To assess directly the differential contribution of cyclodextrin species having different degrees of hydroxypropyl substitution, we fractionated a batch of Kleptose® HPB into three pools, respectively having low, medium, and high degrees of hydroxypropyl substitution, and tested the effects of these pooled fractions on gene expression in NPC1 cells.

7.8.2.3.1. Methods (a) Fractionation

Fractions were prepared from Kleptose® HPB batch E0245. The distribution of beta-cyclodextrin species in the E0245 starting material is shown in Table 21 (Example 7), excerpted in relevant part in Table 24 below.

TABLE 24

| Quantification of peak distribution | | | | | | | | | | |
|---|---|---|---|---|---|---|---|---|---|---|
| Batch ID | m/z 1152 (DS-0) | m/z 1210 (DS-1) | m/z 1268 (DS-2) | m/z 1326 (DS3) | m/z 1384 (DS4) | m/z 1442 (DS5) | m/z 1500 (DS6) | m/z 1558 (DS7) | m/z 1618 (DS8) | Total Signal |
| EO245 | 0 | 295840 | 965902 | 1907408 | 2345018 | 1807732 | 880668 | 285778 | 0 | 8488345 |
| | 0.0% | 3.5% | 11.4% | 22.5% | 27.6% | 21.3% | 10.4% | 3.4% | 0.0% | 100.0% |

A 15 g sample of Kleptose® HPB (batch E0245) was separated on a CD-screen column essentially as described in Example 5.3.1 above and fractions were collected. FIG. 40 shows chromatograms of various fractions obtained from the preparative CD-Screen chromatographic separation, annotated to show the degree of substitution of the chromatographically separated hydroxypropyl beta-cyclodextrin species.

Fraction 2 was chosen as the fraction having low degrees of substitution, "L" (CYL-4103). The fraction having species with medium degrees of substitution, fraction "M" (CYL-4104), is a pool of fractions 4-15. The fraction having high degrees of substitution, fraction "H" (CYL-4105), is a pool of fractions 16-24. FIG. 41A-D show electrospray MS spectra of (A) Kleptose® HPB batch E0245, annotated to identify the signals by degree of hydroxypropyl substitution; (B) the "L" pooled fraction; (C) the "M" pooled fraction; and (D) the "H" pooled fraction.

(b) Expression Profiling

The NPC cell line GM18453 (500,000 cells per well) was treated in parallel with 1.0 mM of "L", "M", and "H" fractions. RNA was isolated from each treatment followed by the generation of cDNA libraries in accordance with prior methods. Sequencing of cDNA libraries resulted in 28891287 to 50245721 paired reads per sample. For greater mapping quality, base reads were trimmed to 50 base pairs. All color-spaced reads were aligned to human reference genome (Ensembl, release 73) using TopHat v2.1.0_that used Bowtie version 1.0.0. RPKM (reads per kilobase of transcript per million mapped reads) values for gene expression levels were calculated with Cufflinks v2.0.2 and raw counts were retrieved with Illumina BaseSpace Core Apps using gene annotations of protein coding genes downloaded from Ensembl (release 73). Differential expression/fold changes were estimated on raw counts with edgeR. All programs were used with their default parameters with TopHat set to not to find novel junctions. Fold changes for each gene was visualized using TIBCO Spotfire (version 7.0). A combination of treemap and bar graphs were used to display differential gene expression changes.

For comparison, similar analyses were performed using Kleptose® HPB and unfractionated purified batch CYL-4077 (see Example 7).

7.8.2.3.2. Results

We performed whole genome transcriptome analyses to identify the 10 biological pathways most affected, on a statistical basis, by treatment with the "L", "M", and "H" Fractions.

FIG. 42 shows the 10 biological pathways most affected by treatment of the NPC cells with 1.0 mM of the "L", "M", and "H" fractions, ranked in descending order of statistical significance. Consistent with our earlier observations, the "L" fraction did not cause statistically significant changes in the expression of genes in the steroid biosynthesis pathway. In striking contrast, the steroid biosynthesis pathway is statistically the most significantly affected biological pathway upon treatment of NPC1 cells with the "M" fraction. The "M" fraction consists primarily of beta-cyclodextrin species having 3, 4, 5 and 6 hydroxypropyl substitutions (DS3, DS4, DS5, and DS6). The "H" fraction, which includes primarily DS5, DS6, and DS7, also causes changes in expression of the genes of the cholesterol biosynthesis pathway, with the cholesterol biosynthesis pathway appearing as the second most significant pathway.

These results provide direct evidence that the ability to restore cholesterol homeostasis resides in the cyclodextrin species present in Kleptose® HPB that have higher degrees of hydroxypropyl substitution.

7.8.2.4. Comparison of Fractions to Unfractionated Compositions

A corollary to our observation that species of cyclodextrin having different degrees of hydroxypropyl substitution differentially affect gene expression in NPC cells is that the overall pharmacological activity of the composition as a whole must depend on the compositional fingerprint, that is, on the relative proportions of the differentially hydroxypropylated species present in the composition.

We confirmed this hypothesis by comparing gene expression changes on a specific gene-by-specific gene (that is, on a GeneID) basis after treatment of NPC cells with 1.0 mM of either (i) unfractionated Kleptose® HPB, (ii) unfractionated CYL-4077, which had been purified from Kleptose® HPB by absorption chromatography on alumina and selective solvent precipitation, (iii) the “L” fraction, (iv) “M” fraction, or (v) “H” fraction.

We observed that 64% of genes whose expression is significantly affected by Kleptose® HPB at 1.0 mM are also significantly affected by treatment with the purified batch (Batch CYL-4077) at 1.0 mM.

This shared percentage is markedly higher than the percentage of genes whose expression is significantly affected both by treatment with 1.0 mM Kleptose® HPB and by 1.0 mM of any one of the “L”, “M”, and “H” fractions (37%, 43% and 48%, respectively).

Analogously, the 64% shared identity in genes affected both by Kleptose® HPB and CYL-4077 is markedly higher than the percentage of genes whose expression is significantly affected both by treatment with 1.0 mM CYL-4077 and 1.0 mM of any one of the “L”, “M”, and “H” fractions (41%, 38% and 44%, respectively).

7.8.2.5. Genes Involved in Autophagy

Hydroxypropyl beta-cyclodextrin has been demonstrated to enhance autophagic clearance of proteolipids aggregates that accumulate in NPC disease. (Song et al., 2014, *J. Biol. Chem.* vol. 289 (14), pages 10211-10222). We therefore analyzed the effects in GM18453 NPC cells of treatment with 1.0 mM and 10.0 mM Kleptose® HPB, CYL-4077, and each of the “H”, “M”, and “L” fractions on the expression of autophagy-related genes.

Table 25 shows all autophagy genes whose change in expression upon treatment was statistically significant ($p<0.05$), and demonstrates that 1.0 mM concentrations had little effect on autophagy-related genes.

TABLE 25

| Analysis of Autophagy Genes of GM18453 Cells (1.0 mM) | | | | | | | | | |
|---|---|---|---|---|---|---|---|---|---|
| Kleptose ® HPB | | CYL-4077 | | “H” | | “M” | | “L” | |
| Gene ID | fold changes | Gene ID | fold changes | Gene ID | fold changes | Gene ID | fold change | Gene ID | fold changes |
| ATG2B | −0.995 | ATG2B | 1.1123 | — | — | — | — | — | — |

Table 26 shows all autophagy genes whose change in expression upon treatment was statistically significant ($p<0.05$) at 10.0 mM concentrations.

TABLE 26

| Analysis of Autophagy Genes of GM18453 Cells (10.0 mM) | | | | | | | | | |
|---|---|---|---|---|---|---|---|---|---|
| Kleptose ® HPB | | CYL-4077 | | “H” | | “M” | | “L” | |
| Gene ID | fold changes | Gene ID | fold changes | Gene ID | fold changes | Gene ID | fold changes | Gene ID | fold changes |
| ATG10 | 1.23 | ATG10 | 1.045 | ATG5 | 3.11 | ATG5 | 4.332 | ATG10 | 2.7 |
| ATG2A | −0.53 | ATG12 | 0.79 | ATG2 | −2.65 | ATG10 | 2.705 | | |
| ATG16L2 | 0.57 | ATG2A | −0.53 | ATG10 | −5.4 | ATG16 | 11.294 | | |
| ATG3 | −0.71 | ATG2B | 1.1023 | ATG18 | 4.5 | ATG12 | 8.34 | | |
| ATG4A | 1.72 | ATG3 | −0.68 | ATG101 | 2 | BECN1 | 2.7 | | |
| BECN1 | 0.45 | BECN1 | 0.96 | BECN1 | 7.12 | VPS15 | 3.356 | | |
| | | | | VPS15 | 5.63 | VPS13B | 9.28 | | |
| | | | | VPS13B | −4.793 | VPS36 | −4.899 | | |
| | | | | VPS36 | −4.112 | VPS37B | -4.897 | | |
| | | | | VPS37B | 4.42 | | | | |

The results using 10.0 mM demonstrate Kleptose® HPB and CYL-4077 have similar effect on the expression of the genes involved in autophagy, and further demonstrate that these effects are contributed by species having higher degrees of substitution, with the "L" fraction having the least effect on expression of genes involved in autophagy, compared with "H" fraction and "M" fraction.

7.8.3. Discussion

Using gene expression profile experiments, we have demonstrated that the parenteral grade hydroxypropyl beta-cyclodextrin composition, Kleptose® HPB, is capable of restoring expression levels of cholesterol homeostasis genes in cells homozygous for the NPC1 mutation, and increasing expression of autophagy-related genes. These data are consistent with data from the phase I human clinical trial demonstrating that intrathecal administration of Kleptose® HPB is effective to stabilize or slow progression of symptoms in patients with NPC disease. Correlation with the clinical data demonstrates that the gene expression assay can provide an in vitro measure of potency.

Electrospray MS demonstrates that Kleptose® HPB is a complex mixture, containing beta-cyclodextrin molecules having different degrees of hydroxypropylation in reproducible proportions.

The purification process that we have developed to remove process-related and other impurities from Kleptose® HPB adventitiously removes beta-cyclodextrin species with low degrees of substitution, altering the compositional fingerprint. Gene expression profile experiments demonstrated that despite this change in compositional fingerprint, there was no significant change in the ability of the composition to normalize expression of genes in the cholesterol biosynthesis pathway in cells homozygous for the NPC mutation.

These data suggested that the relevant pharmacological activity is contributed primarily by species having greater degrees of substitution than those eliminated during purification.

We confirmed this inference by fractionating the complex mixture into pools having beta-cyclodextrin species with low ("L"), medium ("M"), and high ("H") degrees of hydroxypropyl substitution, and assessing effects on gene expression in NPC cells. The results demonstrated that the "L" fraction has no apparent effect on expression of genes in the cholesterol biosynthesis pathway or autophagy, whereas the "M" and "H" fractions significantly affect expression of cholesterol biosynthesis and autophagy genes. These experiments further demonstrated that the pharmacological activity of the composition as a whole is a composite of the activities separately contributed by beta-cyclodextrin species having different degrees of hydroxypropyl substitution; the overall pharmacological activity depends on the compositional fingerprint, that is, on the relative proportions of the differentially hydroxypropylated species present in the composition.

Although the pharmacological activity of the composition as a whole is a composite of the activities separately contributed by beta-cyclodextrin species having different degrees of hydroxypropyl substitution, fortuitously, the species that are removed by our purification process, those with low degrees of hydroxypropyl substitution, contribute little, if at all, to the particular activities of the mixture that are pharmacologically relevant to treatment of NPC disease. This discovery will allow the novel, more highly purified, and compositionally distinct HPBCD composition we have developed to be administered by intrathecal or intracerebroventricular route to the CSF of patients with NPC disease for longer periods, with therapeutic effect and increased safety.

7.9. Example 9: Alternative Preparative Fraction Methodology

As discussed in Example 8, three fractions having different average degrees of substitution were prepared for use in gene expression profiling experiments using a CD-Screen column for chromatographic separation.

As an alternative, we also prepared fractions of Kleptose® HPB (batch E0245) using an alumina column, essentially as described in Example 5.7.2 above. The sample was applied to the alumina column and eluted isocratically with 100% methanol. FIG. 43 shows chromatograms of various fractions, annotated to show the numerical fractions pooled to produce fractions "A"-"F" and "K", and further annotated to show the degree of substitution of the chromatographically separated hydroxypropyl beta-cyclodextrin species.

The experimental parameters were further optimized to remove unsubstituted BCD and DS1 HPBCD as much as possible from Kleptose® HPB, with the least loss of DS2 and DS3 HPBCD. The details of the purification methods are described as below:

Identical Parameters for Each Tested Method (Methods II-XI):

210 g alumina column;
30 ml/min flow rate;
100 sec/fraction;
60 sec delay time.

Only MeOH as Eluent:

Method II. 21 g Kleptose, 30 fractions, eluent: 100% MeOH isocratic elution, yield: 79.4% Method III. 10.5 g Kleptose, 30 fractions, eluent: 100% MeOH isocratic elution, yield: 72.3%

Method IV. 15 g Kleptose, 30 fractions, eluent: 100% MeOH isocratic elution, yield: 77.7%

MeOH+Water, as Eluents:

Method V. 10.4 g Kleptose, 30 fractions, eluent: 100% MeOH isocratic elution (yield: 73.8%)+30 fractions, 100% MeOH isocratic elution (total yield of the 60 fractions: 75.9%)+30 fractions, 3-step isocratic elution (90, 80, 70% MeOH, 15 min each) with short (100 sec) transition gradient elutions between each step, total yield of the 90 fractions: 83.1%

Method VI. 10.5 g Kleptose, eluent: MeOH+water, 75 fractions, 20 min 100→80% MeOH gradient elution, 106 min 80% MeOH isocratic elution, yield: 82.8%

Method VII. Same as Method VI., but 70% MeOH instead of the 80%, yield: 91.2%

Method VIII. 10.5 g Kleptose, eluent: MeOH+water, 75% MeOH isocratic elution, 30 fractions, yield: 86.4%

Method IX. 10.6 g Kleptose, eluent: MeOH+water, 70% MeOH isocratic elution, 30 fractions, yield: 89.2%

EtOH (96% Purity)+Water, as Eluents:

Method X. 10.5 g Kleptose, 30 fractions, eluent: 100% EtOH isocratic elution (yield: 27.6%)+30 fractions, 70% EtOH isocratic elution, total yield of the 60 fractions: 82.1%

Method XI. 10.5 g Kleptose, 60 fractions, eluent: 80% EtOH isocratic elution, yield: 82.3%

FIG. 44A-B show chromatograms of the HPBCD mixture after different methods of purification. The ratio of the DS2/DS1 in the mixture after purification is summarized in Table 27.

TABLE 27

| DS2/DS1 Ratio | | | |
|---|---|---|---|
| Sample | DS1 area | DS2 area | DS2/DS1 |
| Method II. | 790.2 | 10187.9 | 12.893 |
| Method III. | 282.8 | 7836.0 | 27.706 |
| Method IV. | 607.1 | 10563.8 | 17.400 |
| Method V. | 537.5 | 11873.2 | 22.090 |
| Method VI. | 344.7 | 11678.9 | 33.885 |
| Method VII. | 982.1 | 14857.8 | 15.129 |
| Method VIII. | 318.9 | 10708.8 | 33.577 |
| Method IX. | 729.9 | 13698.6 | 18.768 |
| Starting HPBCD (for Method II-IX) | 5013.215 | 16290.0 | 3.249 |
| Method X. | 1371.7 | 14023.1 | 10.223 |
| Method XI. | 274.1 | 9445.5 | 34.464 |
| Starting HPBCD (for Method X-XI) | 5161.88 | 17371.5 | 3.365 |

7.10. Example 10: Phase I Clinical Trial for NPC at 18 Month

Further analyses were conducted on the data from phase I clinical trial for Niemann-Pick Disease Type C, including efficacy results at 18 months. Results are shown in FIGS. 45-50. As summarized in FIG. 45, annualized slope, change from baseline, and responder analysis were used to analyze the 18 months phase I clinical trial data. From annualized rate of change, the 18 months treatment results reveal that the HPBCD mixture is a disease modifying therapy (FIG. 46). The HPBCD mixture shows consistent improvement or stabilization of disease from the baseline in NPC patients (FIG. 47). The HPBCD mixture treatment also shows a greater percentage of responders showing stable or improving disease (FIG. 48). The impact of treatment on hearing is primarily in high frequency range, and the impact is correctable with hearing aids (FIG. 49). FIG. 50 summarizes the conclusions to date with respect to impact of treatment on hearing.

8. EQUIVALENTS AND INCORPORATION BY REFERENCE

All publications, patents, patent applications and other documents cited in this application are hereby incorporated by reference in their entireties for all purposes to the same extent as if each individual publication, patent, patent application or other document were individually indicated to be incorporated by reference for all purposes.

While various specific embodiments have been illustrated and described, it will be appreciated that various changes can be made without departing from the spirit and scope of the disclosure.

What is claimed is:

1. A composition for intrathecal administration comprising a mixture of beta-cyclodextrin molecules substituted at one or more hydroxyl positions by hydroxypropyl groups, wherein the composition is pharmaceutically acceptable for intrathecal administration and the composition comprises less than 8 International Units (IU) of endotoxins per gram.

2. The composition of claim 1, wherein the composition comprises less than 6 International Units (IU) of endotoxins per gram.

3. The composition of claim 1, wherein the composition comprises less than 5 International Units (IU) of endotoxins per gram.

4. The composition of claim 1, wherein the composition comprises less than 4 International Units (IU) of endotoxins per gram.

5. The composition of claim 1, wherein the composition comprises less than 3 International Units (IU) of endotoxins per gram.

6. The composition of claim 1, wherein the composition comprises less than 1 ppm propylene oxide.

7. The composition of claim 1, wherein the composition comprises less than 0.8 ppm propylene oxide.

8. The composition of claim 1, wherein the composition comprises less than 0.6 ppm propylene oxide.

9. The composition of claim 1, wherein the composition comprises less than 0.5 ppm propylene oxide.

10. The composition of claim 1, wherein the mixture of beta-cyclodextrin molecules comprises less than 1% unsubstituted beta-cyclodextrin ("DS-0").

11. The composition of claim 1, wherein the mixture of beta-cyclodextrin molecules comprises 10% to 30% molecules having three hydroxypropyl substitutions ("DS-3").

12. The composition of claim 1, wherein the mixture of beta-cyclodextrin molecules comprises at least 75% molecules having three, four, five, and six hydroxypropyl substitutions, collectively ("DS-3", "DS-4", "DS-5", and "DS-6").

13. The composition of claim 1, wherein the mixture of beta-cyclodextrin molecules comprises less than 1% molecules having nine and ten hydroxypropyl substitutions, collectively ("DS-9" and "DS-10").

14. The composition of claim 1, wherein the mixture of beta-cyclodextrin molecules comprises less than 0.1% molecules having nine and ten hydroxypropyl substitutions, collectively ("DS-9" and "DS-10").

15. The composition of claim 1, wherein the composition comprises less than 0.9% propylene glycol.

16. The composition of claim 1, wherein the composition comprises less than 0.8% propylene glycol.

17. The composition of claim 1, wherein the composition comprises less than 0.7% propylene glycol.

18. The composition of claim 1, wherein the composition comprises less than 0.6% propylene glycol.

19. The composition of claim 1, wherein the composition further comprises sodium chloride and is suitable for lumbar injection.

20. A composition for intrathecal administration comprising a mixture of beta-cyclodextrin molecules substituted at one or more hydroxyl positions by hydroxypropyl groups, wherein the composition is pharmaceutically acceptable for intrathecal administration, the composition comprises less than 8 Endotoxin Units (EU) of endotoxins per gram, and no more than 1% propylene glycol.

21. The composition of claim 20, wherein the composition comprises less than 6 International Units (IU) of endotoxins per gram.

22. The composition of claim 20, wherein the composition comprises less than 5 International Units (IU) of endotoxins per gram.

23. The composition of claim 20, wherein the composition comprises less than 4 International Units (IU) of endotoxins per gram.

24. The composition of claim 20, wherein the composition comprises less than 3 International Units (IU) of endotoxins per gram.

25. The composition of claim 20, wherein the mixture of beta-cyclodextrin molecules comprises less than 1% unsubstituted beta-cyclodextrin ("DS-0").

26. The composition of claim 20, wherein the mixture of beta-cyclodextrin molecules comprises 10% to 30% molecules having three hydroxypropyl substitutions ("DS-3").

27. The composition of claim 20, wherein the mixture of beta-cyclodextrin molecules comprises at least 75% molecules having three, four, five, and six hydroxypropyl substitutions, collectively ("DS-3", "DS-4", "DS-5", and "DS-6").

28. The composition of claim 20, wherein the mixture of beta-cyclodextrin molecules comprises less than 1% molecules having nine and ten hydroxypropyl substitutions, collectively ("DS-9" and "DS-10").

29. The composition of claim 20, wherein the mixture of beta-cyclodextrin molecules comprises less than 0.1% molecules having nine and ten hydroxypropyl substitutions, collectively ("DS-9" and "DS-10").

30. A composition for intrathecal administration comprising a mixture of beta-cyclodextrin molecules substituted at one or more hydroxyl positions by hydroxypropyl groups, wherein the composition is pharmaceutically acceptable for intrathecal administration, the composition comprises less than 8 Endotoxin Units (EU) of endotoxins per gram, the mixture of beta-cyclodextrin molecules comprises less than 1% unsubstituted beta-cyclodextrin ("DS-0"), and less than 1% molecules having nine and ten hydroxypropyl substitutions, collectively ("DS-9" and "DS-10").

* * * * *